US007202339B2

(12) United States Patent
Alekshun et al.

(10) Patent No.: US 7,202,339 B2
(45) Date of Patent: Apr. 10, 2007

(54) CRYSTALS OF MARR POLYPEPTIDES, REGULATORS OF MULTIPLE ANTIBIOTIC RESISTANCE

(75) Inventors: Michael N. Alekshun, Wakefield, MA (US); Stuart B. Levy, Boston, MA (US); James F. Head, Newton, MA (US); Barbara A. Seaton, Newton, MA (US)

(73) Assignees: Trustees of Tufts College, Medford, MA (US); Trustees of Boston University, Boston, MA (US)

( * ) Notice: Subject to any disclaimer, the term of this patent is extended or adjusted under 35 U.S.C. 154(b) by 362 days.

(21) Appl. No.: 10/196,655

(22) Filed: Jul. 15, 2002

(65) Prior Publication Data

US 2003/0148492 A1 Aug. 7, 2003

Related U.S. Application Data

(60) Provisional application No. 60/388,622, filed on Jun. 13, 2002, provisional application No. 60/305,404, filed on Jul. 13, 2001.

(51) Int. Cl.
*A61K 14/00* (2006.01)

(52) U.S. Cl. ..................................... 530/350

(58) Field of Classification Search ...................... None
See application file for complete search history.

(56) References Cited

U.S. PATENT DOCUMENTS

| | | | |
|---|---|---|---|
| 5,817,793 A | 10/1998 | Levy | |
| 6,346,391 B1 | 2/2002 | Oethinger et al. | |
| 6,391,545 B1 | 5/2002 | Levy | |
| 6,448,006 B1 | 9/2002 | Levy | |

FOREIGN PATENT DOCUMENTS

| WO | WO 03/056294 A2 | 7/2003 |
|---|---|---|
| WO | WO 03/056294 A3 | 7/2003 |

OTHER PUBLICATIONS

Giege et al., "Crystallogenesis of Biological Macromolecules: Facts and Perspectives", Jul. 1994, Acta Crystallographica Section D, vol. 50, pp. 339-350.*
Martinez-Hackert et al., The DNA-binding domain of OmpR: crystal structure of a winged helix transcription factor, Jan. 1997, Structure, vol. 5, pp. 109-124.*
McPherson et al., "The science of macromolecular crystallization", Aug. 1995, Structure, vol. 3, pp. 759-768.*
Drenth, "Principles of Protein X-ray Crystallography", Springer Advanced Texts in Chemistry, 2nd Edition, pp. 89-92.*
Drenth, "Principles of Protein X-ray Crystallography", Springer Advanced Texts in Chemistry, 2nd Edition, Chapter 1, pp. 1-21.*
Alekshun, M.N. et al. "Regulation of chromosomally mediated multiple antibiotic resistance: the *mar* regulon." *Antimicrob. Agents Chemother.* Oct. 1997;41(10):2067-75.

Alekshun, M.N. et al. "Characterization of MarR superrepressor mutants." *J. Bacteriol.* May 1999;181(10):3303-6.
Alekshun, M.N. et al. "Alteration of the repressor activity of MarR, the negative regulator of the *Escherichia coli marRAB* locus, by multiple chemicals *in vitro.*" *J. Bacteriol.* Aug. 1999; 181(15):4669-72.
Alekshun, M.N. et al. "The *mar* regulon: multiple resistance to antibiotics and other toxic chemicals." *Trends Microbiol.* Oct. 1999;7(10):410-3.
Alekshun, M.N. et al. "Mutational analysis of MarR, the negative regulator of *marRAB* expression in *Escherichia coli*, suggests the presence of two regions required for DNA binding." *Mol. Microbiol.* Mar. 2000;35(6):1394-404.
Barbosa, T.M. et al. "Differential expression of over 60 chromosomal genes in *Escherichia coli* by constitutive expression of MarA." *J. Bacteriol.* Jun. 2000;182(12):3467-74.
Brooun, A. et al. "Purification and ligand binding of EmrR, a regulator of a multidrug transporter." *J. Bacteriol.* Aug. 1999;181(16):5131-3.
Drenth, J. "Chapter 1: Crystallizing a protein." from *Principles of Protein X-ray Crystallography* pp. 1-18, 1994 Springer-Verlag New York, Inc.
Gajiwala, K.S. et al. "Winged helix proteins." *Curr. Opin. Struct. Biol.* Feb. 2000;10(1):110-6.
Gajiwala, K.S. et al. "Structure of the winged-helix protein hRFX1 reveals a new mode of DNA binding." *Nature* Feb. 24, 2000;403(6772):916-21.
Kern, W.V. et al. "Non-target gene mutations in the development of fluoroquinolone resistance in *Escherichia coli.*" *Antimicrob. Agents Chemother.* Apr. 2000;44(4):814-20.
Koutsolioutsou, A. et al. "A *soxRS*-constitutive mutation contributing to antibiotic resistance in a clinical isolate of *Salmonella enterica* (Serovar typhimurium)." *Antimicrob. Agents Chemother.* Jan. 2001;45(1):38-43.
Linde, H.J. et al. "*In vivo* increase in resistance to ciprofloxacin in *Escherichia coli* associated with deletion of the C-terminal part of MarR." *Antimicrob. Agents Chemother.* Jul. 2000;44(7):1865-8.
Maneewannakul, K. et al. "Identification for *mar* mutants among quinolone-resistant clinical isolates of *Escherichia coli.*" *Antimicrob. Agents Chemother.* Jul. 1996;40(7):1695-8.
Martin, R.G et al. "Binding of purified multiple antibiotic-resistance repressor protein (MarR) to *mar* operator sequences." *Proc. Natl. Acad. Sci. U.S.A.* Jun. 6, 1995;92(12):5456-60.
Martin, R.G. et al. "Autoactivation of the *marRAB* multiple antibiotic resistance operon by the MarA transcriptional activator in *Escherichia coli.*" *J. Bacteriol.* Apr. 1996;178(8):2216-23.
Martin, R.G. et al. "Binding of purified multiple antibiotic-resistance repressor protein (MarR) to *mar* operator sequences." *Proc. Natl. Acad. Sci. U.S.A.* Jun. 1995; 92:5456-5460.

(Continued)

*Primary Examiner*—Robert A. Wax
*Assistant Examiner*—Suzanne M. Noakes
(74) *Attorney, Agent, or Firm*—Lahive & Cookfield, LLP; Elizabeth Hanley, Esq.; Cynthia M. Soroos, Esq.

(57) ABSTRACT

The crystal structure of the product, crystals of the MarR protein, a regulator of multiple antibiotic resistance in *Escherichia coli*, and methods of crystallization of the MarR protein are described.

10 Claims, 56 Drawing Sheets

OTHER PUBLICATIONS

Nikaido, H. "Multiple antibiotic resistance and efflux." *Curr. Opin. Microbiol.* Oct. 1998;1(5):516-23.

Oethinger, M. et al. "Overexpression of the *marA* or *soxS* regulatory gene in clinical topoisomerase mutants of *Escherichia coli.*" *Antimicrob. Agents Chemother.* Aug. 1998;42(8):2089-94.

Pohl, E. et al. "Motion of the DNA-binding domain with respect to the core of the diphtheria toxin repressor (DtxR) revealed in the crystal structures of apo- and holo-DtxR." *J. Biol. Chem.* Aug. 28, 1998;273(35):22420-7.

Providenti, M.A. et al. "Identification and functional characterization of CbaR, a MarR-like modulator of the *cbaABC*-encoded chlorobenzoate catabolism pathway." *Applied and Environmental Microbiology* Aug. 2001; 67(8):3530-41.

Randall, L.P. et al. "Multiple antibiotic resistance (*mar*) locus in *Salmonella enterica* serovar typhimurium DT104." *Applied and Experimental Microbiology.* Mar. 2001;67(3):1190-1197.

Sulavik, M.C. et al. "The MarR repressor of the multiple antibiotic resistance (*mar*) operon in *Escherichia coli*: prototypic member of a family of bacterial regulatory proteins involved in sensing phenolic compounds." May 1995; 1(4):436-446.

Sulavik, M.C. et al. "The *Salmonella typhimurium mar* locus: molecular and genetic analyses and assessment of its role in virulence." *J. Bacteriol.* Mar. 1997;179(6):1857-66.

White, A. et al. "Structure of the metal-ion-activated diphtheria toxin repressor/*tox* operator complex." *Nature* Jul. 30, 1998;394(6692):502-6.

Zheng, N. et al. "Structural basis of DNA recognition by the heterodimeric cell cycle transcription factor E2F-DP." *Genes Dev.* Mar. 15, 1999;13(6):666-74.

Ziha-Zarifi, I. et al. "*In vivo* emergence of multidrug-resistant mutants of *Pseudomonas aeruginosa* overexpressing the active efflux system MexA-MexB-OprM." *Antimicrob. Agents Chemother.*Feb. 1999;43(2):287-91.

Alekshun, et al. The crystal structure of MarR, a regulator of multiple antibiotic resistance, at 2.3 A resolution. Nat Struct Biol. Aug. 2001;8(8):710-4.

Geneseq_101002 database, AAR4977, dated Oct. 14, 1994, Result #1.

* cited by examiner

Appendix C

```
HEADER    TRANSCRIPTION                           26-JUN-01   1JGS
TITLE     MULTIPLE ANTIBIOTIC RESISTANCE REPRESSOR, MARR WITH SALICYLATE
COMPND    MOL_ID: 1; RESIDUES 7-144 OF SEQ ID NO:2;
COMPND    2 MOLECULE: MULTIPLE ANTIBIOTIC RESISTANCE PROTEIN MARR;
COMPND    3 CHAIN: A;
COMPND    4 ENGINEERED: YES
SOURCE    MOL_ID: 1;
SOURCE    2 ORGANISM_SCIENTIFIC: ESCHERICHIA COLI;
SOURCE    3 ORGANISM_COMMON: BACTERIA;
SOURCE    4 EXPRESSION_SYSTEM: ESCHERICHIA COLI;
SOURCE    5 EXPRESSION_SYSTEM_COMMON: BACTERIA;
SOURCE    6 EXPRESSION_SYSTEM_STRAIN: BL21(DE3)
KEYWDS    TRANSCRIPTION REGULATION, DNA-BINDING, REPRESSOR,
KEYWDS    2 ANTIBIOTIC RESISTANCE
EXPDTA    X-RAY DIFFRACTION
AUTHOR    M.N.ALEKSHUN,S.B.LEVY,T.R.MEALY,B.A.SEATON,J.F.HEAD
REVDAT    1   28-DEC-01 1JGS    0
JRNL         AUTH   M.N.ALEKSHUN,S.B.LEVY,T.R.MEALY,B.A.SEATON,J.F.HEAD
JRNL         TITL   THE CRYSTAL STRUCTURE OF MARR, A REGULATOR OF
JRNL         TITL 2 MULTIPLE ANTIBIOTIC RESISTANCE, AT 2.3 A
JRNL         TITL 3 RESOLUTION.
JRNL         REF    NAT.STRUCT.BIOL.              V.   8   710 2001
JRNL         REFN   ASTM NSBIEW  US ISSN 1072-8368
REMARK    1
REMARK    2
REMARK    2 RESOLUTION. 2.30 ANGSTROMS.
REMARK    3
REMARK    3 REFINEMENT.
REMARK    3   PROGRAM     : CNS 1.0
REMARK    3   AUTHORS     : BRUNGER,ADAMS,CLORE,DELANO,GROS,GROSSE-
REMARK    3               : KUNSTLEVE,JIANG,KUSZEWSKI,NILGES, PANNU,
REMARK    3               : READ,RICE,SIMONSON,WARREN
REMARK    3
REMARK    3   REFINEMENT TARGET : NULL
REMARK    3
REMARK    3  DATA USED IN REFINEMENT.
REMARK    3   RESOLUTION RANGE HIGH (ANGSTROMS) : 2.30
REMARK    3   RESOLUTION RANGE LOW  (ANGSTROMS) : 50.00
REMARK    3   DATA CUTOFF            (SIGMA(F)) : NULL
REMARK    3   OUTLIER CUTOFF HIGH (RMS(ABS(F))) : NULL
REMARK    3   COMPLETENESS (WORKING+TEST)   (%) : NULL
REMARK    3   NUMBER OF REFLECTIONS             : 5968
REMARK    3
REMARK    3  FIT TO DATA USED IN REFINEMENT.
REMARK    3   CROSS-VALIDATION METHOD          : THROUGHOUT
REMARK    3   FREE R VALUE TEST SET SELECTION  : RANDOM
REMARK    3   R VALUE            (WORKING SET) : 0.247
REMARK    3   FREE R VALUE                     : 0.287
REMARK    3   FREE R VALUE TEST SET SIZE   (%) : NULL
REMARK    3   FREE R VALUE TEST SET COUNT      : 506
REMARK    3   ESTIMATED ERROR OF FREE R VALUE  : NULL
REMARK    3
REMARK    3  FIT IN THE HIGHEST RESOLUTION BIN.
REMARK    3   TOTAL NUMBER OF BINS USED             : NULL
REMARK    3   BIN RESOLUTION RANGE HIGH       (A)   : NULL
REMARK    3   BIN RESOLUTION RANGE LOW        (A)   : NULL
REMARK    3   BIN COMPLETENESS (WORKING+TEST) (%)   : NULL
REMARK    3   REFLECTIONS IN BIN    (WORKING SET)   : NULL
REMARK    3   BIN R VALUE           (WORKING SET)   : NULL
REMARK    3   BIN FREE R VALUE                      : NULL
REMARK    3   BIN FREE R VALUE TEST SET SIZE  (%)   : NULL
REMARK    3   BIN FREE R VALUE TEST SET COUNT       : NULL
REMARK    3   ESTIMATED ERROR OF BIN FREE R VALUE   : NULL
REMARK    3
REMARK    3  NUMBER OF NON-HYDROGEN ATOMS USED IN REFINEMENT.
REMARK    3   PROTEIN ATOMS        : 1078
REMARK    3   NUCLEIC ACID ATOMS   : 0
REMARK    3   HETEROGEN ATOMS      : 20
REMARK    3   SOLVENT ATOMS        : 0
REMARK    3
REMARK    3  B VALUES.
REMARK    3   FROM WILSON PLOT         (A**2) : NULL
REMARK    3   MEAN B VALUE   (OVERALL, A**2) : NULL
REMARK    3   OVERALL ANISOTROPIC B VALUE.
REMARK    3     B11 (A**2) : NULL
```

Figure 7-1

```
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3     ESD FROM LUZZATI PLOT        (A) : NULL
REMARK   3     ESD FROM SIGMAA              (A) : NULL
REMARK   3     LOW RESOLUTION CUTOFF        (A) : NULL
REMARK   3
REMARK   3   CROSS-VALIDATED ESTIMATED COORDINATE ERROR.
REMARK   3     ESD FROM C-V LUZZATI PLOT    (A) : NULL
REMARK   3     ESD FROM C-V SIGMAA          (A) : NULL
REMARK   3
REMARK   3   RMS DEVIATIONS FROM IDEAL VALUES.
REMARK   3     BOND LENGTHS                 (A) : 0.007
REMARK   3     BOND ANGLES            (DEGREES) : NULL
REMARK   3     DIHEDRAL ANGLES        (DEGREES) : NULL
REMARK   3     IMPROPER ANGLES        (DEGREES) : NULL
REMARK   3
REMARK   3   ISOTROPIC THERMAL MODEL : NULL
REMARK   3
REMARK   3   ISOTROPIC THERMAL FACTOR RESTRAINTS.    RMS     SIGMA
REMARK   3     MAIN-CHAIN BOND              (A**2) : NULL ; NULL
REMARK   3     MAIN-CHAIN ANGLE             (A**2) : NULL ; NULL
REMARK   3     SIDE-CHAIN BOND              (A**2) : NULL ; NULL
REMARK   3     SIDE-CHAIN ANGLE             (A**2) : NULL ; NULL
REMARK   3
REMARK   3   BULK SOLVENT MODELING.
REMARK   3     METHOD USED : NULL
REMARK   3     KSOL        : NULL
REMARK   3     BSOL        : NULL
REMARK   3
REMARK   3   NCS MODEL : NULL
REMARK   3
REMARK   3   NCS RESTRAINTS.                         RMS    SIGMA/WEIGHT
REMARK   3     GROUP  1  POSITIONAL            (A) : NULL ; NULL
REMARK   3     GROUP  1  B-FACTOR           (A**2) : NULL ; NULL
REMARK   3
REMARK   3   PARAMETER FILE  1  : NULL
REMARK   3   TOPOLOGY FILE   1  : NULL
REMARK   3
REMARK   3   OTHER REFINEMENT REMARKS: NULL
REMARK   4
REMARK   4 1JGS COMPLIES WITH FORMAT V. 2.3, 09-JULY-1998
REMARK 100
REMARK 100 THIS ENTRY HAS BEEN PROCESSED BY RCSB ON 15-JUL-2001.
REMARK 100 THE RCSB ID CODE IS RCSB013753.
REMARK 200
REMARK 200 EXPERIMENTAL DETAILS
REMARK 200   EXPERIMENT TYPE                : X-RAY DIFFRACTION
REMARK 200   DATE OF DATA COLLECTION        : NULL
REMARK 200   TEMPERATURE           (KELVIN) : 100.0
REMARK 200   PH                             : 5.50
REMARK 200   NUMBER OF CRYSTALS USED        : 1
REMARK 200
REMARK 200   SYNCHROTRON              (Y/N) : Y
REMARK 200   RADIATION SOURCE               : NSLS X8C
REMARK 200   BEAMLINE                       : NULL
REMARK 200   X-RAY GENERATOR MODEL          : NULL
REMARK 200   MONOCHROMATIC OR LAUE    (M/L) : M
REMARK 200   WAVELENGTH OR RANGE        (A) : 1.072
REMARK 200   MONOCHROMATOR                  : NULL
REMARK 200   OPTICS                         : NULL
REMARK 200
REMARK 200   DETECTOR TYPE                  : CCD
REMARK 200   DETECTOR MANUFACTURER          : ADSC QUANTUM 4
REMARK 200   INTENSITY-INTEGRATION SOFTWARE : DENZO
REMARK 200   DATA SCALING SOFTWARE          : SCALEPACK
REMARK 200
REMARK 200   NUMBER OF UNIQUE REFLECTIONS   : 6069
REMARK 200   RESOLUTION RANGE HIGH      (A) : 2.300
REMARK 200   RESOLUTION RANGE LOW       (A) : 50.000
REMARK 200   REJECTION CRITERIA  (SIGMA(I)) : NULL
```

Figure 7-2

```
REMARK 200
REMARK 200 OVERALL.
REMARK 200  COMPLETENESS FOR RANGE     (%) : 99.5
REMARK 200  DATA REDUNDANCY                : 9.500
REMARK 200  R MERGE                    (I) : 0.06000
REMARK 200  R SYM                      (I) : NULL
REMARK 200  <I/SIGMA(I)> FOR THE DATA SET  : 21.1000
REMARK 200
REMARK 200 IN THE HIGHEST RESOLUTION SHELL.
REMARK 200  HIGHEST RESOLUTION SHELL, RANGE HIGH (A) : 2.30
REMARK 200  HIGHEST RESOLUTION SHELL, RANGE LOW  (A) : 2.38
REMARK 200  COMPLETENESS FOR SHELL     (%) : 100.0
REMARK 200  DATA REDUNDANCY IN SHELL       : NULL
REMARK 200  R MERGE FOR SHELL          (I) : 0.20000
REMARK 200  R SYM FOR SHELL            (I) : NULL
REMARK 200  <I/SIGMA(I)> FOR SHELL         : 12.000
REMARK 200
REMARK 200 DIFFRACTION PROTOCOL: MAD
REMARK 200 METHOD USED TO DETERMINE THE STRUCTURE: MAD
REMARK 200 SOFTWARE USED: SOLVE
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): NULL
REMARK 280 MATTHEWS COEFFICIENT, VM (ANGSTROMS**3/DA): NULL
REMARK 280
REMARK 280 CRYSTALLIZATION CONDITIONS: PEG MME 5000, AMMONIUM SULFATE,
REMARK 280  SODIUM SALICYLATE, HEPTANETRIOL, GLYCEROL, DTT
REMARK 290
REMARK 290 CRYSTALLOGRAPHIC SYMMETRY
REMARK 290 SYMMETRY OPERATORS FOR SPACE GROUP: I 41 2 2
REMARK 290
REMARK 290      SYMOP    SYMMETRY
REMARK 290     NNNMMM    OPERATOR
REMARK 290       1555    X,Y,Z
REMARK 290       2555    1/2-X,1/2-Y,1/2+Z
REMARK 290       3555    -Y,1/2+X,1/4+Z
REMARK 290       4555    1/2+Y,-X,3/4+Z
REMARK 290       5555    1/2-X,Y,3/4-Z
REMARK 290       6555    X,1/2-Y,1/4-Z
REMARK 290       7555    1/2+Y,1/2+X,1/2-Z
REMARK 290       8555    -Y,-X,-Z
REMARK 290       9555    1/2+X,1/2+Y,1/2+Z
REMARK 290      10555    1/1-X,1/1-Y,1/1+Z
REMARK 290      11555    1/2-Y,1/1+X,3/4+Z
REMARK 290      12555    1/1+Y,1/2-X,5/4+Z
REMARK 290      13555    1/1-X,1/2+Y,5/4-Z
REMARK 290      14555    1/2+X,1/1-Y,3/4-Z
REMARK 290      15555    1/1+Y,1/1+X,1/1-Z
REMARK 290      16555    1/2-Y,1/2-X,1/2-Z
REMARK 290
REMARK 290      WHERE NNN -> OPERATOR NUMBER
REMARK 290            MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290     SMTRY1   1  1.000000  0.000000  0.000000        0.00000
REMARK 290     SMTRY2   1  0.000000  1.000000  0.000000        0.00000
REMARK 290     SMTRY3   1  0.000000  0.000000  1.000000        0.00000
REMARK 290     SMTRY1   2 -1.000000  0.000000  0.000000       31.00000
REMARK 290     SMTRY2   2  0.000000 -1.000000  0.000000       31.00000
REMARK 290     SMTRY3   2  0.000000  0.000000  1.000000       66.44500
REMARK 290     SMTRY1   3  0.000000 -1.000000  0.000000        0.00000
REMARK 290     SMTRY2   3  1.000000  0.000000  0.000000       31.00000
REMARK 290     SMTRY3   3  0.000000  0.000000  1.000000       33.22250
REMARK 290     SMTRY1   4  0.000000  1.000000  0.000000       31.00000
REMARK 290     SMTRY2   4 -1.000000  0.000000  0.000000        0.00000
REMARK 290     SMTRY3   4  0.000000  0.000000  1.000000       99.66750
REMARK 290     SMTRY1   5 -1.000000  0.000000  0.000000       31.00000
REMARK 290     SMTRY2   5  0.000000  1.000000  0.000000        0.00000
REMARK 290     SMTRY3   5  0.000000  0.000000 -1.000000       99.66750
```

Figure 7-3

```
REMARK 290    SMTRY1    6   1.000000   0.000000   0.000000        0.00000
REMARK 290    SMTRY2    6   0.000000  -1.000000   0.000000       31.00000
REMARK 290    SMTRY3    6   0.000000   0.000000  -1.000000       33.22250
REMARK 290    SMTRY1    7   0.000000   1.000000   0.000000       31.00000
REMARK 290    SMTRY2    7   1.000000   0.000000   0.000000       31.00000
REMARK 290    SMTRY3    7   0.000000   0.000000  -1.000000       66.44500
REMARK 290    SMTRY1    8   0.000000  -1.000000   0.000000        0.00000
REMARK 290    SMTRY2    8  -1.000000   0.000000   0.000000        0.00000
REMARK 290    SMTRY3    8   0.000000   0.000000  -1.000000        0.00000
REMARK 290    SMTRY1    9   1.000000   0.000000   0.000000       31.00000
REMARK 290    SMTRY2    9   0.000000   1.000000   0.000000       31.00000
REMARK 290    SMTRY3    9   0.000000   0.000000   1.000000       66.44500
REMARK 290    SMTRY1   10  -1.000000   0.000000   0.000000       62.00000
REMARK 290    SMTRY2   10   0.000000  -1.000000   0.000000       62.00000
REMARK 290    SMTRY3   10   0.000000   0.000000   1.000000      132.89000
REMARK 290    SMTRY1   11   0.000000  -1.000000   0.000000       31.00000
REMARK 290    SMTRY2   11   1.000000   0.000000   0.000000       62.00000
REMARK 290    SMTRY3   11   0.000000   0.000000   1.000000       99.66750
REMARK 290    SMTRY1   12   0.000000   1.000000   0.000000       62.00000
REMARK 290    SMTRY2   12  -1.000000   0.000000   0.000000       31.00000
REMARK 290    SMTRY3   12   0.000000   0.000000   1.000000      166.11250
REMARK 290    SMTRY1   13  -1.000000   0.000000   0.000000       62.00000
REMARK 290    SMTRY2   13   0.000000   1.000000   0.000000       31.00000
REMARK 290    SMTRY3   13   0.000000   0.000000  -1.000000      166.11250
REMARK 290    SMTRY1   14   1.000000   0.000000   0.000000       31.00000
REMARK 290    SMTRY2   14   0.000000  -1.000000   0.000000       62.00000
REMARK 290    SMTRY3   14   0.000000   0.000000  -1.000000       99.66750
REMARK 290    SMTRY1   15   0.000000   1.000000   0.000000       62.00000
REMARK 290    SMTRY2   15   1.000000   0.000000   0.000000       62.00000
REMARK 290    SMTRY3   15   0.000000   0.000000  -1.000000      132.89000
REMARK 290    SMTRY1   16   0.000000  -1.000000   0.000000       31.00000
REMARK 290    SMTRY2   16  -1.000000   0.000000   0.000000       31.00000
REMARK 290    SMTRY3   16   0.000000   0.000000  -1.000000       66.44500
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350    BIOMT1   1   1.000000   0.000000   0.000000        0.00000
REMARK 350    BIOMT2   1   0.000000   1.000000   0.000000        0.00000
REMARK 350    BIOMT3   1   0.000000   0.000000   1.000000        0.00000
REMARK 350    BIOMT1   2  -1.000000   0.000000   0.000000       62.00000
REMARK 350    BIOMT2   2   0.000000  -1.000000   0.000000       62.00000
REMARK 350    BIOMT3   2   0.000000   0.000000   1.000000      132.89000
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
REMARK 500
REMARK 500 EXPECTED VALUES: ENGH AND HUBER, 1991
REMARK 500
REMARK 500  M RES CSSEQI ATM1   RES CSSEQI ATM2   DEVIATION
REMARK 500    MET A   74   CE   MET A   74   SD     0.043
REMARK 500    GLU A  131   CA   GLU A  131   N      0.046
REMARK 500
REMARK 500 GEOMETRY AND STEREOCHEMISTRY
```

Figure 7-4

```
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1   ATM2   ATM3
REMARK 500    LEU A  97   N  -  CA  -  C    ANGL. DEV. = -8.4 DEGREES
REMARK 500    THR A 101   N  -  CA  -  C    ANGL. DEV. = -8.9 DEGREES
REMARK 500    GLU A 131   N  -  CA  -  C    ANGL. DEV. =  9.5 DEGREES
REMARK 500    LEU A 143   N  -  CA  -  C    ANGL. DEV. =  8.6 DEGREES
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M=MODEL NUMBER; RES=RESIDUE NAME; C=CHAIN IDENTIFIER;
REMARK 500 SSEQ=SEQUENCE NUMBER; I=INSERTION CODE).
REMARK 500
REMARK 500 STANDARD TABLE:
REMARK 500 FORMAT:(10X,I3,1X,A3,1X,A1,I4,A1,4X,F7.2,3X,F7.2)
REMARK 500
REMARK 500  M RES CSSEQI        PSI       PHI
REMARK 500    ALA A  53      -60.18     70.65
DBREF  1JGS A    7   144  SWS    P27245   MARR_ECOLI       7    144
SEQRES   1 A  138  LEU PHE ASN GLU ILE ILE PRO LEU GLY ARG LEU ILE HIS
SEQRES   2 A  138  MET VAL ASN GLN LYS LYS ASP ARG LEU LEU ASN GLU TYR
SEQRES   3 A  138  LEU SER PRO LEU ASP ILE THR ALA ALA GLN PHE LYS VAL
SEQRES   4 A  138  LEU CYS SER ILE ARG CYS ALA ALA CYS ILE THR PRO VAL
SEQRES   5 A  138  GLU LEU LYS LYS VAL LEU SER VAL ASP LEU GLY ALA LEU
SEQRES   6 A  138  THR ARG MET LEU ASP ARG LEU VAL CYS LYS GLY TRP VAL
SEQRES   7 A  138  GLU ARG LEU PRO ASN PRO ASN ASP LYS ARG GLY VAL LEU
SEQRES   8 A  138  VAL LYS LEU THR THR GLY GLY ALA ALA ILE CYS GLU GLN
SEQRES   9 A  138  CYS HIS GLN LEU VAL GLY ASP LEU HIS GLN GLU LEU
SEQRES  10 A  138  THR LYS ASN LEU THR ALA ASP GLU VAL ALA THR LEU GLU
SEQRES  11 A  138  TYR LEU LEU LYS LYS VAL LEU PRO
HET     SAL  256      10
HET     SAL  257      10
HETNAM     SAL 2-HYDROXYBENZOIC ACID
HETSYN     SAL SALICYLIC ACID
FORMUL   2  SAL    2(C7 H6 O3)
HELIX    1   1 PRO A   13  SER A   34  1                                  22
HELIX    2   2 THR A   39  ALA A   53  1                                  15
HELIX    3   3 THR A   56  SER A   65  1                                  10
HELIX    4   4 ASP A   67  LYS A   81  1                                  15
HELIX    5   5 THR A  101  LYS A  125  1                                  25
HELIX    6   6 GLU A  131  LYS A  141  1                                  11
SHEET    1   A 2 VAL A  84  PRO A  88  0
SHEET    2   A 2 VAL A  96  LEU A 100 -1  N  LEU A  97   O  LEU A  87
CRYST1   62.000   62.000  132.890  90.00  90.00  90.00 I 41 2 2      16
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.016129  0.000000  0.000000        0.00000
SCALE2      0.000000  0.016129  0.000000        0.00000
SCALE3      0.000000  0.000000  0.007525        0.00000
ATOM      1  N   LEU A   7      36.956  -0.266  22.798  1.00 63.50           N
ATOM      2  CA  LEU A   7      36.482   0.956  22.088  1.00 63.50           C
ATOM      3  C   LEU A   7      37.614   1.498  21.226  1.00 63.50           C
ATOM      4  O   LEU A   7      37.388   1.940  20.097  1.00 63.50           O
ATOM      5  CB  LEU A   7      36.033   2.021  23.097  1.00 65.57           C
ATOM      6  CG  LEU A   7      35.117   3.140  22.579  1.00 65.57           C
ATOM      7  CD1 LEU A   7      33.812   2.545  22.096  1.00 65.57           C
ATOM      8  CD2 LEU A   7      34.848   4.157  23.684  1.00 65.57           C
ATOM      9  N   PHE A   8      38.833   1.465  21.760  1.00 68.87           N
ATOM     10  CA  PHE A   8      40.004   1.938  21.022  1.00 68.87           C
ATOM     11  C   PHE A   8      40.644   0.777  20.278  1.00 68.87           C
ATOM     12  O   PHE A   8      41.758   0.889  19.768  1.00 68.87           O
ATOM     13  CB  PHE A   8      41.034   2.571  21.964  1.00 79.70           C
```

Figure 7-5

```
ATOM     14  CG  PHE A   8      40.611   3.901  22.524  1.00 79.70           C
ATOM     15  CD1 PHE A   8      39.571   3.988  23.450  1.00 79.70           C
ATOM     16  CD2 PHE A   8      41.249   5.072  22.122  1.00 79.70           C
ATOM     17  CE1 PHE A   8      39.174   5.220  23.967  1.00 79.70           C
ATOM     18  CE2 PHE A   8      40.858   6.311  22.634  1.00 79.70           C
ATOM     19  CZ  PHE A   8      39.820   6.383  23.557  1.00 79.70           C
ATOM     20  N   ASN A   9      39.933  -0.344  20.236  1.00 96.16           N
ATOM     21  CA  ASN A   9      40.416  -1.528  19.540  1.00 96.16           C
ATOM     22  C   ASN A   9      39.437  -1.875  18.426  1.00 96.16           C
ATOM     23  O   ASN A   9      39.503  -2.953  17.833  1.00 96.16           O
ATOM     24  CB  ASN A   9      40.551  -2.706  20.510  1.00 93.11           C
ATOM     25  CG  ASN A   9      41.643  -2.489  21.548  1.00 93.11           C
ATOM     26  OD1 ASN A   9      41.894  -3.351  22.395  1.00 93.11           O
ATOM     27  ND2 ASN A   9      42.298  -1.333  21.486  1.00 93.11           N
ATOM     28  N   GLU A  10      38.530  -0.944  18.143  1.00 59.45           N
ATOM     29  CA  GLU A  10      37.525  -1.142  17.105  1.00 59.45           C
ATOM     30  C   GLU A  10      37.512   0.040  16.141  1.00 59.45           C
ATOM     31  O   GLU A  10      37.604   1.191  16.561  1.00 59.45           O
ATOM     32  CB  GLU A  10      36.143  -1.305  17.747  1.00 65.56           C
ATOM     33  CG  GLU A  10      35.257  -2.304  17.033  1.00 65.56           C
ATOM     34  CD  GLU A  10      35.908  -3.673  16.912  1.00 65.56           C
ATOM     35  OE1 GLU A  10      36.330  -4.238  17.943  1.00 65.56           O
ATOM     36  OE2 GLU A  10      35.995  -4.186  15.778  1.00 65.56           O
ATOM     37  N   ILE A  11      37.403  -0.247  14.847  1.00 60.35           N
ATOM     38  CA  ILE A  11      37.383   0.812  13.846  1.00 60.35           C
ATOM     39  C   ILE A  11      35.962   1.288  13.573  1.00 60.35           C
ATOM     40  O   ILE A  11      35.271   0.780  12.687  1.00 60.35           O
ATOM     41  CB  ILE A  11      38.020   0.354  12.519  1.00 49.41           C
ATOM     42  CG1 ILE A  11      39.485  -0.019  12.752  1.00 49.41           C
ATOM     43  CG2 ILE A  11      37.925   1.470  11.475  1.00 49.41           C
ATOM     44  CD1 ILE A  11      40.133  -0.692  11.564  1.00 49.41           C
ATOM     45  N   ILE A  12      35.537   2.270  14.357  1.00 57.24           N
ATOM     46  CA  ILE A  12      34.213   2.852  14.227  1.00 57.24           C
ATOM     47  C   ILE A  12      34.362   4.041  13.286  1.00 57.24           C
ATOM     48  O   ILE A  12      35.210   4.918  13.503  1.00 57.24           O
ATOM     49  CB  ILE A  12      33.697   3.328  15.609  1.00 44.12           C
ATOM     50  CG1 ILE A  12      33.711   2.147  16.591  1.00 44.12           C
ATOM     51  CG2 ILE A  12      32.294   3.907  15.481  1.00 44.12           C
ATOM     52  CD1 ILE A  12      33.624   2.551  18.061  1.00 44.12           C
ATOM     53  N   PRO A  13      33.559   4.074  12.208  1.00 56.35           N
ATOM     54  CA  PRO A  13      33.607   5.166  11.228  1.00 56.35           C
ATOM     55  C   PRO A  13      33.175   6.508  11.834  1.00 56.35           C
ATOM     56  O   PRO A  13      32.278   6.558  12.678  1.00 56.35           O
ATOM     57  CB  PRO A  13      32.659   4.679  10.134  1.00 44.76           C
ATOM     58  CG  PRO A  13      31.628   3.905  10.919  1.00 44.76           C
ATOM     59  CD  PRO A  13      32.497   3.110  11.868  1.00 44.76           C
ATOM     60  N   LEU A  14      33.816   7.583  11.384  1.00 50.54           N
ATOM     61  CA  LEU A  14      33.547   8.938  11.865  1.00 50.54           C
ATOM     62  C   LEU A  14      32.060   9.240  12.081  1.00 50.54           C
ATOM     63  O   LEU A  14      31.652   9.658  13.179  1.00 50.54           O
ATOM     64  CB  LEU A  14      34.145   9.947  10.880  1.00 41.30           C
ATOM     65  CG  LEU A  14      34.006  11.443  11.136  1.00 41.30           C
ATOM     66  CD1 LEU A  14      34.719  11.839  12.423  1.00 41.30           C
ATOM     67  CD2 LEU A  14      34.603  12.185   9.952  1.00 41.30           C
ATOM     68  N   GLY A  15      31.260   9.028  11.034  1.00 49.82           N
ATOM     69  CA  GLY A  15      29.829   9.276  11.115  1.00 49.82           C
ATOM     70  C   GLY A  15      29.180   8.770  12.390  1.00 49.82           C
ATOM     71  O   GLY A  15      28.489   9.521  13.080  1.00 49.82           O
ATOM     72  N   ARG A  16      29.389   7.496  12.708  1.00 56.39           N
ATOM     73  CA  ARG A  16      28.807   6.925  13.917  1.00 56.39           C
ATOM     74  C   ARG A  16      29.406   7.557  15.172  1.00 56.39           C
ATOM     75  O   ARG A  16      28.698   7.776  16.154  1.00 56.39           O
ATOM     76  CB  ARG A  16      29.013   5.409  13.947  1.00100.64           C
ATOM     77  CG  ARG A  16      28.044   4.622  13.073  1.00100.64           C
ATOM     78  CD  ARG A  16      28.476   3.163  12.974  1.00100.64           C
ATOM     79  NE  ARG A  16      28.621   2.532  14.287  1.00100.64           N
ATOM     80  CZ  ARG A  16      29.280   1.395  14.502  1.00100.64           C
ATOM     81  NH1 ARG A  16      29.861   0.758  13.492  1.00100.64           N
ATOM     82  NH2 ARG A  16      29.360   0.893  15.727  1.00100.64           N
ATOM     83  N   LEU A  17      30.707   7.853  15.147  1.00 42.87           N
ATOM     84  CA  LEU A  17      31.341   8.466  16.308  1.00 42.87           C
ATOM     85  C   LEU A  17      30.735   9.844  16.572  1.00 42.87           C
ATOM     86  O   LEU A  17      30.456  10.187  17.716  1.00 42.87           O
ATOM     87  CB  LEU A  17      32.859   8.587  16.115  1.00 41.77           C
ATOM     88  CG  LEU A  17      33.683   7.296  16.205  1.00 41.77           C
```

Figure 7-6

```
ATOM     89  CD1 LEU A  17      35.166   7.592  15.962  1.00 41.77           C
ATOM     90  CD2 LEU A  17      33.487   6.677  17.571  1.00 41.77           C
ATOM     91  N   ILE A  18      30.558  10.634  15.516  1.00 40.19           N
ATOM     92  CA  ILE A  18      29.959  11.962  15.643  1.00 40.19           C
ATOM     93  C   ILE A  18      28.557  11.779  16.234  1.00 40.19           C
ATOM     94  O   ILE A  18      28.113  12.567  17.072  1.00 40.19           O
ATOM     95  CB  ILE A  18      29.821  12.662  14.270  1.00 50.02           C
ATOM     96  CG1 ILE A  18      31.203  13.011  13.716  1.00 50.02           C
ATOM     97  CG2 ILE A  18      29.008  13.933  14.409  1.00 50.02           C
ATOM     98  CD1 ILE A  18      31.156  13.614  12.312  1.00 50.02           C
ATOM     99  N   HIS A  19      27.875  10.726  15.792  1.00 61.33           N
ATOM    100  CA  HIS A  19      26.534  10.419  16.262  1.00 61.33           C
ATOM    101  C   HIS A  19      26.592  10.158  17.755  1.00 61.33           C
ATOM    102  O   HIS A  19      26.050  10.922  18.557  1.00 61.33           O
ATOM    103  CB  HIS A  19      26.007   9.186  15.532  1.00 71.93           C
ATOM    104  CG  HIS A  19      24.670   8.715  16.009  1.00 71.93           C
ATOM    105  ND1 HIS A  19      23.556   9.526  16.029  1.00 71.93           N
ATOM    106  CD2 HIS A  19      24.257   7.501  16.445  1.00 71.93           C
ATOM    107  CE1 HIS A  19      22.515   8.833  16.454  1.00 71.93           C
ATOM    108  NE2 HIS A  19      22.913   7.600  16.712  1.00 71.93           N
ATOM    109  N   MET A  20      27.264   9.072  18.116  1.00 42.03           N
ATOM    110  CA  MET A  20      27.426   8.676  19.511  1.00 42.03           C
ATOM    111  C   MET A  20      27.796   9.844  20.414  1.00 42.03           C
ATOM    112  O   MET A  20      27.316   9.923  21.535  1.00 42.03           O
ATOM    113  CB  MET A  20      28.515   7.608  19.634  1.00 67.14           C
ATOM    114  CG  MET A  20      28.159   6.249  19.067  1.00 67.14           C
ATOM    115  SD  MET A  20      29.602   5.147  19.075  1.00 67.14           S
ATOM    116  CE  MET A  20      29.707   4.719  20.836  1.00 67.14           C
ATOM    117  N   VAL A  21      28.664  10.735  19.938  1.00 52.70           N
ATOM    118  CA  VAL A  21      29.092  11.885  20.733  1.00 52.70           C
ATOM    119  C   VAL A  21      28.002  12.948  20.875  1.00 52.70           C
ATOM    120  O   VAL A  21      27.875  13.592  21.933  1.00 52.70           O
ATOM    121  CB  VAL A  21      30.346  12.560  20.137  1.00 37.15           C
ATOM    122  CG1 VAL A  21      30.727  13.763  20.989  1.00 37.15           C
ATOM    123  CG2 VAL A  21      31.517  11.556  20.086  1.00 37.15           C
ATOM    124  N   ASN A  22      27.231  13.149  19.810  1.00 51.65           N
ATOM    125  CA  ASN A  22      26.161  14.131  19.863  1.00 51.65           C
ATOM    126  C   ASN A  22      25.157  13.551  20.836  1.00 51.65           C
ATOM    127  O   ASN A  22      24.591  14.263  21.671  1.00 51.65           O
ATOM    128  CB  ASN A  22      25.502  14.323  18.497  1.00 36.79           C
ATOM    129  CG  ASN A  22      24.601  15.544  18.465  1.00 36.79           C
ATOM    130  OD1 ASN A  22      25.067  16.671  18.633  1.00 36.79           O
ATOM    131  ND2 ASN A  22      23.304  15.326  18.257  1.00 36.79           N
ATOM    132  N   GLN A  23      24.957  12.241  20.723  1.00 53.66           N
ATOM    133  CA  GLN A  23      24.040  11.521  21.592  1.00 53.66           C
ATOM    134  C   GLN A  23      24.419  11.899  23.018  1.00 53.66           C
ATOM    135  O   GLN A  23      23.649  12.543  23.728  1.00 53.66           O
ATOM    136  CB  GLN A  23      24.205  10.015  21.384  1.00 84.11           C
ATOM    137  CG  GLN A  23      23.100   9.154  21.974  1.00 84.11           C
ATOM    138  CD  GLN A  23      22.270   8.458  20.903  1.00 84.11           C
ATOM    139  OE1 GLN A  23      22.789   7.665  20.109  1.00 84.11           O
ATOM    140  NE2 GLN A  23      20.972   8.752  20.877  1.00 84.11           N
ATOM    141  N   LYS A  24      25.631  11.519  23.412  1.00 47.08           N
ATOM    142  CA  LYS A  24      26.142  11.801  24.746  1.00 47.08           C
ATOM    143  C   LYS A  24      25.873  13.245  25.140  1.00 47.08           C
ATOM    144  O   LYS A  24      25.342  13.516  26.213  1.00 47.08           O
ATOM    145  CB  LYS A  24      27.651  11.540  24.817  1.00 49.11           C
ATOM    146  CG  LYS A  24      28.214  11.723  26.218  1.00 49.11           C
ATOM    147  CD  LYS A  24      29.725  11.840  26.227  1.00 49.11           C
ATOM    148  CE  LYS A  24      30.273  12.007  27.651  1.00 49.11           C
ATOM    149  NZ  LYS A  24      30.669  10.711  28.286  1.00 49.11           N
ATOM    150  N   LYS A  25      26.253  14.161  24.260  1.00 49.08           N
ATOM    151  CA  LYS A  25      26.082  15.592  24.491  1.00 49.08           C
ATOM    152  C   LYS A  25      24.650  15.955  24.881  1.00 49.08           C
ATOM    153  O   LYS A  25      24.428  16.784  25.767  1.00 49.08           O
ATOM    154  CB  LYS A  25      26.504  16.365  23.235  1.00 88.21           C
ATOM    155  CG  LYS A  25      26.525  17.878  23.381  1.00 88.21           C
ATOM    156  CD  LYS A  25      25.257  18.516  22.837  1.00 88.21           C
ATOM    157  CE  LYS A  25      25.373  20.036  22.832  1.00 88.21           C
ATOM    158  NZ  LYS A  25      24.213  20.700  22.173  1.00 88.21           N
ATOM    159  N   ASP A  26      23.677  15.331  24.227  1.00 49.82           N
ATOM    160  CA  ASP A  26      22.291  15.635  24.539  1.00 49.82           C
ATOM    161  C   ASP A  26      21.908  15.027  25.873  1.00 49.82           C
ATOM    162  O   ASP A  26      21.190  15.650  26.661  1.00 49.82           O
ATOM    163  CB  ASP A  26      21.356  15.137  23.432  1.00 69.22           C
```

Figure 7-7

```
ATOM    164  CG  ASP A  26      21.429  15.997  22.174  1.00 69.22           C
ATOM    165  OD1 ASP A  26      21.641  17.227  22.294  1.00 69.22           O
ATOM    166  OD2 ASP A  26      21.259  15.444  21.065  1.00 69.22           O
ATOM    167  N   ARG A  27      22.403  13.819  26.129  1.00 55.02           N
ATOM    168  CA  ARG A  27      22.117  13.123  27.381  1.00 55.02           C
ATOM    169  C   ARG A  27      22.570  13.967  28.562  1.00 55.02           C
ATOM    170  O   ARG A  27      21.902  14.023  29.590  1.00 55.02           O
ATOM    171  CB  ARG A  27      22.823  11.765  27.426  1.00107.80           C
ATOM    172  CG  ARG A  27      22.687  11.072  28.770  1.00107.80           C
ATOM    173  CD  ARG A  27      23.372   9.722  28.799  1.00107.80           C
ATOM    174  NE  ARG A  27      23.381   9.171  30.151  1.00107.80           N
ATOM    175  CZ  ARG A  27      23.926   8.005  30.485  1.00107.80           C
ATOM    176  NH1 ARG A  27      24.513   7.256  29.559  1.00107.80           N
ATOM    177  NH2 ARG A  27      23.884   7.585  31.746  1.00107.80           N
ATOM    178  N   LEU A  28      23.715  14.619  28.410  1.00 41.40           N
ATOM    179  CA  LEU A  28      24.232  15.464  29.469  1.00 41.40           C
ATOM    180  C   LEU A  28      23.314  16.674  29.610  1.00 41.40           C
ATOM    181  O   LEU A  28      23.000  17.105  30.720  1.00 41.40           O
ATOM    182  CB  LEU A  28      25.662  15.913  29.142  1.00 54.85           C
ATOM    183  CG  LEU A  28      26.672  14.768  29.009  1.00 54.85           C
ATOM    184  CD1 LEU A  28      28.074  15.320  28.812  1.00 54.85           C
ATOM    185  CD2 LEU A  28      26.629  13.914  30.259  1.00 54.85           C
ATOM    186  N   LEU A  29      22.887  17.207  28.472  1.00 46.97           N
ATOM    187  CA  LEU A  29      22.001  18.359  28.432  1.00 46.97           C
ATOM    188  C   LEU A  29      20.738  18.053  29.245  1.00 46.97           C
ATOM    189  O   LEU A  29      20.399  18.793  30.172  1.00 46.97           O
ATOM    190  CB  LEU A  29      21.639  18.670  26.982  1.00 54.42           C
ATOM    191  CG  LEU A  29      20.751  19.884  26.737  1.00 54.42           C
ATOM    192  CD1 LEU A  29      21.413  21.122  27.319  1.00 54.42           C
ATOM    193  CD2 LEU A  29      20.510  20.042  25.250  1.00 54.42           C
ATOM    194  N   ASN A  30      20.043  16.965  28.903  1.00 36.87           N
ATOM    195  CA  ASN A  30      18.849  16.583  29.648  1.00 36.87           C
ATOM    196  C   ASN A  30      19.174  16.503  31.144  1.00 36.87           C
ATOM    197  O   ASN A  30      18.399  16.977  31.981  1.00 36.87           O
ATOM    198  CB  ASN A  30      18.302  15.220  29.189  1.00 52.27           C
ATOM    199  CG  ASN A  30      17.560  15.296  27.862  1.00 52.27           C
ATOM    200  OD1 ASN A  30      18.148  15.107  26.795  1.00 52.27           O
ATOM    201  ND2 ASN A  30      16.259  15.583  27.925  1.00 52.27           N
ATOM    202  N   GLU A  31      20.320  15.905  31.474  1.00 57.43           N
ATOM    203  CA  GLU A  31      20.733  15.760  32.874  1.00 57.43           C
ATOM    204  C   GLU A  31      20.946  17.092  33.588  1.00 57.43           C
ATOM    205  O   GLU A  31      20.661  17.214  34.776  1.00 57.43           O
ATOM    206  CB  GLU A  31      22.004  14.908  32.981  1.00 80.57           C
ATOM    207  CG  GLU A  31      21.742  13.406  32.919  1.00 80.57           C
ATOM    208  CD  GLU A  31      23.005  12.566  33.095  1.00 80.57           C
ATOM    209  OE1 GLU A  31      23.742  12.795  34.081  1.00 80.57           O
ATOM    210  OE2 GLU A  31      23.253  11.672  32.253  1.00 80.57           O
ATOM    211  N   TYR A  32      21.436  18.090  32.863  1.00 46.41           N
ATOM    212  CA  TYR A  32      21.676  19.408  33.446  1.00 46.41           C
ATOM    213  C   TYR A  32      20.393  20.212  33.627  1.00 46.41           C
ATOM    214  O   TYR A  32      20.319  21.063  34.511  1.00 46.41           O
ATOM    215  CB  TYR A  32      22.622  20.219  32.565  1.00 77.48           C
ATOM    216  CG  TYR A  32      23.960  19.576  32.316  1.00 77.48           C
ATOM    217  CD1 TYR A  32      24.590  19.716  31.080  1.00 77.48           C
ATOM    218  CD2 TYR A  32      24.610  18.853  33.315  1.00 77.48           C
ATOM    219  CE1 TYR A  32      25.834  19.154  30.838  1.00 77.48           C
ATOM    220  CE2 TYR A  32      25.859  18.285  33.089  1.00 77.48           C
ATOM    221  CZ  TYR A  32      26.465  18.441  31.845  1.00 77.48           C
ATOM    222  OH  TYR A  32      27.703  17.894  31.601  1.00 77.48           O
ATOM    223  N   LEU A  33      19.393  19.955  32.784  1.00 41.53           N
ATOM    224  CA  LEU A  33      18.120  20.684  32.858  1.00 41.53           C
ATOM    225  C   LEU A  33      17.058  19.961  33.689  1.00 41.53           C
ATOM    226  O   LEU A  33      15.980  20.502  33.943  1.00 41.53           O
ATOM    227  CB  LEU A  33      17.566  20.931  31.450  1.00 35.85           C
ATOM    228  CG  LEU A  33      18.493  21.636  30.462  1.00 35.85           C
ATOM    229  CD1 LEU A  33      17.719  21.961  29.198  1.00 35.85           C
ATOM    230  CD2 LEU A  33      19.038  22.907  31.080  1.00 35.85           C
ATOM    231  N   SER A  34      17.385  18.740  34.102  1.00 49.29           N
ATOM    232  CA  SER A  34      16.500  17.900  34.892  1.00 49.29           C
ATOM    233  C   SER A  34      15.924  18.583  36.131  1.00 49.29           C
ATOM    234  O   SER A  34      14.755  18.387  36.458  1.00 49.29           O
ATOM    235  CB  SER A  34      17.240  16.623  35.304  1.00 54.11           C
ATOM    236  OG  SER A  34      16.391  15.733  36.002  1.00 54.11           O
ATOM    237  N   PRO A  35      16.733  19.374  36.853  1.00 36.68           N
ATOM    238  CA  PRO A  35      16.216  20.049  38.054  1.00 36.68           C
```

Figure 7-8

```
ATOM    239  C   PRO A  35      15.460  21.353  37.760  1.00 36.68           C
ATOM    240  O   PRO A  35      14.772  21.893  38.638  1.00 36.68           O
ATOM    241  CB  PRO A  35      17.481  20.331  38.883  1.00 44.90           C
ATOM    242  CG  PRO A  35      18.530  19.429  38.291  1.00 44.90           C
ATOM    243  CD  PRO A  35      18.204  19.432  36.823  1.00 44.90           C
ATOM    244  N   LEU A  36      15.618  21.868  36.543  1.00 37.76           N
ATOM    245  CA  LEU A  36      14.978  23.120  36.141  1.00 37.76           C
ATOM    246  C   LEU A  36      13.610  22.879  35.491  1.00 37.76           C
ATOM    247  O   LEU A  36      13.374  21.840  34.862  1.00 37.76           O
ATOM    248  CB  LEU A  36      15.889  23.882  35.170  1.00 41.54           C
ATOM    249  CG  LEU A  36      17.362  24.080  35.557  1.00 41.54           C
ATOM    250  CD1 LEU A  36      18.086  24.902  34.476  1.00 41.54           C
ATOM    251  CD2 LEU A  36      17.451  24.788  36.901  1.00 41.54           C
ATOM    252  N   ASP A  37      12.721  23.857  35.630  1.00 31.59           N
ATOM    253  CA  ASP A  37      11.368  23.757  35.090  1.00 31.59           C
ATOM    254  C   ASP A  37      11.369  24.064  33.583  1.00 31.59           C
ATOM    255  O   ASP A  37      10.747  25.019  33.109  1.00 31.59           O
ATOM    256  CB  ASP A  37      10.469  24.730  35.856  1.00 32.69           C
ATOM    257  CG  ASP A  37       8.990  24.479  35.628  1.00 32.69           C
ATOM    258  OD1 ASP A  37       8.186  25.361  35.988  1.00 32.69           O
ATOM    259  OD2 ASP A  37       8.619  23.420  35.101  1.00 32.69           O
ATOM    260  N   ILE A  38      12.089  23.245  32.832  1.00 37.25           N
ATOM    261  CA  ILE A  38      12.169  23.417  31.392  1.00 37.25           C
ATOM    262  C   ILE A  38      12.734  22.157  30.781  1.00 37.25           C
ATOM    263  O   ILE A  38      13.564  21.488  31.402  1.00 37.25           O
ATOM    264  CB  ILE A  38      13.100  24.574  31.018  1.00 29.59           C
ATOM    265  CG1 ILE A  38      13.047  24.798  29.502  1.00 29.59           C
ATOM    266  CG2 ILE A  38      14.536  24.258  31.500  1.00 29.59           C
ATOM    267  CD1 ILE A  38      13.782  26.019  29.034  1.00 29.59           C
ATOM    268  N   THR A  39      12.308  21.844  29.559  1.00 37.34           N
ATOM    269  CA  THR A  39      12.798  20.656  28.875  1.00 37.34           C
ATOM    270  C   THR A  39      13.852  20.986  27.800  1.00 37.34           C
ATOM    271  O   THR A  39      13.901  22.097  27.270  1.00 37.34           O
ATOM    272  CB  THR A  39      11.648  19.897  28.216  1.00 28.45           C
ATOM    273  OG1 THR A  39      11.152  20.664  27.114  1.00 28.45           O
ATOM    274  CG2 THR A  39      10.502  19.671  29.227  1.00 28.45           C
ATOM    275  N   ALA A  40      14.693  20.001  27.489  1.00 40.45           N
ATOM    276  CA  ALA A  40      15.741  20.147  26.487  1.00 40.45           C
ATOM    277  C   ALA A  40      15.144  20.691  25.198  1.00 40.45           C
ATOM    278  O   ALA A  40      15.680  21.623  24.601  1.00 40.45           O
ATOM    279  CB  ALA A  40      16.406  18.789  26.227  1.00 37.38           C
ATOM    280  N   ALA A  41      14.024  20.112  24.774  1.00 36.96           N
ATOM    281  CA  ALA A  41      13.368  20.562  23.555  1.00 36.96           C
ATOM    282  C   ALA A  41      12.948  22.027  23.647  1.00 36.96           C
ATOM    283  O   ALA A  41      13.127  22.777  22.686  1.00 36.96           O
ATOM    284  CB  ALA A  41      12.164  19.677  23.237  1.00 24.45           C
ATOM    285  N   GLN A  42      12.386  22.434  24.790  1.00 35.44           N
ATOM    286  CA  GLN A  42      11.981  23.836  24.971  1.00 35.44           C
ATOM    287  C   GLN A  42      13.219  24.723  24.874  1.00 35.44           C
ATOM    288  O   GLN A  42      13.185  25.786  24.247  1.00 35.44           O
ATOM    289  CB  GLN A  42      11.303  24.050  26.334  1.00 33.78           C
ATOM    290  CG  GLN A  42       9.873  23.514  26.443  1.00 33.78           C
ATOM    291  CD  GLN A  42       9.324  23.554  27.870  1.00 33.78           C
ATOM    292  OE1 GLN A  42       9.838  24.264  28.735  1.00 33.78           O
ATOM    293  NE2 GLN A  42       8.270  22.801  28.111  1.00 33.78           N
ATOM    294  N   PHE A  43      14.316  24.280  25.484  1.00 35.55           N
ATOM    295  CA  PHE A  43      15.562  25.053  25.453  1.00 35.55           C
ATOM    296  C   PHE A  43      16.062  25.232  24.013  1.00 35.55           C
ATOM    297  O   PHE A  43      16.431  26.337  23.606  1.00 35.55           O
ATOM    298  CB  PHE A  43      16.633  24.365  26.299  1.00 45.48           C
ATOM    299  CG  PHE A  43      17.937  25.100  26.337  1.00 45.48           C
ATOM    300  CD1 PHE A  43      17.973  26.470  26.599  1.00 45.48           C
ATOM    301  CD2 PHE A  43      19.134  24.426  26.127  1.00 45.48           C
ATOM    302  CE1 PHE A  43      19.180  27.163  26.652  1.00 45.48           C
ATOM    303  CE2 PHE A  43      20.351  25.110  26.178  1.00 45.48           C
ATOM    304  CZ  PHE A  43      20.372  26.486  26.441  1.00 45.48           C
ATOM    305  N   LYS A  44      16.049  24.149  23.241  1.00 38.60           N
ATOM    306  CA  LYS A  44      16.479  24.191  21.844  1.00 38.60           C
ATOM    307  C   LYS A  44      15.600  25.174  21.054  1.00 38.60           C
ATOM    308  O   LYS A  44      16.107  26.007  20.297  1.00 38.60           O
ATOM    309  CB  LYS A  44      16.379  22.794  21.222  1.00 82.69           C
ATOM    310  CG  LYS A  44      17.267  21.744  21.877  1.00 82.69           C
ATOM    311  CD  LYS A  44      16.994  20.355  21.302  1.00 82.69           C
ATOM    312  CE  LYS A  44      17.924  19.296  21.891  1.00 82.69           C
ATOM    313  NZ  LYS A  44      19.348  19.510  21.502  1.00 82.69           N
```

Figure 7-9

```
ATOM    314  N    VAL A  45      14.284  25.078  21.221  1.00 34.06           N
ATOM    315  CA   VAL A  45      13.396  25.997  20.517  1.00 34.06           C
ATOM    316  C    VAL A  45      13.710  27.448  20.877  1.00 34.06           C
ATOM    317  O    VAL A  45      13.619  28.324  20.019  1.00 34.06           O
ATOM    318  CB   VAL A  45      11.913  25.708  20.829  1.00 30.26           C
ATOM    319  CG1  VAL A  45      11.034  26.859  20.357  1.00 30.26           C
ATOM    320  CG2  VAL A  45      11.490  24.411  20.137  1.00 30.26           C
ATOM    321  N    LEU A  46      14.085  27.710  22.129  1.00 42.08           N
ATOM    322  CA   LEU A  46      14.408  29.086  22.530  1.00 42.08           C
ATOM    323  C    LEU A  46      15.721  29.573  21.899  1.00 42.08           C
ATOM    324  O    LEU A  46      15.816  30.704  21.423  1.00 42.08           O
ATOM    325  CB   LEU A  46      14.529  29.228  24.059  1.00 33.35           C
ATOM    326  CG   LEU A  46      13.316  29.155  24.989  1.00 33.35           C
ATOM    327  CD1  LEU A  46      13.772  29.485  26.416  1.00 33.35           C
ATOM    328  CD2  LEU A  46      12.243  30.120  24.554  1.00 33.35           C
ATOM    329  N    CYS A  47      16.734  28.720  21.903  1.00 47.51           N
ATOM    330  CA   CYS A  47      18.015  29.103  21.334  1.00 47.51           C
ATOM    331  C    CYS A  47      17.874  29.371  19.841  1.00 47.51           C
ATOM    332  O    CYS A  47      18.515  30.275  19.303  1.00 47.51           O
ATOM    333  CB   CYS A  47      19.045  28.004  21.577  1.00 47.01           C
ATOM    334  SG   CYS A  47      19.407  27.720  23.319  1.00 47.01           S
ATOM    335  N    SER A  48      17.029  28.590  19.176  1.00 42.18           N
ATOM    336  CA   SER A  48      16.814  28.747  17.737  1.00 42.18           C
ATOM    337  C    SER A  48      16.060  30.018  17.367  1.00 42.18           C
ATOM    338  O    SER A  48      16.352  30.638  16.356  1.00 42.18           O
ATOM    339  CB   SER A  48      16.047  27.547  17.180  1.00 30.64           C
ATOM    340  OG   SER A  48      16.769  26.345  17.382  1.00 30.64           O
ATOM    341  N    ILE A  49      15.068  30.390  18.171  1.00 41.78           N
ATOM    342  CA   ILE A  49      14.287  31.585  17.893  1.00 41.78           C
ATOM    343  C    ILE A  49      15.181  32.789  18.171  1.00 41.78           C
ATOM    344  O    ILE A  49      15.177  33.767  17.427  1.00 41.78           O
ATOM    345  CB   ILE A  49      13.039  31.650  18.796  1.00 41.13           C
ATOM    346  CG1  ILE A  49      12.068  30.527  18.418  1.00 41.13           C
ATOM    347  CG2  ILE A  49      12.363  33.009  18.671  1.00 41.13           C
ATOM    348  CD1  ILE A  49      10.746  30.559  19.184  1.00 41.13           C
ATOM    349  N    ARG A  50      15.948  32.692  19.253  1.00 49.26           N
ATOM    350  CA   ARG A  50      16.858  33.747  19.644  1.00 49.26           C
ATOM    351  C    ARG A  50      17.766  34.163  18.479  1.00 49.26           C
ATOM    352  O    ARG A  50      17.680  35.299  17.978  1.00 49.26           O
ATOM    353  CB   ARG A  50      17.712  33.279  20.827  1.00 66.71           C
ATOM    354  CG   ARG A  50      18.819  34.249  21.219  1.00 66.71           C
ATOM    355  CD   ARG A  50      19.567  33.783  22.449  1.00 66.71           C
ATOM    356  NE   ARG A  50      20.818  34.514  22.581  1.00 66.71           N
ATOM    357  CZ   ARG A  50      21.761  34.242  23.476  1.00 66.71           C
ATOM    358  NH1  ARG A  50      21.606  33.248  24.344  1.00 66.71           N
ATOM    359  NH2  ARG A  50      22.879  34.953  23.485  1.00 66.71           N
ATOM    360  N    CYS A  51      18.626  33.232  18.062  1.00 56.95           N
ATOM    361  CA   CYS A  51      19.585  33.437  16.975  1.00 56.95           C
ATOM    362  C    CYS A  51      19.000  34.159  15.790  1.00 56.95           C
ATOM    363  O    CYS A  51      19.623  35.058  15.216  1.00 56.95           O
ATOM    364  CB   CYS A  51      20.128  32.096  16.499  1.00 55.83           C
ATOM    365  SG   CYS A  51      21.019  31.209  17.754  1.00 55.83           S
ATOM    366  N    ALA A  52      17.799  33.746  15.421  1.00 43.02           N
ATOM    367  CA   ALA A  52      17.107  34.328  14.295  1.00 43.02           C
ATOM    368  C    ALA A  52      16.401  35.650  14.628  1.00 43.02           C
ATOM    369  O    ALA A  52      15.889  36.319  13.718  1.00 43.02           O
ATOM    370  CB   ALA A  52      16.112  33.325  13.764  1.00 30.40           C
ATOM    371  N    ALA A  53      16.373  36.025  15.914  1.00 45.66           N
ATOM    372  CA   ALA A  53      15.711  37.257  16.362  1.00 45.66           C
ATOM    373  C    ALA A  53      14.196  37.112  16.249  1.00 45.66           C
ATOM    374  O    ALA A  53      13.465  37.222  17.239  1.00 45.66           O
ATOM    375  CB   ALA A  53      16.166  38.446  15.526  1.00 34.46           C
ATOM    376  N    CYS A  54      13.749  36.877  15.021  1.00 42.13           N
ATOM    377  CA   CYS A  54      12.347  36.690  14.686  1.00 42.13           C
ATOM    378  C    CYS A  54      12.290  35.612  13.605  1.00 42.13           C
ATOM    379  O    CYS A  54      13.032  35.672  12.626  1.00 42.13           O
ATOM    380  CB   CYS A  54      11.741  37.976  14.119  1.00 63.33           C
ATOM    381  SG   CYS A  54      11.425  39.280  15.311  1.00 63.33           S
ATOM    382  N    ILE A  55      11.407  34.636  13.765  1.00 45.27           N
ATOM    383  CA   ILE A  55      11.300  33.580  12.771  1.00 45.27           C
ATOM    384  C    ILE A  55       9.881  33.051  12.687  1.00 45.27           C
ATOM    385  O    ILE A  55       9.140  33.064  13.681  1.00 45.27           O
ATOM    386  CB   ILE A  55      12.243  32.408  13.102  1.00 41.76           C
ATOM    387  CG1  ILE A  55      12.130  31.329  12.018  1.00 41.76           C
ATOM    388  CG2  ILE A  55      11.902  31.846  14.481  1.00 41.76           C
```

Figure 7-10

```
ATOM    389  CD1 ILE A  55      13.119  30.197  12.173  1.00 41.76           C
ATOM    390  N   THR A  56       9.500  32.596  11.500  1.00 37.37           N
ATOM    391  CA  THR A  56       8.161  32.049  11.302  1.00 37.37           C
ATOM    392  C   THR A  56       8.092  30.637  11.890  1.00 37.37           C
ATOM    393  O   THR A  56       9.103  29.929  11.974  1.00 37.37           O
ATOM    394  CB  THR A  56       7.799  31.988   9.811  1.00 68.07           C
ATOM    395  OG1 THR A  56       8.687  31.086   9.137  1.00 68.07           O
ATOM    396  CG2 THR A  56       7.901  33.371   9.189  1.00 68.07           C
ATOM    397  N   PRO A  57       6.904  30.212  12.327  1.00 37.02           N
ATOM    398  CA  PRO A  57       6.837  28.864  12.887  1.00 37.02           C
ATOM    399  C   PRO A  57       7.275  27.811  11.870  1.00 37.02           C
ATOM    400  O   PRO A  57       8.020  26.875  12.208  1.00 37.02           O
ATOM    401  CB  PRO A  57       5.379  28.741  13.290  1.00 39.03           C
ATOM    402  CG  PRO A  57       5.043  30.143  13.708  1.00 39.03           C
ATOM    403  CD  PRO A  57       5.662  30.958  12.596  1.00 39.03           C
ATOM    404  N   VAL A  58       6.847  27.973  10.619  1.00 50.69           N
ATOM    405  CA  VAL A  58       7.218  27.019   9.579  1.00 50.69           C
ATOM    406  C   VAL A  58       8.726  26.999   9.335  1.00 50.69           C
ATOM    407  O   VAL A  58       9.318  25.929   9.193  1.00 50.69           O
ATOM    408  CB  VAL A  58       6.503  27.324   8.267  1.00 56.43           C
ATOM    409  CG1 VAL A  58       6.909  26.304   7.223  1.00 56.43           C
ATOM    410  CG2 VAL A  58       4.990  27.308   8.484  1.00 56.43           C
ATOM    411  N   GLU A  59       9.349  28.175   9.280  1.00 44.74           N
ATOM    412  CA  GLU A  59      10.796  28.248   9.087  1.00 44.74           C
ATOM    413  C   GLU A  59      11.443  27.568  10.299  1.00 44.74           C
ATOM    414  O   GLU A  59      12.412  26.816  10.176  1.00 44.74           O
ATOM    415  CB  GLU A  59      11.251  29.707   9.008  1.00 89.17           C
ATOM    416  CG  GLU A  59      12.746  29.900   8.766  1.00 89.17           C
ATOM    417  CD  GLU A  59      13.151  29.678   7.319  1.00 89.17           C
ATOM    418  OE1 GLU A  59      12.953  28.557   6.803  1.00 89.17           O
ATOM    419  OE2 GLU A  59      13.671  30.630   6.696  1.00 89.17           O
ATOM    420  N   LEU A  60      10.892  27.837  11.478  1.00 41.66           N
ATOM    421  CA  LEU A  60      11.405  27.241  12.702  1.00 41.66           C
ATOM    422  C   LEU A  60      11.215  25.721  12.625  1.00 41.66           C
ATOM    423  O   LEU A  60      12.053  24.940  13.088  1.00 41.66           O
ATOM    424  CB  LEU A  60      10.651  27.817  13.907  1.00 44.47           C
ATOM    425  CG  LEU A  60      11.044  27.322  15.300  1.00 44.47           C
ATOM    426  CD1 LEU A  60      12.533  27.525  15.539  1.00 44.47           C
ATOM    427  CD2 LEU A  60      10.219  28.080  16.333  1.00 44.47           C
ATOM    428  N   LYS A  61      10.101  25.314  12.028  1.00 54.28           N
ATOM    429  CA  LYS A  61       9.778  23.902  11.863  1.00 54.28           C
ATOM    430  C   LYS A  61      10.870  23.222  11.028  1.00 54.28           C
ATOM    431  O   LYS A  61      11.294  22.102  11.319  1.00 54.28           O
ATOM    432  CB  LYS A  61       8.413  23.769  11.165  1.00 53.54           C
ATOM    433  CG  LYS A  61       7.943  22.338  10.945  1.00 53.54           C
ATOM    434  CD  LYS A  61       7.356  22.167   9.548  1.00 53.54           C
ATOM    435  CE  LYS A  61       7.057  20.693   9.231  1.00 53.54           C
ATOM    436  NZ  LYS A  61       8.259  19.782   9.328  1.00 53.54           N
ATOM    437  N   LYS A  62      11.324  23.919   9.992  1.00 55.89           N
ATOM    438  CA  LYS A  62      12.359  23.401   9.103  1.00 55.89           C
ATOM    439  C   LYS A  62      13.716  23.356   9.784  1.00 55.89           C
ATOM    440  O   LYS A  62      14.466  22.396   9.624  1.00 55.89           O
ATOM    441  CB  LYS A  62      12.473  24.267   7.843  1.00 90.82           C
ATOM    442  CG  LYS A  62      11.240  24.274   6.954  1.00 90.82           C
ATOM    443  CD  LYS A  62      11.501  25.040   5.654  1.00 90.82           C
ATOM    444  CE  LYS A  62      12.551  24.348   4.783  1.00 90.82           C
ATOM    445  NZ  LYS A  62      12.107  22.996   4.325  1.00 90.82           N
ATOM    446  N   VAL A  63      14.035  24.403  10.539  1.00 51.21           N
ATOM    447  CA  VAL A  63      15.317  24.473  11.228  1.00 51.21           C
ATOM    448  C   VAL A  63      15.476  23.407  12.302  1.00 51.21           C
ATOM    449  O   VAL A  63      16.573  22.915  12.532  1.00 51.21           O
ATOM    450  CB  VAL A  63      15.508  25.834  11.897  1.00 72.29           C
ATOM    451  CG1 VAL A  63      16.841  25.867  12.624  1.00 72.29           C
ATOM    452  CG2 VAL A  63      15.427  26.933  10.854  1.00 72.29           C
ATOM    453  N   LEU A  64      14.379  23.063  12.967  1.00 55.82           N
ATOM    454  CA  LEU A  64      14.419  22.074  14.034  1.00 55.82           C
ATOM    455  C   LEU A  64      14.203  20.642  13.548  1.00 55.82           C
ATOM    456  O   LEU A  64      14.568  19.695  14.249  1.00 55.82           O
ATOM    457  CB  LEU A  64      13.359  22.413  15.088  1.00 42.64           C
ATOM    458  CG  LEU A  64      13.549  23.683  15.926  1.00 42.64           C
ATOM    459  CD1 LEU A  64      12.256  23.980  16.678  1.00 42.64           C
ATOM    460  CD2 LEU A  64      14.727  23.505  16.898  1.00 42.64           C
ATOM    461  N   SER A  65      13.616  20.490  12.358  1.00 57.55           N
ATOM    462  CA  SER A  65      13.320  19.167  11.793  1.00 57.55           C
ATOM    463  C   SER A  65      12.399  18.480  12.783  1.00 57.55           C
```

Figure 7-11

```
ATOM    464  O    SER A  65      12.774  17.504  13.423  1.00 57.55           O
ATOM    465  CB   SER A  65      14.596  18.336  11.626  1.00 69.01           C
ATOM    466  OG   SER A  65      15.462  18.903  10.657  1.00 69.01           O
ATOM    467  N    VAL A  66      11.185  18.998  12.900  1.00 48.95           N
ATOM    468  CA   VAL A  66      10.221  18.464  13.850  1.00 48.95           C
ATOM    469  C    VAL A  66       8.820  18.454  13.262  1.00 48.95           C
ATOM    470  O    VAL A  66       8.541  19.120  12.254  1.00 48.95           O
ATOM    471  CB   VAL A  66      10.229  19.329  15.144  1.00 70.40           C
ATOM    472  CG1  VAL A  66       9.074  18.956  16.050  1.00 70.40           C
ATOM    473  CG2  VAL A  66      11.561  19.155  15.879  1.00 70.40           C
ATOM    474  N    ASP A  67       7.944  17.676  13.885  1.00 54.83           N
ATOM    475  CA   ASP A  67       6.558  17.592  13.455  1.00 54.83           C
ATOM    476  C    ASP A  67       5.940  18.961  13.731  1.00 54.83           C
ATOM    477  O    ASP A  67       6.140  19.539  14.807  1.00 54.83           O
ATOM    478  CB   ASP A  67       5.821  16.516  14.259  1.00 69.23           C
ATOM    479  CG   ASP A  67       4.334  16.480  13.963  1.00 69.23           C
ATOM    480  OD1  ASP A  67       3.572  15.961  14.803  1.00 69.23           O
ATOM    481  OD2  ASP A  67       3.922  16.962  12.891  1.00 69.23           O
ATOM    482  N    LEU A  68       5.187  19.475  12.767  1.00 57.37           N
ATOM    483  CA   LEU A  68       4.567  20.776  12.933  1.00 57.37           C
ATOM    484  C    LEU A  68       3.620  20.750  14.123  1.00 57.37           C
ATOM    485  O    LEU A  68       3.573  21.694  14.913  1.00 57.37           O
ATOM    486  CB   LEU A  68       3.799  21.175  11.668  1.00 70.92           C
ATOM    487  CG   LEU A  68       3.297  22.624  11.655  1.00 70.92           C
ATOM    488  CD1  LEU A  68       4.489  23.553  11.713  1.00 70.92           C
ATOM    489  CD2  LEU A  68       2.473  22.900  10.410  1.00 70.92           C
ATOM    490  N    GLY A  69       2.871  19.661  14.249  1.00 42.69           N
ATOM    491  CA   GLY A  69       1.921  19.541  15.341  1.00 42.69           C
ATOM    492  C    GLY A  69       2.550  19.715  16.711  1.00 42.69           C
ATOM    493  O    GLY A  69       2.001  20.399  17.577  1.00 42.69           O
ATOM    494  N    ALA A  70       3.714  19.107  16.907  1.00 34.08           N
ATOM    495  CA   ALA A  70       4.401  19.180  18.192  1.00 34.08           C
ATOM    496  C    ALA A  70       5.008  20.556  18.412  1.00 34.08           C
ATOM    497  O    ALA A  70       5.237  20.961  19.549  1.00 34.08           O
ATOM    498  CB   ALA A  70       5.484  18.120  18.259  1.00 29.39           C
ATOM    499  N    LEU A  71       5.265  21.272  17.320  1.00 36.90           N
ATOM    500  CA   LEU A  71       5.846  22.605  17.401  1.00 36.90           C
ATOM    501  C    LEU A  71       4.790  23.591  17.883  1.00 36.90           C
ATOM    502  O    LEU A  71       5.045  24.420  18.768  1.00 36.90           O
ATOM    503  CB   LEU A  71       6.368  23.040  16.030  1.00 46.47           C
ATOM    504  CG   LEU A  71       7.126  24.370  16.062  1.00 46.47           C
ATOM    505  CD1  LEU A  71       8.395  24.172  16.864  1.00 46.47           C
ATOM    506  CD2  LEU A  71       7.444  24.845  14.654  1.00 46.47           C
ATOM    507  N    THR A  72       3.603  23.477  17.296  1.00 33.18           N
ATOM    508  CA   THR A  72       2.467  24.323  17.620  1.00 33.18           C
ATOM    509  C    THR A  72       2.140  24.230  19.093  1.00 33.18           C
ATOM    510  O    THR A  72       1.956  25.249  19.761  1.00 33.18           O
ATOM    511  CB   THR A  72       1.210  23.895  16.825  1.00 64.50           C
ATOM    512  OG1  THR A  72       1.554  23.697  15.448  1.00 64.50           O
ATOM    513  CG2  THR A  72       0.129  24.965  16.921  1.00 64.50           C
ATOM    514  N    ARG A  73       2.048  23.003  19.600  1.00 32.09           N
ATOM    515  CA   ARG A  73       1.749  22.803  21.016  1.00 32.09           C
ATOM    516  C    ARG A  73       2.917  23.358  21.808  1.00 32.09           C
ATOM    517  O    ARG A  73       2.734  23.989  22.834  1.00 32.09           O
ATOM    518  CB   ARG A  73       1.558  21.309  21.343  1.00 47.77           C
ATOM    519  CG   ARG A  73       0.393  20.651  20.620  1.00 47.77           C
ATOM    520  CD   ARG A  73      -0.084  19.386  21.337  1.00 47.77           C
ATOM    521  NE   ARG A  73       0.966  18.382  21.494  1.00 47.77           N
ATOM    522  CZ   ARG A  73       1.445  17.634  20.504  1.00 47.77           C
ATOM    523  NH1  ARG A  73       0.973  17.766  19.269  1.00 47.77           N
ATOM    524  NH2  ARG A  73       2.399  16.747  20.748  1.00 47.77           N
ATOM    525  N    MET A  74       4.122  23.114  21.312  1.00 37.17           N
ATOM    526  CA   MET A  74       5.341  23.599  21.954  1.00 37.17           C
ATOM    527  C    MET A  74       5.328  25.131  22.049  1.00 37.17           C
ATOM    528  O    MET A  74       5.598  25.709  23.109  1.00 37.17           O
ATOM    529  CB   MET A  74       6.566  23.155  21.144  1.00 41.38           C
ATOM    530  CG   MET A  74       7.852  23.892  21.493  1.00 41.38           C
ATOM    531  SD   MET A  74       8.444  23.481  23.126  1.00 41.38           S
ATOM    532  CE   MET A  74       9.524  22.058  22.712  1.00 41.38           C
ATOM    533  N    LEU A  75       5.021  25.787  20.934  1.00 30.84           N
ATOM    534  CA   LEU A  75       5.001  27.240  20.930  1.00 30.84           C
ATOM    535  C    LEU A  75       3.944  27.762  21.910  1.00 30.84           C
ATOM    536  O    LEU A  75       4.182  28.744  22.628  1.00 30.84           O
ATOM    537  CB   LEU A  75       4.770  27.755  19.506  1.00 25.28           C
ATOM    538  CG   LEU A  75       5.960  27.583  18.535  1.00 25.28           C
```

Figure 7-12

```
ATOM    539  CD1 LEU A   75       5.565  28.044  17.136  1.00 25.28           C
ATOM    540  CD2 LEU A   75       7.150  28.427  19.001  1.00 25.28           C
ATOM    541  N   ASP A   76       2.795  27.084  21.971  1.00 31.28           N
ATOM    542  CA  ASP A   76       1.734  27.500  22.888  1.00 31.28           C
ATOM    543  C   ASP A   76       2.203  27.312  24.323  1.00 31.28           C
ATOM    544  O   ASP A   76       1.954  28.161  25.167  1.00 31.28           O
ATOM    545  CB  ASP A   76       0.445  26.703  22.661  1.00 35.21           C
ATOM    546  CG  ASP A   76      -0.433  27.287  21.544  1.00 35.21           C
ATOM    547  OD1 ASP A   76      -0.126  28.381  21.008  1.00 35.21           O
ATOM    548  OD2 ASP A   76      -1.451  26.643  21.211  1.00 35.21           O
ATOM    549  N   ARG A   77       2.874  26.205  24.618  1.00 31.46           N
ATOM    550  CA  ARG A   77       3.355  26.008  25.980  1.00 31.46           C
ATOM    551  C   ARG A   77       4.351  27.119  26.322  1.00 31.46           C
ATOM    552  O   ARG A   77       4.332  27.665  27.422  1.00 31.46           O
ATOM    553  CB  ARG A   77       4.031  24.640  26.134  1.00 37.99           C
ATOM    554  CG  ARG A   77       4.678  24.387  27.497  1.00 37.99           C
ATOM    555  CD  ARG A   77       3.701  24.641  28.652  1.00 37.99           C
ATOM    556  NE  ARG A   77       2.503  23.796  28.598  1.00 37.99           N
ATOM    557  CZ  ARG A   77       2.490  22.492  28.858  1.00 37.99           C
ATOM    558  NH1 ARG A   77       3.617  21.869  29.192  1.00 37.99           N
ATOM    559  NH2 ARG A   77       1.353  21.809  28.799  1.00 37.99           N
ATOM    560  N   LEU A   78       5.221  27.462  25.380  1.00 29.78           N
ATOM    561  CA  LEU A   78       6.216  28.507  25.645  1.00 29.78           C
ATOM    562  C   LEU A   78       5.564  29.868  25.889  1.00 29.78           C
ATOM    563  O   LEU A   78       6.054  30.661  26.695  1.00 29.78           O
ATOM    564  CB  LEU A   78       7.228  28.574  24.494  1.00 25.32           C
ATOM    565  CG  LEU A   78       8.171  27.356  24.470  1.00 25.32           C
ATOM    566  CD1 LEU A   78       9.043  27.324  23.235  1.00 25.32           C
ATOM    567  CD2 LEU A   78       9.009  27.399  25.725  1.00 25.32           C
ATOM    568  N   VAL A   79       4.460  30.145  25.199  1.00 31.60           N
ATOM    569  CA  VAL A   79       3.759  31.412  25.412  1.00 31.60           C
ATOM    570  C   VAL A   79       3.161  31.379  26.815  1.00 31.60           C
ATOM    571  O   VAL A   79       3.244  32.367  27.536  1.00 31.60           O
ATOM    572  CB  VAL A   79       2.641  31.623  24.370  1.00 28.89           C
ATOM    573  CG1 VAL A   79       1.816  32.851  24.709  1.00 28.89           C
ATOM    574  CG2 VAL A   79       3.271  31.765  22.982  1.00 28.89           C
ATOM    575  N   CYS A   80       2.588  30.235  27.214  1.00 35.75           N
ATOM    576  CA  CYS A   80       2.011  30.091  28.560  1.00 35.75           C
ATOM    577  C   CYS A   80       3.069  30.345  29.628  1.00 35.75           C
ATOM    578  O   CYS A   80       2.763  30.825  30.722  1.00 35.75           O
ATOM    579  CB  CYS A   80       1.448  28.686  28.787  1.00 46.08           C
ATOM    580  SG  CYS A   80      -0.183  28.381  28.120  1.00 46.08           S
ATOM    581  N   LYS A   81       4.311  29.996  29.331  1.00 40.46           N
ATOM    582  CA  LYS A   81       5.372  30.215  30.299  1.00 40.46           C
ATOM    583  C   LYS A   81       5.877  31.658  30.213  1.00 40.46           C
ATOM    584  O   LYS A   81       6.719  32.082  31.014  1.00 40.46           O
ATOM    585  CB  LYS A   81       6.518  29.233  30.057  1.00 28.93           C
ATOM    586  CG  LYS A   81       6.207  27.809  30.479  1.00 28.93           C
ATOM    587  CD  LYS A   81       7.410  26.901  30.212  1.00 28.93           C
ATOM    588  CE  LYS A   81       7.281  25.556  30.910  1.00 28.93           C
ATOM    589  NZ  LYS A   81       8.603  24.910  31.080  1.00 28.93           N
ATOM    590  N   GLY A   82       5.350  32.406  29.244  1.00 34.82           N
ATOM    591  CA  GLY A   82       5.755  33.794  29.074  1.00 34.82           C
ATOM    592  C   GLY A   82       7.146  33.950  28.468  1.00 34.82           C
ATOM    593  O   GLY A   82       7.778  34.999  28.604  1.00 34.82           O
ATOM    594  N   TRP A   83       7.632  32.914  27.786  1.00 32.56           N
ATOM    595  CA  TRP A   83       8.956  32.985  27.198  1.00 32.56           C
ATOM    596  C   TRP A   83       8.961  33.366  25.730  1.00 32.56           C
ATOM    597  O   TRP A   83       9.981  33.799  25.209  1.00 32.56           O
ATOM    598  CB  TRP A   83       9.683  31.649  27.365  1.00 37.53           C
ATOM    599  CG  TRP A   83       9.919  31.242  28.782  1.00 37.53           C
ATOM    600  CD1 TRP A   83       9.854  32.040  29.884  1.00 37.53           C
ATOM    601  CD2 TRP A   83      10.243  29.929  29.253  1.00 37.53           C
ATOM    602  NE1 TRP A   83      10.111  31.307  31.018  1.00 37.53           N
ATOM    603  CE2 TRP A   83      10.353  30.006  30.660  1.00 37.53           C
ATOM    604  CE3 TRP A   83      10.448  28.696  28.625  1.00 37.53           C
ATOM    605  CZ2 TRP A   83      10.658  28.897  31.454  1.00 37.53           C
ATOM    606  CZ3 TRP A   83      10.755  27.584  29.415  1.00 37.53           C
ATOM    607  CH2 TRP A   83      10.856  27.695  30.817  1.00 37.53           C
ATOM    608  N   VAL A   84       7.822  33.218  25.062  1.00 30.33           N
ATOM    609  CA  VAL A   84       7.727  33.519  23.640  1.00 30.33           C
ATOM    610  C   VAL A   84       6.473  34.323  23.329  1.00 30.33           C
ATOM    611  O   VAL A   84       5.472  34.212  24.034  1.00 30.33           O
ATOM    612  CB  VAL A   84       7.703  32.198  22.825  1.00 28.67           C
ATOM    613  CG1 VAL A   84       7.370  32.466  21.374  1.00 28.67           C
```

Figure 7-13

```
ATOM    614  CG2 VAL A  84       9.051  31.487  22.946  1.00 28.67           C
ATOM    615  N   GLU A  85       6.532  35.145  22.287  1.00 32.27           N
ATOM    616  CA  GLU A  85       5.373  35.931  21.891  1.00 32.27           C
ATOM    617  C   GLU A  85       5.314  35.967  20.373  1.00 32.27           C
ATOM    618  O   GLU A  85       6.344  35.837  19.694  1.00 32.27           O
ATOM    619  CB  GLU A  85       5.428  37.355  22.470  1.00 48.71           C
ATOM    620  CG  GLU A  85       6.386  38.324  21.809  1.00 48.71           C
ATOM    621  CD  GLU A  85       6.466  39.642  22.578  1.00 48.71           C
ATOM    622  OE1 GLU A  85       6.858  39.604  23.753  1.00 48.71           O
ATOM    623  OE2 GLU A  85       6.134  40.719  22.031  1.00 48.71           O
ATOM    624  N   ARG A  86       4.101  36.129  19.862  1.00 41.63           N
ATOM    625  CA  ARG A  86       3.823  36.156  18.436  1.00 41.63           C
ATOM    626  C   ARG A  86       3.509  37.557  17.913  1.00 41.63           C
ATOM    627  O   ARG A  86       2.742  38.307  18.525  1.00 41.63           O
ATOM    628  CB  ARG A  86       2.625  35.255  18.156  1.00 42.32           C
ATOM    629  CG  ARG A  86       2.826  34.245  17.066  1.00 42.32           C
ATOM    630  CD  ARG A  86       1.630  33.345  17.037  1.00 42.32           C
ATOM    631  NE  ARG A  86       1.424  32.786  18.363  1.00 42.32           N
ATOM    632  CZ  ARG A  86       1.572  31.503  18.679  1.00 42.32           C
ATOM    633  NH1 ARG A  86       1.923  30.627  17.753  1.00 42.32           N
ATOM    634  NH2 ARG A  86       1.377  31.105  19.932  1.00 42.32           N
ATOM    635  N   LEU A  87       4.095  37.909  16.775  1.00 39.77           N
ATOM    636  CA  LEU A  87       3.826  39.209  16.180  1.00 39.77           C
ATOM    637  C   LEU A  87       3.519  39.000  14.703  1.00 39.77           C
ATOM    638  O   LEU A  87       3.853  37.963  14.131  1.00 39.77           O
ATOM    639  CB  LEU A  87       5.018  40.151  16.333  1.00 48.09           C
ATOM    640  CG  LEU A  87       6.305  39.730  15.630  1.00 48.09           C
ATOM    641  CD1 LEU A  87       7.061  40.968  15.171  1.00 48.09           C
ATOM    642  CD2 LEU A  87       7.156  38.884  16.578  1.00 48.09           C
ATOM    643  N   PRO A  88       2.860  39.983  14.070  1.00 54.80           N
ATOM    644  CA  PRO A  88       2.522  39.864  12.649  1.00 54.80           C
ATOM    645  C   PRO A  88       3.785  39.853  11.804  1.00 54.80           C
ATOM    646  O   PRO A  88       4.753  40.548  12.119  1.00 54.80           O
ATOM    647  CB  PRO A  88       1.661  41.101  12.392  1.00 66.77           C
ATOM    648  CG  PRO A  88       1.049  41.386  13.751  1.00 66.77           C
ATOM    649  CD  PRO A  88       2.235  41.180  14.661  1.00 66.77           C
ATOM    650  N   ASN A  89       3.785  39.046  10.748  1.00 61.50           N
ATOM    651  CA  ASN A  89       4.938  38.963   9.860  1.00 61.50           C
ATOM    652  C   ASN A  89       4.808  40.089   8.839  1.00 61.50           C
ATOM    653  O   ASN A  89       3.838  40.145   8.089  1.00 61.50           O
ATOM    654  CB  ASN A  89       4.973  37.609   9.139  1.00 63.20           C
ATOM    655  CG  ASN A  89       6.230  37.427   8.298  1.00 63.20           C
ATOM    656  OD1 ASN A  89       6.643  38.335   7.585  1.00 63.20           O
ATOM    657  ND2 ASN A  89       6.837  36.249   8.372  1.00 63.20           N
ATOM    658  N   PRO A  90       5.779  41.015   8.815  1.00 66.40           N
ATOM    659  CA  PRO A  90       5.762  42.142   7.878  1.00 66.40           C
ATOM    660  C   PRO A  90       5.812  41.709   6.415  1.00 66.40           C
ATOM    661  O   PRO A  90       4.973  42.114   5.613  1.00 66.40           O
ATOM    662  CB  PRO A  90       6.993  42.944   8.288  1.00 66.93           C
ATOM    663  CG  PRO A  90       7.079  42.679   9.759  1.00 66.93           C
ATOM    664  CD  PRO A  90       6.854  41.187   9.805  1.00 66.93           C
ATOM    665  N   ASN A  91       6.794  40.881   6.074  1.00 79.71           N
ATOM    666  CA  ASN A  91       6.944  40.391   4.705  1.00 79.71           C
ATOM    667  C   ASN A  91       5.781  39.490   4.271  1.00 79.71           C
ATOM    668  O   ASN A  91       5.840  38.856   3.216  1.00 79.71           O
ATOM    669  CB  ASN A  91       8.266  39.628   4.556  1.00119.06           C
ATOM    670  CG  ASN A  91       9.477  40.490   4.867  1.00119.06           C
ATOM    671  OD1 ASN A  91       9.685  41.537   4.251  1.00119.06           O
ATOM    672  ND2 ASN A  91      10.284  40.051   5.826  1.00119.06           N
ATOM    673  N   ASP A  92       4.736  39.430   5.093  1.00 89.89           N
ATOM    674  CA  ASP A  92       3.551  38.631   4.792  1.00 89.89           C
ATOM    675  C   ASP A  92       2.332  39.408   5.282  1.00 89.89           C
ATOM    676  O   ASP A  92       2.299  40.635   5.183  1.00 89.89           O
ATOM    677  CB  ASP A  92       3.627  37.262   5.483  1.00 66.82           C
ATOM    678  CG  ASP A  92       2.587  36.275   4.955  1.00 66.82           C
ATOM    679  OD1 ASP A  92       2.716  35.061   5.229  1.00 66.82           O
ATOM    680  OD2 ASP A  92       1.637  36.709   4.272  1.00 66.82           O
ATOM    681  N   LYS A  93       1.339  38.700   5.813  1.00 72.63           N
ATOM    682  CA  LYS A  93       0.124  39.337   6.317  1.00 72.63           C
ATOM    683  C   LYS A  93      -0.865  38.247   6.700  1.00 72.63           C
ATOM    684  O   LYS A  93      -1.854  38.496   7.387  1.00 72.63           O
ATOM    685  CB  LYS A  93      -0.486  40.247   5.244  1.00 83.15           C
ATOM    686  CG  LYS A  93      -1.673  41.088   5.699  1.00 83.15           C
ATOM    687  CD  LYS A  93      -1.307  42.071   6.811  1.00 83.15           C
ATOM    688  CE  LYS A  93      -1.321  41.416   8.191  1.00 83.15           C
```

Figure 7-14

| | | | | | | | | | |
|---|---|---|---|---|---|---|---|---|---|
| ATOM | 689 | NZ | LYS A | 93 | -1.016 | 42.381 | 9.286 | 1.00 83.15 | N |
| ATOM | 690 | N | ARG A | 94 | -0.581 | 37.034 | 6.240 | 1.00 58.78 | N |
| ATOM | 691 | CA | ARG A | 94 | -1.414 | 35.878 | 6.527 | 1.00 58.78 | C |
| ATOM | 692 | C | ARG A | 94 | -0.651 | 35.036 | 7.546 | 1.00 58.78 | C |
| ATOM | 693 | O | ARG A | 94 | -1.072 | 33.943 | 7.913 | 1.00 58.78 | O |
| ATOM | 694 | CB | ARG A | 94 | -1.639 | 35.066 | 5.246 | 1.00 92.71 | C |
| ATOM | 695 | CG | ARG A | 94 | -2.651 | 33.937 | 5.385 | 1.00 92.71 | C |
| ATOM | 696 | CD | ARG A | 94 | -4.081 | 34.467 | 5.370 | 1.00 92.71 | C |
| ATOM | 697 | NE | ARG A | 94 | -4.493 | 34.880 | 4.032 | 1.00 92.71 | N |
| ATOM | 698 | CZ | ARG A | 94 | -4.746 | 34.035 | 3.039 | 1.00 92.71 | C |
| ATOM | 699 | NH1 | ARG A | 94 | -4.634 | 32.728 | 3.236 | 1.00 92.71 | N |
| ATOM | 700 | NH2 | ARG A | 94 | -5.091 | 34.497 | 1.844 | 1.00 92.71 | N |
| ATOM | 701 | N | GLY A | 95 | 0.479 | 35.562 | 8.005 | 1.00 44.29 | N |
| ATOM | 702 | CA | GLY A | 95 | 1.294 | 34.827 | 8.954 | 1.00 44.29 | C |
| ATOM | 703 | C | GLY A | 95 | 1.842 | 35.630 | 10.111 | 1.00 44.29 | C |
| ATOM | 704 | O | GLY A | 95 | 1.608 | 36.836 | 10.228 | 1.00 44.29 | O |
| ATOM | 705 | N | VAL A | 96 | 2.580 | 34.949 | 10.978 | 1.00 40.14 | N |
| ATOM | 706 | CA | VAL A | 96 | 3.159 | 35.592 | 12.143 | 1.00 40.14 | C |
| ATOM | 707 | C | VAL A | 96 | 4.587 | 35.156 | 12.346 | 1.00 40.14 | C |
| ATOM | 708 | O | VAL A | 96 | 5.074 | 34.230 | 11.689 | 1.00 40.14 | O |
| ATOM | 709 | CB | VAL A | 96 | 2.387 | 35.253 | 13.441 | 1.00 35.66 | C |
| ATOM | 710 | CG1 | VAL A | 96 | 0.964 | 35.734 | 13.329 | 1.00 35.66 | C |
| ATOM | 711 | CG2 | VAL A | 96 | 2.439 | 33.759 | 13.718 | 1.00 35.66 | C |
| ATOM | 712 | N | LEU A | 97 | 5.256 | 35.838 | 13.263 | 1.00 30.82 | N |
| ATOM | 713 | CA | LEU A | 97 | 6.631 | 35.530 | 13.591 | 1.00 30.82 | C |
| ATOM | 714 | C | LEU A | 97 | 6.568 | 35.265 | 15.078 | 1.00 30.82 | C |
| ATOM | 715 | O | LEU A | 97 | 5.615 | 35.665 | 15.752 | 1.00 30.82 | O |
| ATOM | 716 | CB | LEU A | 97 | 7.560 | 36.736 | 13.335 | 1.00 43.64 | C |
| ATOM | 717 | CG | LEU A | 97 | 7.811 | 37.285 | 11.917 | 1.00 43.64 | C |
| ATOM | 718 | CD1 | LEU A | 97 | 8.354 | 38.693 | 12.030 | 1.00 43.64 | C |
| ATOM | 719 | CD2 | LEU A | 97 | 8.795 | 36.407 | 11.137 | 1.00 43.64 | C |
| ATOM | 720 | N | VAL A | 98 | 7.570 | 34.577 | 15.590 | 1.00 40.02 | N |
| ATOM | 721 | CA | VAL A | 98 | 7.614 | 34.333 | 17.007 | 1.00 40.02 | C |
| ATOM | 722 | C | VAL A | 98 | 8.980 | 34.805 | 17.425 | 1.00 40.02 | C |
| ATOM | 723 | O | VAL A | 98 | 9.962 | 34.607 | 16.704 | 1.00 40.02 | O |
| ATOM | 724 | CB | VAL A | 98 | 7.442 | 32.836 | 17.356 | 1.00 33.09 | C |
| ATOM | 725 | CG1 | VAL A | 98 | 6.027 | 32.355 | 16.945 | 1.00 33.09 | C |
| ATOM | 726 | CG2 | VAL A | 98 | 8.519 | 32.015 | 16.669 | 1.00 33.09 | C |
| ATOM | 727 | N | LYS A | 99 | 9.035 | 35.472 | 18.568 | 1.00 35.95 | N |
| ATOM | 728 | CA | LYS A | 99 | 10.295 | 35.956 | 19.100 | 1.00 35.95 | C |
| ATOM | 729 | C | LYS A | 99 | 10.212 | 35.734 | 20.593 | 1.00 35.95 | C |
| ATOM | 730 | O | LYS A | 99 | 9.127 | 35.487 | 21.137 | 1.00 35.95 | O |
| ATOM | 731 | CB | LYS A | 99 | 10.461 | 37.444 | 18.793 | 1.00 43.93 | C |
| ATOM | 732 | CG | LYS A | 99 | 9.512 | 38.352 | 19.556 | 1.00 43.93 | C |
| ATOM | 733 | CD | LYS A | 99 | 9.590 | 39.769 | 19.029 | 1.00 43.93 | C |
| ATOM | 734 | CE | LYS A | 99 | 9.757 | 40.761 | 20.153 | 1.00 43.93 | C |
| ATOM | 735 | NZ | LYS A | 99 | 11.015 | 40.516 | 20.922 | 1.00 43.93 | N |
| ATOM | 736 | N | LEU A | 100 | 11.349 | 35.823 | 21.262 | 1.00 44.66 | N |
| ATOM | 737 | CA | LEU A | 100 | 11.378 | 35.640 | 22.696 | 1.00 44.66 | C |
| ATOM | 738 | C | LEU A | 100 | 10.928 | 36.902 | 23.401 | 1.00 44.66 | C |
| ATOM | 739 | O | LEU A | 100 | 11.148 | 38.006 | 22.914 | 1.00 44.66 | O |
| ATOM | 740 | CB | LEU A | 100 | 12.791 | 35.312 | 23.158 | 1.00 32.99 | C |
| ATOM | 741 | CG | LEU A | 100 | 13.480 | 34.081 | 22.554 | 1.00 32.99 | C |
| ATOM | 742 | CD1 | LEU A | 100 | 14.715 | 33.774 | 23.409 | 1.00 32.99 | C |
| ATOM | 743 | CD2 | LEU A | 100 | 12.517 | 32.864 | 22.532 | 1.00 32.99 | C |
| ATOM | 744 | N | THR A | 101 | 10.276 | 36.737 | 24.543 | 1.00 38.68 | N |
| ATOM | 745 | CA | THR A | 101 | 9.871 | 37.886 | 25.332 | 1.00 38.68 | C |
| ATOM | 746 | C | THR A | 101 | 11.131 | 38.172 | 26.167 | 1.00 38.68 | C |
| ATOM | 747 | O | THR A | 101 | 12.059 | 37.348 | 26.179 | 1.00 38.68 | O |
| ATOM | 748 | CB | THR A | 101 | 8.708 | 37.523 | 26.256 | 1.00 35.09 | C |
| ATOM | 749 | OG1 | THR A | 101 | 9.092 | 36.406 | 27.073 | 1.00 35.09 | O |
| ATOM | 750 | CG2 | THR A | 101 | 7.474 | 37.153 | 25.449 | 1.00 35.09 | C |
| ATOM | 751 | N | THR A | 102 | 11.183 | 39.310 | 26.857 | 1.00 50.83 | N |
| ATOM | 752 | CA | THR A | 102 | 12.364 | 39.638 | 27.673 | 1.00 50.83 | C |
| ATOM | 753 | C | THR A | 102 | 12.678 | 38.510 | 28.647 | 1.00 50.83 | C |
| ATOM | 754 | O | THR A | 102 | 13.816 | 38.061 | 28.745 | 1.00 50.83 | O |
| ATOM | 755 | CB | THR A | 102 | 12.168 | 40.931 | 28.506 | 1.00 38.42 | C |
| ATOM | 756 | OG1 | THR A | 102 | 11.800 | 42.012 | 27.645 | 1.00 38.42 | O |
| ATOM | 757 | CG2 | THR A | 102 | 13.470 | 41.293 | 29.231 | 1.00 38.42 | C |
| ATOM | 758 | N | GLY A | 103 | 11.665 | 38.065 | 29.381 | 1.00 42.94 | N |
| ATOM | 759 | CA | GLY A | 103 | 11.872 | 36.976 | 30.312 | 1.00 42.94 | C |
| ATOM | 760 | C | GLY A | 103 | 12.371 | 35.723 | 29.602 | 1.00 42.94 | C |
| ATOM | 761 | O | GLY A | 103 | 13.289 | 35.053 | 30.082 | 1.00 42.94 | O |
| ATOM | 762 | N | GLY A | 104 | 11.762 | 35.404 | 28.459 | 1.00 38.70 | N |
| ATOM | 763 | CA | GLY A | 104 | 12.178 | 34.234 | 27.707 | 1.00 38.70 | C |

Figure 7-15

```
ATOM    764  C   GLY A 104      13.656  34.336  27.384  1.00 38.70           C
ATOM    765  O   GLY A 104      14.398  33.359  27.510  1.00 38.70           O
ATOM    766  N   ALA A 105      14.076  35.534  26.979  1.00 47.24           N
ATOM    767  CA  ALA A 105      15.471  35.799  26.634  1.00 47.24           C
ATOM    768  C   ALA A 105      16.390  35.514  27.812  1.00 47.24           C
ATOM    769  O   ALA A 105      17.438  34.893  27.650  1.00 47.24           O
ATOM    770  CB  ALA A 105      15.634  37.256  26.183  1.00 42.30           C
ATOM    771  N   ALA A 106      15.989  35.967  28.997  1.00 52.11           N
ATOM    772  CA  ALA A 106      16.778  35.763  30.201  1.00 52.11           C
ATOM    773  C   ALA A 106      16.876  34.267  30.503  1.00 52.11           C
ATOM    774  O   ALA A 106      17.966  33.730  30.719  1.00 52.11           O
ATOM    775  CB  ALA A 106      16.141  36.505  31.372  1.00 50.48           C
ATOM    776  N   ILE A 107      15.735  33.592  30.519  1.00 47.20           N
ATOM    777  CA  ILE A 107      15.731  32.160  30.772  1.00 47.20           C
ATOM    778  C   ILE A 107      16.728  31.464  29.818  1.00 47.20           C
ATOM    779  O   ILE A 107      17.558  30.652  30.241  1.00 47.20           O
ATOM    780  CB  ILE A 107      14.325  31.563  30.528  1.00 46.42           C
ATOM    781  CG1 ILE A 107      13.312  32.166  31.507  1.00 46.42           C
ATOM    782  CG2 ILE A 107      14.380  30.052  30.642  1.00 46.42           C
ATOM    783  CD1 ILE A 107      13.619  31.905  32.956  1.00 46.42           C
ATOM    784  N   CYS A 108      16.637  31.789  28.531  1.00 55.20           N
ATOM    785  CA  CYS A 108      17.508  31.187  27.526  1.00 55.20           C
ATOM    786  C   CYS A 108      18.981  31.472  27.763  1.00 55.20           C
ATOM    787  O   CYS A 108      19.839  30.689  27.346  1.00 55.20           O
ATOM    788  CB  CYS A 108      17.126  31.665  26.125  1.00 50.25           C
ATOM    789  SG  CYS A 108      18.283  31.139  24.836  1.00 50.25           S
ATOM    790  N   GLU A 109      19.275  32.590  28.425  1.00 53.61           N
ATOM    791  CA  GLU A 109      20.660  32.952  28.708  1.00 53.61           C
ATOM    792  C   GLU A 109      21.128  32.294  30.007  1.00 53.61           C
ATOM    793  O   GLU A 109      22.275  31.864  30.109  1.00 53.61           O
ATOM    794  CB  GLU A 109      20.813  34.472  28.795  1.00109.75           C
ATOM    795  CG  GLU A 109      22.263  34.944  28.795  1.00109.75           C
ATOM    796  CD  GLU A 109      23.044  34.423  27.598  1.00109.75           C
ATOM    797  OE1 GLU A 109      22.620  34.679  26.453  1.00109.75           O
ATOM    798  OE2 GLU A 109      24.084  33.759  27.799  1.00109.75           O
ATOM    799  N   GLN A 110      20.253  32.211  31.002  1.00 70.78           N
ATOM    800  CA  GLN A 110      20.635  31.560  32.249  1.00 70.78           C
ATOM    801  C   GLN A 110      21.020  30.123  31.918  1.00 70.78           C
ATOM    802  O   GLN A 110      22.045  29.621  32.382  1.00 70.78           O
ATOM    803  CB  GLN A 110      19.476  31.522  33.240  1.00 56.91           C
ATOM    804  CG  GLN A 110      19.214  32.789  34.020  1.00 56.91           C
ATOM    805  CD  GLN A 110      17.892  32.707  34.780  1.00 56.91           C
ATOM    806  OE1 GLN A 110      17.620  31.722  35.481  1.00 56.91           O
ATOM    807  NE2 GLN A 110      17.063  33.738  34.640  1.00 56.91           N
ATOM    808  N   CYS A 111      20.180  29.471  31.116  1.00 60.37           N
ATOM    809  CA  CYS A 111      20.397  28.087  30.714  1.00 60.37           C
ATOM    810  C   CYS A 111      21.614  27.911  29.822  1.00 60.37           C
ATOM    811  O   CYS A 111      22.456  27.047  30.077  1.00 60.37           O
ATOM    812  CB  CYS A 111      19.177  27.546  29.964  1.00 52.09           C
ATOM    813  SG  CYS A 111      17.688  27.268  30.941  1.00 52.09           S
ATOM    814  N   HIS A 112      21.693  28.716  28.767  1.00 61.76           N
ATOM    815  CA  HIS A 112      22.801  28.632  27.818  1.00 61.76           C
ATOM    816  C   HIS A 112      24.160  28.735  28.502  1.00 61.76           C
ATOM    817  O   HIS A 112      25.108  28.032  28.138  1.00 61.76           O
ATOM    818  CB  HIS A 112      22.663  29.727  26.762  1.00 68.17           C
ATOM    819  CG  HIS A 112      23.616  29.585  25.617  1.00 68.17           C
ATOM    820  ND1 HIS A 112      24.964  29.851  25.730  1.00 68.17           N
ATOM    821  CD2 HIS A 112      23.416  29.199  24.335  1.00 68.17           C
ATOM    822  CE1 HIS A 112      25.552  29.637  24.567  1.00 68.17           C
ATOM    823  NE2 HIS A 112      24.634  29.240  23.704  1.00 68.17           N
ATOM    824  N   GLN A 113      24.243  29.603  29.503  1.00 60.30           N
ATOM    825  CA  GLN A 113      25.480  29.792  30.240  1.00 60.30           C
ATOM    826  C   GLN A 113      25.812  28.603  31.125  1.00 60.30           C
ATOM    827  O   GLN A 113      26.940  28.117  31.105  1.00 60.30           O
ATOM    828  CB  GLN A 113      25.406  31.059  31.093  1.00102.85           C
ATOM    829  CG  GLN A 113      25.241  32.328  30.281  1.00102.85           C
ATOM    830  CD  GLN A 113      25.367  33.575  31.125  1.00102.85           C
ATOM    831  OE1 GLN A 113      24.708  33.707  32.155  1.00102.85           O
ATOM    832  NE2 GLN A 113      26.212  34.503  30.689  1.00102.85           N
ATOM    833  N   LEU A 114      24.836  28.132  31.896  1.00 64.71           N
ATOM    834  CA  LEU A 114      25.057  27.001  32.798  1.00 64.71           C
ATOM    835  C   LEU A 114      25.417  25.713  32.056  1.00 64.71           C
ATOM    836  O   LEU A 114      26.468  25.123  32.295  1.00 64.71           O
ATOM    837  CB  LEU A 114      23.819  26.766  33.671  1.00 66.45           C
ATOM    838  CG  LEU A 114      23.238  28.013  34.349  1.00 66.45           C
```

Figure 7-16

```
ATOM    839  CD1 LEU A 114      22.189  27.587  35.387  1.00 66.45           C
ATOM    840  CD2 LEU A 114      24.353  28.830  35.002  1.00 66.45           C
ATOM    841  N   VAL A 115      24.545  25.272  31.160  1.00115.02           N
ATOM    842  CA  VAL A 115      24.811  24.054  30.412  1.00115.02           C
ATOM    843  C   VAL A 115      26.134  24.163  29.661  1.00115.02           C
ATOM    844  O   VAL A 115      26.908  23.206  29.606  1.00115.02           O
ATOM    845  CB  VAL A 115      23.670  23.755  29.420  1.00 64.88           C
ATOM    846  CG1 VAL A 115      24.073  22.627  28.477  1.00 64.88           C
ATOM    847  CG2 VAL A 115      22.409  23.383  30.194  1.00 64.88           C
ATOM    848  N   GLY A 116      26.393  25.335  29.089  1.00119.74           N
ATOM    849  CA  GLY A 116      27.629  25.538  28.358  1.00119.74           C
ATOM    850  C   GLY A 116      28.847  25.403  29.253  1.00119.74           C
ATOM    851  O   GLY A 116      29.936  25.088  28.779  1.00119.74           O
ATOM    852  N   GLN A 117      28.661  25.636  30.549  1.00 73.12           N
ATOM    853  CA  GLN A 117      29.750  25.546  31.523  1.00 73.12           C
ATOM    854  C   GLN A 117      29.944  24.137  32.084  1.00 73.12           C
ATOM    855  O   GLN A 117      31.019  23.815  32.587  1.00 73.12           O
ATOM    856  CB  GLN A 117      29.504  26.520  32.678  1.00 96.60           C
ATOM    857  CG  GLN A 117      29.577  27.984  32.282  1.00 96.60           C
ATOM    858  CD  GLN A 117      29.080  28.919  33.374  1.00 96.60           C
ATOM    859  OE1 GLN A 117      29.094  30.141  33.215  1.00 96.60           O
ATOM    860  NE2 GLN A 117      28.632  28.347  34.488  1.00 96.60           N
ATOM    861  N   ASP A 118      28.905  23.308  32.006  1.00 69.89           N
ATOM    862  CA  ASP A 118      28.981  21.937  32.507  1.00 69.89           C
ATOM    863  C   ASP A 118      29.402  20.966  31.416  1.00 69.89           C
ATOM    864  O   ASP A 118      30.112  19.995  31.680  1.00 69.89           O
ATOM    865  CB  ASP A 118      27.632  21.487  33.070  1.00 86.01           C
ATOM    866  CG  ASP A 118      27.261  22.204  34.348  1.00 86.01           C
ATOM    867  OD1 ASP A 118      26.218  21.849  34.935  1.00 86.01           O
ATOM    868  OD2 ASP A 118      28.004  23.117  34.767  1.00 86.01           O
ATOM    869  N   LEU A 119      28.947  21.223  30.194  1.00 80.62           N
ATOM    870  CA  LEU A 119      29.285  20.368  29.065  1.00 80.62           C
ATOM    871  C   LEU A 119      30.769  20.458  28.772  1.00 80.62           C
ATOM    872  O   LEU A 119      31.467  19.448  28.731  1.00 80.62           O
ATOM    873  CB  LEU A 119      28.499  20.784  27.819  1.00 80.69           C
ATOM    874  CG  LEU A 119      27.053  20.307  27.695  1.00 80.69           C
ATOM    875  CD1 LEU A 119      26.407  20.940  26.465  1.00 80.69           C
ATOM    876  CD2 LEU A 119      27.029  18.790  27.586  1.00 80.69           C
ATOM    877  N   HIS A 120      31.244  21.680  28.569  1.00 76.91           N
ATOM    878  CA  HIS A 120      32.647  21.911  28.275  1.00 76.91           C
ATOM    879  C   HIS A 120      33.491  21.044  29.192  1.00 76.91           C
ATOM    880  O   HIS A 120      34.372  20.317  28.734  1.00 76.91           O
ATOM    881  CB  HIS A 120      32.998  23.384  28.494  1.00119.42           C
ATOM    882  CG  HIS A 120      34.363  23.758  28.006  1.00119.42           C
ATOM    883  ND1 HIS A 120      35.504  23.094  28.401  1.00119.42           N
ATOM    884  CD2 HIS A 120      34.770  24.736  27.162  1.00119.42           C
ATOM    885  CE1 HIS A 120      36.555  23.646  27.821  1.00119.42           C
ATOM    886  NE2 HIS A 120      36.137  24.644  27.065  1.00119.42           N
ATOM    887  N   GLN A 121      33.207  21.118  30.489  1.00 79.07           N
ATOM    888  CA  GLN A 121      33.940  20.340  31.480  1.00 79.07           C
ATOM    889  C   GLN A 121      33.760  18.848  31.239  1.00 79.07           C
ATOM    890  O   GLN A 121      34.724  18.140  30.952  1.00 79.07           O
ATOM    891  CB  GLN A 121      33.458  20.685  32.889  1.00 96.87           C
ATOM    892  CG  GLN A 121      33.479  22.169  33.202  1.00 96.87           C
ATOM    893  CD  GLN A 121      34.837  22.800  32.959  1.00 96.87           C
ATOM    894  OE1 GLN A 121      35.846  22.357  33.510  1.00 96.87           O
ATOM    895  NE2 GLN A 121      34.870  23.843  32.134  1.00 96.87           N
ATOM    896  N   GLU A 122      32.523  18.375  31.349  1.00 53.54           N
ATOM    897  CA  GLU A 122      32.235  16.958  31.158  1.00 53.54           C
ATOM    898  C   GLU A 122      32.783  16.358  29.873  1.00 53.54           C
ATOM    899  O   GLU A 122      33.365  15.271  29.897  1.00 53.54           O
ATOM    900  CB  GLU A 122      30.729  16.703  31.233  1.00 88.00           C
ATOM    901  CG  GLU A 122      30.187  16.610  32.650  1.00 88.00           C
ATOM    902  CD  GLU A 122      30.991  15.657  33.510  1.00 88.00           C
ATOM    903  OE1 GLU A 122      32.017  16.091  34.076  1.00 88.00           O
ATOM    904  OE2 GLU A 122      30.604  14.472  33.606  1.00 88.00           O
ATOM    905  N   LEU A 123      32.596  17.056  28.756  1.00 72.38           N
ATOM    906  CA  LEU A 123      33.074  16.579  27.460  1.00 72.38           C
ATOM    907  C   LEU A 123      34.593  16.554  27.402  1.00 72.38           C
ATOM    908  O   LEU A 123      35.199  15.644  26.829  1.00 72.38           O
ATOM    909  CB  LEU A 123      32.564  17.484  26.331  1.00 59.40           C
ATOM    910  CG  LEU A 123      31.065  17.540  26.049  1.00 59.40           C
ATOM    911  CD1 LEU A 123      30.789  18.535  24.929  1.00 59.40           C
ATOM    912  CD2 LEU A 123      30.580  16.147  25.675  1.00 59.40           C
ATOM    913  N   THR A 124      35.195  17.573  28.000  1.00 64.43           N
```

Figure 7-17

```
ATOM    914  CA  THR A 124      36.641  17.737  28.022  1.00 64.43           C
ATOM    915  C   THR A 124      37.288  17.074  29.234  1.00 64.43           C
ATOM    916  O   THR A 124      38.507  17.043  29.341  1.00 64.43           O
ATOM    917  CB  THR A 124      36.984  19.256  28.002  1.00 67.40           C
ATOM    918  OG1 THR A 124      36.866  19.751  26.663  1.00 67.40           O
ATOM    919  CG2 THR A 124      38.376  19.527  28.528  1.00 67.40           C
ATOM    920  N   LYS A 125      36.470  16.523  30.129  1.00 52.23           N
ATOM    921  CA  LYS A 125      36.966  15.900  31.358  1.00 52.23           C
ATOM    922  C   LYS A 125      38.170  14.973  31.201  1.00 52.23           C
ATOM    923  O   LYS A 125      39.044  14.944  32.068  1.00 52.23           O
ATOM    924  CB  LYS A 125      35.846  15.127  32.065  1.00 85.46           C
ATOM    925  CG  LYS A 125      35.460  13.806  31.400  1.00 85.46           C
ATOM    926  CD  LYS A 125      34.492  13.017  32.281  1.00 85.46           C
ATOM    927  CE  LYS A 125      34.044  11.712  31.633  1.00 85.46           C
ATOM    928  NZ  LYS A 125      33.098  10.969  32.515  1.00 85.46           N
ATOM    929  N   ASN A 126      38.224  14.215  30.108  1.00 50.93           N
ATOM    930  CA  ASN A 126      39.333  13.295  29.917  1.00 50.93           C
ATOM    931  C   ASN A 126      40.208  13.447  28.682  1.00 50.93           C
ATOM    932  O   ASN A 126      41.262  12.826  28.604  1.00 50.93           O
ATOM    933  CB  ASN A 126      38.833  11.844  30.023  1.00 72.05           C
ATOM    934  CG  ASN A 126      37.528  11.609  29.285  1.00 72.05           C
ATOM    935  OD1 ASN A 126      36.929  10.535  29.393  1.00 72.05           O
ATOM    936  ND2 ASN A 126      37.080  12.610  28.530  1.00 72.05           N
ATOM    937  N   LEU A 127      39.824  14.263  27.714  1.00113.27           N
ATOM    938  CA  LEU A 127      40.699  14.382  26.560  1.00113.27           C
ATOM    939  C   LEU A 127      41.620  15.594  26.688  1.00113.27           C
ATOM    940  O   LEU A 127      42.582  15.727  25.931  1.00113.27           O
ATOM    941  CB  LEU A 127      39.882  14.443  25.260  1.00 65.66           C
ATOM    942  CG  LEU A 127      39.297  15.758  24.754  1.00 65.66           C
ATOM    943  CD1 LEU A 127      40.410  16.733  24.365  1.00 65.66           C
ATOM    944  CD2 LEU A 127      38.436  15.466  23.538  1.00 65.66           C
ATOM    945  N   THR A 128      41.333  16.458  27.662  1.00 81.99           N
ATOM    946  CA  THR A 128      42.112  17.679  27.901  1.00 81.99           C
ATOM    947  C   THR A 128      43.609  17.562  27.596  1.00 81.99           C
ATOM    948  O   THR A 128      44.210  18.480  27.029  1.00 81.99           O
ATOM    949  CB  THR A 128      41.964  18.170  29.361  1.00 99.66           C
ATOM    950  OG1 THR A 128      40.575  18.315  29.685  1.00 99.66           O
ATOM    951  CG2 THR A 128      42.649  19.523  29.537  1.00 99.66           C
ATOM    952  N   ALA A 129      44.212  16.445  27.987  1.00102.35           N
ATOM    953  CA  ALA A 129      45.628  16.228  27.731  1.00102.35           C
ATOM    954  C   ALA A 129      45.851  16.337  26.228  1.00102.35           C
ATOM    955  O   ALA A 129      46.619  17.183  25.764  1.00102.35           O
ATOM    956  CB  ALA A 129      46.048  14.850  28.225  1.00 76.05           C
ATOM    957  N   ASP A 130      45.198  15.448  25.473  1.00 89.67           N
ATOM    958  CA  ASP A 130      45.262  15.470  24.013  1.00 89.67           C
ATOM    959  C   ASP A 130      44.908  16.860  23.521  1.00 89.67           C
ATOM    960  O   ASP A 130      45.261  17.257  22.398  1.00 89.67           O
ATOM    961  CB  ASP A 130      44.285  14.455  23.410  1.00103.50           C
ATOM    962  CG  ASP A 130      44.420  13.104  24.094  1.00103.50           C
ATOM    963  OD1 ASP A 130      44.236  13.026  25.328  1.00103.50           O
ATOM    964  OD2 ASP A 130      44.715  12.125  23.377  1.00103.50           O
ATOM    965  N   GLU A 131      44.167  17.618  24.366  1.00 61.61           N
ATOM    966  CA  GLU A 131      43.848  19.075  24.175  1.00 61.61           C
ATOM    967  C   GLU A 131      42.658  19.507  23.329  1.00 61.61           C
ATOM    968  O   GLU A 131      42.751  19.518  22.098  1.00 61.61           O
ATOM    969  CB  GLU A 131      45.075  19.734  23.589  1.00 59.54           C
ATOM    970  CG  GLU A 131      44.935  21.220  23.744  1.00 59.54           C
ATOM    971  CD  GLU A 131      44.602  21.536  25.176  1.00 59.54           C
ATOM    972  OE1 GLU A 131      43.619  22.275  25.430  1.00 59.54           O
ATOM    973  OE2 GLU A 131      45.308  21.040  26.070  1.00 59.54           O
ATOM    974  N   VAL A 132      41.502  19.874  23.920  1.00 61.80           N
ATOM    975  CA  VAL A 132      40.251  20.217  23.175  1.00 61.80           C
ATOM    976  C   VAL A 132      40.452  21.036  21.890  1.00 61.80           C
ATOM    977  O   VAL A 132      39.666  20.967  20.961  1.00 61.80           O
ATOM    978  CB  VAL A 132      39.280  20.917  24.135  1.00 77.83           C
ATOM    979  CG1 VAL A 132      37.860  20.909  23.588  1.00 77.83           C
ATOM    980  CG2 VAL A 132      39.321  20.254  25.499  1.00 77.83           C
ATOM    981  N   ALA A 133      41.519  21.812  21.920  1.00 74.99           N
ATOM    982  CA  ALA A 133      41.904  22.678  20.812  1.00 74.99           C
ATOM    983  C   ALA A 133      42.214  21.873  19.546  1.00 74.99           C
ATOM    984  O   ALA A 133      41.925  22.323  18.441  1.00 74.99           O
ATOM    985  CB  ALA A 133      43.099  23.540  21.186  1.00 70.55           C
ATOM    986  N   THR A 134      42.808  20.694  19.703  1.00 59.60           N
ATOM    987  CA  THR A 134      43.129  19.845  18.557  1.00 59.60           C
ATOM    988  C   THR A 134      41.852  19.236  17.961  1.00 59.60           C
```

Figure 7-18

| | | | | | | | | | |
|---|---|---|---|---|---|---|---|---|---|
| ATOM | 989 | O | THR | A | 134 | 41.649 | 19.255 | 16.747 | 1.00 59.60 | O |
| ATOM | 990 | CB | THR | A | 134 | 44.076 | 18.714 | 18.978 | 1.00 48.57 | C |
| ATOM | 991 | OG1 | THR | A | 134 | 45.208 | 19.286 | 19.647 | 1.00 48.57 | O |
| ATOM | 992 | CG2 | THR | A | 134 | 44.550 | 17.909 | 17.765 | 1.00 48.57 | C |
| ATOM | 993 | N | LEU | A | 135 | 40.997 | 18.687 | 18.818 | 1.00 52.11 | N |
| ATOM | 994 | CA | LEU | A | 135 | 39.748 | 18.106 | 18.357 | 1.00 52.11 | C |
| ATOM | 995 | C | LEU | A | 135 | 38.950 | 19.211 | 17.683 | 1.00 52.11 | C |
| ATOM | 996 | O | LEU | A | 135 | 38.387 | 19.019 | 16.604 | 1.00 52.11 | O |
| ATOM | 997 | CB | LEU | A | 135 | 38.953 | 17.542 | 19.532 | 1.00 28.91 | C |
| ATOM | 998 | CG | LEU | A | 135 | 37.563 | 16.938 | 19.216 | 1.00 28.91 | C |
| ATOM | 999 | CD1 | LEU | A | 135 | 37.675 | 15.855 | 18.148 | 1.00 28.91 | C |
| ATOM | 1000 | CD2 | LEU | A | 135 | 36.964 | 16.366 | 20.504 | 1.00 28.91 | C |
| ATOM | 1001 | N | GLU | A | 136 | 38.922 | 20.379 | 18.315 | 1.00 51.30 | N |
| ATOM | 1002 | CA | GLU | A | 136 | 38.188 | 21.509 | 17.766 | 1.00 51.30 | C |
| ATOM | 1003 | C | GLU | A | 136 | 38.750 | 21.874 | 16.396 | 1.00 51.30 | C |
| ATOM | 1004 | O | GLU | A | 136 | 38.007 | 22.136 | 15.458 | 1.00 51.30 | O |
| ATOM | 1005 | CB | GLU | A | 136 | 38.282 | 22.704 | 18.716 | 1.00 50.36 | C |
| ATOM | 1006 | CG | GLU | A | 136 | 37.995 | 22.341 | 20.160 | 1.00 50.36 | C |
| ATOM | 1007 | CD | GLU | A | 136 | 37.849 | 23.550 | 21.070 | 1.00 50.36 | C |
| ATOM | 1008 | OE1 | GLU | A | 136 | 38.667 | 24.495 | 20.971 | 1.00 50.36 | O |
| ATOM | 1009 | OE2 | GLU | A | 136 | 36.915 | 23.542 | 21.904 | 1.00 50.36 | O |
| ATOM | 1010 | N | TYR | A | 137 | 40.070 | 21.871 | 16.286 | 1.00 48.14 | N |
| ATOM | 1011 | CA | TYR | A | 137 | 40.728 | 22.197 | 15.038 | 1.00 48.14 | C |
| ATOM | 1012 | C | TYR | A | 137 | 40.267 | 21.258 | 13.934 | 1.00 48.14 | C |
| ATOM | 1013 | O | TYR | A | 137 | 39.753 | 21.704 | 12.908 | 1.00 48.14 | O |
| ATOM | 1014 | CB | TYR | A | 137 | 42.244 | 22.088 | 15.199 | 1.00 62.08 | C |
| ATOM | 1015 | CG | TYR | A | 137 | 42.995 | 22.317 | 13.914 | 1.00 62.08 | C |
| ATOM | 1016 | CD1 | TYR | A | 137 | 43.121 | 23.595 | 13.380 | 1.00 62.08 | C |
| ATOM | 1017 | CD2 | TYR | A | 137 | 43.543 | 21.247 | 13.209 | 1.00 62.08 | C |
| ATOM | 1018 | CE1 | TYR | A | 137 | 43.774 | 23.810 | 12.172 | 1.00 62.08 | C |
| ATOM | 1019 | CE2 | TYR | A | 137 | 44.200 | 21.444 | 11.996 | 1.00 62.08 | C |
| ATOM | 1020 | CZ | TYR | A | 137 | 44.310 | 22.732 | 11.483 | 1.00 62.08 | C |
| ATOM | 1021 | OH | TYR | A | 137 | 44.939 | 22.938 | 10.274 | 1.00 62.08 | O |
| ATOM | 1022 | N | LEU | A | 138 | 40.468 | 19.958 | 14.138 | 1.00 37.88 | N |
| ATOM | 1023 | CA | LEU | A | 138 | 40.059 | 18.962 | 13.150 | 1.00 37.88 | C |
| ATOM | 1024 | C | LEU | A | 138 | 38.554 | 19.022 | 12.848 | 1.00 37.88 | C |
| ATOM | 1025 | O | LEU | A | 138 | 38.146 | 18.864 | 11.700 | 1.00 37.88 | O |
| ATOM | 1026 | CB | LEU | A | 138 | 40.439 | 17.555 | 13.624 | 1.00 65.29 | C |
| ATOM | 1027 | CG | LEU | A | 138 | 41.937 | 17.223 | 13.657 | 1.00 65.29 | C |
| ATOM | 1028 | CD1 | LEU | A | 138 | 42.152 | 15.798 | 14.136 | 1.00 65.29 | C |
| ATOM | 1029 | CD2 | LEU | A | 138 | 42.513 | 17.393 | 12.266 | 1.00 65.29 | C |
| ATOM | 1030 | N | LEU | A | 139 | 37.731 | 19.256 | 13.868 | 1.00 37.74 | N |
| ATOM | 1031 | CA | LEU | A | 139 | 36.291 | 19.329 | 13.654 | 1.00 37.74 | C |
| ATOM | 1032 | C | LEU | A | 139 | 35.939 | 20.500 | 12.749 | 1.00 37.74 | C |
| ATOM | 1033 | O | LEU | A | 139 | 34.915 | 20.479 | 12.068 | 1.00 37.74 | O |
| ATOM | 1034 | CB | LEU | A | 139 | 35.547 | 19.468 | 14.987 | 1.00 35.40 | C |
| ATOM | 1035 | CG | LEU | A | 139 | 35.320 | 18.190 | 15.805 | 1.00 35.40 | C |
| ATOM | 1036 | CD1 | LEU | A | 139 | 34.645 | 18.554 | 17.126 | 1.00 35.40 | C |
| ATOM | 1037 | CD2 | LEU | A | 139 | 34.461 | 17.208 | 15.019 | 1.00 35.40 | C |
| ATOM | 1038 | N | LYS | A | 140 | 36.778 | 21.529 | 12.750 | 1.00 53.22 | N |
| ATOM | 1039 | CA | LYS | A | 140 | 36.527 | 22.689 | 11.900 | 1.00 53.22 | C |
| ATOM | 1040 | C | LYS | A | 140 | 36.822 | 22.323 | 10.459 | 1.00 53.22 | C |
| ATOM | 1041 | O | LYS | A | 140 | 36.089 | 22.718 | 9.554 | 1.00 53.22 | O |
| ATOM | 1042 | CB | LYS | A | 140 | 37.392 | 23.883 | 12.319 | 1.00 43.83 | C |
| ATOM | 1043 | CG | LYS | A | 140 | 36.966 | 24.525 | 13.634 | 1.00 43.83 | C |
| ATOM | 1044 | CD | LYS | A | 140 | 37.829 | 25.733 | 13.976 | 1.00 43.83 | C |
| ATOM | 1045 | CE | LYS | A | 140 | 37.341 | 26.425 | 15.238 | 1.00 43.83 | C |
| ATOM | 1046 | NZ | LYS | A | 140 | 38.091 | 27.695 | 15.494 | 1.00 43.83 | N |
| ATOM | 1047 | N | LYS | A | 141 | 37.889 | 21.554 | 10.251 | 1.00 43.02 | N |
| ATOM | 1048 | CA | LYS | A | 141 | 38.279 | 21.133 | 8.910 | 1.00 43.02 | C |
| ATOM | 1049 | C | LYS | A | 141 | 37.210 | 20.276 | 8.245 | 1.00 43.02 | C |
| ATOM | 1050 | O | LYS | A | 141 | 37.316 | 19.946 | 7.063 | 1.00 43.02 | O |
| ATOM | 1051 | CB | LYS | A | 141 | 39.609 | 20.366 | 8.939 | 1.00 56.38 | C |
| ATOM | 1052 | CG | LYS | A | 141 | 40.801 | 21.198 | 9.383 | 1.00 56.38 | C |
| ATOM | 1053 | CD | LYS | A | 141 | 42.119 | 20.601 | 8.900 | 1.00 56.38 | C |
| ATOM | 1054 | CE | LYS | A | 141 | 42.286 | 20.774 | 7.384 | 1.00 56.38 | C |
| ATOM | 1055 | NZ | LYS | A | 141 | 43.556 | 20.185 | 6.830 | 1.00 56.38 | N |
| ATOM | 1056 | N | VAL | A | 142 | 36.178 | 19.918 | 9.001 | 1.00 64.66 | N |
| ATOM | 1057 | CA | VAL | A | 142 | 35.081 | 19.119 | 8.470 | 1.00 64.66 | C |
| ATOM | 1058 | C | VAL | A | 142 | 33.940 | 20.008 | 7.952 | 1.00 64.66 | C |
| ATOM | 1059 | O | VAL | A | 142 | 33.198 | 19.611 | 7.053 | 1.00 64.66 | O |
| ATOM | 1060 | CB | VAL | A | 142 | 34.502 | 18.170 | 9.556 | 1.00 36.71 | C |
| ATOM | 1061 | CG1 | VAL | A | 142 | 33.236 | 17.503 | 9.044 | 1.00 36.71 | C |
| ATOM | 1062 | CG2 | VAL | A | 142 | 35.533 | 17.118 | 9.945 | 1.00 36.71 | C |
| ATOM | 1063 | N | LEU | A | 143 | 33.815 | 21.212 | 8.504 | 1.00 55.78 | N |

Figure 7-19

```
ATOM   1064 CA  LEU A 143      32.736  22.126   8.125  1.00 55.78           C
ATOM   1065 C   LEU A 143      32.745  22.784   6.733  1.00 55.78           C
ATOM   1066 O   LEU A 143      31.732  22.766   6.021  1.00 55.78           O
ATOM   1067 CB  LEU A 143      32.591  23.210   9.202  1.00 39.23           C
ATOM   1068 CG  LEU A 143      32.052  22.650  10.517  1.00 39.23           C
ATOM   1069 CD1 LEU A 143      31.874  23.748  11.529  1.00 39.23           C
ATOM   1070 CD2 LEU A 143      30.736  21.952  10.247  1.00 39.23           C
ATOM   1071 N   PRO A 144      33.874  23.375   6.323  1.00 58.86           N
ATOM   1072 CA  PRO A 144      33.870  24.001   4.997  1.00 58.86           C
ATOM   1073 C   PRO A 144      33.622  23.019   3.840  1.00 58.86           C
ATOM   1074 O   PRO A 144      33.792  21.797   4.034  1.00 58.86           O
ATOM   1075 CB  PRO A 144      35.250  24.659   4.928  1.00 69.58           C
ATOM   1076 CG  PRO A 144      36.096  23.742   5.760  1.00 69.58           C
ATOM   1077 CD  PRO A 144      35.207  23.454   6.945  1.00 69.58           C
ATOM   1078 OXT PRO A 144      33.265  23.490   2.742  1.00 69.58           O
TER    1079     PRO A 144
HETATM 1080 C1' SAL   256       1.600  28.984  14.971  1.00 44.77           C
HETATM 1081 O1' SAL   256       1.140  30.228  15.037  1.00 44.77           O
HETATM 1082 O2' SAL   256       1.829  28.336  16.002  1.00 44.77           O
HETATM 1083 C1  SAL   256       1.818  28.433  13.617  1.00 44.77           C
HETATM 1084 C2  SAL   256       2.324  27.078  13.453  1.00 44.77           C
HETATM 1085 C3  SAL   256       2.546  26.526  12.169  1.00 44.77           C
HETATM 1086 C4  SAL   256       2.286  27.268  11.019  1.00 44.77           C
HETATM 1087 C5  SAL   256       1.734  28.740  11.167  1.00 44.77           C
HETATM 1088 C6  SAL   256       1.535  29.234  12.452  1.00 44.77           C
HETATM 1089 O2  SAL   256       2.610  26.273  14.510  1.00 44.77           O
HETATM 1090 C1' SAL   257       6.631  20.720  25.251  1.00 42.17           C
HETATM 1091 O1' SAL   257       7.014  21.247  26.407  1.00 42.17           O
HETATM 1092 O2' SAL   257       5.545  21.061  24.701  1.00 42.17           O
HETATM 1093 C1  SAL   257       7.558  19.723  24.673  1.00 42.17           C
HETATM 1094 C2  SAL   257       7.247  19.073  23.396  1.00 42.17           C
HETATM 1095 C3  SAL   257       8.133  18.108  22.827  1.00 42.17           C
HETATM 1096 C4  SAL   257       9.326  17.754  23.481  1.00 42.17           C
HETATM 1097 C5  SAL   257       9.668  18.454  24.869  1.00 42.17           C
HETATM 1098 C6  SAL   257       8.767  19.390  25.369  1.00 42.17           C
HETATM 1099 O2  SAL   257       6.103  19.348  22.680  1.00 42.17           O
CONECT 1080 1081 1082 1083
CONECT 1081 1080
CONECT 1082 1080
CONECT 1083 1080 1084 1088
CONECT 1084 1083 1085 1089
CONECT 1085 1084 1086
CONECT 1086 1085 1087
CONECT 1087 1086 1088
CONECT 1088 1083 1087
CONECT 1089 1084
CONECT 1090 1091 1092 1093
CONECT 1091 1090
CONECT 1092 1090
CONECT 1093 1090 1094 1098
CONECT 1094 1093 1095 1099
CONECT 1095 1094 1096
CONECT 1096 1095 1097
CONECT 1097 1096 1098
CONECT 1098 1093 1097
CONECT 1099 1094
MASTER      306    0    2    6    2    0    0    6 1098    1   20   11
END
```

Figure 7-20

Appendix E

```
REMARK  Apo-MarR; Residues 12-144 of SEQ ID NO:2
REMARK  Written by O version 6.2.1
REMARK  DATE:10-May-02   11:21:32
CRYST1   65.8    137.7    96.4   90.00  90.00  90.00  C222
ATOM       1  CB   ILE A  12      59.905  14.106  45.475  1.00 67.94      A
ATOM       2  CG2  ILE A  12      59.418  13.830  44.055  1.00 67.94      A
ATOM       3  CG1  ILE A  12      58.771  13.864  46.472  1.00 67.94      A
ATOM       4  CD1  ILE A  12      58.227  12.461  46.458  1.00 67.94      A
ATOM       5  C    ILE A  12      61.444  13.384  47.291  1.00123.94      A
ATOM       6  O    ILE A  12      61.003  12.599  48.130  1.00123.94      A
ATOM       7  N    ILE A  12      60.812  11.760  45.543  1.00123.94      A
ATOM       8  CA   ILE A  12      61.114  13.198  45.814  1.00123.94      A
ATOM       9  N    PRO A  13      62.238  14.420  47.627  1.00130.37      A
ATOM      10  CD   PRO A  13      62.932  15.390  46.760  1.00 80.29      A
ATOM      11  CA   PRO A  13      62.578  14.645  49.035  1.00130.37      A
ATOM      12  CB   PRO A  13      63.297  15.990  49.002  1.00 80.29      A
ATOM      13  CG   PRO A  13      64.011  15.937  47.685  1.00 80.29      A
ATOM      14  C    PRO A  13      61.294  14.670  49.862  1.00130.37      A
ATOM      15  O    PRO A  13      60.232  15.061  49.371  1.00130.37      A
ATOM      16  N    LEU A  14      61.396  14.254  51.115  1.00 79.03      A
ATOM      17  CA   LEU A  14      60.236  14.183  51.985  1.00 79.03      A
ATOM      18  CB   LEU A  14      60.652  13.546  53.315  1.00 46.83      A
ATOM      19  CG   LEU A  14      59.567  13.009  54.251  1.00 46.83      A
ATOM      20  CD1  LEU A  14      58.532  12.213  53.467  1.00 46.83      A
ATOM      21  CD2  LEU A  14      60.223  12.134  55.316  1.00 46.83      A
ATOM      22  C    LEU A  14      59.542  15.528  52.206  1.00 79.03      A
ATOM      23  O    LEU A  14      58.310  15.596  52.261  1.00 79.03      A
ATOM      24  N    GLY A  15      60.332  16.593  52.312  1.00 52.34      A
ATOM      25  CA   GLY A  15      59.775  17.919  52.530  1.00 52.34      A
ATOM      26  C    GLY A  15      58.591  18.254  51.642  1.00 52.34      A
ATOM      27  O    GLY A  15      57.551  18.705  52.138  1.00 52.34      A
ATOM      28  N    ARG A  16      58.741  18.039  50.335  1.00 52.47      A
ATOM      29  CA   ARG A  16      57.664  18.331  49.393  1.00 52.47      A
ATOM      30  CB   ARG A  16      58.173  18.263  47.949  1.00111.16      A
ATOM      31  CG   ARG A  16      58.538  19.623  47.367  1.00111.16      A
ATOM      32  CD   ARG A  16      58.915  19.527  45.896  1.00111.16      A
ATOM      33  NE   ARG A  16      60.105  18.707  45.692  1.00111.16      A
ATOM      34  CZ   ARG A  16      61.304  18.988  46.193  1.00111.16      A
ATOM      35  NH1  ARG A  16      61.485  20.073  46.933  1.00111.16      A
ATOM      36  NH2  ARG A  16      62.324  18.179  45.957  1.00111.16      A
ATOM      37  C    ARG A  16      56.482  17.393  49.561  1.00 52.47      A
ATOM      38  O    ARG A  16      55.330  17.786  49.361  1.00 52.47      A
ATOM      39  N    LEU A  17      56.765  16.154  49.939  1.00 37.85      A
ATOM      40  CA   LEU A  17      55.706  15.175  50.117  1.00 37.85      A
ATOM      41  CB   LEU A  17      56.315  13.788  50.319  1.00 47.48      A
ATOM      42  CG   LEU A  17      55.704  12.665  49.481  1.00 47.48      A
ATOM      43  CD1  LEU A  17      55.356  13.152  48.075  1.00 47.48      A
ATOM      44  CD2  LEU A  17      56.702  11.515  49.432  1.00 47.48      A
ATOM      45  C    LEU A  17      54.832  15.562  51.303  1.00 37.85      A
ATOM      46  O    LEU A  17      53.600  15.578  51.199  1.00 37.85      A
ATOM      47  N    ILE A  18      55.475  15.889  52.423  1.00 32.29      A
ATOM      48  CA   ILE A  18      54.749  16.282  53.628  1.00 32.29      A
ATOM      49  CB   ILE A  18      55.715  16.537  54.819  1.00 22.79      A
ATOM      50  CG2  ILE A  18      54.938  17.003  56.048  1.00 22.79      A
ATOM      51  CG1  ILE A  18      56.487  15.247  55.131  1.00 22.79      A
ATOM      52  CD1  ILE A  18      57.543  15.383  56.248  1.00 22.79      A
ATOM      53  C    ILE A  18      53.983  17.550  53.307  1.00 32.29      A
ATOM      54  O    ILE A  18      52.900  17.792  53.836  1.00 32.29      A
ATOM      55  N    HIS A  19      54.545  18.353  52.416  1.00 38.61      A
ATOM      56  CA   HIS A  19      53.893  19.587  52.022  1.00 38.61      A
ATOM      57  CB   HIS A  19      54.837  20.437  51.178  1.00 36.15      A
ATOM      58  CG   HIS A  19      54.378  21.850  51.011  1.00 36.15      A
ATOM      59  CD2  HIS A  19      53.819  22.714  51.890  1.00 36.15      A
ATOM      60  ND1  HIS A  19      54.490  22.534  49.819  1.00 36.15      A
ATOM      61  CE1  HIS A  19      54.019  23.758  49.971  1.00 36.15      A
ATOM      62  NE2  HIS A  19      53.606  23.892  51.217  1.00 36.15      A
ATOM      63  C    HIS A  19      52.613  19.294  51.235  1.00 38.61      A
ATOM      64  O    HIS A  19      51.550  19.822  51.567  1.00 38.61      A
ATOM      65  N    MET A  20      52.706  18.447  50.208  1.00 40.71      A
ATOM      66  CA   MET A  20      51.529  18.134  49.397  1.00 40.71      A
ATOM      67  CB   MET A  20      51.932  17.320  48.167  1.00 37.11      A
ATOM      68  CG   MET A  20      52.702  18.147  47.140  1.00 37.11      A
ATOM      69  SD   MET A  20      53.466  17.123  45.859  1.00 37.11      A
ATOM      70  CE   MET A  20      54.894  16.449  46.755  1.00 37.11      A
ATOM      71  C    MET A  20      50.455  17.415  50.201  1.00 40.71      A
```

Figure 8-1

```
ATOM   72  O    MET A  20      49.265  17.732  50.088  1.00 40.71      A
ATOM   73  N    VAL A  21      50.873  16.456  51.020  1.00 34.62      A
ATOM   74  CA   VAL A  21      49.920  15.737  51.845  1.00 34.62      A
ATOM   75  CB   VAL A  21      50.623  14.669  52.700  1.00 33.69      A
ATOM   76  CG1  VAL A  21      49.651  14.074  53.696  1.00 33.69      A
ATOM   77  CG2  VAL A  21      51.181  13.583  51.798  1.00 33.69      A
ATOM   78  C    VAL A  21      49.240  16.760  52.755  1.00 34.62      A
ATOM   79  O    VAL A  21      48.009  16.759  52.909  1.00 34.62      A
ATOM   80  N    ASN A  22      50.041  17.652  53.336  1.00 31.08      A
ATOM   81  CA   ASN A  22      49.489  18.656  54.230  1.00 31.08      A
ATOM   82  CB   ASN A  22      50.576  19.546  54.827  1.00 26.87      A
ATOM   83  CG   ASN A  22      50.032  20.418  55.951  1.00 26.87      A
ATOM   84  OD1  ASN A  22      49.760  19.919  57.052  1.00 26.87      A
ATOM   85  ND2  ASN A  22      49.830  21.713  55.672  1.00 26.87      A
ATOM   86  C    ASN A  22      48.457  19.556  53.555  1.00 31.08      A
ATOM   87  O    ASN A  22      47.397  19.850  54.130  1.00 31.08      A
ATOM   88  N    GLN A  23      48.765  20.015  52.349  1.00 22.48      A
ATOM   89  CA   GLN A  23      47.828  20.871  51.670  1.00 22.48      A
ATOM   90  CB   GLN A  23      48.401  21.383  50.354  1.00 42.54      A
ATOM   91  CG   GLN A  23      49.576  22.309  50.520  1.00 42.54      A
ATOM   92  CD   GLN A  23      49.739  23.255  49.337  1.00 42.54      A
ATOM   93  OE1  GLN A  23      49.522  22.876  48.173  1.00 42.54      A
ATOM   94  NE2  GLN A  23      50.132  24.498  49.629  1.00 42.54      A
ATOM   95  C    GLN A  23      46.528  20.110  51.432  1.00 22.48      A
ATOM   96  O    GLN A  23      45.447  20.683  51.600  1.00 22.48      A
ATOM   97  N    LYS A  24      46.616  18.829  51.064  1.00 27.17      A
ATOM   98  CA   LYS A  24      45.393  18.068  50.835  1.00 27.17      A
ATOM   99  CB   LYS A  24      45.693  16.643  50.362  1.00 41.13      A
ATOM  100  CG   LYS A  24      44.450  15.943  49.835  1.00 41.13      A
ATOM  101  CD   LYS A  24      44.684  14.486  49.469  1.00 41.13      A
ATOM  102  CE   LYS A  24      43.406  13.866  48.908  1.00 41.13      A
ATOM  103  NZ   LYS A  24      43.411  12.372  49.000  1.00 41.13      A
ATOM  104  C    LYS A  24      44.595  18.021  52.144  1.00 27.17      A
ATOM  105  O    LYS A  24      43.381  18.296  52.151  1.00 27.17      A
ATOM  106  N    LYS A  25      45.274  17.696  53.248  1.00 23.70      A
ATOM  107  CA   LYS A  25      44.588  17.631  54.536  1.00 23.70      A
ATOM  108  CB   LYS A  25      45.565  17.431  55.704  1.00 36.11      A
ATOM  109  CG   LYS A  25      44.843  17.459  57.063  1.00 36.11      A
ATOM  110  CD   LYS A  25      45.789  17.520  58.266  1.00 36.11      A
ATOM  111  CE   LYS A  25      46.615  18.813  58.323  1.00 36.11      A
ATOM  112  NZ   LYS A  25      45.775  20.034  58.447  1.00 36.11      A
ATOM  113  C    LYS A  25      43.811  18.928  54.762  1.00 23.70      A
ATOM  114  O    LYS A  25      42.604  18.904  55.046  1.00 23.70      A
ATOM  115  N    ASP A  26      44.509  20.055  54.620  1.00 27.62      A
ATOM  116  CA   ASP A  26      43.892  21.359  54.822  1.00 27.62      A
ATOM  117  CB   ASP A  26      44.909  22.477  54.572  1.00 48.95      A
ATOM  118  CG   ASP A  26      45.908  22.639  55.721  1.00 48.95      A
ATOM  119  OD1  ASP A  26      46.897  23.399  55.548  1.00 48.95      A
ATOM  120  OD2  ASP A  26      45.706  22.016  56.791  1.00 48.95      A
ATOM  121  C    ASP A  26      42.656  21.576  53.959  1.00 27.62      A
ATOM  122  O    ASP A  26      41.662  22.114  54.448  1.00 27.62      A
ATOM  123  N    ARG A  27      42.708  21.168  52.685  1.00 22.30      A
ATOM  124  CA   ARG A  27      41.563  21.343  51.798  1.00 22.30      A
ATOM  125  CB   ARG A  27      41.952  21.014  50.354  1.00 52.90      A
ATOM  126  CG   ARG A  27      42.798  22.123  49.697  1.00 52.90      A
ATOM  127  CD   ARG A  27      43.108  21.870  48.208  1.00 52.90      A
ATOM  128  NE   ARG A  27      44.493  21.445  47.986  1.00 52.90      A
ATOM  129  CZ   ARG A  27      44.883  20.184  47.786  1.00 52.90      A
ATOM  130  NH1  ARG A  27      43.994  19.196  47.771  1.00 52.90      A
ATOM  131  NH2  ARG A  27      46.169  19.908  47.600  1.00 52.90      A
ATOM  132  C    ARG A  27      40.388  20.484  52.284  1.00 22.30      A
ATOM  133  O    ARG A  27      39.249  20.970  52.381  1.00 22.30      A
ATOM  134  N    LEU A  28      40.668  19.226  52.625  1.00 28.23      A
ATOM  135  CA   LEU A  28      39.628  18.342  53.124  1.00 28.23      A
ATOM  136  CB   LEU A  28      40.204  16.951  53.384  1.00 19.62      A
ATOM  137  CG   LEU A  28      40.644  16.188  52.133  1.00 19.62      A
ATOM  138  CD1  LEU A  28      41.264  14.854  52.538  1.00 19.62      A
ATOM  139  CD2  LEU A  28      39.431  15.979  51.225  1.00 19.62      A
ATOM  140  C    LEU A  28      39.108  18.939  54.421  1.00 28.23      A
ATOM  141  O    LEU A  28      37.902  19.103  54.606  1.00 28.23      A
ATOM  142  N    LEU A  29      40.041  19.271  55.310  1.00 32.81      A
ATOM  143  CA   LEU A  29      39.723  19.844  56.610  1.00 32.81      A
ATOM  144  CB   LEU A  29      41.009  20.264  57.301  1.00 30.88      A
ATOM  145  CG   LEU A  29      40.893  20.746  58.740  1.00 30.88      A
ATOM  146  CD1  LEU A  29      39.898  19.883  59.510  1.00 30.88      A
```

Figure 8-2

```
ATOM    147  CD2 LEU A  29      42.282  20.693  59.379  1.00 30.88       A
ATOM    148  C   LEU A  29      38.794  21.038  56.471  1.00 32.81       A
ATOM    149  O   LEU A  29      37.873  21.226  57.273  1.00 32.81       A
ATOM    150  N   ASN A  30      39.030  21.839  55.437  1.00 33.15       A
ATOM    151  CA  ASN A  30      38.206  23.010  55.202  1.00 33.15       A
ATOM    152  CB  ASN A  30      38.812  23.879  54.106  1.00 37.23       A
ATOM    153  CG  ASN A  30      38.967  25.325  54.527  1.00 37.23       A
ATOM    154  OD1 ASN A  30      39.241  26.196  53.706  1.00 37.23       A
ATOM    155  ND2 ASN A  30      38.805  25.587  55.813  1.00 37.23       A
ATOM    156  C   ASN A  30      36.791  22.614  54.813  1.00 33.15       A
ATOM    157  O   ASN A  30      35.847  23.304  55.156  1.00 33.15       A
ATOM    158  N   GLU A  31      36.643  21.499  54.106  1.00 45.74       A
ATOM    159  CA  GLU A  31      35.320  21.055  53.681  1.00 45.74       A
ATOM    160  CB  GLU A  31      35.443  20.018  52.573  1.00111.71       A
ATOM    161  CG  GLU A  31      36.048  20.569  51.302  1.00111.71       A
ATOM    162  CD  GLU A  31      36.235  19.500  50.255  1.00111.71       A
ATOM    163  OE1 GLU A  31      35.229  18.863  49.877  1.00111.71       A
ATOM    164  OE2 GLU A  31      37.385  19.292  49.813  1.00111.71       A
ATOM    165  C   GLU A  31      34.502  20.493  54.829  1.00 45.74       A
ATOM    166  O   GLU A  31      33.325  20.802  54.962  1.00 45.74       A
ATOM    167  N   TYR A  32      35.119  19.677  55.668  1.00 43.75       A
ATOM    168  CA  TYR A  32      34.393  19.110  56.790  1.00 43.75       A
ATOM    169  CB  TYR A  32      35.171  17.926  57.355  1.00 50.30       A
ATOM    170  CG  TYR A  32      35.296  16.793  56.364  1.00 50.30       A
ATOM    171  CD1 TYR A  32      36.534  16.445  55.823  1.00 50.30       A
ATOM    172  CE1 TYR A  32      36.646  15.423  54.881  1.00 50.30       A
ATOM    173  CD2 TYR A  32      34.168  16.089  55.941  1.00 50.30       A
ATOM    174  CE2 TYR A  32      34.264  15.069  55.001  1.00 50.30       A
ATOM    175  CZ  TYR A  32      35.506  14.740  54.471  1.00 50.30       A
ATOM    176  OH  TYR A  32      35.601  13.741  53.520  1.00 50.30       A
ATOM    177  C   TYR A  32      34.117  20.154  57.876  1.00 43.75       A
ATOM    178  O   TYR A  32      33.278  19.951  58.746  1.00 43.75       A
ATOM    179  N   LEU A  33      34.806  21.286  57.805  1.00 31.02       A
ATOM    180  CA  LEU A  33      34.628  22.343  58.785  1.00 31.02       A
ATOM    181  CB  LEU A  33      35.933  23.120  58.969  1.00 26.92       A
ATOM    182  CG  LEU A  33      36.988  22.548  59.905  1.00 26.92       A
ATOM    183  CD1 LEU A  33      38.137  23.523  59.973  1.00 26.92       A
ATOM    184  CD2 LEU A  33      36.399  22.324  61.291  1.00 26.92       A
ATOM    185  C   LEU A  33      33.529  23.327  58.397  1.00 31.02       A
ATOM    186  O   LEU A  33      32.846  23.877  59.266  1.00 31.02       A
ATOM    187  N   SER A  34      33.379  23.561  57.094  1.00 47.63       A
ATOM    188  CA  SER A  34      32.380  24.498  56.584  1.00 47.63       A
ATOM    189  CB  SER A  34      32.121  24.237  55.097  1.00 75.10       A
ATOM    190  OG  SER A  34      31.147  25.133  54.585  1.00 75.10       A
ATOM    191  C   SER A  34      31.053  24.459  57.353  1.00 47.63       A
ATOM    192  O   SER A  34      30.504  25.507  57.706  1.00 47.63       A
ATOM    193  N   PRO A  35      30.528  23.249  57.632  1.00 43.33       A
ATOM    194  CD  PRO A  35      31.030  21.949  57.157  1.00 63.21       A
ATOM    195  CA  PRO A  35      29.263  23.069  58.359  1.00 43.33       A
ATOM    196  CB  PRO A  35      29.049  21.559  58.317  1.00 63.21       A
ATOM    197  CG  PRO A  35      29.764  21.146  57.072  1.00 63.21       A
ATOM    198  C   PRO A  35      29.293  23.578  59.794  1.00 43.33       A
ATOM    199  O   PRO A  35      28.296  23.501  60.504  1.00 43.33       A
ATOM    200  N   LEU A  36      30.441  24.090  60.222  1.00 41.82       A
ATOM    201  CA  LEU A  36      30.587  24.589  61.587  1.00 41.82       A
ATOM    202  CB  LEU A  36      31.673  23.792  62.320  1.00 53.45       A
ATOM    203  CG  LEU A  36      31.335  23.115  63.659  1.00 53.45       A
ATOM    204  CD1 LEU A  36      32.514  22.238  64.077  1.00 53.45       A
ATOM    205  CD2 LEU A  36      31.026  24.153  64.741  1.00 53.45       A
ATOM    206  C   LEU A  36      30.925  26.078  61.636  1.00 41.82       A
ATOM    207  O   LEU A  36      31.226  26.612  62.700  1.00 41.82       A
ATOM    208  N   ASP A  37      30.878  26.750  60.489  1.00 34.90       A
ATOM    209  CA  ASP A  37      31.178  28.176  60.451  1.00 34.90       A
ATOM    210  CB  ASP A  37      30.202  28.950  61.337  1.00 88.32       A
ATOM    211  CG  ASP A  37      29.042  29.523  60.558  1.00 88.32       A
ATOM    212  OD1 ASP A  37      29.289  30.383  59.684  1.00 88.32       A
ATOM    213  OD2 ASP A  37      27.888  29.115  60.816  1.00 88.32       A
ATOM    214  C   ASP A  37      32.606  28.506  60.883  1.00 34.90       A
ATOM    215  O   ASP A  37      32.828  29.476  61.610  1.00 34.90       A
ATOM    216  N   ILE A  38      33.570  27.702  60.442  1.00 28.88       A
ATOM    217  CA  ILE A  38      34.964  27.952  60.779  1.00 28.88       A
ATOM    218  CB  ILE A  38      35.350  27.274  62.108  1.00 20.06       A
ATOM    219  CG2 ILE A  38      35.702  25.822  61.878  1.00 20.06       A
ATOM    220  CG1 ILE A  38      36.545  28.010  62.722  1.00 20.06       A
ATOM    221  CD1 ILE A  38      37.305  27.243  63.816  1.00 20.06       A
```

Figure 8-3

```
ATOM    222  C   ILE A  38      35.896  27.461  59.663  1.00 28.88      A
ATOM    223  O   ILE A  38      35.651  26.422  59.041  1.00 28.88      A
ATOM    224  N   THR A  39      36.959  28.215  59.399  1.00 29.25      A
ATOM    225  CA  THR A  39      37.904  27.840  58.349  1.00 29.25      A
ATOM    226  CB  THR A  39      38.426  29.068  57.605  1.00  9.47      A
ATOM    227  OG1 THR A  39      39.300  29.807  58.477  1.00  9.47      A
ATOM    228  CG2 THR A  39      37.291  29.959  57.169  1.00  9.47      A
ATOM    229  C   THR A  39      39.127  27.121  58.923  1.00 29.25      A
ATOM    230  O   THR A  39      39.458  27.278  60.101  1.00 29.25      A
ATOM    231  N   ALA A  40      39.801  26.347  58.078  1.00 29.21      A
ATOM    232  CA  ALA A  40      40.994  25.610  58.480  1.00 29.21      A
ATOM    233  CB  ALA A  40      41.616  24.918  57.280  1.00  1.00      A
ATOM    234  C   ALA A  40      42.010  26.565  59.080  1.00 29.21      A
ATOM    235  O   ALA A  40      42.684  26.245  60.064  1.00 29.21      A
ATOM    236  N   ALA A  41      42.129  27.740  58.476  1.00 28.55      A
ATOM    237  CA  ALA A  41      43.087  28.719  58.972  1.00 28.55      A
ATOM    238  CB  ALA A  41      43.012  30.003  58.145  1.00 30.67      A
ATOM    239  C   ALA A  41      42.801  29.025  60.442  1.00 28.55      A
ATOM    240  O   ALA A  41      43.675  28.890  61.309  1.00 28.55      A
ATOM    241  N   GLN A  42      41.567  29.430  60.717  1.00 23.69      A
ATOM    242  CA  GLN A  42      41.180  29.775  62.069  1.00 23.69      A
ATOM    243  CB  GLN A  42      39.712  30.183  62.088  1.00 31.90      A
ATOM    244  CG  GLN A  42      39.421  31.267  61.070  1.00 31.90      A
ATOM    245  CD  GLN A  42      37.966  31.641  61.012  1.00 31.90      A
ATOM    246  OE1 GLN A  42      37.092  30.776  60.997  1.00 31.90      A
ATOM    247  NE2 GLN A  42      37.692  32.938  60.967  1.00 31.90      A
ATOM    248  C   GLN A  42      41.417  28.596  62.988  1.00 23.69      A
ATOM    249  O   GLN A  42      42.026  28.730  64.058  1.00 23.69      A
ATOM    250  N   PHE A  43      40.949  27.429  62.561  1.00 20.02      A
ATOM    251  CA  PHE A  43      41.099  26.232  63.368  1.00 20.02      A
ATOM    252  CB  PHE A  43      40.441  25.042  62.665  1.00 21.86      A
ATOM    253  CG  PHE A  43      40.607  23.738  63.394  1.00 21.86      A
ATOM    254  CD1 PHE A  43      40.118  23.582  64.692  1.00 21.86      A
ATOM    255  CD2 PHE A  43      41.250  22.659  62.778  1.00 21.86      A
ATOM    256  CE1 PHE A  43      40.264  22.368  65.375  1.00 21.86      A
ATOM    257  CE2 PHE A  43      41.402  21.441  63.448  1.00 21.86      A
ATOM    258  CZ  PHE A  43      40.907  21.293  64.754  1.00 21.86      A
ATOM    259  C   PHE A  43      42.575  25.962  63.646  1.00 20.02      A
ATOM    260  O   PHE A  43      42.946  25.641  64.776  1.00 20.02      A
ATOM    261  N   LYS A  44      43.425  26.105  62.632  1.00 25.04      A
ATOM    262  CA  LYS A  44      44.856  25.883  62.839  1.00 25.04      A
ATOM    263  CB  LYS A  44      45.648  26.125  61.550  1.00 46.29      A
ATOM    264  CG  LYS A  44      45.596  24.991  60.552  1.00 46.29      A
ATOM    265  CD  LYS A  44      46.639  25.210  59.467  1.00 46.29      A
ATOM    266  CE  LYS A  44      46.797  23.984  58.585  1.00 46.29      A
ATOM    267  NZ  LYS A  44      48.034  24.060  57.757  1.00 46.29      A
ATOM    268  C   LYS A  44      45.402  26.802  63.940  1.00 25.04      A
ATOM    269  O   LYS A  44      46.092  26.334  64.861  1.00 25.04      A
ATOM    270  N   VAL A  45      45.103  28.102  63.836  1.00 24.20      A
ATOM    271  CA  VAL A  45      45.563  29.073  64.830  1.00 24.20      A
ATOM    272  CB  VAL A  45      45.056  30.508  64.511  1.00 17.46      A
ATOM    273  CG1 VAL A  45      45.349  31.440  65.670  1.00 17.46      A
ATOM    274  CG2 VAL A  45      45.736  31.036  63.238  1.00 17.46      A
ATOM    275  C   VAL A  45      45.053  28.665  66.213  1.00 24.20      A
ATOM    276  O   VAL A  45      45.818  28.590  67.183  1.00 24.20      A
ATOM    277  N   LEU A  46      43.755  28.398  66.294  1.00 22.98      A
ATOM    278  CA  LEU A  46      43.144  27.979  67.542  1.00 22.98      A
ATOM    279  CB  LEU A  46      41.701  27.570  67.277  1.00 18.73      A
ATOM    280  CG  LEU A  46      40.618  28.396  67.970  1.00 18.73      A
ATOM    281  CD1 LEU A  46      40.946  29.880  67.928  1.00 18.73      A
ATOM    282  CD2 LEU A  46      39.276  28.083  67.296  1.00 18.73      A
ATOM    283  C   LEU A  46      43.918  26.808  68.170  1.00 22.98      A
ATOM    284  O   LEU A  46      44.198  26.809  69.374  1.00 22.98      A
ATOM    285  N   CYS A  47      44.276  25.816  67.356  1.00 25.10      A
ATOM    286  CA  CYS A  47      45.027  24.657  67.853  1.00 25.10      A
ATOM    287  CB  CYS A  47      45.147  23.588  66.764  1.00 37.95      A
ATOM    288  SG  CYS A  47      43.614  22.685  66.463  1.00 37.95      A
ATOM    289  C   CYS A  47      46.426  24.997  68.367  1.00 25.10      A
ATOM    290  O   CYS A  47      46.885  24.424  69.350  1.00 25.10      A
ATOM    291  N   SER A  48      47.113  25.920  67.703  1.00 26.62      A
ATOM    292  CA  SER A  48      48.460  26.286  68.128  1.00 26.62      A
ATOM    293  CB  SER A  48      49.082  27.220  67.100  1.00 43.10      A
ATOM    294  OG  SER A  48      49.034  26.614  65.824  1.00 43.10      A
ATOM    295  C   SER A  48      48.423  26.954  69.502  1.00 26.62      A
ATOM    296  O   SER A  48      49.246  26.667  70.385  1.00 26.62      A
```

Figure 8-4

```
ATOM    297  N    ILE A  49      47.459  27.850  69.678  1.00 23.50           A
ATOM    298  CA   ILE A  49      47.301  28.534  70.946  1.00 23.50           A
ATOM    299  CB   ILE A  49      46.226  29.642  70.852  1.00 14.67           A
ATOM    300  CG2  ILE A  49      45.970  30.242  72.234  1.00 14.67           A
ATOM    301  CG1  ILE A  49      46.683  30.720  69.857  1.00 14.67           A
ATOM    302  CD1  ILE A  49      45.560  31.560  69.315  1.00 14.67           A
ATOM    303  C    ILE A  49      46.906  27.512  72.016  1.00 23.50           A
ATOM    304  O    ILE A  49      47.507  27.476  73.092  1.00 23.50           A
ATOM    305  N    ARG A  50      45.916  26.669  71.726  1.00 25.93           A
ATOM    306  CA   ARG A  50      45.505  25.671  72.713  1.00 25.93           A
ATOM    307  CB   ARG A  50      44.391  24.766  72.189  1.00 51.02           A
ATOM    308  CG   ARG A  50      44.109  23.617  73.147  1.00 51.02           A
ATOM    309  CD   ARG A  50      42.736  23.006  72.969  1.00 51.02           A
ATOM    310  NE   ARG A  50      42.773  21.759  72.211  1.00 51.02           A
ATOM    311  CZ   ARG A  50      41.765  20.890  72.165  1.00 51.02           A
ATOM    312  NH1  ARG A  50      40.645  21.142  72.839  1.00 51.02           A
ATOM    313  NH2  ARG A  50      41.872  19.772  71.449  1.00 51.02           A
ATOM    314  C    ARG A  50      46.678  24.791  73.124  1.00 25.93           A
ATOM    315  O    ARG A  50      46.873  24.491  74.307  1.00 25.93           A
ATOM    316  N    CYS A  51      47.459  24.373  72.138  1.00 40.32           A
ATOM    317  CA   CYS A  51      48.597  23.523  72.411  1.00 40.32           A
ATOM    318  CB   CYS A  51      49.253  23.092  71.107  1.00 66.88           A
ATOM    319  SG   CYS A  51      50.555  21.891  71.373  1.00 66.88           A
ATOM    320  C    CYS A  51      49.609  24.233  73.303  1.00 40.32           A
ATOM    321  O    CYS A  51      50.189  23.621  74.192  1.00 40.32           A
ATOM    322  N    ALA A  52      49.805  25.528  73.076  1.00 38.59           A
ATOM    323  CA   ALA A  52      50.757  26.304  73.866  1.00 38.59           A
ATOM    324  CB   ALA A  52      51.221  27.516  73.067  1.00 22.10           A
ATOM    325  C    ALA A  52      50.193  26.770  75.209  1.00 38.59           A
ATOM    326  O    ALA A  52      50.948  27.036  76.145  1.00 38.59           A
ATOM    327  N    ALA A  53      48.869  26.876  75.291  1.00 28.02           A
ATOM    328  CA   ALA A  53      48.184  27.343  76.498  1.00 28.02           A
ATOM    329  CB   ALA A  53      48.779  26.719  77.746  1.00  8.31           A
ATOM    330  C    ALA A  53      48.266  28.857  76.597  1.00 28.02           A
ATOM    331  O    ALA A  53      47.250  29.519  76.808  1.00 28.02           A
ATOM    332  N    CYS A  54      49.475  29.399  76.451  1.00 17.61           A
ATOM    333  CA   CYS A  54      49.706  30.850  76.508  1.00 17.61           A
ATOM    334  CB   CYS A  54      49.977  31.291  77.939  1.00 33.17           A
ATOM    335  SG   CYS A  54      49.981  33.078  78.102  1.00 33.17           A
ATOM    336  C    CYS A  54      50.918  31.140  75.628  1.00 17.61           A
ATOM    337  O    CYS A  54      51.918  30.424  75.698  1.00 17.61           A
ATOM    338  N    ILE A  55      50.856  32.185  74.811  1.00 19.43           A
ATOM    339  CA   ILE A  55      51.969  32.434  73.889  1.00 19.43           A
ATOM    340  CB   ILE A  55      51.881  31.396  72.727  1.00 24.10           A
ATOM    341  CG2  ILE A  55      50.660  31.703  71.856  1.00 24.10           A
ATOM    342  CG1  ILE A  55      53.142  31.411  71.865  1.00 24.10           A
ATOM    343  CD1  ILE A  55      53.142  30.324  70.750  1.00 24.10           A
ATOM    344  C    ILE A  55      51.977  33.858  73.309  1.00 19.43           A
ATOM    345  O    ILE A  55      50.928  34.492  73.181  1.00 19.43           A
ATOM    346  N    THR A  56      53.157  34.359  72.957  1.00 31.11           A
ATOM    347  CA   THR A  56      53.253  35.704  72.396  1.00 31.11           A
ATOM    348  CB   THR A  56      54.633  36.338  72.605  1.00 27.01           A
ATOM    349  OG1  THR A  56      55.611  35.560  71.903  1.00 27.01           A
ATOM    350  CG2  THR A  56      54.995  36.395  74.081  1.00 27.01           A
ATOM    351  C    THR A  56      53.041  35.598  70.898  1.00 31.11           A
ATOM    352  O    THR A  56      53.252  34.532  70.306  1.00 31.11           A
ATOM    353  N    PRO A  57      52.621  36.701  70.257  1.00 39.22           A
ATOM    354  CD   PRO A  57      52.134  37.964  70.836  1.00 28.66           A
ATOM    355  CA   PRO A  57      52.392  36.688  68.816  1.00 39.22           A
ATOM    356  CB   PRO A  57      51.892  38.098  68.541  1.00 28.66           A
ATOM    357  CG   PRO A  57      51.148  38.419  69.793  1.00 28.66           A
ATOM    358  C    PRO A  57      53.653  36.357  68.038  1.00 39.22           A
ATOM    359  O    PRO A  57      53.606  35.641  67.037  1.00 39.22           A
ATOM    360  N    VAL A  58      54.788  36.878  68.485  1.00 41.76           A
ATOM    361  CA   VAL A  58      56.020  36.585  67.778  1.00 41.76           A
ATOM    362  CB   VAL A  58      57.233  37.319  68.397  1.00 36.94           A
ATOM    363  CG1  VAL A  58      58.538  36.680  67.928  1.00 36.94           A
ATOM    364  CG2  VAL A  58      57.211  38.777  67.969  1.00 36.94           A
ATOM    365  C    VAL A  58      56.263  35.086  67.800  1.00 41.76           A
ATOM    366  O    VAL A  58      56.427  34.469  66.748  1.00 41.76           A
ATOM    367  N    GLU A  59      56.259  34.497  68.994  1.00 42.87           A
ATOM    368  CA   GLU A  59      56.506  33.068  69.117  1.00 42.87           A
ATOM    369  CB   GLU A  59      56.554  32.665  70.588  1.00 79.89           A
ATOM    370  CG   GLU A  59      57.670  31.681  70.885  1.00 79.89           A
ATOM    371  CD   GLU A  59      59.000  32.113  70.274  1.00 79.89           A
```

Figure 8-5

```
ATOM    372  OE1 GLU A  59      59.378  33.295  70.431  1.00 79.89      A
ATOM    373  OE2 GLU A  59      59.672  31.269  69.641  1.00 79.89      A
ATOM    374  C   GLU A  59      55.466  32.235  68.374  1.00 42.87      A
ATOM    375  O   GLU A  59      55.738  31.096  67.974  1.00 42.87      A
ATOM    376  N   LEU A  60      54.280  32.802  68.171  1.00 30.72      A
ATOM    377  CA  LEU A  60      53.229  32.075  67.468  1.00 30.72      A
ATOM    378  CB  LEU A  60      51.842  32.625  67.818  1.00 25.76      A
ATOM    379  CG  LEU A  60      50.703  31.829  67.164  1.00 25.76      A
ATOM    380  CD1 LEU A  60      50.673  30.422  67.744  1.00 25.76      A
ATOM    381  CD2 LEU A  60      49.367  32.514  67.412  1.00 25.76      A
ATOM    382  C   LEU A  60      53.399  32.115  65.953  1.00 30.72      A
ATOM    383  O   LEU A  60      53.043  31.160  65.262  1.00 30.72      A
ATOM    384  N   LYS A  61      53.919  33.223  65.429  1.00 59.73      A
ATOM    385  CA  LYS A  61      54.104  33.322  63.988  1.00 59.73      A
ATOM    386  CB  LYS A  61      54.420  34.768  63.560  1.00 50.33      A
ATOM    387  CG  LYS A  61      55.814  35.288  63.899  1.00 50.33      A
ATOM    388  CD  LYS A  61      56.731  35.255  62.677  1.00 50.33      A
ATOM    389  CE  LYS A  61      58.029  36.018  62.915  1.00 50.33      A
ATOM    390  NZ  LYS A  61      58.852  35.406  63.994  1.00 50.33      A
ATOM    391  C   LYS A  61      55.208  32.364  63.560  1.00 59.73      A
ATOM    392  O   LYS A  61      55.184  31.844  62.448  1.00 59.73      A
ATOM    393  N   LYS A  62      56.168  32.113  64.445  1.00 50.25      A
ATOM    394  CA  LYS A  62      57.237  31.190  64.112  1.00 50.25      A
ATOM    395  CB  LYS A  62      58.297  31.165  65.212  1.00 70.74      A
ATOM    396  CG  LYS A  62      59.040  32.475  65.350  1.00 70.74      A
ATOM    397  CD  LYS A  62      60.177  32.384  66.357  1.00 70.74      A
ATOM    398  CE  LYS A  62      60.894  33.727  66.474  1.00 70.74      A
ATOM    399  NZ  LYS A  62      62.121  33.639  67.314  1.00 70.74      A
ATOM    400  C   LYS A  62      56.609  29.812  63.953  1.00 50.25      A
ATOM    401  O   LYS A  62      56.801  29.144  62.938  1.00 50.25      A
ATOM    402  N   VAL A  63      55.837  29.404  64.953  1.00 44.77      A
ATOM    403  CA  VAL A  63      55.168  28.107  64.944  1.00 44.77      A
ATOM    404  CB  VAL A  63      54.325  27.922  66.226  1.00 51.34      A
ATOM    405  CG1 VAL A  63      53.707  26.543  66.249  1.00 51.34      A
ATOM    406  CG2 VAL A  63      55.200  28.130  67.455  1.00 51.34      A
ATOM    407  C   VAL A  63      54.268  27.913  63.720  1.00 44.77      A
ATOM    408  O   VAL A  63      54.313  26.872  63.072  1.00 44.77      A
ATOM    409  N   LEU A  64      53.447  28.908  63.405  1.00 32.87      A
ATOM    410  CA  LEU A  64      52.553  28.821  62.248  1.00 32.87      A
ATOM    411  CB  LEU A  64      51.406  29.836  62.367  1.00 41.38      A
ATOM    412  CG  LEU A  64      50.173  29.587  63.236  1.00 41.38      A
ATOM    413  CD1 LEU A  64      49.310  28.505  62.617  1.00 41.38      A
ATOM    414  CD2 LEU A  64      50.606  29.195  64.630  1.00 41.38      A
ATOM    415  C   LEU A  64      53.296  29.101  60.948  1.00 32.87      A
ATOM    416  O   LEU A  64      52.736  28.918  59.870  1.00 32.87      A
ATOM    417  N   SER A  65      54.548  29.548  61.047  1.00 42.60      A
ATOM    418  CA  SER A  65      55.333  29.889  59.859  1.00 42.60      A
ATOM    419  CB  SER A  65      55.719  28.626  59.081  1.00 59.96      A
ATOM    420  OG  SER A  65      56.738  27.908  59.759  1.00 59.96      A
ATOM    421  C   SER A  65      54.534  30.841  58.960  1.00 42.60      A
ATOM    422  O   SER A  65      54.162  30.501  57.833  1.00 42.60      A
ATOM    423  N   VAL A  66      54.266  32.037  59.473  1.00 37.30      A
ATOM    424  CA  VAL A  66      53.515  33.026  58.721  1.00 37.30      A
ATOM    425  CB  VAL A  66      51.992  32.916  59.032  1.00 65.92      A
ATOM    426  CG1 VAL A  66      51.434  31.630  58.447  1.00 65.92      A
ATOM    427  CG2 VAL A  66      51.754  32.927  60.533  1.00 65.92      A
ATOM    428  C   VAL A  66      54.004  34.436  59.024  1.00 37.30      A
ATOM    429  O   VAL A  66      54.865  34.641  59.894  1.00 37.30      A
ATOM    430  N   ASP A  67      53.455  35.396  58.285  1.00 42.15      A
ATOM    431  CA  ASP A  67      53.787  36.812  58.429  1.00 42.15      A
ATOM    432  CB  ASP A  67      53.186  37.587  57.243  1.00 69.98      A
ATOM    433  CG  ASP A  67      53.562  39.059  57.239  1.00 69.98      A
ATOM    434  OD1 ASP A  67      54.770  39.367  57.146  1.00 69.98      A
ATOM    435  OD2 ASP A  67      52.644  39.908  57.321  1.00 69.98      A
ATOM    436  C   ASP A  67      53.194  37.304  59.753  1.00 42.15      A
ATOM    437  O   ASP A  67      52.018  37.047  60.046  1.00 42.15      A
ATOM    438  N   LEU A  68      54.006  37.995  60.551  1.00 43.19      A
ATOM    439  CA  LEU A  68      53.542  38.516  61.836  1.00 43.19      A
ATOM    440  CB  LEU A  68      54.655  39.303  62.521  1.00 28.99      A
ATOM    441  CG  LEU A  68      54.292  39.876  63.890  1.00 28.99      A
ATOM    442  CD1 LEU A  68      53.785  38.755  64.802  1.00 28.99      A
ATOM    443  CD2 LEU A  68      55.507  40.546  64.507  1.00 28.99      A
ATOM    444  C   LEU A  68      52.320  39.416  61.645  1.00 43.19      A
ATOM    445  O   LEU A  68      51.379  39.404  62.452  1.00 43.19      A
ATOM    446  N   GLY A  69      52.338  40.186  60.563  1.00 24.15      A
```

Figure 8-6

```
ATOM    447  CA  GLY A  69      51.236  41.076  60.276  1.00 24.15      A
ATOM    448  C   GLY A  69      49.977  40.315  59.920  1.00 24.15      A
ATOM    449  O   GLY A  69      48.871  40.711  60.307  1.00 24.15      A
ATOM    450  N   ALA A  70      50.122  39.227  59.172  1.00 34.42      A
ATOM    451  CA  ALA A  70      48.949  38.434  58.799  1.00 34.42      A
ATOM    452  CB  ALA A  70      49.316  37.387  57.762  1.00 25.53      A
ATOM    453  C   ALA A  70      48.412  37.758  60.053  1.00 34.42      A
ATOM    454  O   ALA A  70      47.199  37.606  60.225  1.00 34.42      A
ATOM    455  N   LEU A  71      49.321  37.356  60.933  1.00 33.80      A
ATOM    456  CA  LEU A  71      48.905  36.718  62.166  1.00 33.80      A
ATOM    457  CB  LEU A  71      50.117  36.208  62.948  1.00 27.48      A
ATOM    458  CG  LEU A  71      49.810  35.500  64.269  1.00 27.48      A
ATOM    459  CD1 LEU A  71      48.665  34.512  64.089  1.00 27.48      A
ATOM    460  CD2 LEU A  71      51.069  34.784  64.748  1.00 27.48      A
ATOM    461  C   LEU A  71      48.136  37.726  63.003  1.00 33.80      A
ATOM    462  O   LEU A  71      47.015  37.459  63.446  1.00 33.80      A
ATOM    463  N   THR A  72      48.730  38.895  63.203  1.00 29.00      A
ATOM    464  CA  THR A  72      48.082  39.914  64.008  1.00 29.00      A
ATOM    465  CB  THR A  72      48.895  41.210  64.002  1.00 31.46      A
ATOM    466  OG1 THR A  72      50.117  40.983  64.719  1.00 31.46      A
ATOM    467  CG2 THR A  72      48.106  42.349  64.663  1.00 31.46      A
ATOM    468  C   THR A  72      46.657  40.181  63.555  1.00 29.00      A
ATOM    469  O   THR A  72      45.741  40.242  64.384  1.00 29.00      A
ATOM    470  N   ARG A  73      46.460  40.333  62.249  1.00 39.42      A
ATOM    471  CA  ARG A  73      45.120  40.580  61.728  1.00 39.42      A
ATOM    472  CB  ARG A  73      45.136  40.709  60.204  1.00 68.23      A
ATOM    473  CG  ARG A  73      45.743  41.993  59.689  1.00 68.23      A
ATOM    474  CD  ARG A  73      45.392  42.203  58.226  1.00 68.23      A
ATOM    475  NE  ARG A  73      46.042  43.386  57.676  1.00 68.23      A
ATOM    476  CZ  ARG A  73      47.361  43.536  57.580  1.00 68.23      A
ATOM    477  NH1 ARG A  73      48.180  42.576  57.999  1.00 68.23      A
ATOM    478  NH2 ARG A  73      47.868  44.651  57.064  1.00 68.23      A
ATOM    479  C   ARG A  73      44.207  39.423  62.117  1.00 39.42      A
ATOM    480  O   ARG A  73      43.056  39.630  62.507  1.00 39.42      A
ATOM    481  N   MET A  74      44.733  38.207  62.006  1.00 34.55      A
ATOM    482  CA  MET A  74      43.972  37.006  62.342  1.00 34.55      A
ATOM    483  CB  MET A  74      44.764  35.751  61.921  1.00 18.52      A
ATOM    484  CG  MET A  74      44.122  34.405  62.282  1.00 18.52      A
ATOM    485  SD  MET A  74      42.438  34.164  61.672  1.00 18.52      A
ATOM    486  CE  MET A  74      42.765  32.941  60.397  1.00 18.52      A
ATOM    487  C   MET A  74      43.651  36.973  63.840  1.00 34.55      A
ATOM    488  O   MET A  74      42.504  36.704  64.235  1.00 34.55      A
ATOM    489  N   LEU A  75      44.656  37.247  64.675  1.00 29.89      A
ATOM    490  CA  LEU A  75      44.429  37.251  66.115  1.00 29.89      A
ATOM    491  CB  LEU A  75      45.728  37.581  66.870  1.00 15.40      A
ATOM    492  CG  LEU A  75      46.720  36.410  66.867  1.00 15.40      A
ATOM    493  CD1 LEU A  75      48.069  36.851  67.405  1.00 15.40      A
ATOM    494  CD2 LEU A  75      46.141  35.244  67.689  1.00 15.40      A
ATOM    495  C   LEU A  75      43.349  38.277  66.422  1.00 29.89      A
ATOM    496  O   LEU A  75      42.408  37.996  67.171  1.00 29.89      A
ATOM    497  N   ASP A  76      43.477  39.456  65.811  1.00 31.44      A
ATOM    498  CA  ASP A  76      42.508  40.524  66.013  1.00 31.44      A
ATOM    499  CB  ASP A  76      42.846  41.722  65.136  1.00 97.34      A
ATOM    500  CG  ASP A  76      43.324  42.895  65.948  1.00 97.34      A
ATOM    501  OD1 ASP A  76      42.531  43.382  66.781  1.00 97.34      A
ATOM    502  OD2 ASP A  76      44.484  43.322  65.770  1.00 97.34      A
ATOM    503  C   ASP A  76      41.096  40.053  65.734  1.00 31.44      A
ATOM    504  O   ASP A  76      40.204  40.244  66.555  1.00 31.44      A
ATOM    505  N   ARG A  77      40.898  39.416  64.586  1.00 31.21      A
ATOM    506  CA  ARG A  77      39.576  38.914  64.217  1.00 31.21      A
ATOM    507  CB  ARG A  77      39.600  38.275  62.818  1.00 77.50      A
ATOM    508  CG  ARG A  77      40.061  39.194  61.696  1.00 77.50      A
ATOM    509  CD  ARG A  77      39.341  38.870  60.393  1.00 77.50      A
ATOM    510  NE  ARG A  77      39.526  37.486  59.971  1.00 77.50      A
ATOM    511  CZ  ARG A  77      40.620  37.019  59.375  1.00 77.50      A
ATOM    512  NH1 ARG A  77      41.645  37.829  59.120  1.00 77.50      A
ATOM    513  NH2 ARG A  77      40.687  35.734  59.032  1.00 77.50      A
ATOM    514  C   ARG A  77      39.088  37.878  65.233  1.00 31.21      A
ATOM    515  O   ARG A  77      37.913  37.885  65.628  1.00 31.21      A
ATOM    516  N   LEU A  78      39.998  36.994  65.654  1.00 31.76      A
ATOM    517  CA  LEU A  78      39.657  35.945  66.608  1.00 31.76      A
ATOM    518  CB  LEU A  78      40.786  34.916  66.696  1.00 22.72      A
ATOM    519  CG  LEU A  78      41.060  34.145  65.394  1.00 22.72      A
ATOM    520  CD1 LEU A  78      42.129  33.095  65.622  1.00 22.72      A
ATOM    521  CD2 LEU A  78      39.769  33.474  64.917  1.00 22.72      A
```

Figure 8-7

```
ATOM    522  C   LEU A  78      39.318  36.488  67.993  1.00 31.76      A
ATOM    523  O   LEU A  78      38.544  35.876  68.730  1.00 31.76      A
ATOM    524  N   VAL A  79      39.889  37.632  68.355  1.00 25.81      A
ATOM    525  CA  VAL A  79      39.568  38.209  69.649  1.00 25.81      A
ATOM    526  CB  VAL A  79      40.581  39.316  70.056  1.00 14.52      A
ATOM    527  CG1 VAL A  79      40.103  40.047  71.328  1.00 14.52      A
ATOM    528  CG2 VAL A  79      41.977  38.675  70.305  1.00 14.52      A
ATOM    529  C   VAL A  79      38.159  38.766  69.514  1.00 25.81      A
ATOM    530  O   VAL A  79      37.359  38.688  70.447  1.00 25.81      A
ATOM    531  N   CYS A  80      37.834  39.297  68.338  1.00 30.46      A
ATOM    532  CA  CYS A  80      36.488  39.825  68.103  1.00 30.46      A
ATOM    533  CB  CYS A  80      36.381  40.469  66.724  1.00 75.62      A
ATOM    534  SG  CYS A  80      37.191  42.062  66.616  1.00 75.62      A
ATOM    535  C   CYS A  80      35.454  38.718  68.217  1.00 30.46      A
ATOM    536  O   CYS A  80      34.404  38.925  68.802  1.00 30.46      A
ATOM    537  N   LYS A  81      35.747  37.541  67.666  1.00 26.41      A
ATOM    538  CA  LYS A  81      34.797  36.430  67.728  1.00 26.41      A
ATOM    539  CB  LYS A  81      35.261  35.250  66.870  1.00 27.80      A
ATOM    540  CG  LYS A  81      35.336  35.482  65.354  1.00 27.80      A
ATOM    541  CD  LYS A  81      35.801  34.183  64.666  1.00 27.80      A
ATOM    542  CE  LYS A  81      36.220  34.388  63.206  1.00 27.80      A
ATOM    543  NZ  LYS A  81      35.067  34.552  62.277  1.00 27.80      A
ATOM    544  C   LYS A  81      34.639  35.935  69.157  1.00 26.41      A
ATOM    545  O   LYS A  81      33.690  35.219  69.473  1.00 26.41      A
ATOM    546  N   GLY A  82      35.574  36.306  70.025  1.00 28.59      A
ATOM    547  CA  GLY A  82      35.512  35.847  71.401  1.00 28.59      A
ATOM    548  C   GLY A  82      36.158  34.482  71.602  1.00 28.59      A
ATOM    549  O   GLY A  82      35.887  33.804  72.591  1.00 28.59      A
ATOM    550  N   TRP A  83      37.019  34.067  70.679  1.00 24.24      A
ATOM    551  CA  TRP A  83      37.678  32.764  70.797  1.00 24.24      A
ATOM    552  CB  TRP A  83      37.796  32.088  69.410  1.00 17.27      A
ATOM    553  CG  TRP A  83      36.457  31.894  68.722  1.00 17.27      A
ATOM    554  CD2 TRP A  83      36.236  31.502  67.365  1.00 17.27      A
ATOM    555  CE2 TRP A  83      34.838  31.467  67.158  1.00 17.27      A
ATOM    556  CE3 TRP A  83      37.083  31.178  66.297  1.00 17.27      A
ATOM    557  CD1 TRP A  83      35.215  32.073  69.273  1.00 17.27      A
ATOM    558  NE1 TRP A  83      34.237  31.819  68.338  1.00 17.27      A
ATOM    559  CZ2 TRP A  83      34.272  31.124  65.935  1.00 17.27      A
ATOM    560  CZ3 TRP A  83      36.514  30.839  65.077  1.00 17.27      A
ATOM    561  CH2 TRP A  83      35.120  30.816  64.911  1.00 17.27      A
ATOM    562  C   TRP A  83      39.061  32.899  71.428  1.00 24.24      A
ATOM    563  O   TRP A  83      39.547  31.973  72.083  1.00 24.24      A
ATOM    564  N   VAL A  84      39.688  34.058  71.231  1.00 30.33      A
ATOM    565  CA  VAL A  84      41.014  34.326  71.777  1.00 30.33      A
ATOM    566  CB  VAL A  84      42.046  34.570  70.659  1.00 10.78      A
ATOM    567  CG1 VAL A  84      43.398  34.887  71.274  1.00 10.78      A
ATOM    568  CG2 VAL A  84      42.144  33.354  69.763  1.00 10.78      A
ATOM    569  C   VAL A  84      40.982  35.570  72.654  1.00 30.33      A
ATOM    570  O   VAL A  84      40.268  36.530  72.359  1.00 30.33      A
ATOM    571  N   GLU A  85      41.785  35.552  73.712  1.00 30.48      A
ATOM    572  CA  GLU A  85      41.883  36.651  74.671  1.00 30.48      A
ATOM    573  CB  GLU A  85      41.482  36.121  76.051  1.00 48.81      A
ATOM    574  CG  GLU A  85      41.723  37.057  77.224  1.00 48.81      A
ATOM    575  CD  GLU A  85      41.513  36.359  78.567  1.00 48.81      A
ATOM    576  OE1 GLU A  85      41.467  37.055  79.610  1.00 48.81      A
ATOM    577  OE2 GLU A  85      41.399  35.110  78.581  1.00 48.81      A
ATOM    578  C   GLU A  85      43.322  37.187  74.715  1.00 30.48      A
ATOM    579  O   GLU A  85      44.273  36.401  74.689  1.00 30.48      A
ATOM    580  N   ARG A  86      43.486  38.511  74.775  1.00 26.85      A
ATOM    581  CA  ARG A  86      44.830  39.118  74.855  1.00 26.85      A
ATOM    582  CB  ARG A  86      44.903  40.444  74.097  1.00 38.70      A
ATOM    583  CG  ARG A  86      44.744  40.394  72.600  1.00 38.70      A
ATOM    584  CD  ARG A  86      44.769  41.827  72.082  1.00 38.70      A
ATOM    585  NE  ARG A  86      44.228  41.997  70.733  1.00 38.70      A
ATOM    586  CZ  ARG A  86      44.744  41.439  69.642  1.00 38.70      A
ATOM    587  NH1 ARG A  86      45.820  40.656  69.729  1.00 38.70      A
ATOM    588  NH2 ARG A  86      44.201  41.687  68.456  1.00 38.70      A
ATOM    589  C   ARG A  86      45.162  39.426  76.315  1.00 26.85      A
ATOM    590  O   ARG A  86      44.304  39.887  77.059  1.00 26.85      A
ATOM    591  N   LEU A  87      46.401  39.183  76.724  1.00 25.04      A
ATOM    592  CA  LEU A  87      46.815  39.474  78.097  1.00 25.04      A
ATOM    593  CB  LEU A  87      47.118  38.184  78.858  1.00 36.39      A
ATOM    594  CG  LEU A  87      45.922  37.372  79.349  1.00 36.39      A
ATOM    595  CD1 LEU A  87      46.416  36.090  79.986  1.00 36.39      A
ATOM    596  CD2 LEU A  87      45.134  38.181  80.360  1.00 36.39      A
```

Figure 8-8

```
ATOM    597  C    LEU A  87      48.053  40.366  78.090  1.00 25.04           A
ATOM    598  O    LEU A  87      48.894  40.291  77.174  1.00 25.04           A
ATOM    599  N    PRO A  88      48.185  41.237  79.101  1.00 41.37           A
ATOM    600  CD   PRO A  88      47.257  41.606  80.178  1.00 36.25           A
ATOM    601  CA   PRO A  88      49.370  42.099  79.109  1.00 41.37           A
ATOM    602  CB   PRO A  88      49.106  43.057  80.271  1.00 36.25           A
ATOM    603  CG   PRO A  88      47.602  43.063  80.385  1.00 36.25           A
ATOM    604  C    PRO A  88      50.613  41.257  79.333  1.00 41.37           A
ATOM    605  O    PRO A  88      50.626  40.363  80.192  1.00 41.37           A
ATOM    606  N    ASN A  89      51.642  41.530  78.540  1.00 40.92           A
ATOM    607  CA   ASN A  89      52.890  40.806  78.668  1.00 40.92           A
ATOM    608  CB   ASN A  89      53.757  40.990  77.426  1.00 48.54           A
ATOM    609  CG   ASN A  89      54.948  40.063  77.424  1.00 48.54           A
ATOM    610  OD1  ASN A  89      55.520  39.784  78.482  1.00 48.54           A
ATOM    611  ND2  ASN A  89      55.334  39.581  76.244  1.00 48.54           A
ATOM    612  C    ASN A  89      53.612  41.376  79.881  1.00 40.92           A
ATOM    613  O    ASN A  89      54.057  42.526  79.864  1.00 40.92           A
ATOM    614  N    PRO A  90      53.727  40.578  80.955  1.00 44.27           A
ATOM    615  CD   PRO A  90      53.271  39.176  80.997  1.00 40.09           A
ATOM    616  CA   PRO A  90      54.381  40.941  82.216  1.00 44.27           A
ATOM    617  CB   PRO A  90      54.617  39.586  82.875  1.00 40.09           A
ATOM    618  CG   PRO A  90      53.392  38.836  82.477  1.00 40.09           A
ATOM    619  C    PRO A  90      55.668  41.769  82.115  1.00 44.27           A
ATOM    620  O    PRO A  90      55.866  42.688  82.911  1.00 44.27           A
ATOM    621  N    ASN A  91      56.544  41.462  81.158  1.00 69.68           A
ATOM    622  CA   ASN A  91      57.785  42.226  81.060  1.00 69.68           A
ATOM    623  CB   ASN A  91      59.005  41.288  81.081  1.00 76.88           A
ATOM    624  CG   ASN A  91      59.169  40.493  79.797  1.00 76.88           A
ATOM    625  OD1  ASN A  91      59.444  41.050  78.732  1.00 76.88           A
ATOM    626  ND2  ASN A  91      59.008  39.179  79.896  1.00 76.88           A
ATOM    627  C    ASN A  91      57.897  43.179  79.876  1.00 69.68           A
ATOM    628  O    ASN A  91      58.384  44.303  80.029  1.00 69.68           A
ATOM    629  N    ASP A  92      57.447  42.745  78.702  1.00 97.47           A
ATOM    630  CA   ASP A  92      57.533  43.585  77.513  1.00 97.47           A
ATOM    631  CB   ASP A  92      56.898  42.886  76.310  1.00 77.46           A
ATOM    632  CG   ASP A  92      57.184  43.608  75.009  1.00 77.46           A
ATOM    633  OD1  ASP A  92      56.846  44.808  74.915  1.00 77.46           A
ATOM    634  OD2  ASP A  92      57.749  42.980  74.087  1.00 77.46           A
ATOM    635  C    ASP A  92      56.869  44.941  77.721  1.00 97.47           A
ATOM    636  O    ASP A  92      57.351  45.956  77.222  1.00 97.47           A
ATOM    637  N    LYS A  93      55.758  44.951  78.451  1.00 79.22           A
ATOM    638  CA   LYS A  93      55.035  46.187  78.735  1.00 79.22           A
ATOM    639  CB   LYS A  93      55.964  47.188  79.439  1.00105.99           A
ATOM    640  CG   LYS A  93      56.461  46.727  80.813  1.00105.99           A
ATOM    641  CD   LYS A  93      57.584  47.619  81.345  1.00105.99           A
ATOM    642  CE   LYS A  93      57.140  49.067  81.530  1.00105.99           A
ATOM    643  NZ   LYS A  93      56.095  49.203  82.577  1.00105.99           A
ATOM    644  C    LYS A  93      54.434  46.831  77.481  1.00 79.22           A
ATOM    645  O    LYS A  93      53.643  47.770  77.575  1.00 79.22           A
ATOM    646  N    ARG A  94      54.812  46.328  76.309  1.00101.34           A
ATOM    647  CA   ARG A  94      54.298  46.854  75.047  1.00101.34           A
ATOM    648  CB   ARG A  94      55.382  47.656  74.312  1.00133.25           A
ATOM    649  CG   ARG A  94      55.380  49.164  74.590  1.00133.25           A
ATOM    650  CD   ARG A  94      55.552  49.481  76.072  1.00133.25           A
ATOM    651  NE   ARG A  94      55.707  50.913  76.325  1.00133.25           A
ATOM    652  CZ   ARG A  94      55.877  51.447  77.533  1.00133.25           A
ATOM    653  NH1  ARG A  94      55.911  50.670  78.610  1.00133.25           A
ATOM    654  NH2  ARG A  94      56.026  52.759  77.663  1.00133.25           A
ATOM    655  C    ARG A  94      53.808  45.722  74.152  1.00101.34           A
ATOM    656  O    ARG A  94      53.294  45.965  73.060  1.00101.34           A
ATOM    657  N    GLY A  95      53.974  44.486  74.618  1.00 68.05           A
ATOM    658  CA   GLY A  95      53.537  43.336  73.846  1.00 68.05           A
ATOM    659  C    GLY A  95      52.361  42.639  74.503  1.00 68.05           A
ATOM    660  O    GLY A  95      51.963  42.995  75.611  1.00 68.05           A
ATOM    661  N    VAL A  96      51.799  41.644  73.826  1.00 32.70           A
ATOM    662  CA   VAL A  96      50.662  40.914  74.378  1.00 32.70           A
ATOM    663  CB   VAL A  96      49.384  41.151  73.540  1.00 46.59           A
ATOM    664  CG1  VAL A  96      49.061  42.631  73.489  1.00 46.59           A
ATOM    665  CG2  VAL A  96      49.576  40.582  72.134  1.00 46.59           A
ATOM    666  C    VAL A  96      50.880  39.401  74.464  1.00 32.70           A
ATOM    667  O    VAL A  96      51.871  38.864  73.975  1.00 32.70           A
ATOM    668  N    LEU A  97      49.938  38.729  75.112  1.00 23.07           A
ATOM    669  CA   LEU A  97      49.964  37.282  75.251  1.00 23.07           A
ATOM    670  CB   LEU A  97      50.225  36.883  76.703  1.00 46.89           A
ATOM    671  CG   LEU A  97      51.491  37.474  77.318  1.00 46.89           A
```

Figure 8-9

```
ATOM    672  CD1 LEU A   97      51.666  36.944  78.730  1.00 46.89           A
ATOM    673  CD2 LEU A   97      52.692  37.111  76.456  1.00 46.89           A
ATOM    674  C   LEU A   97      48.570  36.839  74.831  1.00 23.07           A
ATOM    675  O   LEU A   97      47.575  37.517  75.125  1.00 23.07           A
ATOM    676  N   VAL A   98      48.492  35.724  74.120  1.00 29.54           A
ATOM    677  CA  VAL A   98      47.199  35.243  73.682  1.00 29.54           A
ATOM    678  CB  VAL A   98      47.075  35.216  72.143  1.00 16.38           A
ATOM    679  CG1 VAL A   98      47.126  36.631  71.597  1.00 16.38           A
ATOM    680  CG2 VAL A   98      48.186  34.384  71.553  1.00 16.38           A
ATOM    681  C   VAL A   98      46.968  33.859  74.208  1.00 29.54           A
ATOM    682  O   VAL A   98      47.908  33.076  74.396  1.00 29.54           A
ATOM    683  N   LYS A   99      45.699  33.575  74.453  1.00 22.55           A
ATOM    684  CA  LYS A   99      45.273  32.289  74.960  1.00 22.55           A
ATOM    685  CB  LYS A   99      45.310  32.298  76.491  1.00 25.06           A
ATOM    686  CG  LYS A   99      44.402  33.337  77.130  1.00 25.06           A
ATOM    687  CD  LYS A   99      44.394  33.234  78.669  1.00 25.06           A
ATOM    688  CE  LYS A   99      43.619  32.009  79.172  1.00 25.06           A
ATOM    689  NZ  LYS A   99      42.150  32.101  78.900  1.00 25.06           A
ATOM    690  C   LYS A   99      43.841  32.074  74.469  1.00 22.55           A
ATOM    691  O   LYS A   99      43.173  33.020  74.042  1.00 22.55           A
ATOM    692  N   LEU A  100      43.369  30.837  74.507  1.00 21.07           A
ATOM    693  CA  LEU A  100      42.010  30.576  74.080  1.00 21.07           A
ATOM    694  CB  LEU A  100      41.818  29.095  73.759  1.00 18.76           A
ATOM    695  CG  LEU A  100      42.598  28.488  72.578  1.00 18.76           A
ATOM    696  CD1 LEU A  100      41.992  27.126  72.253  1.00 18.76           A
ATOM    697  CD2 LEU A  100      42.526  29.400  71.343  1.00 18.76           A
ATOM    698  C   LEU A  100      41.053  30.956  75.195  1.00 21.07           A
ATOM    699  O   LEU A  100      41.399  30.864  76.387  1.00 21.07           A
ATOM    700  N   THR A  101      39.857  31.412  74.827  1.00 17.16           A
ATOM    701  CA  THR A  101      38.858  31.711  75.849  1.00 17.16           A
ATOM    702  CB  THR A  101      37.775  32.645  75.357  1.00  7.57           A
ATOM    703  OG1 THR A  101      37.178  32.067  74.189  1.00  7.57           A
ATOM    704  CG2 THR A  101      38.361  34.025  75.019  1.00  7.57           A
ATOM    705  C   THR A  101      38.243  30.341  76.029  1.00 17.16           A
ATOM    706  O   THR A  101      38.624  29.393  75.332  1.00 17.16           A
ATOM    707  N   THR A  102      37.292  30.210  76.943  1.00 17.61           A
ATOM    708  CA  THR A  102      36.710  28.892  77.142  1.00 17.61           A
ATOM    709  CB  THR A  102      35.924  28.813  78.492  1.00 19.84           A
ATOM    710  OG1 THR A  102      34.558  29.190  78.309  1.00 19.84           A
ATOM    711  CG2 THR A  102      36.566  29.748  79.500  1.00 19.84           A
ATOM    712  C   THR A  102      35.861  28.546  75.929  1.00 17.61           A
ATOM    713  O   THR A  102      35.781  27.387  75.529  1.00 17.61           A
ATOM    714  N   GLY A  103      35.266  29.560  75.313  1.00 30.04           A
ATOM    715  CA  GLY A  103      34.470  29.318  74.121  1.00 30.04           A
ATOM    716  C   GLY A  103      35.353  28.847  72.972  1.00 30.04           A
ATOM    717  O   GLY A  103      34.990  27.928  72.224  1.00 30.04           A
ATOM    718  N   GLY A  104      36.517  29.479  72.829  1.00 27.12           A
ATOM    719  CA  GLY A  104      37.445  29.106  71.777  1.00 27.12           A
ATOM    720  C   GLY A  104      37.986  27.703  71.976  1.00 27.12           A
ATOM    721  O   GLY A  104      38.169  26.959  71.005  1.00 27.12           A
ATOM    722  N   ALA A  105      38.244  27.330  73.228  1.00 31.63           A
ATOM    723  CA  ALA A  105      38.762  25.993  73.512  1.00 31.63           A
ATOM    724  CB  ALA A  105      39.180  25.866  74.977  1.00  1.17           A
ATOM    725  C   ALA A  105      37.679  24.976  73.191  1.00 31.63           A
ATOM    726  O   ALA A  105      37.965  23.900  72.667  1.00 31.63           A
ATOM    727  N   ALA A  106      36.435  25.327  73.509  1.00 15.93           A
ATOM    728  CA  ALA A  106      35.304  24.439  73.238  1.00 15.93           A
ATOM    729  CB  ALA A  106      34.008  25.061  73.734  1.00 34.73           A
ATOM    730  C   ALA A  106      35.218  24.191  71.739  1.00 15.93           A
ATOM    731  O   ALA A  106      35.118  23.049  71.291  1.00 15.93           A
ATOM    732  N   ILE A  107      35.265  25.264  70.964  1.00 24.47           A
ATOM    733  CA  ILE A  107      35.198  25.144  69.516  1.00 24.47           A
ATOM    734  CB  ILE A  107      35.361  26.531  68.844  1.00 27.19           A
ATOM    735  CG2 ILE A  107      35.734  26.378  67.377  1.00 27.19           A
ATOM    736  CG1 ILE A  107      34.070  27.324  69.009  1.00 27.19           A
ATOM    737  CD1 ILE A  107      34.170  28.743  68.513  1.00 27.19           A
ATOM    738  C   ILE A  107      36.300  24.211  69.023  1.00 24.47           A
ATOM    739  O   ILE A  107      36.071  23.338  68.179  1.00 24.47           A
ATOM    740  N   CYS A  108      37.497  24.390  69.565  1.00 23.24           A
ATOM    741  CA  CYS A  108      38.627  23.572  69.145  1.00 23.24           A
ATOM    742  CB  CYS A  108      39.869  23.955  69.948  1.00 44.34           A
ATOM    743  SG  CYS A  108      41.387  23.261  69.295  1.00 44.34           A
ATOM    744  C   CYS A  108      38.307  22.095  69.336  1.00 23.24           A
ATOM    745  O   CYS A  108      38.444  21.286  68.411  1.00 23.24           A
ATOM    746  N   GLU A  109      37.864  21.755  70.543  1.00 34.17           A
```

Figure 8-10

```
ATOM    747  CA   GLU A 109      37.525  20.379  70.867  1.00 34.17      A
ATOM    748  CB   GLU A 109      37.121  20.269  72.342  1.00 54.06      A
ATOM    749  CG   GLU A 109      36.882  18.841  72.820  1.00 54.06      A
ATOM    750  CD   GLU A 109      38.027  17.892  72.469  1.00 54.06      A
ATOM    751  OE1  GLU A 109      39.195  18.212  72.790  1.00 54.06      A
ATOM    752  OE2  GLU A 109      37.755  16.822  71.876  1.00 54.06      A
ATOM    753  C    GLU A 109      36.407  19.868  69.965  1.00 34.17      A
ATOM    754  O    GLU A 109      36.491  18.775  69.423  1.00 34.17      A
ATOM    755  N    GLN A 110      35.371  20.672  69.781  1.00 31.70      A
ATOM    756  CA   GLN A 110      34.263  20.243  68.954  1.00 31.70      A
ATOM    757  CB   GLN A 110      33.130  21.268  69.050  1.00 54.33      A
ATOM    758  CG   GLN A 110      31.790  20.641  69.442  1.00 54.33      A
ATOM    759  CD   GLN A 110      31.943  19.486  70.440  1.00 54.33      A
ATOM    760  OE1  GLN A 110      32.444  19.662  71.559  1.00 54.33      A
ATOM    761  NE2  GLN A 110      31.515  18.295  70.026  1.00 54.33      A
ATOM    762  C    GLN A 110      34.680  19.988  67.498  1.00 31.70      A
ATOM    763  O    GLN A 110      34.241  19.008  66.885  1.00 31.70      A
ATOM    764  N    CYS A 111      35.535  20.852  66.947  1.00 20.80      A
ATOM    765  CA   CYS A 111      35.990  20.679  65.572  1.00 20.80      A
ATOM    766  CB   CYS A 111      36.893  21.841  65.156  1.00 32.98      A
ATOM    767  SG   CYS A 111      35.999  23.387  64.796  1.00 32.98      A
ATOM    768  C    CYS A 111      36.731  19.352  65.412  1.00 20.80      A
ATOM    769  O    CYS A 111      36.511  18.632  64.443  1.00 20.80      A
ATOM    770  N    HIS A 112      37.606  19.025  66.360  1.00 36.28      A
ATOM    771  CA   HIS A 112      38.344  17.761  66.308  1.00 36.28      A
ATOM    772  CB   HIS A 112      39.294  17.635  67.504  1.00 32.43      A
ATOM    773  CG   HIS A 112      40.594  18.365  67.339  1.00 32.43      A
ATOM    774  CD2  HIS A 112      41.170  19.340  68.085  1.00 32.43      A
ATOM    775  ND1  HIS A 112      41.493  18.072  66.334  1.00 32.43      A
ATOM    776  CE1  HIS A 112      42.566  18.830  66.470  1.00 32.43      A
ATOM    777  NE2  HIS A 112      42.397  19.608  67.525  1.00 32.43      A
ATOM    778  C    HIS A 112      37.379  16.570  66.330  1.00 36.28      A
ATOM    779  O    HIS A 112      37.537  15.610  65.575  1.00 36.28      A
ATOM    780  N    GLN A 113      36.373  16.642  67.194  1.00 32.58      A
ATOM    781  CA   GLN A 113      35.416  15.556  67.321  1.00 32.58      A
ATOM    782  CB   GLN A 113      34.575  15.737  68.585  1.00 64.21      A
ATOM    783  CG   GLN A 113      35.383  15.675  69.869  1.00 64.21      A
ATOM    784  CD   GLN A 113      34.518  15.624  71.116  1.00 64.21      A
ATOM    785  OE1  GLN A 113      35.030  15.690  72.236  1.00 64.21      A
ATOM    786  NE2  GLN A 113      33.203  15.501  70.933  1.00 64.21      A
ATOM    787  C    GLN A 113      34.493  15.334  66.133  1.00 32.58      A
ATOM    788  O    GLN A 113      34.194  14.193  65.793  1.00 32.58      A
ATOM    789  N    LEU A 114      34.050  16.406  65.487  1.00 43.53      A
ATOM    790  CA   LEU A 114      33.124  16.267  64.370  1.00 43.53      A
ATOM    791  CB   LEU A 114      32.095  17.399  64.416  1.00 83.39      A
ATOM    792  CG   LEU A 114      31.191  17.440  65.658  1.00 83.39      A
ATOM    793  CD1  LEU A 114      30.424  18.760  65.725  1.00 83.39      A
ATOM    794  CD2  LEU A 114      30.231  16.258  65.615  1.00 83.39      A
ATOM    795  C    LEU A 114      33.801  16.262  63.022  1.00 43.53      A
ATOM    796  O    LEU A 114      33.144  16.383  61.995  1.00 43.53      A
ATOM    797  N    VAL A 115      35.113  16.094  63.016  1.00 22.15      A
ATOM    798  CA   VAL A 115      35.867  16.129  61.768  1.00 22.15      A
ATOM    799  CB   VAL A 115      36.511  17.528  61.597  1.00 22.88      A
ATOM    800  CG1  VAL A 115      37.978  17.412  61.200  1.00 22.88      A
ATOM    801  CG2  VAL A 115      35.728  18.329  60.572  1.00 22.88      A
ATOM    802  C    VAL A 115      36.948  15.064  61.712  1.00 22.15      A
ATOM    803  O    VAL A 115      37.257  14.522  60.642  1.00 22.15      A
ATOM    804  N    GLY A 116      37.522  14.779  62.873  1.00 30.44      A
ATOM    805  CA   GLY A 116      38.581  13.797  62.966  1.00 30.44      A
ATOM    806  C    GLY A 116      38.384  12.527  62.163  1.00 30.44      A
ATOM    807  O    GLY A 116      39.139  12.257  61.224  1.00 30.44      A
ATOM    808  N    GLN A 117      37.363  11.749  62.511  1.00 39.45      A
ATOM    809  CA   GLN A 117      37.117  10.483  61.823  1.00 39.45      A
ATOM    810  CB   GLN A 117      35.899   9.783  62.424  1.00 99.18      A
ATOM    811  CG   GLN A 117      36.100   8.289  62.577  1.00 99.18      A
ATOM    812  CD   GLN A 117      37.439   7.956  63.222  1.00 99.18      A
ATOM    813  OE1  GLN A 117      37.735   8.397  64.336  1.00 99.18      A
ATOM    814  NE2  GLN A 117      38.259   7.179  62.520  1.00 99.18      A
ATOM    815  C    GLN A 117      36.947  10.619  60.317  1.00 39.45      A
ATOM    816  O    GLN A 117      37.662   9.982  59.543  1.00 39.45      A
ATOM    817  N    ASP A 118      36.004  11.453  59.901  1.00 47.18      A
ATOM    818  CA   ASP A 118      35.759  11.662  58.480  1.00 47.18      A
ATOM    819  CB   ASP A 118      34.688  12.740  58.281  1.00 77.40      A
ATOM    820  CG   ASP A 118      33.306  12.275  58.704  1.00 77.40      A
ATOM    821  OD1  ASP A 118      32.401  13.127  58.810  1.00 77.40      A
```

Figure 8-11

```
ATOM    822  OD2 ASP A 118      33.121  11.057  58.923  1.00 77.40      A
ATOM    823  C   ASP A 118      37.032  12.053  57.733  1.00 47.18      A
ATOM    824  O   ASP A 118      37.314  11.517  56.663  1.00 47.18      A
ATOM    825  N   LEU A 119      37.796  12.985  58.300  1.00 42.24      A
ATOM    826  CA  LEU A 119      39.032  13.447  57.675  1.00 42.24      A
ATOM    827  CB  LEU A 119      39.676  14.561  58.515  1.00 15.97      A
ATOM    828  CG  LEU A 119      41.092  14.941  58.055  1.00 15.97      A
ATOM    829  CD1 LEU A 119      41.020  15.406  56.612  1.00 15.97      A
ATOM    830  CD2 LEU A 119      41.684  16.010  58.936  1.00 15.97      A
ATOM    831  C   LEU A 119      40.015  12.295  57.531  1.00 42.24      A
ATOM    832  O   LEU A 119      40.662  12.137  56.496  1.00 42.24      A
ATOM    833  N   HIS A 120      40.129  11.507  58.594  1.00 39.36      A
ATOM    834  CA  HIS A 120      41.026  10.365  58.619  1.00 39.36      A
ATOM    835  CB  HIS A 120      40.947   9.655  59.959  1.00 36.14      A
ATOM    836  CG  HIS A 120      41.656   8.342  59.971  1.00 36.14      A
ATOM    837  CD2 HIS A 120      41.204   7.084  59.763  1.00 36.14      A
ATOM    838  ND1 HIS A 120      43.015   8.233  60.172  1.00 36.14      A
ATOM    839  CE1 HIS A 120      43.369   6.963  60.089  1.00 36.14      A
ATOM    840  NE2 HIS A 120      42.289   6.245  59.842  1.00 36.14      A
ATOM    841  C   HIS A 120      40.619   9.377  57.549  1.00 39.36      A
ATOM    842  O   HIS A 120      41.449   8.780  56.865  1.00 39.36      A
ATOM    843  N   GLN A 121      39.317   9.191  57.436  1.00 35.35      A
ATOM    844  CA  GLN A 121      38.738   8.281  56.467  1.00 35.35      A
ATOM    845  CB  GLN A 121      37.223   8.336  56.618  1.00 61.52      A
ATOM    846  CG  GLN A 121      36.466   7.174  56.059  1.00 61.52      A
ATOM    847  CD  GLN A 121      35.049   7.152  56.584  1.00 61.52      A
ATOM    848  OE1 GLN A 121      34.827   7.055  57.798  1.00 61.52      A
ATOM    849  NE2 GLN A 121      34.077   7.253  55.679  1.00 61.52      A
ATOM    850  C   GLN A 121      39.149   8.675  55.047  1.00 35.35      A
ATOM    851  O   GLN A 121      39.795   7.907  54.335  1.00 35.35      A
ATOM    852  N   GLU A 122      38.779   9.885  54.643  1.00 27.29      A
ATOM    853  CA  GLU A 122      39.096  10.380  53.309  1.00 27.29      A
ATOM    854  CB  GLU A 122      38.586  11.815  53.155  1.00 50.77      A
ATOM    855  CG  GLU A 122      38.783  12.414  51.772  1.00 50.77      A
ATOM    856  CD  GLU A 122      38.039  11.659  50.681  1.00 50.77      A
ATOM    857  OE1 GLU A 122      38.145  12.066  49.499  1.00 50.77      A
ATOM    858  OE2 GLU A 122      37.349  10.663  51.004  1.00 50.77      A
ATOM    859  C   GLU A 122      40.597  10.318  52.996  1.00 27.29      A
ATOM    860  O   GLU A 122      40.991   9.922  51.895  1.00 27.29      A
ATOM    861  N   LEU A 123      41.436  10.693  53.956  1.00 37.09      A
ATOM    862  CA  LEU A 123      42.871  10.675  53.718  1.00 37.09      A
ATOM    863  CB  LEU A 123      43.628  11.267  54.915  1.00 42.11      A
ATOM    864  CG  LEU A 123      43.574  12.766  55.229  1.00 42.11      A
ATOM    865  CD1 LEU A 123      44.474  13.051  56.431  1.00 42.11      A
ATOM    866  CD2 LEU A 123      44.036  13.575  54.027  1.00 42.11      A
ATOM    867  C   LEU A 123      43.406   9.269  53.443  1.00 37.09      A
ATOM    868  O   LEU A 123      44.435   9.106  52.775  1.00 37.09      A
ATOM    869  N   THR A 124      42.710   8.256  53.948  1.00 47.34      A
ATOM    870  CA  THR A 124      43.165   6.881  53.779  1.00 47.34      A
ATOM    871  CB  THR A 124      43.280   6.189  55.147  1.00 51.95      A
ATOM    872  OG1 THR A 124      41.992   6.173  55.778  1.00 51.95      A
ATOM    873  CG2 THR A 124      44.263   6.935  56.040  1.00 51.95      A
ATOM    874  C   THR A 124      42.293   6.006  52.885  1.00 47.34      A
ATOM    875  O   THR A 124      42.402   4.785  52.926  1.00 47.34      A
ATOM    876  N   LYS A 125      41.441   6.612  52.070  1.00 44.88      A
ATOM    877  CA  LYS A 125      40.572   5.821  51.209  1.00 44.88      A
ATOM    878  CB  LYS A 125      39.633   6.732  50.411  1.00 45.55      A
ATOM    879  CG  LYS A 125      40.317   7.559  49.354  1.00 45.55      A
ATOM    880  CD  LYS A 125      39.353   8.555  48.745  1.00 45.55      A
ATOM    881  CE  LYS A 125      40.063   9.392  47.694  1.00 45.55      A
ATOM    882  NZ  LYS A 125      39.217  10.513  47.202  1.00 45.55      A
ATOM    883  C   LYS A 125      41.338   4.899  50.257  1.00 44.88      A
ATOM    884  O   LYS A 125      40.821   3.854  49.864  1.00 44.88      A
ATOM    885  N   ASN A 126      42.561   5.276  49.886  1.00 32.03      A
ATOM    886  CA  ASN A 126      43.366   4.455  48.979  1.00 32.03      A
ATOM    887  CB  ASN A 126      44.005   5.313  47.885  1.00 55.44      A
ATOM    888  CG  ASN A 126      42.987   6.043  47.047  1.00 55.44      A
ATOM    889  OD1 ASN A 126      42.162   5.422  46.370  1.00 55.44      A
ATOM    890  ND2 ASN A 126      43.034   7.377  47.082  1.00 55.44      A
ATOM    891  C   ASN A 126      44.480   3.711  49.709  1.00 32.03      A
ATOM    892  O   ASN A 126      45.527   3.426  49.124  1.00 32.03      A
ATOM    893  N   LEU A 127      44.280   3.411  50.986  1.00 29.87      A
ATOM    894  CA  LEU A 127      45.289   2.680  51.736  1.00 29.87      A
ATOM    895  CB  LEU A 127      45.969   3.586  52.759  1.00 41.10      A
ATOM    896  CG  LEU A 127      46.688   4.836  52.259  1.00 41.10      A
```

Figure 8-12

| | | | | | | | | | | |
|---|---|---|---|---|---|---|---|---|---|---|
| ATOM | 897 | CD1 | LEU | A | 127 | 47.585 | 5.351 | 53.383 | 1.00 41.10 | A |
| ATOM | 898 | CD2 | LEU | A | 127 | 47.524 | 4.516 | 51.029 | 1.00 41.10 | A |
| ATOM | 899 | C | LEU | A | 127 | 44.689 | 1.482 | 52.465 | 1.00 29.87 | A |
| ATOM | 900 | O | LEU | A | 127 | 43.617 | 1.576 | 53.065 | 1.00 29.87 | A |
| ATOM | 901 | N | THR | A | 128 | 45.381 | 0.350 | 52.410 | 1.00 63.04 | A |
| ATOM | 902 | CA | THR | A | 128 | 44.919 | -0.845 | 53.102 | 1.00 63.04 | A |
| ATOM | 903 | CB | THR | A | 128 | 45.728 | -2.087 | 52.685 | 1.00 36.80 | A |
| ATOM | 904 | OG1 | THR | A | 128 | 47.102 | -1.913 | 53.074 | 1.00 36.80 | A |
| ATOM | 905 | CG2 | THR | A | 128 | 45.638 | -2.304 | 51.164 | 1.00 36.80 | A |
| ATOM | 906 | C | THR | A | 128 | 45.161 | -0.595 | 54.585 | 1.00 63.04 | A |
| ATOM | 907 | O | THR | A | 128 | 45.999 | 0.232 | 54.951 | 1.00 63.04 | A |
| ATOM | 908 | N | ALA | A | 129 | 44.435 | -1.301 | 55.440 | 1.00 39.48 | A |
| ATOM | 909 | CA | ALA | A | 129 | 44.606 | -1.125 | 56.875 | 1.00 39.48 | A |
| ATOM | 910 | CB | ALA | A | 129 | 43.749 | -2.128 | 57.639 | 1.00 39.02 | A |
| ATOM | 911 | C | ALA | A | 129 | 46.072 | -1.277 | 57.271 | 1.00 39.48 | A |
| ATOM | 912 | O | ALA | A | 129 | 46.544 | -0.596 | 58.179 | 1.00 39.48 | A |
| ATOM | 913 | N | ASP | A | 130 | 46.797 | -2.160 | 56.589 | 1.00 50.74 | A |
| ATOM | 914 | CA | ASP | A | 130 | 48.206 | -2.371 | 56.912 | 1.00 50.74 | A |
| ATOM | 915 | CB | ASP | A | 130 | 48.738 | -3.631 | 56.229 | 1.00 98.04 | A |
| ATOM | 916 | CG | ASP | A | 130 | 48.257 | -4.899 | 56.900 | 1.00 98.04 | A |
| ATOM | 917 | OD1 | ASP | A | 130 | 47.035 | -5.156 | 56.873 | 1.00 98.04 | A |
| ATOM | 918 | OD2 | ASP | A | 130 | 49.100 | -5.633 | 57.461 | 1.00 98.04 | A |
| ATOM | 919 | C | ASP | A | 130 | 49.060 | -1.179 | 56.519 | 1.00 50.74 | A |
| ATOM | 920 | O | ASP | A | 130 | 49.963 | -0.781 | 57.265 | 1.00 50.74 | A |
| ATOM | 921 | N | GLU | A | 131 | 48.771 | -0.618 | 55.347 | 1.00 61.99 | A |
| ATOM | 922 | CA | GLU | A | 131 | 49.500 | 0.543 | 54.848 | 1.00 61.99 | A |
| ATOM | 923 | CB | GLU | A | 131 | 49.018 | 0.905 | 53.432 | 1.00 35.87 | A |
| ATOM | 924 | CG | GLU | A | 131 | 49.255 | -0.199 | 52.383 | 1.00 35.87 | A |
| ATOM | 925 | CD | GLU | A | 131 | 48.725 | 0.156 | 50.991 | 1.00 35.87 | A |
| ATOM | 926 | OE1 | GLU | A | 131 | 47.518 | 0.469 | 50.867 | 1.00 35.87 | A |
| ATOM | 927 | OE2 | GLU | A | 131 | 49.514 | 0.116 | 50.019 | 1.00 35.87 | A |
| ATOM | 928 | C | GLU | A | 131 | 49.285 | 1.720 | 55.805 | 1.00 61.99 | A |
| ATOM | 929 | O | GLU | A | 131 | 50.210 | 2.494 | 56.061 | 1.00 61.99 | A |
| ATOM | 930 | N | VAL | A | 132 | 48.066 | 1.835 | 56.338 | 1.00 41.47 | A |
| ATOM | 931 | CA | VAL | A | 132 | 47.716 | 2.899 | 57.282 | 1.00 41.47 | A |
| ATOM | 932 | CB | VAL | A | 132 | 46.227 | 2.827 | 57.703 | 1.00 27.86 | A |
| ATOM | 933 | CG1 | VAL | A | 132 | 45.971 | 3.746 | 58.890 | 1.00 27.86 | A |
| ATOM | 934 | CG2 | VAL | A | 132 | 45.345 | 3.243 | 56.550 | 1.00 27.86 | A |
| ATOM | 935 | C | VAL | A | 132 | 48.566 | 2.789 | 58.541 | 1.00 41.47 | A |
| ATOM | 936 | O | VAL | A | 132 | 49.214 | 3.755 | 58.958 | 1.00 41.47 | A |
| ATOM | 937 | N | ALA | A | 133 | 48.551 | 1.607 | 59.146 | 1.00 41.81 | A |
| ATOM | 938 | CA | ALA | A | 133 | 49.327 | 1.358 | 60.351 | 1.00 41.81 | A |
| ATOM | 939 | CB | ALA | A | 133 | 49.198 | -0.103 | 60.759 | 1.00 40.85 | A |
| ATOM | 940 | C | ALA | A | 133 | 50.790 | 1.700 | 60.096 | 1.00 41.81 | A |
| ATOM | 941 | O | ALA | A | 133 | 51.426 | 2.374 | 60.904 | 1.00 41.81 | A |
| ATOM | 942 | N | THR | A | 134 | 51.320 | 1.232 | 58.970 | 1.00 46.90 | A |
| ATOM | 943 | CA | THR | A | 134 | 52.712 | 1.497 | 58.633 | 1.00 46.90 | A |
| ATOM | 944 | CB | THR | A | 134 | 53.106 | 0.851 | 57.293 | 1.00 46.04 | A |
| ATOM | 945 | OG1 | THR | A | 134 | 53.111 | -0.574 | 57.439 | 1.00 46.04 | A |
| ATOM | 946 | CG2 | THR | A | 134 | 54.494 | 1.324 | 56.857 | 1.00 46.04 | A |
| ATOM | 947 | C | THR | A | 134 | 52.957 | 2.992 | 58.538 | 1.00 46.90 | A |
| ATOM | 948 | O | THR | A | 134 | 53.908 | 3.518 | 59.130 | 1.00 46.90 | A |
| ATOM | 949 | N | LEU | A | 135 | 52.097 | 3.668 | 57.784 | 1.00 53.07 | A |
| ATOM | 950 | CA | LEU | A | 135 | 52.206 | 5.109 | 57.611 | 1.00 53.07 | A |
| ATOM | 951 | CB | LEU | A | 135 | 50.997 | 5.629 | 56.838 | 1.00 28.73 | A |
| ATOM | 952 | CG | LEU | A | 135 | 50.926 | 7.133 | 56.591 | 1.00 28.73 | A |
| ATOM | 953 | CD1 | LEU | A | 135 | 52.240 | 7.647 | 56.003 | 1.00 28.73 | A |
| ATOM | 954 | CD2 | LEU | A | 135 | 49.763 | 7.405 | 55.650 | 1.00 28.73 | A |
| ATOM | 955 | C | LEU | A | 135 | 52.295 | 5.803 | 58.972 | 1.00 53.07 | A |
| ATOM | 956 | O | LEU | A | 135 | 53.204 | 6.601 | 59.214 | 1.00 53.07 | A |
| ATOM | 957 | N | GLU | A | 136 | 51.361 | 5.484 | 59.863 | 1.00 44.05 | A |
| ATOM | 958 | CA | GLU | A | 136 | 51.360 | 6.088 | 61.186 | 1.00 44.05 | A |
| ATOM | 959 | CB | GLU | A | 136 | 50.082 | 5.723 | 61.938 | 1.00 46.25 | A |
| ATOM | 960 | CG | GLU | A | 136 | 48.848 | 6.270 | 61.250 | 1.00 46.25 | A |
| ATOM | 961 | CD | GLU | A | 136 | 47.720 | 6.554 | 62.208 | 1.00 46.25 | A |
| ATOM | 962 | OE1 | GLU | A | 136 | 46.624 | 6.927 | 61.737 | 1.00 46.25 | A |
| ATOM | 963 | OE2 | GLU | A | 136 | 47.932 | 6.413 | 63.433 | 1.00 46.25 | A |
| ATOM | 964 | C | GLU | A | 136 | 52.583 | 5.692 | 62.000 | 1.00 44.05 | A |
| ATOM | 965 | O | GLU | A | 136 | 53.122 | 6.497 | 62.768 | 1.00 44.05 | A |
| ATOM | 966 | N | TYR | A | 137 | 53.034 | 4.457 | 61.836 | 1.00 42.24 | A |
| ATOM | 967 | CA | TYR | A | 137 | 54.205 | 4.012 | 62.572 | 1.00 42.24 | A |
| ATOM | 968 | CB | TYR | A | 137 | 54.504 | 2.545 | 62.263 | 1.00 52.94 | A |
| ATOM | 969 | CG | TYR | A | 137 | 55.858 | 2.111 | 62.761 | 1.00 52.94 | A |
| ATOM | 970 | CD1 | TYR | A | 137 | 56.111 | 1.973 | 64.123 | 1.00 52.94 | A |
| ATOM | 971 | CE1 | TYR | A | 137 | 57.379 | 1.636 | 64.586 | 1.00 52.94 | A |

Figure 8-13

```
ATOM    972  CD2 TYR A 137      56.904   1.897  61.870  1.00 52.94      A
ATOM    973  CE2 TYR A 137      58.174   1.560  62.316  1.00 52.94      A
ATOM    974  CZ  TYR A 137      58.410   1.431  63.674  1.00 52.94      A
ATOM    975  OH  TYR A 137      59.679   1.099  64.109  1.00 52.94      A
ATOM    976  C   TYR A 137      55.402   4.876  62.180  1.00 42.24      A
ATOM    977  O   TYR A 137      56.093   5.425  63.039  1.00 42.24      A
ATOM    978  N   LEU A 138      55.631   4.995  60.874  1.00 37.69      A
ATOM    979  CA  LEU A 138      56.745   5.780  60.351  1.00 37.69      A
ATOM    980  CB  LEU A 138      56.878   5.554  58.836  1.00 52.05      A
ATOM    981  CG  LEU A 138      57.143   4.104  58.390  1.00 52.05      A
ATOM    982  CD1 LEU A 138      57.126   4.020  56.870  1.00 52.05      A
ATOM    983  CD2 LEU A 138      58.482   3.626  58.933  1.00 52.05      A
ATOM    984  C   LEU A 138      56.611   7.275  60.657  1.00 37.69      A
ATOM    985  O   LEU A 138      57.566   7.900  61.111  1.00 37.69      A
ATOM    986  N   LEU A 139      55.437   7.849  60.411  1.00 53.38      A
ATOM    987  CA  LEU A 139      55.238   9.264  60.696  1.00 53.38      A
ATOM    988  CB  LEU A 139      53.782   9.674  60.428  1.00 22.81      A
ATOM    989  CG  LEU A 139      53.510  10.039  58.957  1.00 22.81      A
ATOM    990  CD1 LEU A 139      52.025  10.086  58.665  1.00 22.81      A
ATOM    991  CD2 LEU A 139      54.167  11.368  58.656  1.00 22.81      A
ATOM    992  C   LEU A 139      55.615   9.570  62.144  1.00 53.38      A
ATOM    993  O   LEU A 139      56.289  10.569  62.424  1.00 53.38      A
ATOM    994  N   LYS A 140      55.196   8.708  63.065  1.00 46.77      A
ATOM    995  CA  LYS A 140      55.517   8.912  64.473  1.00 46.77      A
ATOM    996  CB  LYS A 140      54.854   7.830  65.324  1.00 58.30      A
ATOM    997  CG  LYS A 140      53.336   7.886  65.328  1.00 58.30      A
ATOM    998  CD  LYS A 140      52.751   6.751  66.144  1.00 58.30      A
ATOM    999  CE  LYS A 140      51.240   6.713  66.029  1.00 58.30      A
ATOM   1000  NZ  LYS A 140      50.658   5.553  66.765  1.00 58.30      A
ATOM   1001  C   LYS A 140      57.035   8.900  64.696  1.00 46.77      A
ATOM   1002  O   LYS A 140      57.559   9.669  65.503  1.00 46.77      A
ATOM   1003  N   LYS A 141      57.736   8.025  63.980  1.00 52.29      A
ATOM   1004  CA  LYS A 141      59.183   7.927  64.102  1.00 52.29      A
ATOM   1005  CB  LYS A 141      59.733   6.906  63.103  1.00 78.01      A
ATOM   1006  CG  LYS A 141      59.234   5.485  63.304  1.00 78.01      A
ATOM   1007  CD  LYS A 141      59.917   4.803  64.483  1.00 78.01      A
ATOM   1008  CE  LYS A 141      61.401   4.570  64.211  1.00 78.01      A
ATOM   1009  NZ  LYS A 141      61.626   3.676  63.039  1.00 78.01      A
ATOM   1010  C   LYS A 141      59.822   9.283  63.831  1.00 52.29      A
ATOM   1011  O   LYS A 141      60.721   9.710  64.561  1.00 52.29      A
ATOM   1012  N   VAL A 142      59.351   9.962  62.785  1.00 48.93      A
ATOM   1013  CA  VAL A 142      59.889  11.268  62.410  1.00 48.93      A
ATOM   1014  CB  VAL A 142      59.205  11.796  61.126  1.00 31.55      A
ATOM   1015  CG1 VAL A 142      59.666  13.211  60.816  1.00 31.55      A
ATOM   1016  CG2 VAL A 142      59.540  10.881  59.962  1.00 31.55      A
ATOM   1017  C   VAL A 142      59.792  12.321  63.522  1.00 48.93      A
ATOM   1018  O   VAL A 142      60.540  13.297  63.520  1.00 48.93      A
ATOM   1019  N   LEU A 143      58.877  12.129  64.466  1.00 67.04      A
ATOM   1020  CA  LEU A 143      58.737  13.062  65.583  1.00 67.04      A
ATOM   1021  CB  LEU A 143      57.302  13.053  66.120  1.00 42.71      A
ATOM   1022  CG  LEU A 143      56.178  13.434  65.151  1.00 42.71      A
ATOM   1023  CD1 LEU A 143      54.823  13.233  65.821  1.00 42.71      A
ATOM   1024  CD2 LEU A 143      56.355  14.874  64.714  1.00 42.71      A
ATOM   1025  C   LEU A 143      59.695  12.601  66.682  1.00 67.04      A
ATOM   1026  O   LEU A 143      60.170  11.461  66.660  1.00 67.04      A
ATOM   1027  N   PRO A 144      59.987  13.467  67.667  1.00135.51      A
ATOM   1028  CD  PRO A 144      60.809  13.066  68.823  1.00 96.05      A
ATOM   1029  CA  PRO A 144      59.495  14.840  67.835  1.00135.51      A
ATOM   1030  CB  PRO A 144      60.165  15.287  69.135  1.00 96.05      A
ATOM   1031  CG  PRO A 144      60.316  14.001  69.895  1.00 96.05      A
ATOM   1032  C   PRO A 144      59.851  15.747  66.656  1.00135.51      A
ATOM   1033  O   PRO A 144      58.923  16.371  66.093  1.00135.51      A
ATOM   1034  OXT PRO A 144      61.053  15.826  66.317  1.00 96.05      A
REMARK Apo-MarR; Residues 9-144 of SEQ ID NO:2
ATOM   1035  CB  ASN B   9      51.205   2.213  67.233  1.00135.37      B
ATOM   1036  CG  ASN B   9      50.539   1.403  66.123  1.00135.37      B
ATOM   1037  OD1 ASN B   9      50.453   0.173  66.194  1.00135.37      B
ATOM   1038  ND2 ASN B   9      50.060   2.096  65.091  1.00135.37      B
ATOM   1039  C   ASN B   9      48.981   2.335  68.349  1.00 66.09      B
ATOM   1040  O   ASN B   9      48.315   1.572  67.640  1.00 66.09      B
ATOM   1041  N   ASN B   9      50.712   0.757  69.190  1.00 66.09      B
ATOM   1042  CA  ASN B   9      50.471   2.096  68.577  1.00 66.09      B
ATOM   1043  N   GLU B  10      48.458   3.398  68.949  1.00129.71      B
ATOM   1044  CA  GLU B  10      47.050   3.722  68.781  1.00129.71      B
ATOM   1045  CB  GLU B  10      46.538   4.558  69.965  1.00111.04      B
```

Figure 8-14

```
ATOM   1046  CG   GLU B  10      47.613   5.022  70.946  1.00111.04      B
ATOM   1047  CD   GLU B  10      48.429   6.195  70.432  1.00111.04      B
ATOM   1048  OE1  GLU B  10      49.073   6.062  69.369  1.00111.04      B
ATOM   1049  OE2  GLU B  10      48.425   7.253  71.099  1.00111.04      B
ATOM   1050  C    GLU B  10      46.817   4.471  67.472  1.00129.71      B
ATOM   1051  O    GLU B  10      47.241   5.619  67.314  1.00129.71      B
ATOM   1052  N    ILE B  11      46.165   3.803  66.523  1.00 72.20      B
ATOM   1053  CA   ILE B  11      45.859   4.430  65.249  1.00 72.20      B
ATOM   1054  CB   ILE B  11      45.047   3.482  64.321  1.00 44.08      B
ATOM   1055  CG2  ILE B  11      44.363   4.273  63.215  1.00 44.08      B
ATOM   1056  CG1  ILE B  11      45.981   2.447  63.685  1.00 44.08      B
ATOM   1057  CD1  ILE B  11      47.045   3.052  62.771  1.00 44.08      B
ATOM   1058  C    ILE B  11      45.030   5.664  65.570  1.00 72.20      B
ATOM   1059  O    ILE B  11      43.859   5.559  65.931  1.00 72.20      B
ATOM   1060  N    ILE B  12      45.659   6.830  65.468  1.00 83.43      B
ATOM   1061  CA   ILE B  12      44.990   8.093  65.740  1.00 83.43      B
ATOM   1062  CB   ILE B  12      45.914   9.042  66.517  1.00 57.67      B
ATOM   1063  CG2  ILE B  12      46.291   8.415  67.849  1.00 57.67      B
ATOM   1064  CG1  ILE B  12      47.169   9.336  65.696  1.00 57.67      B
ATOM   1065  CD1  ILE B  12      48.155  10.247  66.400  1.00 57.67      B
ATOM   1066  C    ILE B  12      44.614   8.733  64.410  1.00 83.43      B
ATOM   1067  O    ILE B  12      45.108   8.318  63.361  1.00 83.43      B
ATOM   1068  N    PRO B  13      43.734   9.751  64.430  1.00 40.24      B
ATOM   1069  CD   PRO B  13      43.092  10.404  65.582  1.00 21.06      B
ATOM   1070  CA   PRO B  13      43.332  10.404  63.178  1.00 40.24      B
ATOM   1071  CB   PRO B  13      42.435  11.547  63.657  1.00 21.06      B
ATOM   1072  CG   PRO B  13      41.867  11.005  64.948  1.00 21.06      B
ATOM   1073  C    PRO B  13      44.567  10.892  62.428  1.00 40.24      B
ATOM   1074  O    PRO B  13      45.298  11.766  62.903  1.00 40.24      B
ATOM   1075  N    LEU B  14      44.806  10.306  61.262  1.00 44.39      B
ATOM   1076  CA   LEU B  14      45.969  10.670  60.479  1.00 44.39      B
ATOM   1077  CB   LEU B  14      45.908   9.983  59.117  1.00 19.34      B
ATOM   1078  CG   LEU B  14      47.107  10.215  58.191  1.00 19.34      B
ATOM   1079  CD1  LEU B  14      48.395   9.890  58.927  1.00 19.34      B
ATOM   1080  CD2  LEU B  14      46.967   9.347  56.941  1.00 19.34      B
ATOM   1081  C    LEU B  14      46.076  12.185  60.314  1.00 44.39      B
ATOM   1082  O    LEU B  14      47.176  12.743  60.347  1.00 44.39      B
ATOM   1083  N    GLY B  15      44.932  12.848  60.153  1.00 31.14      B
ATOM   1084  CA   GLY B  15      44.931  14.292  59.983  1.00 31.14      B
ATOM   1085  C    GLY B  15      45.771  14.999  61.030  1.00 31.14      B
ATOM   1086  O    GLY B  15      46.495  15.959  60.725  1.00 31.14      B
ATOM   1087  N    ARG B  16      45.673  14.531  62.272  1.00 41.91      B
ATOM   1088  CA   ARG B  16      46.440  15.101  63.382  1.00 41.91      B
ATOM   1089  CB   ARG B  16      45.947  14.523  64.716  1.00 51.45      B
ATOM   1090  CG   ARG B  16      44.787  15.262  65.386  1.00 51.45      B
ATOM   1091  CD   ARG B  16      43.456  15.229  64.609  1.00 51.45      B
ATOM   1092  NE   ARG B  16      43.346  16.273  63.581  1.00 51.45      B
ATOM   1093  CZ   ARG B  16      42.194  16.797  63.167  1.00 51.45      B
ATOM   1094  NH1  ARG B  16      41.052  16.376  63.696  1.00 51.45      B
ATOM   1095  NH2  ARG B  16      42.186  17.736  62.228  1.00 51.45      B
ATOM   1096  C    ARG B  16      47.945  14.811  63.223  1.00 41.91      B
ATOM   1097  O    ARG B  16      48.793  15.676  63.462  1.00 41.91      B
ATOM   1098  N    LEU B  17      48.272  13.588  62.820  1.00 38.48      B
ATOM   1099  CA   LEU B  17      49.667  13.186  62.634  1.00 38.48      B
ATOM   1100  CB   LEU B  17      49.747  11.706  62.251  1.00 42.44      B
ATOM   1101  CG   LEU B  17      50.527  10.781  63.183  1.00 42.44      B
ATOM   1102  CD1  LEU B  17      50.582   9.383  62.577  1.00 42.44      B
ATOM   1103  CD2  LEU B  17      51.933  11.312  63.380  1.00 42.44      B
ATOM   1104  C    LEU B  17      50.318  14.027  61.541  1.00 38.48      B
ATOM   1105  O    LEU B  17      51.416  14.560  61.722  1.00 38.48      B
ATOM   1106  N    ILE B  18      49.639  14.127  60.398  1.00 33.51      B
ATOM   1107  CA   ILE B  18      50.131  14.919  59.273  1.00 33.51      B
ATOM   1108  CB   ILE B  18      49.089  14.986  58.154  1.00 35.12      B
ATOM   1109  CG2  ILE B  18      49.478  16.025  57.131  1.00 35.12      B
ATOM   1110  CG1  ILE B  18      48.953  13.616  57.505  1.00 35.12      B
ATOM   1111  CD1  ILE B  18      47.936  13.574  56.392  1.00 35.12      B
ATOM   1112  C    ILE B  18      50.407  16.335  59.768  1.00 33.51      B
ATOM   1113  O    ILE B  18      51.434  16.926  59.430  1.00 33.51      B
ATOM   1114  N    HIS B  19      49.488  16.865  60.579  1.00 26.80      B
ATOM   1115  CA   HIS B  19      49.634  18.207  61.131  1.00 26.80      B
ATOM   1116  CB   HIS B  19      48.402  18.596  61.953  1.00 38.93      B
ATOM   1117  CG   HIS B  19      48.514  19.943  62.609  1.00 38.93      B
ATOM   1118  CD2  HIS B  19      47.842  21.101  62.391  1.00 38.93      B
ATOM   1119  ND1  HIS B  19      49.422  20.212  63.613  1.00 38.93      B
ATOM   1120  CE1  HIS B  19      49.305  21.474  63.985  1.00 38.93      B
```

Figure 8-15

```
ATOM   1121  NE2 HIS B  19      48.354  22.035  63.259  1.00 38.93      B
ATOM   1122  C   HIS B  19      50.883  18.324  62.010  1.00 26.80      B
ATOM   1123  O   HIS B  19      51.666  19.259  61.852  1.00 26.80      B
ATOM   1124  N   MET B  20      51.063  17.394  62.943  1.00 28.60      B
ATOM   1125  CA  MET B  20      52.232  17.433  63.821  1.00 28.60      B
ATOM   1126  CB  MET B  20      52.227  16.259  64.820  1.00 39.32      B
ATOM   1127  CG  MET B  20      51.096  16.297  65.880  1.00 39.32      B
ATOM   1128  SD  MET B  20      50.911  14.776  66.939  1.00 39.32      B
ATOM   1129  CE  MET B  20      49.664  13.868  66.026  1.00 39.32      B
ATOM   1130  C   MET B  20      53.509  17.374  62.981  1.00 28.60      B
ATOM   1131  O   MET B  20      54.360  18.257  63.067  1.00 28.60      B
ATOM   1132  N   VAL B  21      53.645  16.337  62.165  1.00 44.11      B
ATOM   1133  CA  VAL B  21      54.831  16.202  61.328  1.00 44.11      B
ATOM   1134  CB  VAL B  21      54.750  14.920  60.419  1.00 25.48      B
ATOM   1135  CG1 VAL B  21      55.871  14.909  59.369  1.00 25.48      B
ATOM   1136  CG2 VAL B  21      54.851  13.667  61.296  1.00 25.48      B
ATOM   1137  C   VAL B  21      55.024  17.453  60.472  1.00 44.11      B
ATOM   1138  O   VAL B  21      56.147  17.951  60.365  1.00 44.11      B
ATOM   1139  N   ASN B  22      53.941  17.967  59.880  1.00 30.47      B
ATOM   1140  CA  ASN B  22      54.033  19.161  59.038  1.00 30.47      B
ATOM   1141  CB  ASN B  22      52.663  19.551  58.476  1.00 26.19      B
ATOM   1142  CG  ASN B  22      52.696  20.880  57.708  1.00 26.19      B
ATOM   1143  OD1 ASN B  22      53.363  21.014  56.676  1.00 26.19      B
ATOM   1144  ND2 ASN B  22      51.965  21.867  58.218  1.00 26.19      B
ATOM   1145  C   ASN B  22      54.592  20.317  59.851  1.00 30.47      B
ATOM   1146  O   ASN B  22      55.460  21.061  59.377  1.00 30.47      B
ATOM   1147  N   GLN B  23      54.082  20.460  61.073  1.00 46.49      B
ATOM   1148  CA  GLN B  23      54.518  21.507  61.988  1.00 46.49      B
ATOM   1149  CB  GLN B  23      53.941  21.261  63.380  1.00 78.77      B
ATOM   1150  CG  GLN B  23      52.673  22.015  63.661  1.00 78.77      B
ATOM   1151  CD  GLN B  23      52.923  23.495  63.762  1.00 78.77      B
ATOM   1152  OE1 GLN B  23      53.721  23.937  64.588  1.00 78.77      B
ATOM   1153  NE2 GLN B  23      52.247  24.277  62.921  1.00 78.77      B
ATOM   1154  C   GLN B  23      56.030  21.474  62.075  1.00 46.49      B
ATOM   1155  O   GLN B  23      56.717  22.470  61.805  1.00 46.49      B
ATOM   1156  N   LYS B  24      56.541  20.310  62.463  1.00 34.97      B
ATOM   1157  CA  LYS B  24      57.976  20.100  62.603  1.00 34.97      B
ATOM   1158  CB  LYS B  24      58.270  18.647  62.982  1.00 37.02      B
ATOM   1159  CG  LYS B  24      59.722  18.264  62.762  1.00 37.02      B
ATOM   1160  CD  LYS B  24      60.128  16.985  63.486  1.00 37.02      B
ATOM   1161  CE  LYS B  24      61.567  16.611  63.127  1.00 37.02      B
ATOM   1162  NZ  LYS B  24      62.174  15.628  64.082  1.00 37.02      B
ATOM   1163  C   LYS B  24      58.729  20.448  61.322  1.00 34.97      B
ATOM   1164  O   LYS B  24      59.758  21.123  61.355  1.00 34.97      B
ATOM   1165  N   LYS B  25      58.220  19.976  60.193  1.00 37.64      B
ATOM   1166  CA  LYS B  25      58.855  20.255  58.919  1.00 37.64      B
ATOM   1167  CB  LYS B  25      57.990  19.746  57.762  1.00 42.01      B
ATOM   1168  CG  LYS B  25      58.655  19.922  56.407  1.00 42.01      B
ATOM   1169  CD  LYS B  25      57.650  20.235  55.311  1.00 42.01      B
ATOM   1170  CE  LYS B  25      57.095  21.642  55.459  1.00 42.01      B
ATOM   1171  NZ  LYS B  25      56.097  21.963  54.394  1.00 42.01      B
ATOM   1172  C   LYS B  25      59.075  21.761  58.752  1.00 37.64      B
ATOM   1173  O   LYS B  25      60.199  22.200  58.489  1.00 37.64      B
ATOM   1174  N   ASP B  26      58.001  22.542  58.907  1.00 35.53      B
ATOM   1175  CA  ASP B  26      58.088  23.994  58.748  1.00 35.53      B
ATOM   1176  CB  ASP B  26      56.699  24.640  58.880  1.00 56.04      B
ATOM   1177  CG  ASP B  26      55.787  24.341  57.681  1.00 56.04      B
ATOM   1178  OD1 ASP B  26      56.233  24.520  56.522  1.00 56.04      B
ATOM   1179  OD2 ASP B  26      54.618  23.937  57.897  1.00 56.04      B
ATOM   1180  C   ASP B  26      59.072  24.629  59.739  1.00 35.53      B
ATOM   1181  O   ASP B  26      59.735  25.614  59.417  1.00 35.53      B
ATOM   1182  N   ARG B  27      59.171  24.070  60.940  1.00 25.58      B
ATOM   1183  CA  ARG B  27      60.101  24.602  61.926  1.00 25.58      B
ATOM   1184  CB  ARG B  27      60.023  23.818  63.245  1.00 59.09      B
ATOM   1185  CG  ARG B  27      61.276  23.954  64.121  1.00 59.09      B
ATOM   1186  CD  ARG B  27      61.081  23.472  65.571  1.00 59.09      B
ATOM   1187  NE  ARG B  27      60.843  22.034  65.700  1.00 59.09      B
ATOM   1188  CZ  ARG B  27      59.642  21.475  65.865  1.00 59.09      B
ATOM   1189  NH1 ARG B  27      58.546  22.230  65.922  1.00 59.09      B
ATOM   1190  NH2 ARG B  27      59.537  20.154  65.991  1.00 59.09      B
ATOM   1191  C   ARG B  27      61.492  24.460  61.333  1.00 25.58      B
ATOM   1192  O   ARG B  27      62.217  25.445  61.145  1.00 25.58      B
ATOM   1193  N   LEU B  28      61.866  23.221  61.031  1.00 30.74      B
ATOM   1194  CA  LEU B  28      63.173  22.958  60.454  1.00 30.74      B
ATOM   1195  CB  LEU B  28      63.303  21.490  60.060  1.00 25.37      B
```

Figure 8-16

```
ATOM   1196  CG   LEU B  28      63.317  20.479  61.204  1.00 25.37           B
ATOM   1197  CD1  LEU B  28      63.329  19.085  60.628  1.00 25.37           B
ATOM   1198  CD2  LEU B  28      64.532  20.705  62.088  1.00 25.37           B
ATOM   1199  C    LEU B  28      63.402  23.826  59.227  1.00 30.74           B
ATOM   1200  O    LEU B  28      64.450  24.468  59.100  1.00 30.74           B
ATOM   1201  N    LEU B  29      62.422  23.843  58.323  1.00 35.92           B
ATOM   1202  CA   LEU B  29      62.519  24.635  57.097  1.00 35.92           B
ATOM   1203  CB   LEU B  29      61.193  24.617  56.335  1.00 29.83           B
ATOM   1204  CG   LEU B  29      61.253  25.212  54.924  1.00 29.83           B
ATOM   1205  CD1  LEU B  29      62.079  24.314  54.024  1.00 29.83           B
ATOM   1206  CD2  LEU B  29      59.859  25.341  54.356  1.00 29.83           B
ATOM   1207  C    LEU B  29      62.892  26.083  57.422  1.00 35.92           B
ATOM   1208  O    LEU B  29      63.767  26.675  56.783  1.00 35.92           B
ATOM   1209  N    ASN B  30      62.232  26.652  58.423  1.00 32.28           B
ATOM   1210  CA   ASN B  30      62.519  28.018  58.811  1.00 32.28           B
ATOM   1211  CB   ASN B  30      61.609  28.440  59.960  1.00 55.71           B
ATOM   1212  CG   ASN B  30      60.475  29.325  59.501  1.00 55.71           B
ATOM   1213  OD1  ASN B  30      59.407  29.356  60.118  1.00 55.71           B
ATOM   1214  ND2  ASN B  30      60.699  30.064  58.418  1.00 55.71           B
ATOM   1215  C    ASN B  30      63.977  28.170  59.215  1.00 32.28           B
ATOM   1216  O    ASN B  30      64.655  29.106  58.790  1.00 32.28           B
ATOM   1217  N    GLU B  31      64.464  27.248  60.034  1.00 28.98           B
ATOM   1218  CA   GLU B  31      65.840  27.315  60.492  1.00 28.98           B
ATOM   1219  CB   GLU B  31      66.158  26.172  61.453  1.00 46.83           B
ATOM   1220  CG   GLU B  31      65.361  26.133  62.739  1.00 46.83           B
ATOM   1221  CD   GLU B  31      65.784  24.959  63.607  1.00 46.83           B
ATOM   1222  OE1  GLU B  31      66.487  24.059  63.085  1.00 46.83           B
ATOM   1223  OE2  GLU B  31      65.410  24.926  64.799  1.00 46.83           B
ATOM   1224  C    GLU B  31      66.794  27.222  59.319  1.00 28.98           B
ATOM   1225  O    GLU B  31      67.678  28.054  59.159  1.00 28.98           B
ATOM   1226  N    TYR B  32      66.628  26.193  58.503  1.00 35.77           B
ATOM   1227  CA   TYR B  32      67.506  26.014  57.362  1.00 35.77           B
ATOM   1228  CB   TYR B  32      67.223  24.672  56.668  1.00 40.71           B
ATOM   1229  CG   TYR B  32      67.928  23.494  57.302  1.00 40.71           B
ATOM   1230  CD1  TYR B  32      67.209  22.441  57.873  1.00 40.71           B
ATOM   1231  CE1  TYR B  32      67.861  21.338  58.449  1.00 40.71           B
ATOM   1232  CD2  TYR B  32      69.319  23.426  57.323  1.00 40.71           B
ATOM   1233  CE2  TYR B  32      69.984  22.339  57.896  1.00 40.71           B
ATOM   1234  CZ   TYR B  32      69.251  21.296  58.455  1.00 40.71           B
ATOM   1235  OH   TYR B  32      69.918  20.213  58.998  1.00 40.71           B
ATOM   1236  C    TYR B  32      67.432  27.148  56.346  1.00 35.77           B
ATOM   1237  O    TYR B  32      68.383  27.342  55.581  1.00 35.77           B
ATOM   1238  N    LEU B  33      66.326  27.896  56.335  1.00 52.15           B
ATOM   1239  CA   LEU B  33      66.170  28.996  55.380  1.00 52.15           B
ATOM   1240  CB   LEU B  33      64.707  29.153  54.940  1.00 25.90           B
ATOM   1241  CG   LEU B  33      64.061  28.198  53.921  1.00 25.90           B
ATOM   1242  CD1  LEU B  33      62.616  28.613  53.731  1.00 25.90           B
ATOM   1243  CD2  LEU B  33      64.793  28.219  52.587  1.00 25.90           B
ATOM   1244  C    LEU B  33      66.662  30.348  55.878  1.00 52.15           B
ATOM   1245  O    LEU B  33      67.086  31.182  55.077  1.00 52.15           B
ATOM   1246  N    SER B  34      66.601  30.563  57.191  1.00 35.65           B
ATOM   1247  CA   SER B  34      67.018  31.829  57.809  1.00 35.65           B
ATOM   1248  CB   SER B  34      67.164  31.619  59.319  1.00 47.51           B
ATOM   1249  OG   SER B  34      66.819  32.791  60.039  1.00 47.51           B
ATOM   1250  C    SER B  34      68.309  32.458  57.222  1.00 35.65           B
ATOM   1251  O    SER B  34      68.354  33.664  56.930  1.00 35.65           B
ATOM   1252  N    PRO B  35      69.377  31.657  57.061  1.00 45.02           B
ATOM   1253  CD   PRO B  35      69.647  30.355  57.695  1.00 42.17           B
ATOM   1254  CA   PRO B  35      70.609  32.218  56.502  1.00 45.02           B
ATOM   1255  CB   PRO B  35      71.662  31.150  56.828  1.00 42.17           B
ATOM   1256  CG   PRO B  35      70.878  29.894  56.944  1.00 42.17           B
ATOM   1257  C    PRO B  35      70.562  32.579  55.012  1.00 45.02           B
ATOM   1258  O    PRO B  35      71.604  32.831  54.400  1.00 45.02           B
ATOM   1259  N    LEU B  36      69.365  32.614  54.428  1.00 41.85           B
ATOM   1260  CA   LEU B  36      69.230  32.985  53.021  1.00 41.85           B
ATOM   1261  CB   LEU B  36      68.741  31.794  52.198  1.00 42.76           B
ATOM   1262  CG   LEU B  36      69.454  30.458  52.439  1.00 42.76           B
ATOM   1263  CD1  LEU B  36      69.045  29.466  51.351  1.00 42.76           B
ATOM   1264  CD2  LEU B  36      70.964  30.649  52.427  1.00 42.76           B
ATOM   1265  C    LEU B  36      68.256  34.160  52.893  1.00 41.85           B
ATOM   1266  O    LEU B  36      67.936  34.610  51.785  1.00 41.85           B
ATOM   1267  N    ASP B  37      67.811  34.663  54.043  1.00 46.79           B
ATOM   1268  CA   ASP B  37      66.872  35.782  54.107  1.00 46.79           B
ATOM   1269  CB   ASP B  37      67.464  37.026  53.442  1.00 96.46           B
ATOM   1270  CG   ASP B  37      68.133  37.952  54.441  1.00 96.46           B
```

Figure 8-17

| | | | | | | | | | |
|---|---|---|---|---|---|---|---|---|---|
| ATOM | 1271 | OD1 | ASP | B | 37 | 67.437 | 38.425 | 55.365 | 1.00 96.46 | B |
| ATOM | 1272 | OD2 | ASP | B | 37 | 69.348 | 38.206 | 54.308 | 1.00 96.46 | B |
| ATOM | 1273 | C | ASP | B | 37 | 65.527 | 35.446 | 53.483 | 1.00 46.79 | B |
| ATOM | 1274 | O | ASP | B | 37 | 64.991 | 36.195 | 52.653 | 1.00 46.79 | B |
| ATOM | 1275 | N | ILE | B | 38 | 64.986 | 34.303 | 53.889 | 1.00 41.11 | B |
| ATOM | 1276 | CA | ILE | B | 38 | 63.697 | 33.859 | 53.396 | 1.00 41.11 | B |
| ATOM | 1277 | CB | ILE | B | 38 | 63.835 | 32.886 | 52.230 | 1.00 28.68 | B |
| ATOM | 1278 | CG2 | ILE | B | 38 | 62.540 | 32.872 | 51.436 | 1.00 28.68 | B |
| ATOM | 1279 | CG1 | ILE | B | 38 | 64.997 | 33.300 | 51.337 | 1.00 28.68 | B |
| ATOM | 1280 | CD1 | ILE | B | 38 | 65.143 | 32.438 | 50.104 | 1.00 28.68 | B |
| ATOM | 1281 | C | ILE | B | 38 | 62.980 | 33.113 | 54.499 | 1.00 41.11 | B |
| ATOM | 1282 | O | ILE | B | 38 | 63.599 | 32.360 | 55.253 | 1.00 41.11 | B |
| ATOM | 1283 | N | THR | B | 39 | 61.674 | 33.319 | 54.592 | 1.00 26.87 | B |
| ATOM | 1284 | CA | THR | B | 39 | 60.885 | 32.625 | 55.594 | 1.00 26.87 | B |
| ATOM | 1285 | CB | THR | B | 39 | 59.815 | 33.541 | 56.153 | 1.00 31.96 | B |
| ATOM | 1286 | OG1 | THR | B | 39 | 58.964 | 33.981 | 55.084 | 1.00 31.96 | B |
| ATOM | 1287 | CG2 | THR | B | 39 | 60.466 | 34.752 | 56.837 | 1.00 31.96 | B |
| ATOM | 1288 | C | THR | B | 39 | 60.231 | 31.447 | 54.893 | 1.00 26.87 | B |
| ATOM | 1289 | O | THR | B | 39 | 60.110 | 31.455 | 53.659 | 1.00 26.87 | B |
| ATOM | 1290 | N | ALA | B | 40 | 59.819 | 30.431 | 55.651 | 1.00 35.79 | B |
| ATOM | 1291 | CA | ALA | B | 40 | 59.178 | 29.267 | 55.030 | 1.00 35.79 | B |
| ATOM | 1292 | CB | ALA | B | 40 | 58.996 | 28.135 | 56.047 | 1.00  6.71 | B |
| ATOM | 1293 | C | ALA | B | 40 | 57.836 | 29.700 | 54.459 | 1.00 35.79 | B |
| ATOM | 1294 | O | ALA | B | 40 | 57.346 | 29.121 | 53.490 | 1.00 35.79 | B |
| ATOM | 1295 | N | ALA | B | 41 | 57.266 | 30.742 | 55.056 | 1.00 35.78 | B |
| ATOM | 1296 | CA | ALA | B | 41 | 55.986 | 31.284 | 54.616 | 1.00 35.78 | B |
| ATOM | 1297 | CB | ALA | B | 41 | 55.616 | 32.512 | 55.465 | 1.00 11.87 | B |
| ATOM | 1298 | C | ALA | B | 41 | 56.106 | 31.679 | 53.151 | 1.00 35.78 | B |
| ATOM | 1299 | O | ALA | B | 41 | 55.376 | 31.179 | 52.281 | 1.00 35.78 | B |
| ATOM | 1300 | N | GLN | B | 42 | 57.050 | 32.575 | 52.890 | 1.00 33.53 | B |
| ATOM | 1301 | CA | GLN | B | 42 | 57.291 | 33.061 | 51.538 | 1.00 33.53 | B |
| ATOM | 1302 | CB | GLN | B | 42 | 58.394 | 34.107 | 51.569 | 1.00 34.68 | B |
| ATOM | 1303 | CG | GLN | B | 42 | 58.068 | 35.300 | 52.437 | 1.00 34.68 | B |
| ATOM | 1304 | CD | GLN | B | 42 | 59.279 | 36.195 | 52.665 | 1.00 34.68 | B |
| ATOM | 1305 | OE1 | GLN | B | 42 | 59.133 | 37.359 | 53.034 | 1.00 34.68 | B |
| ATOM | 1306 | NE2 | GLN | B | 42 | 60.485 | 35.647 | 52.460 | 1.00 34.68 | B |
| ATOM | 1307 | C | GLN | B | 42 | 57.679 | 31.915 | 50.613 | 1.00 33.53 | B |
| ATOM | 1308 | O | GLN | B | 42 | 57.219 | 31.847 | 49.470 | 1.00 33.53 | B |
| ATOM | 1309 | N | PHE | B | 43 | 58.514 | 31.013 | 51.123 | 1.00 29.03 | B |
| ATOM | 1310 | CA | PHE | B | 43 | 58.974 | 29.872 | 50.343 | 1.00 29.03 | B |
| ATOM | 1311 | CB | PHE | B | 43 | 59.971 | 29.047 | 51.145 | 1.00 37.88 | B |
| ATOM | 1312 | CG | PHE | B | 43 | 60.544 | 27.894 | 50.377 | 1.00 37.88 | B |
| ATOM | 1313 | CD1 | PHE | B | 43 | 61.275 | 28.114 | 49.210 | 1.00 37.88 | B |
| ATOM | 1314 | CD2 | PHE | B | 43 | 60.350 | 26.583 | 50.808 | 1.00 37.88 | B |
| ATOM | 1315 | CE1 | PHE | B | 43 | 61.804 | 27.041 | 48.479 | 1.00 37.88 | B |
| ATOM | 1316 | CE2 | PHE | B | 43 | 60.876 | 25.501 | 50.082 | 1.00 37.88 | B |
| ATOM | 1317 | CZ | PHE | B | 43 | 61.603 | 25.732 | 48.918 | 1.00 37.88 | B |
| ATOM | 1318 | C | PHE | B | 43 | 57.814 | 28.983 | 49.908 | 1.00 29.03 | B |
| ATOM | 1319 | O | PHE | B | 43 | 57.734 | 28.566 | 48.746 | 1.00 29.03 | B |
| ATOM | 1320 | N | LYS | B | 44 | 56.912 | 28.698 | 50.841 | 1.00 36.68 | B |
| ATOM | 1321 | CA | LYS | B | 44 | 55.768 | 27.851 | 50.532 | 1.00 36.68 | B |
| ATOM | 1322 | CB | LYS | B | 44 | 54.913 | 27.635 | 51.792 | 1.00 86.09 | B |
| ATOM | 1323 | CG | LYS | B | 44 | 55.545 | 26.659 | 52.801 | 1.00 86.09 | B |
| ATOM | 1324 | CD | LYS | B | 44 | 54.913 | 26.748 | 54.194 | 1.00 86.09 | B |
| ATOM | 1325 | CE | LYS | B | 44 | 53.467 | 26.253 | 54.234 | 1.00 86.09 | B |
| ATOM | 1326 | NZ | LYS | B | 44 | 53.345 | 24.763 | 54.191 | 1.00 86.09 | B |
| ATOM | 1327 | C | LYS | B | 44 | 54.947 | 28.466 | 49.399 | 1.00 36.68 | B |
| ATOM | 1328 | O | LYS | B | 44 | 54.622 | 27.786 | 48.431 | 1.00 36.68 | B |
| ATOM | 1329 | N | VAL | B | 45 | 54.629 | 29.750 | 49.508 | 1.00 34.37 | B |
| ATOM | 1330 | CA | VAL | B | 45 | 53.860 | 30.406 | 48.471 | 1.00 34.37 | B |
| ATOM | 1331 | CB | VAL | B | 45 | 53.622 | 31.876 | 48.816 | 1.00 27.32 | B |
| ATOM | 1332 | CG1 | VAL | B | 45 | 52.980 | 32.594 | 47.631 | 1.00 27.32 | B |
| ATOM | 1333 | CG2 | VAL | B | 45 | 52.717 | 31.968 | 50.026 | 1.00 27.32 | B |
| ATOM | 1334 | C | VAL | B | 45 | 54.569 | 30.301 | 47.119 | 1.00 34.37 | B |
| ATOM | 1335 | O | VAL | B | 45 | 53.952 | 29.895 | 46.119 | 1.00 34.37 | B |
| ATOM | 1336 | N | LEU | B | 46 | 55.856 | 30.660 | 47.079 | 1.00 34.02 | B |
| ATOM | 1337 | CA | LEU | B | 46 | 56.630 | 30.574 | 45.837 | 1.00 34.02 | B |
| ATOM | 1338 | CB | LEU | B | 46 | 58.097 | 30.928 | 46.089 | 1.00 41.81 | B |
| ATOM | 1339 | CG | LEU | B | 46 | 58.407 | 32.358 | 46.526 | 1.00 41.81 | B |
| ATOM | 1340 | CD1 | LEU | B | 46 | 59.911 | 32.538 | 46.588 | 1.00 41.81 | B |
| ATOM | 1341 | CD2 | LEU | B | 46 | 57.793 | 33.356 | 45.548 | 1.00 41.81 | B |
| ATOM | 1342 | C | LEU | B | 46 | 56.552 | 29.178 | 45.203 | 1.00 34.02 | B |
| ATOM | 1343 | O | LEU | B | 46 | 56.477 | 29.056 | 43.982 | 1.00 34.02 | B |
| ATOM | 1344 | N | CYS | B | 47 | 56.575 | 28.130 | 46.025 | 1.00 34.11 | B |
| ATOM | 1345 | CA | CYS | B | 47 | 56.495 | 26.762 | 45.509 | 1.00 34.11 | B |

Figure 8-18

```
ATOM   1346  CB  CYS B  47      56.771  25.748  46.620  1.00 73.82      B
ATOM   1347  SG  CYS B  47      58.491  25.691  47.144  1.00 73.82      B
ATOM   1348  C   CYS B  47      55.132  26.467  44.897  1.00 34.11      B
ATOM   1349  O   CYS B  47      55.030  25.800  43.861  1.00 34.11      B
ATOM   1350  N   SER B  48      54.086  26.972  45.540  1.00 30.53      B
ATOM   1351  CA  SER B  48      52.727  26.757  45.068  1.00 30.53      B
ATOM   1352  CB  SER B  48      51.734  27.371  46.055  1.00 28.82      B
ATOM   1353  OG  SER B  48      51.984  26.926  47.380  1.00 28.82      B
ATOM   1354  C   SER B  48      52.546  27.394  43.693  1.00 30.53      B
ATOM   1355  O   SER B  48      51.934  26.811  42.791  1.00 30.53      B
ATOM   1356  N   ILE B  49      53.083  28.596  43.537  1.00 27.84      B
ATOM   1357  CA  ILE B  49      52.971  29.298  42.275  1.00 27.84      B
ATOM   1358  CB  ILE B  49      53.401  30.771  42.439  1.00 22.70      B
ATOM   1359  CG2 ILE B  49      53.243  31.526  41.113  1.00 22.70      B
ATOM   1360  CG1 ILE B  49      52.528  31.421  43.526  1.00 22.70      B
ATOM   1361  CD1 ILE B  49      53.047  32.738  44.026  1.00 22.70      B
ATOM   1362  C   ILE B  49      53.820  28.599  41.224  1.00 27.84      B
ATOM   1363  O   ILE B  49      53.382  28.402  40.092  1.00 27.84      B
ATOM   1364  N   ARG B  50      55.027  28.203  41.607  1.00 18.56      B
ATOM   1365  CA  ARG B  50      55.925  27.512  40.687  1.00 18.56      B
ATOM   1366  CB  ARG B  50      57.239  27.200  41.396  1.00 82.28      B
ATOM   1367  CG  ARG B  50      58.304  26.600  40.514  1.00 82.28      B
ATOM   1368  CD  ARG B  50      59.495  26.222  41.356  1.00 82.28      B
ATOM   1369  NE  ARG B  50      60.697  25.996  40.562  1.00 82.28      B
ATOM   1370  CZ  ARG B  50      61.877  25.682  41.088  1.00 82.28      B
ATOM   1371  NH1 ARG B  50      62.002  25.555  42.405  1.00 82.28      B
ATOM   1372  NH2 ARG B  50      62.933  25.507  40.303  1.00 82.28      B
ATOM   1373  C   ARG B  50      55.271  26.206  40.213  1.00 18.56      B
ATOM   1374  O   ARG B  50      55.241  25.893  39.014  1.00 18.56      B
ATOM   1375  N   CYS B  51      54.740  25.444  41.160  1.00 43.60      B
ATOM   1376  CA  CYS B  51      54.107  24.186  40.819  1.00 43.60      B
ATOM   1377  CB  CYS B  51      53.584  23.504  42.081  1.00 84.70      B
ATOM   1378  SG  CYS B  51      52.553  22.064  41.740  1.00 84.70      B
ATOM   1379  C   CYS B  51      52.961  24.398  39.826  1.00 43.60      B
ATOM   1380  O   CYS B  51      52.780  23.612  38.889  1.00 43.60      B
ATOM   1381  N   ALA B  52      52.198  25.470  40.029  1.00 31.36      B
ATOM   1382  CA  ALA B  52      51.059  25.776  39.172  1.00 31.36      B
ATOM   1383  CB  ALA B  52      50.083  26.633  39.920  1.00 17.44      B
ATOM   1384  C   ALA B  52      51.455  26.474  37.881  1.00 31.36      B
ATOM   1385  O   ALA B  52      50.676  26.510  36.931  1.00 31.36      B
ATOM   1386  N   ALA B  53      52.660  27.037  37.857  1.00 34.68      B
ATOM   1387  CA  ALA B  53      53.156  27.743  36.688  1.00 34.68      B
ATOM   1388  CB  ALA B  53      52.944  26.903  35.440  1.00 31.90      B
ATOM   1389  C   ALA B  53      52.467  29.083  36.518  1.00 34.68      B
ATOM   1390  O   ALA B  53      53.118  30.111  36.368  1.00 34.68      B
ATOM   1391  N   CYS B  54      51.142  29.058  36.567  1.00 32.06      B
ATOM   1392  CA  CYS B  54      50.316  30.245  36.368  1.00 32.06      B
ATOM   1393  CB  CYS B  54      50.058  30.370  34.872  1.00 58.96      B
ATOM   1394  SG  CYS B  54      49.247  31.838  34.359  1.00 58.96      B
ATOM   1395  C   CYS B  54      49.008  30.003  37.137  1.00 32.06      B
ATOM   1396  O   CYS B  54      48.354  28.979  36.949  1.00 32.06      B
ATOM   1397  N   ILE B  55      48.605  30.936  37.990  1.00 18.46      B
ATOM   1398  CA  ILE B  55      47.404  30.692  38.777  1.00 18.46      B
ATOM   1399  CB  ILE B  55      47.762  29.766  39.974  1.00 12.62      B
ATOM   1400  CG2 ILE B  55      48.683  30.502  40.950  1.00 12.62      B
ATOM   1401  CG1 ILE B  55      46.510  29.340  40.734  1.00 12.62      B
ATOM   1402  CD1 ILE B  55      46.796  28.230  41.760  1.00 12.62      B
ATOM   1403  C   ILE B  55      46.739  31.963  39.302  1.00 18.46      B
ATOM   1404  O   ILE B  55      47.411  32.961  39.598  1.00 18.46      B
ATOM   1405  N   THR B  56      45.416  31.925  39.415  1.00 29.52      B
ATOM   1406  CA  THR B  56      44.670  33.066  39.924  1.00 29.52      B
ATOM   1407  CB  THR B  56      43.196  32.976  39.544  1.00 27.79      B
ATOM   1408  OG1 THR B  56      42.613  31.853  40.213  1.00 27.79      B
ATOM   1409  CG2 THR B  56      43.041  32.806  38.039  1.00 27.79      B
ATOM   1410  C   THR B  56      44.765  33.030  41.443  1.00 29.52      B
ATOM   1411  O   THR B  56      44.974  31.964  42.033  1.00 29.52      B
ATOM   1412  N   PRO B  57      44.620  34.194  42.094  1.00 30.29      B
ATOM   1413  CD  PRO B  57      44.561  35.518  41.456  1.00 29.70      B
ATOM   1414  CA  PRO B  57      44.687  34.318  43.555  1.00 30.29      B
ATOM   1415  CB  PRO B  57      44.508  35.812  43.782  1.00 29.70      B
ATOM   1416  CG  PRO B  57      45.119  36.410  42.535  1.00 29.70      B
ATOM   1417  C   PRO B  57      43.600  33.502  44.250  1.00 30.29      B
ATOM   1418  O   PRO B  57      43.823  32.925  45.321  1.00 30.29      B
ATOM   1419  N   VAL B  58      42.420  33.461  43.641  1.00 38.22      B
ATOM   1420  CA  VAL B  58      41.319  32.713  44.221  1.00 38.22      B
```

Figure 8-19

```
ATOM   1421  CB   VAL B  58      39.996  32.966  43.435  1.00 66.42      B
ATOM   1422  CG1  VAL B  58      40.088  32.407  42.020  1.00 66.42      B
ATOM   1423  CG2  VAL B  58      38.828  32.372  44.192  1.00 66.42      B
ATOM   1424  C    VAL B  58      41.668  31.219  44.260  1.00 38.22      B
ATOM   1425  O    VAL B  58      41.516  30.572  45.295  1.00 38.22      B
ATOM   1426  N    GLU B  59      42.153  30.673  43.149  1.00 36.09      B
ATOM   1427  CA   GLU B  59      42.534  29.262  43.114  1.00 36.09      B
ATOM   1428  CB   GLU B  59      42.827  28.833  41.678  1.00 40.02      B
ATOM   1429  CG   GLU B  59      41.640  28.926  40.734  1.00 40.02      B
ATOM   1430  CD   GLU B  59      40.609  27.810  40.936  1.00 40.02      B
ATOM   1431  OE1  GLU B  59      39.800  27.876  41.895  1.00 40.02      B
ATOM   1432  OE2  GLU B  59      40.614  26.858  40.122  1.00 40.02      B
ATOM   1433  C    GLU B  59      43.776  29.002  43.991  1.00 36.09      B
ATOM   1434  O    GLU B  59      43.998  27.881  44.455  1.00 36.09      B
ATOM   1435  N    LEU B  60      44.583  30.038  44.207  1.00 32.50      B
ATOM   1436  CA   LEU B  60      45.781  29.912  45.022  1.00 32.50      B
ATOM   1437  CB   LEU B  60      46.677  31.135  44.833  1.00 29.62      B
ATOM   1438  CG   LEU B  60      47.978  31.130  45.642  1.00 29.62      B
ATOM   1439  CD1  LEU B  60      48.835  29.920  45.253  1.00 29.62      B
ATOM   1440  CD2  LEU B  60      48.732  32.435  45.385  1.00 29.62      B
ATOM   1441  C    LEU B  60      45.375  29.789  46.486  1.00 32.50      B
ATOM   1442  O    LEU B  60      45.877  28.939  47.220  1.00 32.50      B
ATOM   1443  N    LYS B  61      44.460  30.654  46.895  1.00 35.36      B
ATOM   1444  CA   LYS B  61      43.933  30.674  48.248  1.00 35.36      B
ATOM   1445  CB   LYS B  61      42.790  31.688  48.315  1.00 67.16      B
ATOM   1446  CG   LYS B  61      41.883  31.550  49.515  1.00 67.16      B
ATOM   1447  CD   LYS B  61      40.659  32.433  49.367  1.00 67.16      B
ATOM   1448  CE   LYS B  61      39.915  32.122  48.078  1.00 67.16      B
ATOM   1449  NZ   LYS B  61      39.618  30.668  47.968  1.00 67.16      B
ATOM   1450  C    LYS B  61      43.424  29.285  48.645  1.00 35.36      B
ATOM   1451  O    LYS B  61      43.628  28.835  49.778  1.00 35.36      B
ATOM   1452  N    LYS B  62      42.746  28.613  47.719  1.00 56.38      B
ATOM   1453  CA   LYS B  62      42.237  27.275  47.991  1.00 56.38      B
ATOM   1454  CB   LYS B  62      41.448  26.744  46.794  1.00 56.12      B
ATOM   1455  CG   LYS B  62      40.146  27.469  46.524  1.00 56.12      B
ATOM   1456  CD   LYS B  62      39.429  26.878  45.313  1.00 56.12      B
ATOM   1457  CE   LYS B  62      38.081  27.546  45.070  1.00 56.12      B
ATOM   1458  NZ   LYS B  62      38.199  29.033  44.949  1.00 56.12      B
ATOM   1459  C    LYS B  62      43.414  26.342  48.275  1.00 56.38      B
ATOM   1460  O    LYS B  62      43.404  25.595  49.257  1.00 56.38      B
ATOM   1461  N    VAL B  63      44.424  26.396  47.407  1.00 37.26      B
ATOM   1462  CA   VAL B  63      45.607  25.567  47.549  1.00 37.26      B
ATOM   1463  CB   VAL B  63      46.641  25.874  46.440  1.00 20.35      B
ATOM   1464  CG1  VAL B  63      48.013  25.281  46.813  1.00 20.35      B
ATOM   1465  CG2  VAL B  63      46.160  25.301  45.125  1.00 20.35      B
ATOM   1466  C    VAL B  63      46.268  25.784  48.899  1.00 37.26      B
ATOM   1467  O    VAL B  63      46.497  24.837  49.652  1.00 37.26      B
ATOM   1468  N    LEU B  64      46.568  27.037  49.203  1.00 37.82      B
ATOM   1469  CA   LEU B  64      47.230  27.377  50.454  1.00 37.82      B
ATOM   1470  CB   LEU B  64      47.786  28.800  50.381  1.00 50.74      B
ATOM   1471  CG   LEU B  64      49.053  29.018  49.560  1.00 50.74      B
ATOM   1472  CD1  LEU B  64      48.961  28.277  48.243  1.00 50.74      B
ATOM   1473  CD2  LEU B  64      49.241  30.520  49.342  1.00 50.74      B
ATOM   1474  C    LEU B  64      46.334  27.258  51.680  1.00 37.82      B
ATOM   1475  O    LEU B  64      46.819  27.268  52.814  1.00 37.82      B
ATOM   1476  N    SER B  65      45.031  27.149  51.454  1.00 47.27      B
ATOM   1477  CA   SER B  65      44.083  27.052  52.552  1.00 47.27      B
ATOM   1478  CB   SER B  65      44.261  25.729  53.302  1.00 79.02      B
ATOM   1479  OG   SER B  65      44.033  24.624  52.444  1.00 79.02      B
ATOM   1480  C    SER B  65      44.288  28.227  53.504  1.00 47.27      B
ATOM   1481  O    SER B  65      44.569  28.037  54.697  1.00 47.27      B
ATOM   1482  N    VAL B  66      44.168  29.444  52.970  1.00 24.67      B
ATOM   1483  CA   VAL B  66      44.321  30.652  53.790  1.00 24.67      B
ATOM   1484  CB   VAL B  66      45.750  31.269  53.701  1.00 43.56      B
ATOM   1485  CG1  VAL B  66      46.801  30.190  53.939  1.00 43.56      B
ATOM   1486  CG2  VAL B  66      45.948  31.969  52.346  1.00 43.56      B
ATOM   1487  C    VAL B  66      43.329  31.753  53.407  1.00 24.67      B
ATOM   1488  O    VAL B  66      42.554  31.620  52.453  1.00 24.67      B
ATOM   1489  N    ASP B  67      43.361  32.840  54.169  1.00 57.77      B
ATOM   1490  CA   ASP B  67      42.490  33.980  53.924  1.00 57.77      B
ATOM   1491  CB   ASP B  67      42.546  34.932  55.127  1.00 65.50      B
ATOM   1492  CG   ASP B  67      41.804  36.236  54.883  1.00 65.50      B
ATOM   1493  OD1  ASP B  67      40.948  36.273  53.973  1.00 65.50      B
ATOM   1494  OD2  ASP B  67      42.067  37.222  55.607  1.00 65.50      B
ATOM   1495  C    ASP B  67      42.931  34.702  52.645  1.00 57.77      B
```

Figure 8-20

| | | | | | | | | | |
|---|---|---|---|---|---|---|---|---|---|
| ATOM | 1496 | O | ASP | B | 67 | 44.105 | 35.057 | 52.504 | 1.00 57.77 | B |
| ATOM | 1497 | N | LEU | B | 68 | 41.990 | 34.912 | 51.722 | 1.00 50.58 | B |
| ATOM | 1498 | CA | LEU | B | 68 | 42.274 | 35.584 | 50.450 | 1.00 50.58 | B |
| ATOM | 1499 | CB | LEU | B | 68 | 40.999 | 35.779 | 49.625 | 1.00 44.31 | B |
| ATOM | 1500 | CG | LEU | B | 68 | 41.160 | 36.605 | 48.337 | 1.00 44.31 | B |
| ATOM | 1501 | CD1 | LEU | B | 68 | 42.422 | 36.198 | 47.587 | 1.00 44.31 | B |
| ATOM | 1502 | CD2 | LEU | B | 68 | 39.943 | 36.407 | 47.453 | 1.00 44.31 | B |
| ATOM | 1503 | C | LEU | B | 68 | 42.934 | 36.933 | 50.637 | 1.00 50.58 | B |
| ATOM | 1504 | O | LEU | B | 68 | 43.783 | 37.332 | 49.832 | 1.00 50.58 | B |
| ATOM | 1505 | N | GLY | B | 69 | 42.528 | 37.647 | 51.682 | 1.00 44.91 | B |
| ATOM | 1506 | CA | GLY | B | 69 | 43.132 | 38.936 | 51.957 | 1.00 44.91 | B |
| ATOM | 1507 | C | GLY | B | 69 | 44.561 | 38.698 | 52.404 | 1.00 44.91 | B |
| ATOM | 1508 | O | GLY | B | 69 | 45.481 | 39.391 | 51.975 | 1.00 44.91 | B |
| ATOM | 1509 | N | ALA | B | 70 | 44.753 | 37.705 | 53.264 | 1.00 46.62 | B |
| ATOM | 1510 | CA | ALA | B | 70 | 46.083 | 37.374 | 53.750 | 1.00 46.62 | B |
| ATOM | 1511 | CB | ALA | B | 70 | 46.016 | 36.136 | 54.632 | 1.00 21.93 | B |
| ATOM | 1512 | C | ALA | B | 70 | 46.988 | 37.106 | 52.552 | 1.00 46.62 | B |
| ATOM | 1513 | O | ALA | B | 70 | 48.123 | 37.609 | 52.482 | 1.00 46.62 | B |
| ATOM | 1514 | N | LEU | B | 71 | 46.472 | 36.304 | 51.619 | 1.00 61.44 | B |
| ATOM | 1515 | CA | LEU | B | 71 | 47.207 | 35.931 | 50.411 | 1.00 61.44 | B |
| ATOM | 1516 | CB | LEU | B | 71 | 46.366 | 35.019 | 49.505 | 1.00 24.15 | B |
| ATOM | 1517 | CG | LEU | B | 71 | 47.104 | 34.526 | 48.251 | 1.00 24.15 | B |
| ATOM | 1518 | CD1 | LEU | B | 71 | 48.421 | 33.875 | 48.657 | 1.00 24.15 | B |
| ATOM | 1519 | CD2 | LEU | B | 71 | 46.241 | 33.525 | 47.488 | 1.00 24.15 | B |
| ATOM | 1520 | C | LEU | B | 71 | 47.581 | 37.168 | 49.631 | 1.00 61.44 | B |
| ATOM | 1521 | O | LEU | B | 71 | 48.746 | 37.375 | 49.281 | 1.00 61.44 | B |
| ATOM | 1522 | N | THR | B | 72 | 46.570 | 37.984 | 49.357 | 1.00 48.36 | B |
| ATOM | 1523 | CA | THR | B | 72 | 46.765 | 39.213 | 48.612 | 1.00 48.36 | B |
| ATOM | 1524 | CB | THR | B | 72 | 45.493 | 40.033 | 48.585 | 1.00 28.65 | B |
| ATOM | 1525 | OG1 | THR | B | 72 | 44.508 | 39.340 | 47.811 | 1.00 28.65 | B |
| ATOM | 1526 | CG2 | THR | B | 72 | 45.754 | 41.376 | 47.959 | 1.00 28.65 | B |
| ATOM | 1527 | C | THR | B | 72 | 47.891 | 40.078 | 49.160 | 1.00 48.36 | B |
| ATOM | 1528 | O | THR | B | 72 | 48.725 | 40.552 | 48.394 | 1.00 48.36 | B |
| ATOM | 1529 | N | ARG | B | 73 | 47.922 | 40.289 | 50.473 | 1.00 34.07 | B |
| ATOM | 1530 | CA | ARG | B | 73 | 48.982 | 41.104 | 51.045 | 1.00 34.07 | B |
| ATOM | 1531 | CB | ARG | B | 73 | 48.726 | 41.380 | 52.527 | 1.00 63.70 | B |
| ATOM | 1532 | CG | ARG | B | 73 | 47.497 | 42.242 | 52.771 | 1.00 63.70 | B |
| ATOM | 1533 | CD | ARG | B | 73 | 47.368 | 42.666 | 54.223 | 1.00 63.70 | B |
| ATOM | 1534 | NE | ARG | B | 73 | 46.082 | 43.311 | 54.459 | 1.00 63.70 | B |
| ATOM | 1535 | CZ | ARG | B | 73 | 44.910 | 42.685 | 54.372 | 1.00 63.70 | B |
| ATOM | 1536 | NH1 | ARG | B | 73 | 44.867 | 41.394 | 54.063 | 1.00 63.70 | B |
| ATOM | 1537 | NH2 | ARG | B | 73 | 43.777 | 43.350 | 54.578 | 1.00 63.70 | B |
| ATOM | 1538 | C | ARG | B | 73 | 50.321 | 40.417 | 50.853 | 1.00 34.07 | B |
| ATOM | 1539 | O | ARG | B | 73 | 51.337 | 41.084 | 50.649 | 1.00 34.07 | B |
| ATOM | 1540 | N | MET | B | 74 | 50.332 | 39.087 | 50.902 | 1.00 33.57 | B |
| ATOM | 1541 | CA | MET | B | 74 | 51.578 | 38.358 | 50.699 | 1.00 33.57 | B |
| ATOM | 1542 | CB | MET | B | 74 | 51.405 | 36.866 | 51.030 | 1.00 28.43 | B |
| ATOM | 1543 | CG | MET | B | 74 | 52.644 | 36.005 | 50.727 | 1.00 28.43 | B |
| ATOM | 1544 | SD | MET | B | 74 | 54.177 | 36.471 | 51.632 | 1.00 28.43 | B |
| ATOM | 1545 | CE | MET | B | 74 | 54.311 | 35.010 | 52.755 | 1.00 28.43 | B |
| ATOM | 1546 | C | MET | B | 74 | 52.020 | 38.524 | 49.240 | 1.00 33.57 | B |
| ATOM | 1547 | O | MET | B | 74 | 53.196 | 38.799 | 48.958 | 1.00 33.57 | B |
| ATOM | 1548 | N | LEU | B | 75 | 51.075 | 38.370 | 48.313 | 1.00 27.16 | B |
| ATOM | 1549 | CA | LEU | B | 75 | 51.396 | 38.502 | 46.892 | 1.00 27.16 | B |
| ATOM | 1550 | CB | LEU | B | 75 | 50.148 | 38.291 | 46.017 | 1.00 20.11 | B |
| ATOM | 1551 | CG | LEU | B | 75 | 49.595 | 36.867 | 46.001 | 1.00 20.11 | B |
| ATOM | 1552 | CD1 | LEU | B | 75 | 48.347 | 36.813 | 45.155 | 1.00 20.11 | B |
| ATOM | 1553 | CD2 | LEU | B | 75 | 50.657 | 35.910 | 45.471 | 1.00 20.11 | B |
| ATOM | 1554 | C | LEU | B | 75 | 51.986 | 39.873 | 46.617 | 1.00 27.16 | B |
| ATOM | 1555 | O | LEU | B | 75 | 52.999 | 39.991 | 45.930 | 1.00 27.16 | B |
| ATOM | 1556 | N | ASP | B | 76 | 51.353 | 40.911 | 47.155 | 1.00 33.17 | B |
| ATOM | 1557 | CA | ASP | B | 76 | 51.846 | 42.262 | 46.954 | 1.00 33.17 | B |
| ATOM | 1558 | CB | ASP | B | 76 | 50.982 | 43.275 | 47.703 | 1.00123.73 | B |
| ATOM | 1559 | CG | ASP | B | 76 | 49.670 | 43.555 | 46.993 | 1.00123.73 | B |
| ATOM | 1560 | OD1 | ASP | B | 76 | 48.815 | 42.646 | 46.923 | 1.00123.73 | B |
| ATOM | 1561 | OD2 | ASP | B | 76 | 49.496 | 44.687 | 46.494 | 1.00123.73 | B |
| ATOM | 1562 | C | ASP | B | 76 | 53.291 | 42.350 | 47.428 | 1.00 33.17 | B |
| ATOM | 1563 | O | ASP | B | 76 | 54.157 | 42.870 | 46.715 | 1.00 33.17 | B |
| ATOM | 1564 | N | ARG | B | 77 | 53.559 | 41.819 | 48.620 | 1.00 43.84 | B |
| ATOM | 1565 | CA | ARG | B | 77 | 54.909 | 41.858 | 49.165 | 1.00 43.84 | B |
| ATOM | 1566 | CB | ARG | B | 77 | 54.921 | 41.315 | 50.599 | 1.00 55.30 | B |
| ATOM | 1567 | CG | ARG | B | 77 | 54.155 | 42.179 | 51.599 | 1.00 55.30 | B |
| ATOM | 1568 | CD | ARG | B | 77 | 54.376 | 41.708 | 53.035 | 1.00 55.30 | B |
| ATOM | 1569 | NE | ARG | B | 77 | 53.743 | 40.420 | 53.322 | 1.00 55.30 | B |
| ATOM | 1570 | CZ | ARG | B | 77 | 52.461 | 40.262 | 53.657 | 1.00 55.30 | B |

Figure 8-21

```
ATOM   1571  NH1  ARG B  77      51.651  41.314  53.758  1.00 55.30      B
ATOM   1572  NH2  ARG B  77      51.979  39.042  53.885  1.00 55.30      B
ATOM   1573  C    ARG B  77      55.873  41.072  48.282  1.00 43.84      B
ATOM   1574  O    ARG B  77      57.025  41.475  48.103  1.00 43.84      B
ATOM   1575  N    LEU B  78      55.399  39.961  47.717  1.00 32.40      B
ATOM   1576  CA   LEU B  78      56.241  39.139  46.849  1.00 32.40      B
ATOM   1577  CB   LEU B  78      55.617  37.750  46.628  1.00 31.07      B
ATOM   1578  CG   LEU B  78      55.564  36.814  47.857  1.00 31.07      B
ATOM   1579  CD1  LEU B  78      54.824  35.526  47.494  1.00 31.07      B
ATOM   1580  CD2  LEU B  78      56.975  36.482  48.350  1.00 31.07      B
ATOM   1581  C    LEU B  78      56.474  39.827  45.513  1.00 32.40      B
ATOM   1582  O    LEU B  78      57.538  39.671  44.903  1.00 32.40      B
ATOM   1583  N    VAL B  79      55.486  40.585  45.046  1.00 62.46      B
ATOM   1584  CA   VAL B  79      55.641  41.298  43.781  1.00 62.46      B
ATOM   1585  CB   VAL B  79      54.293  41.884  43.283  1.00 32.18      B
ATOM   1586  CG1  VAL B  79      54.531  42.947  42.220  1.00 32.18      B
ATOM   1587  CG2  VAL B  79      53.434  40.766  42.690  1.00 32.18      B
ATOM   1588  C    VAL B  79      56.663  42.418  43.981  1.00 62.46      B
ATOM   1589  O    VAL B  79      57.467  42.702  43.089  1.00 62.46      B
ATOM   1590  N    CYS B  80      56.637  43.037  45.160  1.00 54.33      B
ATOM   1591  CA   CYS B  80      57.575  44.102  45.483  1.00 54.33      B
ATOM   1592  CB   CYS B  80      57.187  44.772  46.795  1.00 78.30      B
ATOM   1593  SG   CYS B  80      55.867  45.974  46.623  1.00 78.30      B
ATOM   1594  C    CYS B  80      59.008  43.589  45.585  1.00 54.33      B
ATOM   1595  O    CYS B  80      59.944  44.286  45.207  1.00 54.33      B
ATOM   1596  N    LYS B  81      59.189  42.376  46.096  1.00 65.17      B
ATOM   1597  CA   LYS B  81      60.530  41.825  46.217  1.00 65.17      B
ATOM   1598  CB   LYS B  81      60.546  40.660  47.213  1.00 59.31      B
ATOM   1599  CG   LYS B  81      59.864  40.991  48.543  1.00 59.31      B
ATOM   1600  CD   LYS B  81      60.115  39.938  49.612  1.00 59.31      B
ATOM   1601  CE   LYS B  81      61.515  40.062  50.192  1.00 59.31      B
ATOM   1602  NZ   LYS B  81      61.815  39.005  51.206  1.00 59.31      B
ATOM   1603  C    LYS B  81      61.015  41.367  44.847  1.00 65.17      B
ATOM   1604  O    LYS B  81      62.185  41.025  44.674  1.00 65.17      B
ATOM   1605  N    GLY B  82      60.111  41.364  43.871  1.00 29.81      B
ATOM   1606  CA   GLY B  82      60.480  40.967  42.522  1.00 29.81      B
ATOM   1607  C    GLY B  82      60.550  39.472  42.261  1.00 29.81      B
ATOM   1608  O    GLY B  82      61.260  39.037  41.346  1.00 29.81      B
ATOM   1609  N    TRP B  83      59.821  38.681  43.045  1.00 33.85      B
ATOM   1610  CA   TRP B  83      59.829  37.232  42.860  1.00 33.85      B
ATOM   1611  CB   TRP B  83      59.997  36.524  44.208  1.00 51.71      B
ATOM   1612  CG   TRP B  83      61.213  36.946  44.993  1.00 51.71      B
ATOM   1613  CD2  TRP B  83      61.436  36.753  46.399  1.00 51.71      B
ATOM   1614  CE2  TRP B  83      62.729  37.244  46.689  1.00 51.71      B
ATOM   1615  CE3  TRP B  83      60.670  36.212  47.440  1.00 51.71      B
ATOM   1616  CD1  TRP B  83      62.347  37.532  44.504  1.00 51.71      B
ATOM   1617  NE1  TRP B  83      63.262  37.713  45.517  1.00 51.71      B
ATOM   1618  CZ2  TRP B  83      63.274  37.209  47.979  1.00 51.71      B
ATOM   1619  CZ3  TRP B  83      61.215  36.178  48.727  1.00 51.71      B
ATOM   1620  CH2  TRP B  83      62.504  36.674  48.980  1.00 51.71      B
ATOM   1621  C    TRP B  83      58.539  36.744  42.180  1.00 33.85      B
ATOM   1622  O    TRP B  83      58.519  35.684  41.540  1.00 33.85      B
ATOM   1623  N    VAL B  84      57.471  37.527  42.324  1.00 31.00      B
ATOM   1624  CA   VAL B  84      56.173  37.203  41.741  1.00 31.00      B
ATOM   1625  CB   VAL B  84      55.127  36.956  42.847  1.00 24.28      B
ATOM   1626  CG1  VAL B  84      53.739  36.784  42.239  1.00 24.28      B
ATOM   1627  CG2  VAL B  84      55.508  35.728  43.645  1.00 24.28      B
ATOM   1628  C    VAL B  84      55.692  38.346  40.832  1.00 31.00      B
ATOM   1629  O    VAL B  84      55.840  39.529  41.162  1.00 31.00      B
ATOM   1630  N    GLU B  85      55.104  37.971  39.697  1.00 29.82      B
ATOM   1631  CA   GLU B  85      54.621  38.920  38.706  1.00 29.82      B
ATOM   1632  CB   GLU B  85      55.355  38.673  37.394  1.00 50.76      B
ATOM   1633  CG   GLU B  85      55.113  39.708  36.331  1.00 50.76      B
ATOM   1634  CD   GLU B  85      55.596  39.248  34.968  1.00 50.76      B
ATOM   1635  OE1  GLU B  85      55.594  40.076  34.030  1.00 50.76      B
ATOM   1636  OE2  GLU B  85      55.968  38.057  34.838  1.00 50.76      B
ATOM   1637  C    GLU B  85      53.123  38.759  38.489  1.00 29.82      B
ATOM   1638  O    GLU B  85      52.605  37.638  38.516  1.00 29.82      B
ATOM   1639  N    ARG B  86      52.425  39.875  38.280  1.00 29.70      B
ATOM   1640  CA   ARG B  86      50.976  39.854  38.034  1.00 29.70      B
ATOM   1641  CB   ARG B  86      50.269  40.980  38.782  1.00 41.84      B
ATOM   1642  CG   ARG B  86      50.075  40.752  40.245  1.00 41.84      B
ATOM   1643  CD   ARG B  86      49.029  41.718  40.769  1.00 41.84      B
ATOM   1644  NE   ARG B  86      48.848  41.623  42.215  1.00 41.84      B
ATOM   1645  CZ   ARG B  86      49.639  42.211  43.108  1.00 41.84      B
```

Figure 8-22

| | | | | | | | | | |
|---|---|---|---|---|---|---|---|---|---|
| ATOM | 1646 | NH1 | ARG | B | 86 | 50.674 | 42.947 | 42.705 | 1.00 41.84 | B |
| ATOM | 1647 | NH2 | ARG | B | 86 | 49.388 | 42.069 | 44.404 | 1.00 41.84 | B |
| ATOM | 1648 | C | ARG | B | 86 | 50.657 | 40.015 | 36.548 | 1.00 29.70 | B |
| ATOM | 1649 | O | ARG | B | 86 | 51.264 | 40.826 | 35.857 | 1.00 29.70 | B |
| ATOM | 1650 | N | LEU | B | 87 | 49.688 | 39.242 | 36.071 | 1.00 43.02 | B |
| ATOM | 1651 | CA | LEU | B | 87 | 49.270 | 39.303 | 34.673 | 1.00 43.02 | B |
| ATOM | 1652 | CB | LEU | B | 87 | 49.695 | 38.047 | 33.922 | 1.00 34.18 | B |
| ATOM | 1653 | CG | LEU | B | 87 | 51.161 | 37.829 | 33.616 | 1.00 34.18 | B |
| ATOM | 1654 | CD1 | LEU | B | 87 | 51.319 | 36.505 | 32.877 | 1.00 34.18 | B |
| ATOM | 1655 | CD2 | LEU | B | 87 | 51.673 | 38.999 | 32.779 | 1.00 34.18 | B |
| ATOM | 1656 | C | LEU | B | 87 | 47.760 | 39.421 | 34.522 | 1.00 43.02 | B |
| ATOM | 1657 | O | LEU | B | 87 | 46.993 | 38.931 | 35.356 | 1.00 43.02 | B |
| ATOM | 1658 | N | PRO | B | 88 | 47.313 | 40.072 | 33.440 | 1.00 39.72 | B |
| ATOM | 1659 | CD | PRO | B | 88 | 48.111 | 40.752 | 32.405 | 1.00 25.30 | B |
| ATOM | 1660 | CA | PRO | B | 88 | 45.875 | 40.230 | 33.190 | 1.00 39.72 | B |
| ATOM | 1661 | CB | PRO | B | 88 | 45.827 | 41.092 | 31.934 | 1.00 25.30 | B |
| ATOM | 1662 | CG | PRO | B | 88 | 47.171 | 41.810 | 31.941 | 1.00 25.30 | B |
| ATOM | 1663 | C | PRO | B | 88 | 45.366 | 38.830 | 32.885 | 1.00 39.72 | B |
| ATOM | 1664 | O | PRO | B | 88 | 45.949 | 38.145 | 32.047 | 1.00 39.72 | B |
| ATOM | 1665 | N | ASN | B | 89 | 44.308 | 38.378 | 33.546 | 1.00 30.26 | B |
| ATOM | 1666 | CA | ASN | B | 89 | 43.803 | 37.044 | 33.242 | 1.00 30.26 | B |
| ATOM | 1667 | CB | ASN | B | 89 | 42.859 | 36.566 | 34.338 | 1.00 30.59 | B |
| ATOM | 1668 | CG | ASN | B | 89 | 42.274 | 35.195 | 34.046 | 1.00 30.59 | B |
| ATOM | 1669 | OD1 | ASN | B | 89 | 41.576 | 34.630 | 34.885 | 1.00 30.59 | B |
| ATOM | 1670 | ND2 | ASN | B | 89 | 42.551 | 34.653 | 32.860 | 1.00 30.59 | B |
| ATOM | 1671 | C | ASN | B | 89 | 43.057 | 37.126 | 31.921 | 1.00 30.26 | B |
| ATOM | 1672 | O | ASN | B | 89 | 42.085 | 37.870 | 31.796 | 1.00 30.26 | B |
| ATOM | 1673 | N | PRO | B | 90 | 43.514 | 36.382 | 30.903 | 1.00 32.35 | B |
| ATOM | 1674 | CD | PRO | B | 90 | 44.768 | 35.613 | 30.819 | 1.00 35.64 | B |
| ATOM | 1675 | CA | PRO | B | 90 | 42.838 | 36.419 | 29.600 | 1.00 32.35 | B |
| ATOM | 1676 | CB | PRO | B | 90 | 43.831 | 35.716 | 28.674 | 1.00 35.64 | B |
| ATOM | 1677 | CG | PRO | B | 90 | 44.529 | 34.757 | 29.595 | 1.00 35.64 | B |
| ATOM | 1678 | C | PRO | B | 90 | 41.447 | 35.783 | 29.559 | 1.00 32.35 | B |
| ATOM | 1679 | O | PRO | B | 90 | 40.638 | 36.132 | 28.699 | 1.00 32.35 | B |
| ATOM | 1680 | N | ASN | B | 91 | 41.159 | 34.868 | 30.482 | 1.00 36.98 | B |
| ATOM | 1681 | CA | ASN | B | 91 | 39.855 | 34.199 | 30.506 | 1.00 36.98 | B |
| ATOM | 1682 | CB | ASN | B | 91 | 39.987 | 32.760 | 31.023 | 1.00 38.48 | B |
| ATOM | 1683 | CG | ASN | B | 91 | 41.044 | 31.963 | 30.280 | 1.00 38.48 | B |
| ATOM | 1684 | OD1 | ASN | B | 91 | 41.044 | 31.897 | 29.043 | 1.00 38.48 | B |
| ATOM | 1685 | ND2 | ASN | B | 91 | 41.957 | 31.346 | 31.035 | 1.00 38.48 | B |
| ATOM | 1686 | C | ASN | B | 91 | 38.844 | 34.932 | 31.381 | 1.00 36.98 | B |
| ATOM | 1687 | O | ASN | B | 91 | 37.744 | 34.426 | 31.623 | 1.00 36.98 | B |
| ATOM | 1688 | N | ASP | B | 92 | 39.215 | 36.112 | 31.872 | 1.00 42.26 | B |
| ATOM | 1689 | CA | ASP | B | 92 | 38.317 | 36.880 | 32.720 | 1.00 42.26 | B |
| ATOM | 1690 | CB | ASP | B | 92 | 38.276 | 36.281 | 34.124 | 1.00 70.87 | B |
| ATOM | 1691 | CG | ASP | B | 92 | 37.060 | 36.723 | 34.903 | 1.00 70.87 | B |
| ATOM | 1692 | OD1 | ASP | B | 92 | 35.939 | 36.530 | 34.389 | 1.00 70.87 | B |
| ATOM | 1693 | OD2 | ASP | B | 92 | 37.219 | 37.259 | 36.021 | 1.00 70.87 | B |
| ATOM | 1694 | C | ASP | B | 92 | 38.739 | 38.342 | 32.787 | 1.00 42.26 | B |
| ATOM | 1695 | O | ASP | B | 92 | 39.629 | 38.724 | 33.555 | 1.00 42.26 | B |
| ATOM | 1696 | N | LYS | B | 93 | 38.070 | 39.141 | 31.966 | 1.00 54.34 | B |
| ATOM | 1697 | CA | LYS | B | 93 | 38.290 | 40.575 | 31.834 | 1.00 54.34 | B |
| ATOM | 1698 | CB | LYS | B | 93 | 36.934 | 41.265 | 31.649 | 1.00 66.28 | B |
| ATOM | 1699 | CG | LYS | B | 93 | 37.001 | 42.673 | 31.085 | 1.00 66.28 | B |
| ATOM | 1700 | CD | LYS | B | 93 | 35.604 | 43.180 | 30.748 | 1.00 66.28 | B |
| ATOM | 1701 | CE | LYS | B | 93 | 35.651 | 44.550 | 30.100 | 1.00 66.28 | B |
| ATOM | 1702 | NZ | LYS | B | 93 | 36.332 | 45.540 | 30.977 | 1.00 66.28 | B |
| ATOM | 1703 | C | LYS | B | 93 | 39.071 | 41.265 | 32.951 | 1.00 54.34 | B |
| ATOM | 1704 | O | LYS | B | 93 | 40.190 | 41.728 | 32.736 | 1.00 54.34 | B |
| ATOM | 1705 | N | ARG | B | 94 | 38.496 | 41.326 | 34.145 | 1.00 36.91 | B |
| ATOM | 1706 | CA | ARG | B | 94 | 39.159 | 42.004 | 35.251 | 1.00 36.91 | B |
| ATOM | 1707 | CB | ARG | B | 94 | 38.131 | 42.845 | 36.008 | 1.00 45.25 | B |
| ATOM | 1708 | CG | ARG | B | 94 | 37.482 | 43.880 | 35.114 | 1.00 45.25 | B |
| ATOM | 1709 | CD | ARG | B | 94 | 36.332 | 44.580 | 35.794 | 1.00 45.25 | B |
| ATOM | 1710 | NE | ARG | B | 94 | 35.640 | 45.503 | 34.893 | 1.00 45.25 | B |
| ATOM | 1711 | CZ | ARG | B | 94 | 36.204 | 46.569 | 34.325 | 1.00 45.25 | B |
| ATOM | 1712 | NH1 | ARG | B | 94 | 37.482 | 46.864 | 34.554 | 1.00 45.25 | B |
| ATOM | 1713 | NH2 | ARG | B | 94 | 35.481 | 47.351 | 33.531 | 1.00 45.25 | B |
| ATOM | 1714 | C | ARG | B | 94 | 39.944 | 41.126 | 36.221 | 1.00 36.91 | B |
| ATOM | 1715 | O | ARG | B | 94 | 40.325 | 41.576 | 37.303 | 1.00 36.91 | B |
| ATOM | 1716 | N | GLY | B | 95 | 40.207 | 39.882 | 35.838 | 1.00 47.16 | B |
| ATOM | 1717 | CA | GLY | B | 95 | 40.967 | 39.010 | 36.717 | 1.00 47.16 | B |
| ATOM | 1718 | C | GLY | B | 95 | 42.467 | 39.094 | 36.477 | 1.00 47.16 | B |
| ATOM | 1719 | O | GLY | B | 95 | 42.920 | 39.707 | 35.516 | 1.00 47.16 | B |
| ATOM | 1720 | N | VAL | B | 96 | 43.250 | 38.491 | 37.360 | 1.00 27.95 | B |

Figure 8-23

```
ATOM   1721  CA   VAL B  96      44.698  38.490  37.197  1.00 27.95      B
ATOM   1722  CB   VAL B  96      45.409  39.413  38.197  1.00 23.13      B
ATOM   1723  CG1  VAL B  96      44.808  40.802  38.149  1.00 23.13      B
ATOM   1724  CG2  VAL B  96      45.330  38.820  39.583  1.00 23.13      B
ATOM   1725  C    VAL B  96      45.252  37.101  37.433  1.00 27.95      B
ATOM   1726  O    VAL B  96      44.616  36.253  38.054  1.00 27.95      B
ATOM   1727  N    LEU B  97      46.445  36.872  36.915  1.00 27.10      B
ATOM   1728  CA   LEU B  97      47.118  35.605  37.107  1.00 27.10      B
ATOM   1729  CB   LEU B  97      47.356  34.880  35.778  1.00 15.99      B
ATOM   1730  CG   LEU B  97      46.199  34.238  35.001  1.00 15.99      B
ATOM   1731  CD1  LEU B  97      46.712  33.848  33.610  1.00 15.99      B
ATOM   1732  CD2  LEU B  97      45.656  33.011  35.748  1.00 15.99      B
ATOM   1733  C    LEU B  97      48.455  35.975  37.718  1.00 27.10      B
ATOM   1734  O    LEU B  97      48.999  37.058  37.447  1.00 27.10      B
ATOM   1735  N    VAL B  98      48.972  35.098  38.567  1.00 24.64      B
ATOM   1736  CA   VAL B  98      50.268  35.346  39.165  1.00 24.64      B
ATOM   1737  CB   VAL B  98      50.197  35.434  40.709  1.00 17.53      B
ATOM   1738  CG1  VAL B  98      49.701  36.806  41.128  1.00 17.53      B
ATOM   1739  CG2  VAL B  98      49.287  34.345  41.244  1.00 17.53      B
ATOM   1740  C    VAL B  98      51.187  34.211  38.772  1.00 24.64      B
ATOM   1741  O    VAL B  98      50.752  33.060  38.629  1.00 24.64      B
ATOM   1742  N    LYS B  99      52.452  34.550  38.569  1.00 25.92      B
ATOM   1743  CA   LYS B  99      53.450  33.565  38.216  1.00 25.92      B
ATOM   1744  CB   LYS B  99      53.527  33.410  36.707  1.00 28.24      B
ATOM   1745  CG   LYS B  99      54.279  34.520  36.008  1.00 28.24      B
ATOM   1746  CD   LYS B  99      54.341  34.259  34.515  1.00 28.24      B
ATOM   1747  CE   LYS B  99      55.558  34.910  33.911  1.00 28.24      B
ATOM   1748  NZ   LYS B  99      56.805  34.299  34.459  1.00 28.24      B
ATOM   1749  C    LYS B  99      54.768  34.084  38.783  1.00 25.92      B
ATOM   1750  O    LYS B  99      54.852  35.237  39.226  1.00 25.92      B
ATOM   1751  N    LEU B 100      55.791  33.242  38.801  1.00 23.47      B
ATOM   1752  CA   LEU B 100      57.064  33.678  39.342  1.00 23.47      B
ATOM   1753  CB   LEU B 100      57.900  32.476  39.796  1.00 16.95      B
ATOM   1754  CG   LEU B 100      57.355  31.635  40.952  1.00 16.95      B
ATOM   1755  CD1  LEU B 100      58.353  30.573  41.322  1.00 16.95      B
ATOM   1756  CD2  LEU B 100      57.101  32.522  42.152  1.00 16.95      B
ATOM   1757  C    LEU B 100      57.823  34.449  38.279  1.00 23.47      B
ATOM   1758  O    LEU B 100      57.671  34.181  37.082  1.00 23.47      B
ATOM   1759  N    THR B 101      58.616  35.421  38.724  1.00 21.01      B
ATOM   1760  CA   THR B 101      59.438  36.222  37.833  1.00 21.01      B
ATOM   1761  CB   THR B 101      59.763  37.573  38.446  1.00 28.80      B
ATOM   1762  OG1  THR B 101      60.482  37.365  39.667  1.00 28.80      B
ATOM   1763  CG2  THR B 101      58.494  38.341  38.742  1.00 28.80      B
ATOM   1764  C    THR B 101      60.723  35.427  37.750  1.00 21.01      B
ATOM   1765  O    THR B 101      60.891  34.459  38.488  1.00 21.01      B
ATOM   1766  N    THR B 102      61.629  35.826  36.865  1.00 29.71      B
ATOM   1767  CA   THR B 102      62.906  35.124  36.717  1.00 29.71      B
ATOM   1768  CB   THR B 102      63.881  35.908  35.818  1.00 48.84      B
ATOM   1769  OG1  THR B 102      63.233  36.248  34.585  1.00 48.84      B
ATOM   1770  CG2  THR B 102      65.122  35.070  35.528  1.00 48.84      B
ATOM   1771  C    THR B 102      63.566  34.983  38.081  1.00 29.71      B
ATOM   1772  O    THR B 102      63.982  33.898  38.477  1.00 29.71      B
ATOM   1773  N    GLY B 103      63.654  36.107  38.783  1.00 40.41      B
ATOM   1774  CA   GLY B 103      64.266  36.131  40.096  1.00 40.41      B
ATOM   1775  C    GLY B 103      63.611  35.177  41.061  1.00 40.41      B
ATOM   1776  O    GLY B 103      64.295  34.412  41.743  1.00 40.41      B
ATOM   1777  N    GLY B 104      62.284  35.225  41.122  1.00 39.22      B
ATOM   1778  CA   GLY B 104      61.557  34.341  42.015  1.00 39.22      B
ATOM   1779  C    GLY B 104      61.868  32.872  41.781  1.00 39.22      B
ATOM   1780  O    GLY B 104      62.178  32.140  42.717  1.00 39.22      B
ATOM   1781  N    ALA B 105      61.798  32.437  40.528  1.00 35.18      B
ATOM   1782  CA   ALA B 105      62.072  31.041  40.198  1.00 35.18      B
ATOM   1783  CB   ALA B 105      61.925  30.811  38.696  1.00  1.00      B
ATOM   1784  C    ALA B 105      63.470  30.649  40.644  1.00 35.18      B
ATOM   1785  O    ALA B 105      63.693  29.529  41.104  1.00 35.18      B
ATOM   1786  N    ALA B 106      64.403  31.585  40.497  1.00 35.53      B
ATOM   1787  CA   ALA B 106      65.797  31.382  40.868  1.00 35.53      B
ATOM   1788  CB   ALA B 106      66.624  32.565  40.420  1.00  9.21      B
ATOM   1789  C    ALA B 106      65.901  31.217  42.368  1.00 35.53      B
ATOM   1790  O    ALA B 106      66.643  30.370  42.855  1.00 35.53      B
ATOM   1791  N    ILE B 107      65.162  32.039  43.102  1.00 27.57      B
ATOM   1792  CA   ILE B 107      65.173  31.948  44.559  1.00 27.57      B
ATOM   1793  CB   ILE B 107      64.166  32.933  45.212  1.00 42.27      B
ATOM   1794  CG2  ILE B 107      64.085  32.674  46.715  1.00 42.27      B
ATOM   1795  CG1  ILE B 107      64.598  34.377  44.951  1.00 42.27      B
```

Figure 8-24

```
ATOM   1796  CD1 ILE B 107      65.995  34.708  45.459  1.00 42.27      B
ATOM   1797  C   ILE B 107      64.758  30.531  44.926  1.00 27.57      B
ATOM   1798  O   ILE B 107      65.406  29.868  45.739  1.00 27.57      B
ATOM   1799  N   CYS B 108      63.676  30.069  44.307  1.00 33.42      B
ATOM   1800  CA  CYS B 108      63.186  28.726  44.581  1.00 33.42      B
ATOM   1801  CB  CYS B 108      61.964  28.402  43.725  1.00 38.41      B
ATOM   1802  SG  CYS B 108      60.451  28.849  44.535  1.00 38.41      B
ATOM   1803  C   CYS B 108      64.243  27.673  44.343  1.00 33.42      B
ATOM   1804  O   CYS B 108      64.538  26.873  45.231  1.00 33.42      B
ATOM   1805  N   GLU B 109      64.810  27.668  43.142  1.00 37.97      B
ATOM   1806  CA  GLU B 109      65.818  26.678  42.835  1.00 37.97      B
ATOM   1807  CB  GLU B 109      66.343  26.854  41.412  1.00 73.89      B
ATOM   1808  CG  GLU B 109      67.143  25.648  40.926  1.00 73.89      B
ATOM   1809  CD  GLU B 109      66.377  24.325  41.060  1.00 73.89      B
ATOM   1810  OE1 GLU B 109      66.989  23.259  40.830  1.00 73.89      B
ATOM   1811  OE2 GLU B 109      65.167  24.344  41.391  1.00 73.89      B
ATOM   1812  C   GLU B 109      66.959  26.763  43.843  1.00 37.97      B
ATOM   1813  O   GLU B 109      67.442  25.740  44.323  1.00 37.97      B
ATOM   1814  N   GLN B 110      67.365  27.985  44.182  1.00 42.51      B
ATOM   1815  CA  GLN B 110      68.450  28.208  45.135  1.00 42.51      B
ATOM   1816  CB  GLN B 110      68.719  29.709  45.300  1.00 63.33      B
ATOM   1817  CG  GLN B 110      69.443  30.355  44.133  1.00 63.33      B
ATOM   1818  CD  GLN B 110      70.799  30.905  44.534  1.00 63.33      B
ATOM   1819  OE1 GLN B 110      70.893  31.775  45.403  1.00 63.33      B
ATOM   1820  NE2 GLN B 110      71.861  30.397  43.904  1.00 63.33      B
ATOM   1821  C   GLN B 110      68.151  27.597  46.501  1.00 42.51      B
ATOM   1822  O   GLN B 110      69.008  26.952  47.100  1.00 42.51      B
ATOM   1823  N   CYS B 111      66.941  27.806  47.004  1.00 43.30      B
ATOM   1824  CA  CYS B 111      66.581  27.247  48.294  1.00 43.30      B
ATOM   1825  CB  CYS B 111      65.213  27.750  48.721  1.00 38.30      B
ATOM   1826  SG  CYS B 111      65.269  29.469  49.201  1.00 38.30      B
ATOM   1827  C   CYS B 111      66.598  25.724  48.277  1.00 43.30      B
ATOM   1828  O   CYS B 111      67.238  25.104  49.124  1.00 43.30      B
ATOM   1829  N   HIS B 112      65.903  25.120  47.316  1.00 88.21      B
ATOM   1830  CA  HIS B 112      65.861  23.664  47.220  1.00 88.21      B
ATOM   1831  CB  HIS B 112      65.104  23.229  45.964  1.00 61.47      B
ATOM   1832  CG  HIS B 112      63.620  23.414  46.053  1.00 61.47      B
ATOM   1833  CD2 HIS B 112      62.772  24.180  45.327  1.00 61.47      B
ATOM   1834  ND1 HIS B 112      62.842  22.754  46.980  1.00 61.47      B
ATOM   1835  CE1 HIS B 112      61.578  23.106  46.822  1.00 61.47      B
ATOM   1836  NE2 HIS B 112      61.509  23.970  45.825  1.00 61.47      B
ATOM   1837  C   HIS B 112      67.269  23.098  47.172  1.00 88.21      B
ATOM   1838  O   HIS B 112      67.545  22.030  47.718  1.00 88.21      B
ATOM   1839  N   GLN B 113      68.156  23.843  46.522  1.00 61.47      B
ATOM   1840  CA  GLN B 113      69.546  23.451  46.343  1.00 61.47      B
ATOM   1841  CB  GLN B 113      70.184  24.349  45.280  1.00104.41      B
ATOM   1842  CG  GLN B 113      71.604  23.972  44.906  1.00104.41      B
ATOM   1843  CD  GLN B 113      71.674  22.689  44.100  1.00104.41      B
ATOM   1844  OE1 GLN B 113      71.223  21.631  44.548  1.00104.41      B
ATOM   1845  NE2 GLN B 113      72.245  22.775  42.902  1.00104.41      B
ATOM   1846  C   GLN B 113      70.410  23.483  47.607  1.00 61.47      B
ATOM   1847  O   GLN B 113      71.276  22.624  47.792  1.00 61.47      B
ATOM   1848  N   LEU B 114      70.184  24.468  48.472  1.00 73.58      B
ATOM   1849  CA  LEU B 114      70.991  24.592  49.680  1.00 73.58      B
ATOM   1850  CB  LEU B 114      71.600  25.997  49.761  1.00 50.36      B
ATOM   1851  CG  LEU B 114      71.926  26.724  48.445  1.00 50.36      B
ATOM   1852  CD1 LEU B 114      72.690  28.017  48.745  1.00 50.36      B
ATOM   1853  CD2 LEU B 114      72.742  25.817  47.529  1.00 50.36      B
ATOM   1854  C   LEU B 114      70.215  24.309  50.955  1.00 73.58      B
ATOM   1855  O   LEU B 114      70.520  24.869  52.006  1.00 73.58      B
ATOM   1856  N   VAL B 115      69.218  23.436  50.871  1.00 50.97      B
ATOM   1857  CA  VAL B 115      68.413  23.100  52.040  1.00 50.97      B
ATOM   1858  CB  VAL B 115      67.269  24.127  52.255  1.00 93.44      B
ATOM   1859  CG1 VAL B 115      66.397  23.698  53.419  1.00 93.44      B
ATOM   1860  CG2 VAL B 115      67.841  25.512  52.523  1.00 93.44      B
ATOM   1861  C   VAL B 115      67.797  21.717  51.894  1.00 50.97      B
ATOM   1862  O   VAL B 115      67.458  21.072  52.885  1.00 50.97      B
ATOM   1863  N   GLY B 116      67.657  21.265  50.653  1.00 40.00      B
ATOM   1864  CA  GLY B 116      67.062  19.964  50.401  1.00 40.00      B
ATOM   1865  C   GLY B 116      67.715  18.821  51.152  1.00 40.00      B
ATOM   1866  O   GLY B 116      67.045  18.088  51.892  1.00 40.00      B
ATOM   1867  N   GLN B 117      69.024  18.663  50.963  1.00 36.16      B
ATOM   1868  CA  GLN B 117      69.751  17.593  51.630  1.00 36.16      B
ATOM   1869  CB  GLN B 117      71.205  17.564  51.150  1.00 97.53      B
ATOM   1870  CG  GLN B 117      71.382  16.732  49.894  1.00 97.53      B
```

Figure 8-25

| ATOM | 1871 | CD  | GLN B 117 | 70.848 | 15.326 | 50.086 | 1.00 | 97.53 | B |
|------|------|-----|-----------|--------|--------|--------|------|-------|---|
| ATOM | 1872 | OE1 | GLN B 117 | 71.406 | 14.542 | 50.853 | 1.00 | 97.53 | B |
| ATOM | 1873 | NE2 | GLN B 117 | 69.750 | 15.008 | 49.407 | 1.00 | 97.53 | B |
| ATOM | 1874 | C   | GLN B 117 | 69.685 | 17.695 | 53.149 | 1.00 | 36.16 | B |
| ATOM | 1875 | O   | GLN B 117 | 69.240 | 16.762 | 53.818 | 1.00 | 36.16 | B |
| ATOM | 1876 | N   | ASP B 118 | 70.115 | 18.831 | 53.689 | 1.00 | 45.11 | B |
| ATOM | 1877 | CA  | ASP B 118 | 70.094 | 19.051 | 55.128 | 1.00 | 45.11 | B |
| ATOM | 1878 | CB  | ASP B 118 | 70.466 | 20.497 | 55.422 | 1.00 | 63.00 | B |
| ATOM | 1879 | CG  | ASP B 118 | 71.856 | 20.847 | 54.934 | 1.00 | 63.00 | B |
| ATOM | 1880 | OD1 | ASP B 118 | 72.217 | 22.046 | 54.974 | 1.00 | 63.00 | B |
| ATOM | 1881 | OD2 | ASP B 118 | 72.587 | 19.919 | 54.514 | 1.00 | 63.00 | B |
| ATOM | 1882 | C   | ASP B 118 | 68.722 | 18.741 | 55.725 | 1.00 | 45.11 | B |
| ATOM | 1883 | O   | ASP B 118 | 68.607 | 18.024 | 56.720 | 1.00 | 45.11 | B |
| ATOM | 1884 | N   | LEU B 119 | 67.676 | 19.270 | 55.104 | 1.00 | 38.08 | B |
| ATOM | 1885 | CA  | LEU B 119 | 66.332 | 19.055 | 55.602 | 1.00 | 38.08 | B |
| ATOM | 1886 | CB  | LEU B 119 | 65.329 | 19.879 | 54.790 | 1.00 | 55.08 | B |
| ATOM | 1887 | CG  | LEU B 119 | 63.895 | 19.822 | 55.327 | 1.00 | 55.08 | B |
| ATOM | 1888 | CD1 | LEU B 119 | 63.893 | 20.275 | 56.778 | 1.00 | 55.08 | B |
| ATOM | 1889 | CD2 | LEU B 119 | 62.978 | 20.693 | 54.486 | 1.00 | 55.08 | B |
| ATOM | 1890 | C   | LEU B 119 | 65.954 | 17.586 | 55.549 | 1.00 | 38.08 | B |
| ATOM | 1891 | O   | LEU B 119 | 65.353 | 17.046 | 56.484 | 1.00 | 38.08 | B |
| ATOM | 1892 | N   | HIS B 120 | 66.312 | 16.934 | 54.452 | 1.00 | 37.90 | B |
| ATOM | 1893 | CA  | HIS B 120 | 65.982 | 15.534 | 54.284 | 1.00 | 37.90 | B |
| ATOM | 1894 | CB  | HIS B 120 | 66.324 | 15.107 | 52.866 | 1.00 | 44.03 | B |
| ATOM | 1895 | CG  | HIS B 120 | 65.762 | 13.777 | 52.491 | 1.00 | 44.03 | B |
| ATOM | 1896 | CD2 | HIS B 120 | 64.508 | 13.407 | 52.138 | 1.00 | 44.03 | B |
| ATOM | 1897 | ND1 | HIS B 120 | 66.519 | 12.626 | 52.477 | 1.00 | 44.03 | B |
| ATOM | 1898 | CE1 | HIS B 120 | 65.757 | 11.604 | 52.132 | 1.00 | 44.03 | B |
| ATOM | 1899 | NE2 | HIS B 120 | 64.531 | 12.050 | 51.921 | 1.00 | 44.03 | B |
| ATOM | 1900 | C   | HIS B 120 | 66.723 | 14.680 | 55.308 | 1.00 | 37.90 | B |
| ATOM | 1901 | O   | HIS B 120 | 66.182 | 13.704 | 55.831 | 1.00 | 37.90 | B |
| ATOM | 1902 | N   | GLN B 121 | 67.956 | 15.074 | 55.606 | 1.00 | 42.58 | B |
| ATOM | 1903 | CA  | GLN B 121 | 68.785 | 14.362 | 56.563 | 1.00 | 42.58 | B |
| ATOM | 1904 | CB  | GLN B 121 | 70.195 | 14.959 | 56.555 | 1.00 | 84.48 | B |
| ATOM | 1905 | CG  | GLN B 121 | 71.264 | 14.100 | 57.206 | 1.00 | 84.48 | B |
| ATOM | 1906 | CD  | GLN B 121 | 72.658 | 14.658 | 56.985 | 1.00 | 84.48 | B |
| ATOM | 1907 | OE1 | GLN B 121 | 73.047 | 14.951 | 55.852 | 1.00 | 84.48 | B |
| ATOM | 1908 | NE2 | GLN B 121 | 73.419 | 14.804 | 58.064 | 1.00 | 84.48 | B |
| ATOM | 1909 | C   | GLN B 121 | 68.168 | 14.467 | 57.957 | 1.00 | 42.58 | B |
| ATOM | 1910 | O   | GLN B 121 | 67.945 | 13.449 | 58.618 | 1.00 | 42.58 | B |
| ATOM | 1911 | N   | GLU B 122 | 67.885 | 15.696 | 58.392 | 1.00 | 47.08 | B |
| ATOM | 1912 | CA  | GLU B 122 | 67.299 | 15.949 | 59.709 | 1.00 | 47.08 | B |
| ATOM | 1913 | CB  | GLU B 122 | 67.150 | 17.456 | 59.935 | 1.00 | 73.03 | B |
| ATOM | 1914 | CG  | GLU B 122 | 68.154 | 18.027 | 60.913 | 1.00 | 73.03 | B |
| ATOM | 1915 | CD  | GLU B 122 | 67.966 | 17.476 | 62.312 | 1.00 | 73.03 | B |
| ATOM | 1916 | OE1 | GLU B 122 | 66.934 | 17.789 | 62.944 | 1.00 | 73.03 | B |
| ATOM | 1917 | OE2 | GLU B 122 | 68.847 | 16.722 | 62.777 | 1.00 | 73.03 | B |
| ATOM | 1918 | C   | GLU B 122 | 65.944 | 15.271 | 59.913 | 1.00 | 47.08 | B |
| ATOM | 1919 | O   | GLU B 122 | 65.693 | 14.664 | 60.959 | 1.00 | 47.08 | B |
| ATOM | 1920 | N   | LEU B 123 | 65.068 | 15.385 | 58.917 | 1.00 | 59.13 | B |
| ATOM | 1921 | CA  | LEU B 123 | 63.745 | 14.783 | 59.000 | 1.00 | 59.13 | B |
| ATOM | 1922 | CB  | LEU B 123 | 62.905 | 15.155 | 57.776 | 1.00 | 52.32 | B |
| ATOM | 1923 | CG  | LEU B 123 | 62.127 | 16.471 | 57.797 | 1.00 | 52.32 | B |
| ATOM | 1924 | CD1 | LEU B 123 | 61.355 | 16.622 | 56.488 | 1.00 | 52.32 | B |
| ATOM | 1925 | CD2 | LEU B 123 | 61.173 | 16.482 | 58.979 | 1.00 | 52.32 | B |
| ATOM | 1926 | C   | LEU B 123 | 63.787 | 13.266 | 59.117 | 1.00 | 59.13 | B |
| ATOM | 1927 | O   | LEU B 123 | 63.037 | 12.682 | 59.901 | 1.00 | 59.13 | B |
| ATOM | 1928 | N   | THR B 124 | 64.664 | 12.631 | 58.341 | 1.00 | 49.05 | B |
| ATOM | 1929 | CA  | THR B 124 | 64.768 | 11.174 | 58.341 | 1.00 | 49.05 | B |
| ATOM | 1930 | CB  | THR B 124 | 64.987 | 10.639 | 56.911 | 1.00 | 64.49 | B |
| ATOM | 1931 | OG1 | THR B 124 | 66.173 | 11.221 | 56.363 | 1.00 | 64.49 | B |
| ATOM | 1932 | CG2 | THR B 124 | 63.813 | 10.993 | 56.019 | 1.00 | 64.49 | B |
| ATOM | 1933 | C   | THR B 124 | 65.862 | 10.589 | 59.233 | 1.00 | 49.05 | B |
| ATOM | 1934 | O   | THR B 124 | 66.059 |  9.370 | 59.255 | 1.00 | 49.05 | B |
| ATOM | 1935 | N   | LYS B 125 | 66.560 | 11.444 | 59.978 | 1.00 | 66.45 | B |
| ATOM | 1936 | CA  | LYS B 125 | 67.642 | 10.982 | 60.843 | 1.00 | 66.45 | B |
| ATOM | 1937 | CB  | LYS B 125 | 68.193 | 12.143 | 61.671 | 1.00 | 68.58 | B |
| ATOM | 1938 | CG  | LYS B 125 | 67.284 | 12.598 | 62.794 | 1.00 | 68.58 | B |
| ATOM | 1939 | CD  | LYS B 125 | 67.964 | 13.659 | 63.645 | 1.00 | 68.58 | B |
| ATOM | 1940 | CE  | LYS B 125 | 67.083 | 14.099 | 64.803 | 1.00 | 68.58 | B |
| ATOM | 1941 | NZ  | LYS B 125 | 67.767 | 15.137 | 65.628 | 1.00 | 68.58 | B |
| ATOM | 1942 | C   | LYS B 125 | 67.248 |  9.835 | 61.778 | 1.00 | 66.45 | B |
| ATOM | 1943 | O   | LYS B 125 | 68.114 |  9.148 | 62.316 | 1.00 | 66.45 | B |
| ATOM | 1944 | N   | ASN B 126 | 65.950 |  9.628 | 61.973 | 1.00 | 53.40 | B |
| ATOM | 1945 | CA  | ASN B 126 | 65.480 |  8.560 | 62.853 | 1.00 | 53.40 | B |

Figure 8-26

| | | | | | | | | | |
|---|---|---|---|---|---|---|---|---|---|
| ATOM | 1946 | CB | ASN | B | 126 | 64.369 | 9.077 | 63.777 | 1.00 70.54 | B |
| ATOM | 1947 | CG | ASN | B | 126 | 64.877 | 10.066 | 64.818 | 1.00 70.54 | B |
| ATOM | 1948 | OD1 | ASN | B | 126 | 64.086 | 10.728 | 65.494 | 1.00 70.54 | B |
| ATOM | 1949 | ND2 | ASN | B | 126 | 66.196 | 10.162 | 64.958 | 1.00 70.54 | B |
| ATOM | 1950 | C | ASN | B | 126 | 64.952 | 7.373 | 62.058 | 1.00 53.40 | B |
| ATOM | 1951 | O | ASN | B | 126 | 64.430 | 6.418 | 62.632 | 1.00 53.40 | B |
| ATOM | 1952 | N | LEU | B | 127 | 65.090 | 7.433 | 60.738 | 1.00 70.93 | B |
| ATOM | 1953 | CA | LEU | B | 127 | 64.601 | 6.361 | 59.884 | 1.00 70.93 | B |
| ATOM | 1954 | CB | LEU | B | 127 | 63.448 | 6.860 | 59.008 | 1.00 58.67 | B |
| ATOM | 1955 | CG | LEU | B | 127 | 62.158 | 7.291 | 59.707 | 1.00 58.67 | B |
| ATOM | 1956 | CD1 | LEU | B | 127 | 61.174 | 7.793 | 58.668 | 1.00 58.67 | B |
| ATOM | 1957 | CD2 | LEU | B | 127 | 61.565 | 6.126 | 60.480 | 1.00 58.67 | B |
| ATOM | 1958 | C | LEU | B | 127 | 65.671 | 5.771 | 58.985 | 1.00 70.93 | B |
| ATOM | 1959 | O | LEU | B | 127 | 66.562 | 6.473 | 58.512 | 1.00 70.93 | B |
| ATOM | 1960 | N | THR | B | 128 | 65.567 | 4.469 | 58.749 | 1.00 75.76 | B |
| ATOM | 1961 | CA | THR | B | 128 | 66.500 | 3.769 | 57.884 | 1.00 75.76 | B |
| ATOM | 1962 | CB | THR | B | 128 | 66.343 | 2.258 | 58.021 | 1.00 67.91 | B |
| ATOM | 1963 | OG1 | THR | B | 128 | 65.106 | 1.854 | 57.417 | 1.00 67.91 | B |
| ATOM | 1964 | CG2 | THR | B | 128 | 66.330 | 1.863 | 59.495 | 1.00 67.91 | B |
| ATOM | 1965 | C | THR | B | 128 | 66.138 | 4.157 | 56.457 | 1.00 75.76 | B |
| ATOM | 1966 | O | THR | B | 128 | 65.112 | 4.795 | 56.224 | 1.00 75.76 | B |
| ATOM | 1967 | N | ALA | B | 129 | 66.970 | 3.767 | 55.502 | 1.00 76.39 | B |
| ATOM | 1968 | CA | ALA | B | 129 | 66.711 | 4.090 | 54.107 | 1.00 76.39 | B |
| ATOM | 1969 | CB | ALA | B | 129 | 67.891 | 3.657 | 53.249 | 1.00 63.22 | B |
| ATOM | 1970 | C | ALA | B | 129 | 65.431 | 3.411 | 53.623 | 1.00 76.39 | B |
| ATOM | 1971 | O | ALA | B | 129 | 64.695 | 3.960 | 52.801 | 1.00 76.39 | B |
| ATOM | 1972 | N | ASP | B | 130 | 65.167 | 2.217 | 54.141 | 1.00 80.92 | B |
| ATOM | 1973 | CA | ASP | B | 130 | 63.983 | 1.464 | 53.743 | 1.00 80.92 | B |
| ATOM | 1974 | CB | ASP | B | 130 | 64.112 | 0.000 | 54.179 | 1.00118.02 | B |
| ATOM | 1975 | CG | ASP | B | 130 | 65.261 | -0.716 | 53.487 | 1.00118.02 | B |
| ATOM | 1976 | OD1 | ASP | B | 130 | 66.425 | -0.317 | 53.701 | 1.00118.02 | B |
| ATOM | 1977 | OD2 | ASP | B | 130 | 65.002 | -1.673 | 52.726 | 1.00118.02 | B |
| ATOM | 1978 | C | ASP | B | 130 | 62.700 | 2.059 | 54.301 | 1.00 80.92 | B |
| ATOM | 1979 | O | ASP | B | 130 | 61.682 | 2.108 | 53.609 | 1.00 80.92 | B |
| ATOM | 1980 | N | GLU | B | 131 | 62.748 | 2.505 | 55.552 | 1.00 71.60 | B |
| ATOM | 1981 | CA | GLU | B | 131 | 61.575 | 3.102 | 56.180 | 1.00 71.60 | B |
| ATOM | 1982 | CB | GLU | B | 131 | 61.865 | 3.406 | 57.657 | 1.00 50.30 | B |
| ATOM | 1983 | CG | GLU | B | 131 | 62.214 | 2.161 | 58.462 | 1.00 50.30 | B |
| ATOM | 1984 | CD | GLU | B | 131 | 62.588 | 2.448 | 59.915 | 1.00 50.30 | B |
| ATOM | 1985 | OE1 | GLU | B | 131 | 63.536 | 3.232 | 60.154 | 1.00 50.30 | B |
| ATOM | 1986 | OE2 | GLU | B | 131 | 61.938 | 1.872 | 60.822 | 1.00 50.30 | B |
| ATOM | 1987 | C | GLU | B | 131 | 61.216 | 4.376 | 55.416 | 1.00 71.60 | B |
| ATOM | 1988 | O | GLU | B | 131 | 60.043 | 4.651 | 55.156 | 1.00 71.60 | B |
| ATOM | 1989 | N | VAL | B | 132 | 62.242 | 5.133 | 55.038 | 1.00 47.01 | B |
| ATOM | 1990 | CA | VAL | B | 132 | 62.070 | 6.375 | 54.292 | 1.00 47.01 | B |
| ATOM | 1991 | CB | VAL | B | 132 | 63.434 | 7.031 | 53.979 | 1.00 59.53 | B |
| ATOM | 1992 | CG1 | VAL | B | 132 | 63.236 | 8.246 | 53.086 | 1.00 59.53 | B |
| ATOM | 1993 | CG2 | VAL | B | 132 | 64.131 | 7.427 | 55.273 | 1.00 59.53 | B |
| ATOM | 1994 | C | VAL | B | 132 | 61.342 | 6.146 | 52.974 | 1.00 47.01 | B |
| ATOM | 1995 | O | VAL | B | 132 | 60.407 | 6.873 | 52.640 | 1.00 47.01 | B |
| ATOM | 1996 | N | ALA | B | 133 | 61.776 | 5.139 | 52.224 | 1.00 62.22 | B |
| ATOM | 1997 | CA | ALA | B | 133 | 61.156 | 4.832 | 50.939 | 1.00 62.22 | B |
| ATOM | 1998 | CB | ALA | B | 133 | 61.968 | 3.768 | 50.211 | 1.00 45.41 | B |
| ATOM | 1999 | C | ALA | B | 133 | 59.713 | 4.364 | 51.122 | 1.00 62.22 | B |
| ATOM | 2000 | O | ALA | B | 133 | 58.849 | 4.636 | 50.288 | 1.00 62.22 | B |
| ATOM | 2001 | N | THR | B | 134 | 59.456 | 3.656 | 52.216 | 1.00 43.56 | B |
| ATOM | 2002 | CA | THR | B | 134 | 58.112 | 3.162 | 52.507 | 1.00 43.56 | B |
| ATOM | 2003 | CB | THR | B | 134 | 58.128 | 2.233 | 53.728 | 1.00 52.11 | B |
| ATOM | 2004 | OG1 | THR | B | 134 | 59.117 | 1.212 | 53.538 | 1.00 52.11 | B |
| ATOM | 2005 | CG2 | THR | B | 134 | 56.761 | 1.599 | 53.927 | 1.00 52.11 | B |
| ATOM | 2006 | C | THR | B | 134 | 57.187 | 4.346 | 52.817 | 1.00 43.56 | B |
| ATOM | 2007 | O | THR | B | 134 | 56.058 | 4.436 | 52.321 | 1.00 43.56 | B |
| ATOM | 2008 | N | LEU | B | 135 | 57.696 | 5.246 | 53.652 | 1.00 41.37 | B |
| ATOM | 2009 | CA | LEU | B | 135 | 56.980 | 6.439 | 54.067 | 1.00 41.37 | B |
| ATOM | 2010 | CB | LEU | B | 135 | 57.849 | 7.243 | 55.030 | 1.00 38.54 | B |
| ATOM | 2011 | CG | LEU | B | 135 | 57.203 | 8.484 | 55.640 | 1.00 38.54 | B |
| ATOM | 2012 | CD1 | LEU | B | 135 | 56.004 | 8.075 | 56.502 | 1.00 38.54 | B |
| ATOM | 2013 | CD2 | LEU | B | 135 | 58.238 | 9.217 | 56.471 | 1.00 38.54 | B |
| ATOM | 2014 | C | LEU | B | 135 | 56.606 | 7.308 | 52.870 | 1.00 41.37 | B |
| ATOM | 2015 | O | LEU | B | 135 | 55.540 | 7.938 | 52.855 | 1.00 41.37 | B |
| ATOM | 2016 | N | GLU | B | 136 | 57.485 | 7.337 | 51.871 | 1.00 39.88 | B |
| ATOM | 2017 | CA | GLU | B | 136 | 57.249 | 8.137 | 50.675 | 1.00 39.88 | B |
| ATOM | 2018 | CB | GLU | B | 136 | 58.555 | 8.358 | 49.913 | 1.00 58.39 | B |
| ATOM | 2019 | CG | GLU | B | 136 | 59.605 | 9.113 | 50.707 | 1.00 58.39 | B |
| ATOM | 2020 | CD | GLU | B | 136 | 60.620 | 9.807 | 49.820 | 1.00 58.39 | B |

Figure 8-27

```
ATOM   2021  OE1 GLU B 136      61.445  10.575  50.363  1.00 58.39      B
ATOM   2022  OE2 GLU B 136      60.593   9.594  48.585  1.00 58.39      B
ATOM   2023  C   GLU B 136      56.216   7.504  49.749  1.00 39.88      B
ATOM   2024  O   GLU B 136      55.408   8.209  49.136  1.00 39.88      B
ATOM   2025  N   TYR B 137      56.234   6.178  49.643  1.00 45.26      B
ATOM   2026  CA  TYR B 137      55.280   5.506  48.778  1.00 45.26      B
ATOM   2027  CB  TYR B 137      55.630   4.021  48.626  1.00 69.50      B
ATOM   2028  CG  TYR B 137      54.622   3.258  47.795  1.00 69.50      B
ATOM   2029  CD1 TYR B 137      54.160   3.773  46.584  1.00 69.50      B
ATOM   2030  CE1 TYR B 137      53.193   3.106  45.841  1.00 69.50      B
ATOM   2031  CD2 TYR B 137      54.097   2.045  48.240  1.00 69.50      B
ATOM   2032  CE2 TYR B 137      53.130   1.366  47.502  1.00 69.50      B
ATOM   2033  CZ  TYR B 137      52.680   1.904  46.307  1.00 69.50      B
ATOM   2034  OH  TYR B 137      51.701   1.258  45.588  1.00 69.50      B
ATOM   2035  C   TYR B 137      53.876   5.668  49.349  1.00 45.26      B
ATOM   2036  O   TYR B 137      52.938   6.023  48.626  1.00 45.26      B
ATOM   2037  N   LEU B 138      53.736   5.414  50.648  1.00 35.44      B
ATOM   2038  CA  LEU B 138      52.442   5.545  51.307  1.00 35.44      B
ATOM   2039  CB  LEU B 138      52.543   5.088  52.765  1.00 36.43      B
ATOM   2040  CG  LEU B 138      52.936   3.625  52.990  1.00 36.43      B
ATOM   2041  CD1 LEU B 138      52.990   3.326  54.486  1.00 36.43      B
ATOM   2042  CD2 LEU B 138      51.929   2.716  52.305  1.00 36.43      B
ATOM   2043  C   LEU B 138      51.940   6.996  51.242  1.00 35.44      B
ATOM   2044  O   LEU B 138      50.769   7.244  50.932  1.00 35.44      B
ATOM   2045  N   LEU B 139      52.823   7.952  51.534  1.00 33.21      B
ATOM   2046  CA  LEU B 139      52.439   9.355  51.482  1.00 33.21      B
ATOM   2047  CB  LEU B 139      53.616  10.259  51.872  1.00 38.76      B
ATOM   2048  CG  LEU B 139      53.835  10.434  53.383  1.00 38.76      B
ATOM   2049  CD1 LEU B 139      55.119  11.198  53.656  1.00 38.76      B
ATOM   2050  CD2 LEU B 139      52.635  11.170  53.983  1.00 38.76      B
ATOM   2051  C   LEU B 139      51.966   9.685  50.078  1.00 33.21      B
ATOM   2052  O   LEU B 139      50.958  10.368  49.905  1.00 33.21      B
ATOM   2053  N   LYS B 140      52.687   9.190  49.073  1.00 32.26      B
ATOM   2054  CA  LYS B 140      52.315   9.437  47.679  1.00 32.26      B
ATOM   2055  CB  LYS B 140      53.355   8.824  46.735  1.00 53.55      B
ATOM   2056  CG  LYS B 140      54.738   9.452  46.831  1.00 53.55      B
ATOM   2057  CD  LYS B 140      55.753   8.716  45.969  1.00 53.55      B
ATOM   2058  CE  LYS B 140      57.152   9.289  46.159  1.00 53.55      B
ATOM   2059  NZ  LYS B 140      58.197   8.604  45.334  1.00 53.55      B
ATOM   2060  C   LYS B 140      50.926   8.875  47.350  1.00 32.26      B
ATOM   2061  O   LYS B 140      50.256   9.370  46.446  1.00 32.26      B
ATOM   2062  N   LYS B 141      50.496   7.846  48.085  1.00 46.02      B
ATOM   2063  CA  LYS B 141      49.185   7.237  47.852  1.00 46.02      B
ATOM   2064  CB  LYS B 141      49.103   5.840  48.479  1.00 51.68      B
ATOM   2065  CG  LYS B 141      49.941   4.782  47.767  1.00 51.68      B
ATOM   2066  CD  LYS B 141      49.637   3.365  48.258  1.00 51.68      B
ATOM   2067  CE  LYS B 141      48.242   2.904  47.838  1.00 51.68      B
ATOM   2068  NZ  LYS B 141      47.928   1.518  48.308  1.00 51.68      B
ATOM   2069  C   LYS B 141      48.043   8.085  48.383  1.00 46.02      B
ATOM   2070  O   LYS B 141      46.895   7.910  47.981  1.00 46.02      B
ATOM   2071  N   VAL B 142      48.355   9.005  49.285  1.00 38.10      B
ATOM   2072  CA  VAL B 142      47.328   9.864  49.855  1.00 38.10      B
ATOM   2073  CB  VAL B 142      47.785  10.504  51.186  1.00 34.97      B
ATOM   2074  CG1 VAL B 142      46.649  11.321  51.776  1.00 34.97      B
ATOM   2075  CG2 VAL B 142      48.245   9.423  52.166  1.00 34.97      B
ATOM   2076  C   VAL B 142      46.990  10.985  48.886  1.00 38.10      B
ATOM   2077  O   VAL B 142      45.833  11.402  48.784  1.00 38.10      B
ATOM   2078  N   LEU B 143      47.999  11.466  48.166  1.00 45.02      B
ATOM   2079  CA  LEU B 143      47.790  12.565  47.231  1.00 45.02      B
ATOM   2080  CB  LEU B 143      49.105  12.915  46.525  1.00 26.86      B
ATOM   2081  CG  LEU B 143      50.062  13.627  47.486  1.00 26.86      B
ATOM   2082  CD1 LEU B 143      51.383  13.934  46.802  1.00 26.86      B
ATOM   2083  CD2 LEU B 143      49.394  14.906  47.974  1.00 26.86      B
ATOM   2084  C   LEU B 143      46.668  12.370  46.211  1.00 45.02      B
ATOM   2085  O   LEU B 143      45.824  13.256  46.035  1.00 45.02      B
ATOM   2086  N   PRO B 144      46.643  11.220  45.521  1.00136.81      B
ATOM   2087  CD  PRO B 144      47.703  10.213  45.346  1.00119.29      B
ATOM   2088  CA  PRO B 144      45.570  11.019  44.543  1.00136.81      B
ATOM   2089  CB  PRO B 144      46.035   9.785  43.768  1.00119.29      B
ATOM   2090  CG  PRO B 144      47.535   9.845  43.895  1.00119.29      B
ATOM   2091  C   PRO B 144      44.224  10.792  45.237  1.00136.81      B
ATOM   2092  O   PRO B 144      43.451   9.933  44.760  1.00136.81      B
ATOM   2093  OXT PRO B 144      43.955  11.484  46.244  1.00119.29      B
ATOM   2094  O   HOH S   1      48.178  40.496  68.629  1.00 35.76      S
ATOM   2095  O   HOH S   2      46.684  40.021  43.558  1.00 29.93      S
```

Figure 8-28

```
ATOM   2096  O   HOH S   3      34.364  30.965  80.945  1.00 25.52           S
ATOM   2097  O   HOH S   4      40.671  32.039  57.247  1.00 33.95           S
ATOM   2098  O   HOH S   5      54.783  40.457  73.829  1.00 29.99           S
ATOM   2099  O   HOH S   6      44.763  28.859  75.845  1.00 18.35           S
ATOM   2100  O   HOH S   7      68.120  36.357  49.261  1.00 38.62           S
ATOM   2101  O   HOH S   8      41.008  40.210  74.710  1.00 29.13           S
ATOM   2102  O   HOH S   9      58.797  33.370  61.148  1.00 34.94           S
ATOM   2103  O   HOH S  10      51.657  20.370  74.794  1.00 34.89           S
ATOM   2104  O   HOH S  11      34.356  12.998  61.568  1.00 19.59           S
ATOM   2105  O   HOH S  12      31.589  17.449  58.590  1.00 33.06           S
ATOM   2106  O   HOH S  13      51.809  23.559  46.413  1.00 42.58           S
ATOM   2107  O   HOH S  14      41.787  36.216  41.713  1.00 34.36           S
END
```

Figure 8-29

SEQUENCE LISTING

```
<160> NUMBER OF SEQ ID NOS: 1

<210> SEQ ID NO 1
<211> LENGTH: 125
<212> TYPE: PRT
<213> ORGANISM: Escherichia coli

<400> SEQUENCE: 1

Met Val Asn Gln Lys Lys Asp Arg Leu Leu Asn Glu Tyr Leu Ser Pro
 1               5                  10                  15

Leu Asp Ile Thr Ala Ala Gln Phe Lys Val Leu Cys Ser Ile Arg Cys
                20                  25                  30

Ala Ala Cys Ile Thr Pro Val Glu Leu Lys Lys Val Leu Ser Val Asp
            35                  40                  45

Leu Gly Ala Leu Thr Arg Met Leu Asp Arg Leu Val Cys Lys Gly Trp
        50                  55                  60

Val Glu Arg Leu Pro Asn Pro Asn Asp Lys Arg Gly Val Leu Val Lys
65                  70                  75                  80

Leu Thr Thr Gly Gly Ala Ala Ile Cys Glu Gln Cys His Gln Leu Val
                85                  90                  95

Gly Gln Asp Leu His Gln Glu Leu Thr Lys Asn Leu Thr Ala Asp Glu
                100                 105                 110

Val Ala Thr Leu Glu Tyr Leu Leu Lys Lys Val Leu Pro
            115                 120                 125
```

CRYSTALS OF MARR POLYPEPTIDES, REGULATORS OF MULTIPLE ANTIBIOTIC RESISTANCE

RELATED APPLICATIONS

This application claims priority to U.S. Provisional Patent Application Ser. No. 60/388,622, entitled "Crystal Structure of a MarR Family Polypeptide," filed on Jun. 13, 2002; and U.S. Provisional Patent Application Ser. No. 60/305,404, entitled "Crystal Structure of a MarR Family Polypeptide," filed on Jul. 13, 2001, the entire contents of each of these applications are hereby incorporated herein by reference.

GOVERNMENT FUNDING

This invention was made with government support under GM51661 awarded by The National Institutes of Health. The government may, therefore, have certain rights in the invention.

BACKGROUND OF THE INVENTION

The Mar phenotype in *E. coli* is attributed largely to the action of MarA, the expression of which is regulated by MarR (Alekshun, M. N. supra (1997)). MarA is a transcription factor that autoactivates expression of the marRAB operon and regulates the expression of a global network of more than 60 chromosomal genes (Martin, R. G. et al. *J. Bact.* 178, 2216–2223 (1996); Barbosa, T. M. & Levy, S. B. *J. Bact.* 182, 3467–3474 (2000)). Mar mutants in isolates of clinical origin have now been identified (Maneewannakul, K. & Levy, S. B. *Antimicrob. Agents Chemother.* 40, 1695–1698 (1996); Oethinger, M. et al. *Antimicrob. Agents Chemother.* 42, 2089–2094 (1998); Linde, H. J. et al. *Antimicrob. Agents Chemother.* 44, 1865–1868 (2000); Ziha-Zarifi, I., et al. *Antimicrob. Agents Chemother.* 43, 287–291 (1999); Koutsolioutsou, A et al. *Antimicrob. Agents Chemother.* 45, 38–43 (2001)). Constitutive overexpression of MarA or a MarA homolog in many of these strains is a key contributor to the maintenance of the resistance phenotype, particularly with respect to the fluoroquinolones, and recent studies have documented the selection of Mar mutants, bearing mutations in MarR, MexR, or other homologous loci, in *E. coli, Pseudomonas aeruginosa*, and other organisms during antimicrobial chemotherapy (Oethinger, M supra; Linde, H. J. et al.; supra; Ziha-Zarifi, I. et al. supra; Kern, W. V., et al. *Antimicrob. Agents Chemother.* 44, 814–820 (2000)).

MarR is a regulator of multiple antibiotic resistance in *Escherichia coli*. It is the prototypic member of a family of regulatory proteins found in the Bacteria and the Archae that play important roles in the development of antibiotic resistance, a global health problem. In the absence of an appropriate stimulus, MarR negatively regulates expression of the marRAB operon (Cohen, S. P., et al. 1993. *J. Bacteriol.* 175: 1484–1492.; Martin, R. G. and Rosner, J. L. 1995. *Proc. Natl. Acad. Sci.* 92: 5456–5460; Seoane, A. S. and Levy, S. B. 1995. *J. Bacteriol.* 177: 3414–3419., 1995). DNA footprinting experiments suggest that MarR dimerizes at two locations, sites I and II, within the mar operator (marO) (Martin and Rosner, 1995, supra). Site I is positioned among the −35 and −10 hexamers and site II spans the putative MarR ribosome binding site (reviewed in Alekshun, M. N. and Levy, S. B. 1997. *Antimicrob. Agents Chemother.* 10: 2067–2075).

MarR is a member of a newly recognized family of regulatory proteins (Alekshun, M. N. and Levy, S. B. 1997. *Antimicrob. Agents Chemother.* 10: 2067–2075. Sulavik, M. C., et al. 1995. *Mol. Med.* 1: 436–446) and many functional homologues have been identified in a variety of important human pathogens and have been found to regulate a variety of different processes. For example, some MarR homologues have been found to control expression of multiple antibiotic resistance operons, some regulate tissue-specific adhesive properties, some control expression of a cryptic hemolysin, some regulate protease production, and some regulate sporulation. Proteins of the MarR family control an assortment of biological functions including resistance to multiple antibiotics, organic solvents, household disinfectants, and oxidative stress agents, collectively termed the multiple antibiotic resistance (Mar) phenotype (Alekshun, M. N. & Levy, S. B. *Trends Microbiol.* 7, 410–413 (1999)). These proteins also regulate the synthesis of pathogenic factors in microbes that infect humans and plants (Miller, P. F. & Sulavik, M. C. *Mol. Microbiol.* 21, 441–448 (1996)). Insight into the three dimensional structure of MarR family proteins would be of great value in designing drugs that interact with this family of proteins and modulate MarR function, for example, antibiotic resistance and virulence.

SUMMARY OF THE INVENTION

The instant invention advances the prior art by providing the crystal structure of a MarR family polypeptide, MarR. The crystal structure was solved for both the MarR polypeptide and the MarR polypeptide bound to salicylate.

The invention pertains at least in part to a crystallized MarR family polypeptide. The MarR family polypeptide is crystallized under appropriate conditions such that its three dimensional structure can be determined. In another embodiments, the crystallized MarR family polypeptide is given by the atomic coordinates given in FIG. 7 or 8.

In another embodiment, the invention pertains, at least in part, to a method for determining the three dimensional structure of MarR family polypeptide. The method includes crystallizing the MarR family polypeptide under appropriate conditions such that crystals are formed, and analyzing it, such that its three dimensional structure is determined.

In yet another embodiment, the invention pertains to a method of making a crystal of a MarR family polypeptide. The method includes contacting MarR with a modulator to form a complex and allowing crystals of the complex to grow, e.g., by using hanging droplet vapor diffusion.

BRIEF DESCRIPTION OF THE DRAWINGS

FIGS. 7-1 to 7-20 show the atomic coordinates of the MarR-slicylate co-crystal (residues 7-144 of SEQ ID NO:2).

FIGS. 8-1 to 8-29 show the atomic coordinates of the MarR crystal without salicylate (residues 12–144 and 9–144 of SEQ ID NO:2).

FIG. 9 is a ribbon representation of the MarR dimer with the two-fold axis near vertical.

DETAILED DESCRIPTION OF THE INVENTION

The invention pertains, at least in part, to crystallized MarR family polypeptides. The crystallized MarR family polypeptides are crystallized under appropriate conditions such that the three dimensional structure can be determined using methods described herein and/or art recognized techniques.

The term "MarR family polypeptide" includes molecules related to MarR, e.g., having certain shared structural and functional features. MarR family polypeptides also include those which are structural homologs of MarR. The structural homologs include those having a crystallized form which are structurally similar to that of crystallized MarR. MarR family members, in addition to having similarity to MarR, may bind to DNA and regulate transcription. While some MarR family members negatively control transcription (e.g., MarR), others have positive/activator functions (e.g., SlyA, BadR, NhhD, and MexR). MarR family polypeptides comprise DNA and protein binding domains. In addition, MarR family polypeptides can interact with a variety of structurally unrelated compounds that regulate their activity.

Exemplary MarR family members are taught in the art and can be found, e.g., in Sulavik et al. (1995. *Molecular Medicine*. 1:436), Miller and Sulavik (1996. *Molecular Microbiology*. 21:441) in which alignments of MarR and related proteins are shown, or through the use of BLAST searches and other techniques known in the art. Exemplary MarR family polypeptides are also illustrated in the following chart:

| MarR Family Polypeptides | | |
|---|---|---|
| Gram-negative | Gram-positive | Acid-fast |
| *Escherichia coli* | *Bacillus subtilus* | *Mycobacterium tuberculosis* |
| MarR | YdcH | 14.7kD |
| SlyA | YhbI | Rv1404 |
| EmrR (MprA) | YkmA | Rv0737 |
| PapX | YkoM | Rv0042c |
| PrsX | Orf7 | Yz08 (15.6kD) |
| HpcR | YfiV | *Mycobacterium leprae* |
| Ec17kD | YetL | Yz08 (15.6kD) |
| *Salmonella typhimurium* | YdgJ | Archaea |
| MarR | YwoH | *Methanobacterium* |
| SlyA | Ywae | *thermoautotrophicum* |
| EmrR | YwhA | MTH313 |
| *Pseudomonas aeruginosa* | Hpr | *Sulfolobus solfataricus* |
| MexR | YybA | Lrs14 |
| *Erwinia chrysanthemi* | YxaD | *Archaeoglobus fulgidus* |
| PecS | YsmB | CinR |
| *Rhodopseudomonas palustris* | YusO | Purple non-sulfur |
| BadR | YpoP | *Rhodobacter capsulatus* |
| *Burkholderia pseudomallei* | YkvE | PetP |
| OrfE | *Bacillus firmus* | *Sinorhizobium meliloti* |
| | Orf7 | SlyA (E293909) |
| | *Staphylococcus sciuri* | |
| | Orf145 | |
| | Orf141 | |
| | *Butyrivibrio fibrisolvens* | |
| | CinR | |
| | *Sphingomonas aromaticivorans* | |
| | Orf158 | |
| | *Rhodococcus rhodochrous* | |
| | NhhD | |
| | *Streptomyces peucetius* | |
| | Orf1 | |

Preferably, the MarR family polypeptide is MarR. Other preferred MarR family polypeptides include: EmrR, Ec17kD, and MexR.

In a further embodiment, the MarR family polypeptide has a winged-helix structure, such as the three dimensional structure of MarR.

Figure 1:
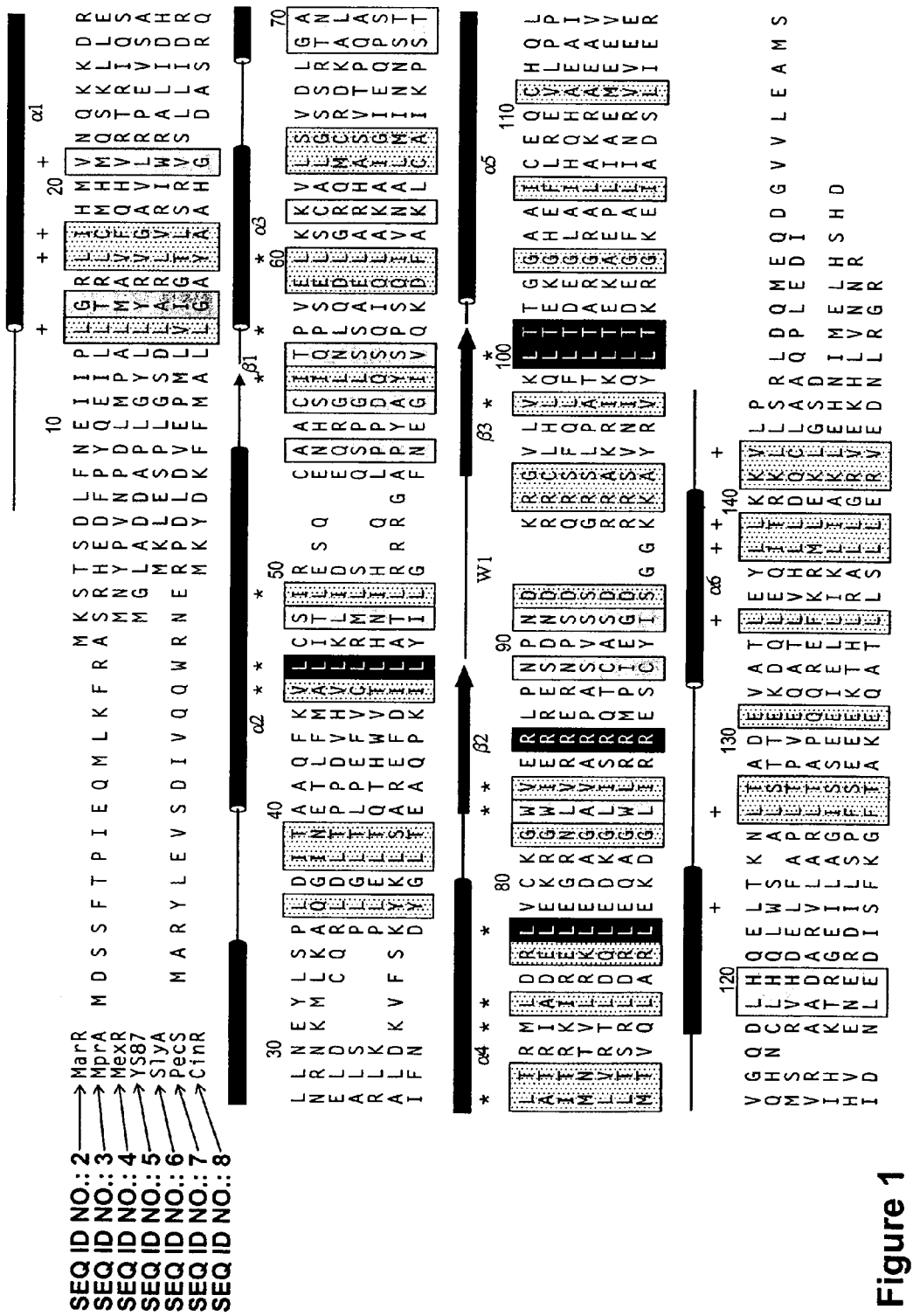
FIG. 1 shows the sequence alignment of MarR with representative members of the MarR family (SEQ ID NOS 2–8, respectively, in order of appearance).

FIG. 1 shows a sequence alignment of MarR with representative MarR family polypeptides. The MarR secondary structure elements were identified in its crystal structure and are illustrated in FIG. 1 (e.g., as tubes for α-helices (α) and arrows for β-sheets (β) and the single wing region (W1)). The numbering in FIG. 1 is according to the MarR primary sequence. The MarR family polypeptides used for the alignment were from the following organisms: MarR, *E. coli*; MprA (EmrR), *E. coli*; MexR, *Pseudomonas aeruginosa*; YS87, *Mycobacterium tuberculosis*; SlyA, *Salmonella typhimurium*; PecS, *Erwinia chrysanthemi*; CinR, *Butyrivibrio fibrisolvens*.

In a further embodiment, MarR comprises, consists essentially of, or consists of the polypeptide sequence shown in Sequence Listing SEQ ID NO:1. Other MarR family polypeptides of interest include EmrR, YS87, PecS, CinR, SlyA, Ec17kD, MexR, etc.

In another embodiment, the MarR family polypeptide is found, for example, in one of the following organisms *Escherichia coli, Salmonella typhimurium, Salmonella enterica, Enterobacter cloacae, Enterobacter aerogenes, Erwinia chrysanthemi, Yrsinia pestis, Yersinia enterocolitica, Kluyvera cryocrescens, Edwardsiella tarda, Pseudomonas aeruginosa, Vibrio cholera, Xanthomonas axonopodis, Xanthomonas campestris, Ralstonia solanacearum, Burkholderia pseudomallei, Burkholderia cepacia, Vogesella indigofera, Mesorhizobium loti, Agrobacterium tumefaciens, Sinorhizobium meliloti, Brucella melitensis, Caulobacter crescentus, Bacillus anthracis, Bacillus subtilis, Bacillus halodurans, Listeria monocytogenes, Listeria innocua, Listeria welshimeri, Staphylococcus sciuri, Streptococcus criceti, Streptococcus pneumoniae, Clostridium perfringens, Clostridium difficile, Streptomyces coelicolor, Streptomyces avermitilis, Mycobacterium tuberculosis, Mycobacterium leprae, Corynebacterium glutamicum, Thermotoga maritima, Methanosarcina acetivorans, Methanosarcina mazei,* and *Sulfolobus solfataricus.*

In another embodiment, the MarR family polypeptide is from an organism belonging to one of the following biological classifications: Enterobacteriaceae, *Enterobacter, Yersinia, Kluyvera, Edwardsiella, Xanthomonas* group, *Xanthomonadales,* Pseudomonaceae/Moraxellaceae group, Pseudomonadaceae, Vibrionaceae group, *Burkholderia/Oxalobacter/Ralstonia* group, *Ralstonia* group, *Burkholderia* group, Neisseriaceae, *Vogesella,* Rhizobiaceae group, Phyllobacteriaceae, *Mesorhizobium,* Rhizobiaceae, *Sinorhizobium,* Brucellaceae, *Brucella, Caulobacter* group, Firmicutes, *Bacillus/Clostridium* group, Bacilli, Bacillales, *Bacillus,* Bacillaceae, *Bacillus cereus* group, *Listeria,* Listeriaceae, Staphylococcaceae, *Staphylococcus, Streptococcus,* Lactobacillales, Streptococcaceae, *Clostridium,* Clostridiaceae, Clostridiales, Clostridia, Actinomycetales, Actinobacteria, Actinobacteridae, *Streptomyces,* Streptomycineae, Streptomycetaceae, Corynebacterineae, Mycobacterium, Mycobacteriaceae, Corynebacteriaceae, *Corynebacterium,* Nostocales, Nostocaceae, *Nostoc,* Thermotogae, Thermotogales, Thermotogaceae; *Thermotoga, Methanosarcina,* Euryarchaeota, Methanococci; Methanosarcinales, Methanosarcinaceae, Crenarchaeota, Thermoprotei; Sulfolobales, Sulfolobaceae, *Sulfolobus,* Proteobacteria, *Pectobacterium,* Cyanobacteria, or Archaea.

In one embodiment, the MarR family polypeptides of the invention are naturally occurring. In another embodiment, the subject crystal structures can be generated using non-naturally occurring forms of MarR family polypeptides, e.g. mutants or synthetic forms of MarR family polypeptides not found in nature.

In one embodiment, the MarR family polypeptide comprises one or more conservative mutations as compared to the wild type protein for the particular MarR family polypeptide. The term "MarR family polypeptide" also includes fragments of MarR family polypeptides which minimally retain at least a portion of the tertiary structure of the MarR family protein.

MarR family member polypeptide sequences are "structurally related" to one or more known MarR family members, preferably to MarR. This structural relatedness is shown by sequence similarity between two MarR family polypeptide sequences or between two MarR family nucleotide sequences. Sequence similarity can be shown, e.g., by optimally aligning MarR family member sequences using an alignment program for purposes of comparison and comparing corresponding positions. To determine the degree of similarity between sequences, they will be aligned for optimal comparison purposes (e.g., gaps may be introduced in the sequence of one protein for nucleic acid molecule for optimal alignment with the other protein or nucleic acid molecules). The amino acid residues or bases and corresponding amino acid positions or bases are then compared. When a position in one sequence is occupied by the same amino acid residue or by the same base as the corresponding position in the other sequence, then the molecules are identical at that position. If amino acid residues are not identical, they may be similar. As used herein, an amino acid residue is "similar" to another amino acid residue if the two amino acid residues are members of the same family of residues having similar side chains. Families of amino acid residues having similar side chains have been defined in the art (see, for example, Altschul et al. 1990. *J. Mol. Biol.* 215:403) including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g, tyrosine, phenylalanine, tryptophan). The degree (percentage) of identity or similarity between sequences, therefore, can be calculated as a function of the number of identical or similar positions shared by two sequences (i.e., % homology=# of identical or similar positions/total # of positions×100). Alignment strategies are well known in the art; see, for example, Altschul et al. supra for optimal sequence alignment.

MarR family polypeptides share some amino acid sequence similarity with MarR. The nucleic acid and amino acid sequences of MarR as well as other MarR family polypeptides are available in the art. For example, the nucleic acid and amino acid sequence of MarR can be found, e.g., on GeneBank (accession number M96235 or in Cohen et al. 1993. J. Bacteriol. 175:1484, or in SEQ ID NO:1).

The nucleic acid and protein sequences of MarR can be used as "query sequences" to perform a search against databases (e.g., either public or private) to, for example, identify other MarR family members having related sequences. Such searches can be performed, e.g., using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to MarR family nucleic acid molecules. BLAST protein searches can be performed with the XBLAST program, score=50, wordlength=3 to obtain amino acid sequences homologous to MarR protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

MarR family members can also be identified as being similar based on their ability to specifically hybridize to the complement of nucleic acid sequences specifying MarR. Such stringent conditions are known to those skilled in the art and can be found e.g., in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Conditions for hybridizations are largely dependent on the melting temperature Tm that is observed for half of the molecules of a substantially pure population of a double-stranded nucleic acid. Tm is the temperature in ° C. at which half the molecules of a given sequence are melted or single-stranded. For nucleic acids of sequence 11 to 23 bases, the Tm can be estimated in degrees C. as 2(number of A+T residues)+4 (number of C+G residues). Hybridization or annealing of nucleic acid molecules should be conducted at a temperature lower than the Tm, e.g., 15° C., 20° C., 25° C. or 30° C. lower than the Tm. The effect of salt concentration (in M of NaCl) can also be calculated, see for example, Brown, A., "Hybridization" pp. 503–506, in *The Encyclopedia of Molec. Biol.*, J. Kendrew, Ed., Blackwell, Oxford (1994).

Preferably, the nucleic acid sequence of a MarR family member identified in this way is at least about 10%, 20%, more preferably at least about 30%, more preferably at least about 40% identical and most preferably at least about 50%, or 60% identical or more with a MarR nucleotide sequence. Preferably, MarR family members have an amino acid sequence at least about 20%, more preferably at least about 30%, more preferably at least about 40% identical and most preferably at least about 50%, or 60% or more identical with a MarR amino acid sequence. However, it will be understood that the level of sequence similarity among microbial regulators of gene transcription, even though members of the same family, is not necessarily high. This is particularly true in the case of divergent genomes where the level of sequence identity may be low, e.g., less than 20% (e.g., *B. burgdorferi* as compared e.g., to *B. subtilis*). For example, the level of amino acid sequence homology between MarR and PecS is about 31% and the level of amino acid sequence homology between MarR and PapX is about 28% when determined as described above. Accordingly, structural similarity among MarR family members can also be determined based on "three-dimensional correspondence" of amino acid residues. As used herein, the language "three-dimensional correspondence" is meant to includes residues which spatially correspond, e.g., are in the same functional position of a MarR family protein member as determined, e.g., by x-ray crystallography, but which may not correspond when aligned using a linear alignment program. The language "three-dimensional correspondence" also includes residues which perform the same function, e.g., bind to DNA or bind the same cofactor, as determined, e.g., by mutational analysis.

Preferred MarR family polypeptides include: MarR, EmrR, Ec17kD, MexR, PapX, SlyA, Hpr, PecS, Hpr, MprA, (EmrR), as well as the other peptides listed in the chart above or known in the art. In a more preferred embodiment, a MarR family polypeptide is selected from the group consisting of: MarR, EmrR, Ec17kD, and MexR. In a particularly preferred embodiment, a MarR family polypeptide is MarR.

In addition to sharing structural similarity, MarR family members have a MarR family polypeptide activity, i.e., they bind to DNA and regulate transcription. Some MarR family members positively regulate transcription (e.g, SlyA, BadR, NhhD, or MexR), while others negatively regulate transcription (e.g., MarR). While all MarR family members bind to DNA and regulate transcription, the different loci controlled by each family member regulate different processes in microbes. For example, MarR family polypeptides can control the expression of microbial loci involved in: regulation of antibiotic resistance [e.g., MarR (Cohen et al. 1993. J. Bacteriol. 175:1484), EmrR (Lomovskaya and Lewis. 1992. Proc. Natl. Acad. Sci. 89:8938), and Ec17kD (Sulavik et al. 1995. Mol. Med. 1:436), and MexR (Poole et al. 1996. Antimicrob. Agents. Chemother. 40:2021)], regulation of tissue-specific adhesive properties [e.g., PapX (Marklund et al., 1992. Mol. Microbiol. 6:2225)], regulation of expression of a cryptic hemolysin [e.g., SlyA (Ludwig et al. 1995 249:4740)], regulation of protease production [e.g., Hpr from *B. subtilis* (Perago and Hoch. 1988. J. Bacteriol. 170:2560) and PecS from *Erwinia chrysanthemi* (Reverchon et al., 1994. Mol. Microbiol. 11:1127)] and regulation of sporulation [e.g., Hpr (Perego and Hoch. 1988. J. Bacteriol. 170:2560)], regulation of the breakdown of plant materials [e.g., CinR (Dalymple and Swadling 1997 Microbiology)] sensing of phenolic compounds [(e.g., Sulvik et al. 1995. Mol. Med. 1:436], and repress marRAB expression when introduced into *E. coli* [e.g., Ec17kd (Marklund et al. 1992. Mol. Microbiol. 6:2225) and MprA (EmrR) (del Castillo et al., 1991. J. Bacteriol. 173:3924)]. The activity of MarR family polypeptides is antagonized by salicylate (Lomovskaya et al., 1995. J. Bacteriol. 177:2328; Sulavik et al. 1995. Mol. Med. 1:436).

Preferred MarR family polypeptide activities include regulation of multiple drug resistance and/or regulation of virulence.

In addition to full length MarR family polypeptide fragments MarR family polypeptide which are useful in making crystals are also within the scope of the invention. Accordingly, MarR family polypeptides for use in the instant invention can be full length MarR family member proteins or fragments thereof. Thus, a MarR family polypeptide can comprise, consist essentially of, or consist of an amino acid sequence derived from the full length amino acid sequence of a MarR family member. For example, in one embodiment, a polypeptide comprising a MarR family polypeptide DNA interacting domain or a polypeptide comprising a MarR family member protein interacting domain can be used.

In addition, naturally or non-naturally occurring variants of these polypeptides and nucleic acid molecules which retain the same functional activity, e.g., the ability to bind to DNA and regulate transcription. Such variants can be made, e.g., by mutation using techniques which are known in the art. Alternatively, variants can be chemically synthesized.

For example, it will be understood that the MarR family polypeptides described herein, are also meant to include equivalents thereof. For instance, mutant forms of MarR family polypeptides which are functionally equivalent, (e.g., have the ability to bind to DNA and to regulate transcription from an operon) can be made using techniques which are well known in the art. Mutations can include, e.g., at least one of a discrete point mutation which can give rise to a substitution, or by at least one deletion or insertion. For example, random mutagenesis can be used. Mutations can be made by random mutagenesis or using cassette mutagenesis. For the former, the entire coding region of a molecule is mutagenized by one of several methods (chemical, PCR, doped oligonucleotide synthesis) and that collection of randomly mutated molecules is subjected to selection or screening procedures. In the latter, discrete regions of a protein, corresponding either to defined structural or functional determinants (e.g., the first or second helix of a helix-turn-helix domain) are subjected to saturating or semi-random mutagenesis and these mutagenized cassettes are re-introduced into the context of the otherwise wild type allele. In one embodiment, PCR mutagenesis can be used. For example, Megaprimer PCR can be used (O. H. Landt, Gene 96:125–128).

In addition, other portions of the above described polypeptides suitable for use in the claimed assays, such as those which retain their function (e.g., the ability to bind to DNA, to regulate transcription from an operon) or those which are critical for binding to regulatory molecules (such as compounds) can be easily determined by one of ordinary skill in the art, e.g, using standard truncation or mutagenesis techniques and used in the instant assays. Exemplary techniques are described by Gallegos et al. (1996. J. Bacteriol. 178:6427).

It shall be understood that the instant invention also pertains to isolated MarR family member polypeptides, portions thereof, and the nucleic acid molecules encoding them, including naturally occurring and mutant forms.

Preparation of MarR Family Polypeptides

Preferred MarR family polypeptides for use in the instant invention are synthesized, isolated or recombinant polypeptides. In one embodiment, MarR family polypeptides can be made from nucleic acid molecules. Nucleic acid molecules encoding MarR family polypeptides can be used to produce MarR family polypeptides for use in the instant assays. For example, nucleic acid molecules encoding a MarR family polypeptide can be isolated (e.g., isolated from the sequences which naturally flank it in the genome and from cellular components) and can be used to produce a MarR family polypeptide. In one embodiment, a nucleic acid molecule which has been (1) amplified in vitro by, for example, polymerase chain reaction (PCR); (2) recombinantly produced by cloning, or (3) purified, as by cleavage and gel separation; or (4) synthesized by, for example, chemical synthesis can be used to produce MarR family polypeptides. As used herein, the term "nucleic acid" refers to polynucleotides such as deoxyribonucleic acid (DNA) or ribonucleic acid (RNA).

Nucleic acid molecules specifying MarR family polypeptides can be placed in a vector. The term "vector" refers to a nucleic acid molecule capable of transporting another nucleic acid molecule to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

Exemplary expression vectors for expression of a gene encoding a MarR family polypeptide and capable of replication in a bacterium, such a bacterium from a genus selected from the group consisting of: *Escherichia, Bacillus, Streptomyces, Streptococcus*, or in a cell of a simple eukaryotic fungus such as a *Saccharomyces* or, *Pichia*, or in a cell of a eukaryotic organism such as an insect, a bird, a mammal, or a plant, are known in the art. Such vectors may carry functional replication-specifying sequences (replicons) both for a host for expression, for example a *Streptomyces*, and for a host, for example, *E. coli*, for genetic manipulations and vector construction. See e.g. U.S. Pat. No. 4,745,056. Suitable vectors for a variety of organisms are described in Ausubel, F. et al., *Short Protocols in Molecular Biology*, Wiley, New York (1995), and for example, for *Pichia*, can be obtained from Invitrogen (Carlsbad, Calif.).

Useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. A useful translational enhancer sequence is described in U.S. Pat. No. 4,820,639.

It should be understood that the design of the expression vector may depend on such factors as the choice of the host cell to be transformed and/or the type of protein desired to be expressed.

"Transcriptional regulatory sequence" is a generic term to refer to DNA sequences, such as initiation signals, enhancers, operators, and promoters, which induce or control transcription of nucleic acid sequences with which they are operably linked. It will also be understood that a recombinant gene encoding a MarR family polypeptide can be under the control of transcriptional regulatory sequences which are the same or which are different from those sequences which control transcription of the naturally-occurring MarR family gene. Exemplary regulatory sequences are described in Goeddel; *Gene Expression Technology: Methods in Enzymology* 185, Academic Press, San Diego, Calif. (1990). For instance, any of a wide variety of expression control sequences, that control the expression of a DNA sequence when operatively linked to it, may be used in these vectors to express DNA sequences encoding the MarR family proteins of this invention.

Appropriate vectors are widely available commercially and it is within the knowledge and discretion of one of ordinary skill in the art to choose a vector which is appropriate for use with a given microbial cell. The sequences encoding MarR family polypeptides can be introduced into a cell on a self-replicating vector or may be introduced into the chromosome of a microbe using homologous recombination or by an insertion element such as a transposon.

Such vectors can be introduced into cells using standard techniques, e.g., transformation or transfection. The terms "transformation" and "transfection" mean the introduction of a nucleic acid, e.g., an expression vector, into a recipient or "host" cell. The term "transduction" means transfer of a nucleic acid sequence, preferably DNA, from a donor to a recipient cell, by means of infection with a virus previously grown in the donor, preferably a bacteriophage. Nucleic acids can also be introduced into microbial cells by transformation using calcium chloride or electroporation.

"Cells," "host cells," "recipient cells, are terms used interchangeably herein. It is understood that such terms refer not only to the particular subject cell but to the progeny or potential progeny of such a cell. In preferred embodiments, cells used to express MarR family polypeptides for purification, e.g., host cells, comprise a mutation which renders any endogenous MarR family polypeptide nonfunctional or causes the endogenous polypeptide to not be expressed. In other embodiments, mutations may also be made in other related genes of the host cell, such that there will be no interference from the endogenous host loci.

Purification of a MarR family polypeptides, e.g, recombinantly expressed polypeptides, can be accomplished using techniques known in the art. For example, if the MarR family polypeptide is expressed in a form that is secreted from cells, the medium can be collected. Alternatively, if the MarR family polypeptide is expressed in a form that is retained by cells, the host cells can be lysed to release the MarR family polypeptide. Such spent medium or cell lysate can be used to concentrate and purify the MarR family polypeptide. For example, the medium or lysate can be passed over a column, e.g., a column to which antibodies specific for the MarR family member polypeptide have been bound. Alternatively, such antibodies can be specific for a non-MarR family member polypeptide which has been fused to the MarR family polypeptide (e.g., as a tag) to facilitate purification of the MarR family member polypeptide. Other means of purifying MarR family member polypeptides are known in the art.

Architecture of the MarR-Salicylate Co-Crystal Structure

The term "three dimensional structure" includes both pictorial representations of MarR family polypeptides (e.g., such as those shown for MarR with salicylate and MarR without salicylate in the Figures) as well as atomic coordinates (e.g., such as those given in FIG. 7 for MarR-salicylate cocrystal, or in FIG. 8 for MarR without salicylate) and other renditions of the shape, size, or symmetry of a MarR family polypeptide of interest. In a further embodiment, the three dimensional structure of the crystallized MarR family polypeptide is determined to a resolution of 5 Å or better, 3 Å or better, 2.5 Å or better, or, advantageously, 2.3 Å or better. The three dimensional structure of MarR, a MarR family polypeptide, is described in greater detail below.

Figure 2:
FIG. 2 is a ribbon representation of the cocrystal structure of the MarR dimer with salicylate viewed with the subunit two-fold axis near vertical.

MarR consists of a dimer with approximate overall dimensions of 50×55×45 Å (corresponding to the width, height and depth of the molecule in the orientation shown in FIG. 2). There is one monomer in the asymmetric unit of the crystal with the dimer composed of subunits related by a crystallographic two-fold rotation. The dimeric structure is consistent with the results of earlier in vitro experiments suggesting that MarR binds the mar operator (marO) as a dimer (Martin, R. G. et al. supra (1996); Martin, R. G. & Rosner, J. L. *Proc. Natl. Acad. Sci. U.S.A.* 92, 5456–5460 (1995)). Another family member, MprA (EmrR) (FIG. 1) is also believed to function as a dimer (Broum, A., et al. *J. Bact.* 181, 5131–5133 (1999)).

Figure 3:
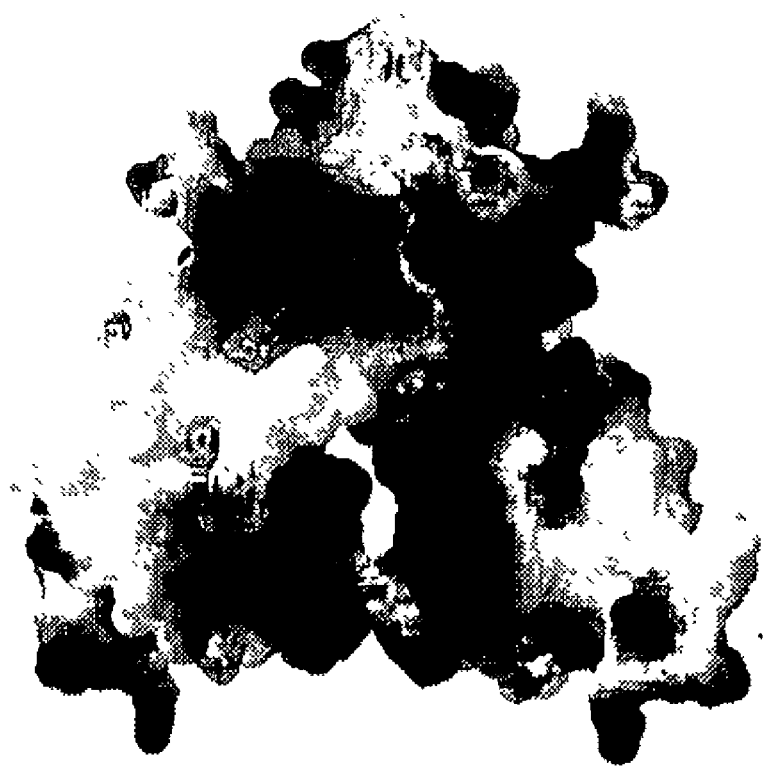
FIG. 3 is an electrostatic surface representation of the MarR dimer.
Figure 4:
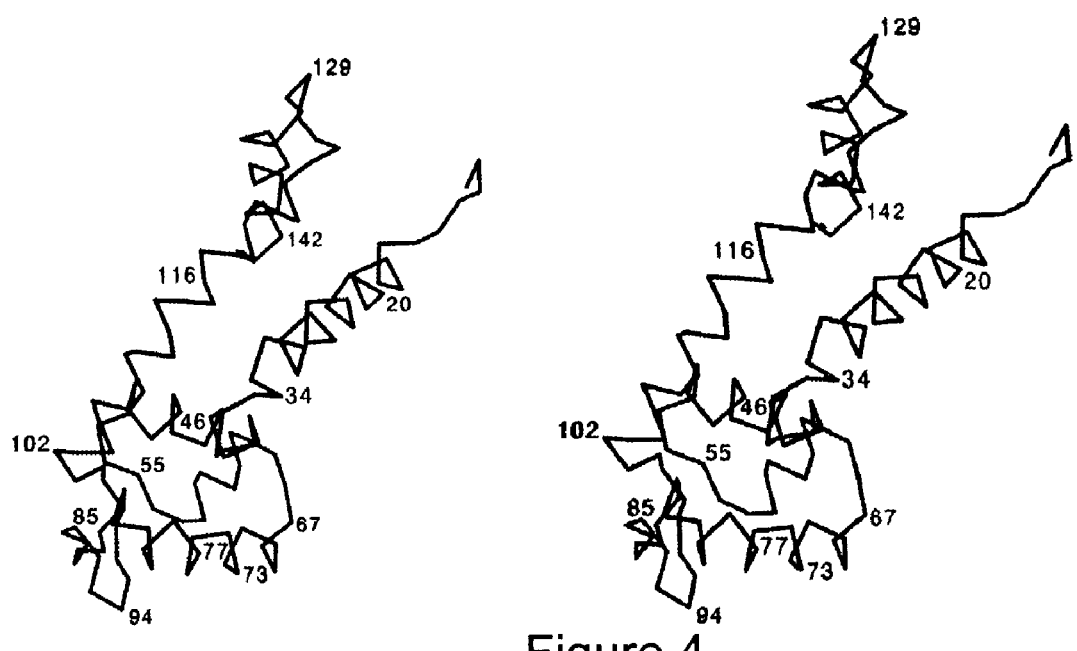
FIG. 4 is a Cα trace of a MarR subunit in stereo representation.
Figure 5:
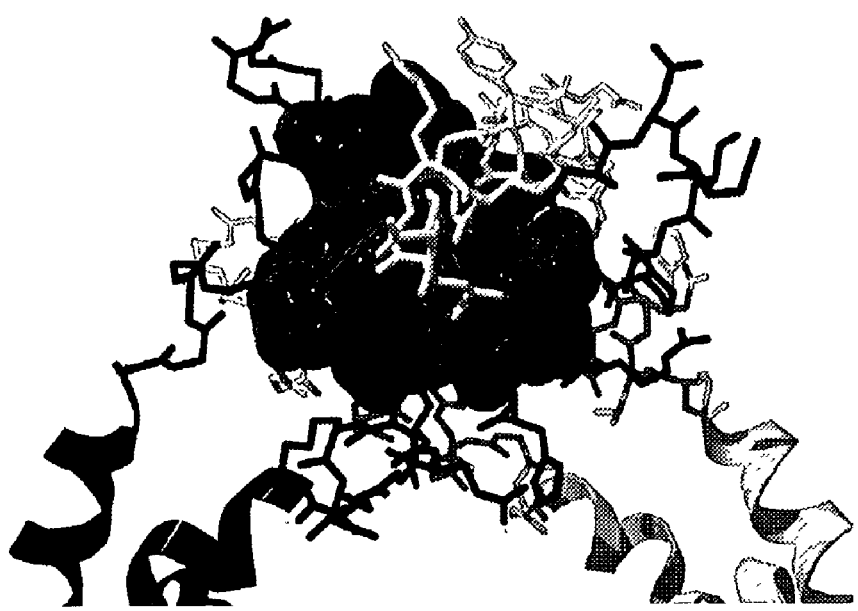
FIG. 5 is a representation of the N-/C-terminal domain represented by a surface around the van der Waals radii of the side chain atoms only of the hydrophobic core residues. Helices leading to and from the domain are shown in ribbon representation.

Each MarR subunit is an $\alpha/\beta$ protein with approximate dimensions of 35×25×60 Å and can be divided into two domains as shown in FIG. 2. FIG. 2 is a ribbon representation of the co-crystal structure of the MarR dimer viewed with the subunit 2-fold axis near vertical. The secondary structure elements of one subunit are colored according to the scheme used in FIG. 1. The N- and C-terminal regions are closely juxtaposed and intertwine with the equivalent regions of the second subunit to form a domain that holds the subunits together (FIG. 5). This N-/C-terminal domain is linked to the remainder of the protein by two long antiparallel helices in each subunit. These helices lead to a globular domain that is likely to be responsible for DNA binding (see below). Although the globular DNA-binding domains of the dimer are adjacent to one another, they make minimal contact with each other and are situated to function independently. The overall organization of the N-/C-terminal domain and the two DNA-binding domains results in the formation of an approximately 6 Å wide channel through the center of the dimer (FIGS. 3 and 4). The electrostatic surface potential (FIG. 3) is consistent with the putative DNA-binding regions being strongly electropositive, as observed in other such winged-helix DNA-binding proteins (Gajiwala, K. S. & Burley, S. K. *Curr. Opin. Str. Biol.* 10, 110–116 (2000)).

Genetic and biochemical data have previously identified the N-terminus of MarR to be important for mediating protein-protein contacts between repressor subunits and have demonstrated that the C-terminus is important for protein function (Alekshun, M. N., et al. *Mol. Adicrobiol.* 35, 1394–404 (2000); Linde, H. J. et al. supra). The present structure shows that α-helices in the N- and C-terminal regions of each monomer fold around and interdigitate with those of the other subunit to form a well-packed hydrophobic core (FIG. 5) burying a surface area of 3,570 $Å^2$ (the total buried surface area for the whole dimer is 3,700 $Å^2$). The dimer is further stabilized in this region by several intermolecular hydrogen bonds, notably that between the $\epsilon$-amino group of Lys 24 and the main chain carbonyl oxygen of Pro 144' in the C-terminus of the second subunit and that between the main chain carbonyl oxygen of Glu 10 and the side chain amino group of Lys 140'.

Figure 6:
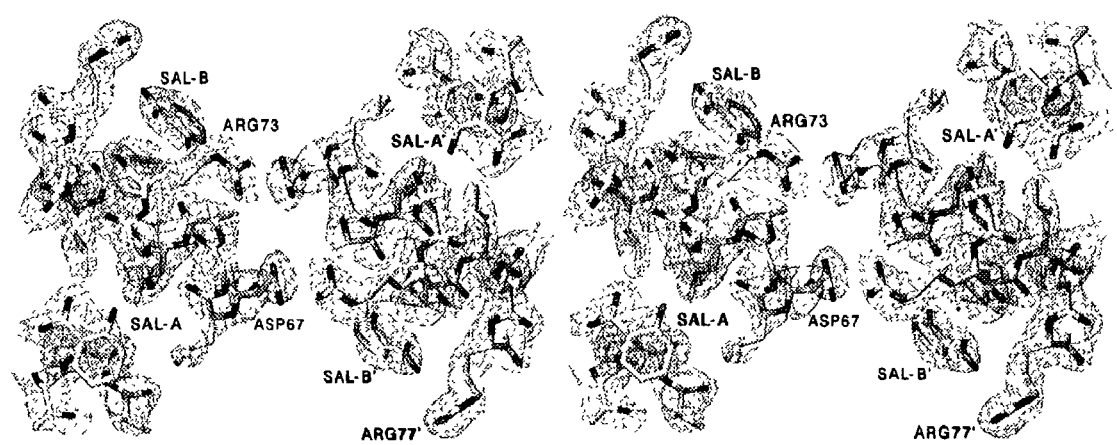
FIG. 6 is a diagram which shows interactions between the DNA-binding domains of the dimer in the region of the Arg 73-Asp 67' salt bridges. The stereo view is coincident with the 2-fold rotation axis of the dimer. Electron density shown is a $2F_O\text{-}F_C$ map contoured at 1σ.

While the DNA-binding lobe of each subunit also forms a well-packed hydrophobic core, the only interactions between these lobes of the two subunits are salt bridges formed between Asp 67 and Arg 73' and the reciprocal pair (FIG. 6). These salt bridges stabilize the relationship between the two lobes of the dimer in the crystal form of the protein but if disrupted by other interactions, such as might occur during the binding of MarR to marO, the two lobes would be able to act independently. Relative movement of the lobes would require distortion of the helices that link them to the N-/C-terminal domain. The long linker helix region encompassing residues 103–126 (α5/α5') (FIG. 2) appears poorly ordered in the region of Gly 116, as is the loop (residues 128–131) that connects this helix to the C-terminal helix (α6/α6') (FIGS. 1 and 2). It is possible that flexibility at these sites in MarR helps to accommodate relative shifts of the two lobes of the dimer that might occur on binding to DNA.

Architecture of the MarR Crystal Structure

Figure 9:

The MarR without salicylate structure is a dimer (FIG. 9) and both subunits of the dimer are in the asymmetric unit. These individual subunits are joined by extensive protein-protein interactions mediated by amino acids within both the N- and C-termini of the monomers (FIG. 9). Like the MarR-salicylate structure, MarR without salicylate is an α/β protein. The MarR without salicylate structure is, however, conformationally different from the salicylate bound protein in that the caliper created by the dimer is more closed in the form of the protein without salicylate. Thus, the channel through the center of the dimer has been lost.

The overall architecture of the MarR without salicylate structure is comparable to that of the salicylate bound protein. The presumed DNA binding lobes or domains are linked to the remainder of the protein by two long α-helices. The positioning of the two DNA binding lobes in the MarR without salicylate structure is fixed by hydrogen bonds between the two lobes. This arrangement is believed to be mediated by interactions between Asp 67 and Arg 77'. In addition, Asp 26 is involved in hydrogen bonds with the side chains of Lys 44 and Lys 25. Together, the presumed recognition helices within the DNA binds lobes overlap by approximately one helical turn.

The DNA Binding Domain

Previous studies have shown the region spanning amino acids 61–121 in MarR to be required for its DNA binding activity (Alekshun, M. N et al., supra, (2000)). In the crystal structure, amino acids 55–100 [β1-α3-α4-β2-W1 (wing)-β3] adopt the winged-helix fold (Clark, K. L. et al. *Nature* 364, 412–420 (1993)). The overall topology [H1 (α2)-S1 (β1)-H2 (α3)-H3 (α4, recognition helix)-S2 (β2)-W1-S3 (β3)] of this region is similar to other winged-helix DNA binding proteins (the terminology applied for these and subsequent structural elements is according to Gajiwala and Burley, supra (2000)) except that a third strand of sheet present in most members of the group appears to be represented in this MarR structure by an interaction with Ile 55 (β1) (FIG. 1). The presence of this single residue as the third component in the sheet interaction is very similar to that observed in OmpR (Martínez-Hackert, E. & Stock, A. M. *Structure* 5, 109–124 (1997)), a winged helix protein, where Leu 180 interacts with the two strands of the antiparallel sheet that forms part of the "wing" in this transcription factor.

Within the winged-helix family of DNA-binding proteins, there are multiple modes of DNA binding. Members such as HNF-3γ use the recognition helix (H3) of the motif as the primary determinant for DNA-protein interactions in the major groove, and a wing region(s) (W1) to form minor groove or phosphodiester backbone nucleoprotein contacts (Clark, K. L. et al. supra (1993)). Others, such as hRFX1, use W1 to interact with the major groove and the H3 helix makes only a single minor groove contact (Gajiwala, K. S. et al. *Nature* 403, 916–921 (2000)). The juxtaposition of the DNA-binding lobes in the present structure does not allow for modeling of the whole dimer onto a B-DNA representation of the operator. However, since mutations in both α4 (H3) and W1 affect the DNA binding activity of MarR it is expected that amino acids from each of these regions would contribute to the DNA binding activity of the protein. For example, mutations in α4, including an R73C change, abolish MarR DNA binding activity in whole cells and in vitro(Alekshun, M. N et al., supra, (2000)). In the present crystal structure, it is the side chain of Arg 73 that is hydrogen bonded to Asp 67' of the other subunit, an interaction that stabilizes the relative orientation of the two DNA-binding lobes (FIG. 6). Also, an R94C mutation at the tip of W1 is inactive in a whole cell assay while a G95S "superrepressor" mutation increases the DNA binding activity of MarR 30-fold in vitro (Alekshun, M. N et al., supra, (2000); Alekshun, M. N. & Levy, S. B. *J. Bact.* 181, 3303–3306 (1999)). In the absence of protein-DNA co-crystal structures, the precise mechanism by which these mutations affect the DNA binding activity of the protein is uncertain.

Footprinting experiments have suggested that MarR binds as a dimer at two separate but very similar sites in marO, the protein protects ~21-bp of DNA on both strands at a single site, and does not bend its target (Martin, R. G. et al., supra (1996); Martin, R. G. et al. *Proc. Natl. Acad. Sci. U.S.A.* 92, 5456–5460 (1995)). Each MarR binding site is composed of two half-sites whose organization is such that they are on different faces of the DNA double helix (Alekshun, M. N. et al. *Mol. Microbiol.* 35, 1394–404 (2000)), an arrangement that is very similar to the hRFX1 binding site (Gajiwala, K. S. et al. *Nature* 403, 916–921 (2000)). For MarR to bind as a dimer, with each winged-helix DNA binding domain contacting one half-site on B-DNA, geometric constraints suggest only a few possible modes of binding. One scenario, involving the binding of a single dimer to one MarR binding site, would require reorientation of the DNA binding lobes so that each could reach one half-site. This would be analogous to the binding of an E2F-DP heterodimer (a eukaryotic transcription factor in which each subunit also has a winged-helix DNA binding domain) to its cognate binding site (Zheng, N. et al. *Genes Dev.* 13, 666–74. (1999)). A second scenario would involve the binding of two dimers, on opposite faces of the double helix, to a single MarR binding site. This model would be analogous to the binding of DtxR (a bacterial protein with a winged-helix DNA binding domain) to its target, although in DtxR the half-sites are on the same face of the DNA helix (Pohl, E. et al. *J. Biol. Chem.* 273, 22420–22427 (1998); White, A. et al. *Nature* 394, 502–506 (1998)).

The term "appropriate conditions" include those conditions which result in the formation of a crystal which can by analyzed to a resolution of 5.0 Å or less. The crystals may be formed using suitable art recognized techniques, such as hanging droplet vapor diffusion. In one embodiment, the temperature of crystallization of the MarR family polypeptide is from about 1° C. to about 30° C., from about 10° C. to about 25° C., from about 15° C. to about 20° C., or abut 17° C. In a further embodiment, the conditions are selected such that crystals of said MarR family polypeptide grow within an acceptable time and reach dimensions which are suitable for structural determination, e.g., by using X-ray diffraction. In one embodiment, the acceptable time is 8 weeks or less, 6 weeks or less, 4 weeks or less, or 3 weeks or less. In an embodiment, the dimensions of the crystal are approximately 0.1 mm or greater per side, 0.2 mm or greater per said, or approximately 0.3 mm per side or greater.

In a further embodiment, the appropriate conditions include a cocrystallization agent which interacts with the protein such that the three dimensional structure of the protein can be determined.

The term "cocrystallization agent" includes substances which can be crystallized with the MarR family polypeptide such that the three dimensional structure can be determined. In an embodiment, the coocrystallization agent is a MarR family polypeptide modulator. The term "MarR family polypeptide modulator" includes compounds which interact with MarR, either to inhibit or enhance the activity of MarR, such that they alter its activity in its non-crystallized form. In one embodiment, the MarR family polypeptide modulator is a MarR inhibitor (e.g., salicylate, plombagin, or DNP). In an embodiment, the concentration of the salicylate is about 100 mM or less, 150 mM or less, 200 mM or less, or 250 mM or less.

The crystal structure or MarR has been solved using crystals grown in the presence and in the absence of high concentrations (250 mM) of sodium salicylate. This agent, at millimolar concentrations, is known to inhibit MarR activity both in vitro and in whole cells (Alekshun, M. N. supra (1999)). It is routinely used as a model inhibitor of MarR to induce MarA expression in *E. coli* and *S. typhimurium* (Cohen, S. P. et al. *J. Bact.* 175, 7856–7862 (1993); Sulavik, M. C. et al. *J. Bact.* 179, 1857–1866 (1997)) and thus, to confer a Mar phenotype (Alekshun, M. N. supra (1999)). In one example, salicylate was included in the current crystal growth conditions to provide stable crystals. In another example, the crystal structure of MarR was determined using MarR without salicylate.

Electron density that is consistent with bound salicylate is apparent at two sites on each subunit in the present structure (FIG. 6). These sites are on the surface of the molecule on either side of the proposed DNA-binding helix α4 (H3). In one site (SAL-A), the salicylate hydroxyl is hydrogen bonded to the hydroxyl side chain of Thr 72 in the α4 (H3) helix and the salicylate carboxylate hydrogen bonds to the guanidinium group of Arg 86. In the other site (SAL-B), the salicylate hydroxyl hydrogen bonds to the backbone carbonyl of Ala 70 and its carboxyl hydrogen bonds to Arg 77. In each of these sites, the salicylate ring sits over a hydrophobic side chain in the pocket; Pro 57 in SAL-A and Met 74 in SAL-B and other surface hydrophobes are also located laterally within 3.5 Å of the unsubstituted side of the ring. Although SAL-B is solvent exposed, SAL-A packs in the crystal with Val 96 of a symmetry mate situated 3.6 Å above the salicylate ring and adjacent to the SAL-A site of this symmetry mate. Since both SAL-A and SAL-B are close to the DNA binding helix, they may be positioned to influence DNA binding.

The crystal structure of MarR was solved by multiwavelength anomalous dispersion methods using protein containing selenomethionine. Diffraction data were collected to 2.3 Å from crystals of both seleno and native protein.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

EXAMPLE 1

Crystallization of MarR with Salicylate

Protein Production and Purification

Native and selenomethionine (Se-Met) containing MarR was prepared from *E. coli* BL21 (DE3) (Novagen) bearing pMarR-WT, a wild type MarR expression vector that has been previously described (Alekshun, M. N. & Levy, S. B. *J. Bact.* 181, 4669–4672 (1999)). Native MarR was produced in whole cells according to previous methods (Alekshun, M. N. & Levy, S. B. *J. Bact.* 181, 4669–4672 (1999)). Se-Met MarR was produced by diluting an overnight culture of *E. coli* BL21 (DE3)+pMarR-WT 1:1000 in M9 medium supplemented with 2 mM $MgSO_4$, 0.2% glucose, 0.1 mM $CaCl_2$, 0.00005% thiamine, 0.04 mg $ml^{-1}$ each of the following amino acids phenylalanine, leucine, isoleucine, valine, serine, threonine, tyrosine, histidine, lysine, aspartic acid, glutamic acid, tryptophan, and tryptophan, and kanamycin (Miller, J. H. In *Experiments in Molecular Genetics*. (Cold Spring Harbor Laboratories, Cold Spring Harbor, N.Y.; 1972). This culture was grown at 37° C. to an OD600≈0.6 and 100 mg each of amino acids threonine, lysine-hydrochloride, phenylalanine, 50 mg each of amino acids leucine, isoleucine, and valine (single letter abbreviations), and 60 mg L-(+)-selenomethionine (Sigma) were then added. The culture was grown for 15 min at 37° C.; IPTG was subsequently added to a final concentration of 1 mM and protein production was allowed to proceed for 14.5 hr at 37° C. Cell pellets were collected and processed as previously described (Alekshun, M. N. & Levy, S. B. *J. Bact.* 181, 4669–4672 (1999)).

Frozen cell pellets containing native or Se-Met MarR were resuspended in 100 mM sodium phosphate buffer (pH 7.4) containing a bacterial protease inhibitor cocktail (Sigma) and sonicated on ice. All buffers contained 2 mM DTT when Se-Met MarR was prepared. Insoluble matter was removed by centrifugation at 4° C. at 30,000×g for 40 min. The supernatant was passed over prepacked 5 ml SP-sepharose HiTrap columns (Amersham Pharmacia Biotech) previously equilibrated with 10 mM sodium phosphate buffer (pH 7.4). The column was washed with 50 ml of 10 mM sodium phosphate buffer (pH 7.4) and the pure proteins were eluted with a linear gradient (0–0.5 M) of NaCl in 10 mM sodium phosphate buffer (pH 7.4). Protein containing fractions were dialyzed vs. 10 mM HEPES (pH 7.4), 200 mM NaCl, and 1 mM DTT, or 2 mM DTT in the case of Se-Met MarR, and the protein in these samples was judged to be greater than 99% pure via SDS-PAGE and electrospray ionization mass spectrophotometry. The latter also demonstrated that more than 95% of the three methionine residues in Se-Met MarR were substituted with selenomethionine.

Crystallization:

MarR crystals were originally grown in 18% PEG MME 5000, 200 mM ammonium sulfate, 100 mM citrate buffer (pH 5.6) but showed anisotropic disorder in the diffraction data that made them unsuitable for structure determination. To stabilize the protein, the citrate was substituted by the known inhibitor salicylate. Crystals of the MarR-salicylate complex were grown at 17° C. by hanging droplet vapor diffusion. 6 µl of a 11.4 mg ml$^{-1}$ protein solution in 200 mM NaCl, 20 mM HEPES (pH 7.4), and 10 mM DTT were added to 2 µl of reservoir buffer (18% PEG MME 5000, 50 mM ammonium sulfate, 250 mM sodium salicylate, 10 mM DTT, and 15% glycerol, pH 5.5), and 0.8 µl 15% heptanetriol. The droplets were equilibrated with 1 ml of reservoir buffer. Crystals grew within 1 week reaching dimensions of approximately 0.3 mm per side.

X-ray Data Collection, Structure Determination, and Refinement:

Diffraction data were collected at the Brookhaven National Synchrotron Light Source, beamline X8C. Crystals were flash frozen in mother liquor at the beam line before data collection. All data were processed and reduced using DENZO and SCALEPACK (Otwinowski, Z. In *CCP4 Proceedings*. 56–62 (Daresbury Laboratory, Warrington, UK, 1993). The space group of the MarR-salicylate co-crystals was determined to be $I4_{1}22$ with one molecule in the asymmetric unit and with unit cell dimensions of a=b=62.0 Å, c=132.9 Å, $\alpha=\beta=\gamma=90°$ for both the native and the selenoprotein. Data were collected on the selenoprotein crystals at three wavelengths to enable MAD phasing. Phases were determined from the MAD data using the program SOLVE (Terwilliger, T. C. & Berendzen, J. *Acta Crystallogr. D.* 55, 849–861 (1999)). This showed two selenium sites per asymmetric unit, with the third selenomethionine, at the N-terminus, apparently disordered. Maps were solvent-flattened using the program DM and the model was built into density using the program O (Collaborative Computational Project, Number 4. *Acta Crystallogr. D.* 50, 760–763 (1994); Jones, T. A. et al. *Acta Crystallogr. A* 47, 110–119 (1991)). Model and refinement parameters for salicylate were obtained from the Hetero Compound Information Center (Kleywegt, G. J. & Jones, T. A. *Acta Crystallogr. D.* 54, 1119–1131 (1998)). Model refinement was performed using CNS and cycles of rebuilding and refinement continued to give the final model (Brunger, A. T. et al. *Acta Crystallogr. D.* 54, 905–921 (1998)). Model quality was assessed by sa-omit, Fo-Fc, maps generated over the whole molecule omitting no more than 7% of the structure at a time. The model extends from residue 6 to the C-terminus at residue 144. In common with several other transcription factors (e.g. TetR, (1A6I), ArgR (1B4B) and TreR (1BYK)), MarR shows relatively high thermal mobility throughout the structure, as reflected by the B-factors. Certain regions appear to be particularly mobile, including the extended structure at the N-terminus, the tip of the "wing" (residues 91–94), parts of the α5 helix, especially around Gly 116 and the connecting loop (128–131) between the α5 and the C-terminal α6 helix. Consistent with the high B-factors, the molecule shows few well-ordered solvent molecules. PROCHECK reports overall g-factors of 0.25 (dihedrals) and 0.55 (main chain covalent forces) and shows that 91% of the residues fall within the most favored region of the Ramachandran plot, with only residue Ala 53 in a disallowed region. This residue is located at the start of the loop connecting the α2 and α3 helices.

The coordinates of the MarR-salicylate cocrystal are shown in FIG. 7. Table 1 shows data collection, phasing, and refinement statistics for the MarR-salicylate co-crystal.

TABLE 1

| Data set | Native | Se-met edge | Se-met peak | Se-met remote |
|---|---|---|---|---|
| Wavelength (Å) | 1.072 | 0.9795 | 0.9793 | 0.9500 |
| Resolution range (Å) | 50–2.3 | 50–2.3 | 50–2.3 | 50–2.3 |
| Measured reflections | 56,495 | 84,173 | 96,582 | 87,365 |
| Unique reflections | 6,069 | 5,534 | 5,564 | 5,472 |
| Completeness (%) overall (final | 99.5 (100) | 91.3 (99.8) | 91.7 (99.8) | 90.4 (99.7) |
| <I/σI> (final shell) | 21.1 (12.0) | 12.2 (7.2) | 12.0 (7.0) | 12.9 (7.9) |
| $R_{merge}$ (%) (final shell) | 6.0 (20.0) | 6.4 (29.7) | 5.7 (30.3) | 4.9 (25.5) |
| Rano (%) |  | 4.9 | 5.0 | 3.5 |
| Overall FOM (centric/acentric) | 0.59/0.71 |  |  |  |
| Resolution | 50–2.3 |  |  |  |
| Rfree | 28.7% |  |  |  |
| Rcryst | 24.7% |  |  |  |
| Atoms/AU |  |  |  |  |
| Protein | 1078 |  |  |  |
| Salicylate | 20 |  |  |  |
| Water | 18 |  |  |  |
| Average B (Å$^2$) |  |  |  |  |
| main chain | 49.7 |  |  |  |
| side chain | 59.2 |  |  |  |
| salicylate | 42.7 |  |  |  |
| water | 50.0 |  |  |  |
| R.m.s. deviation |  |  |  |  |
| Bonds (Å) | 0.009 |  |  |  |
| Angles (°) | 1.3 |  |  |  |

EXAMPLE 2

Crystallization of MarR

MarR was produced and purified as described in Example 1.

Crystallization:

Crystals of MarR were grown by hanging droplet vapor diffusion. 3 μl of a 10 mg ml$^{-1}$ 2:1 (mol:mol) DNA-protein solution in 200 mM NaCl, 20 mM HEPES, pH 7.4, 20 mM TRIS-HCl, pH 8.0, and 2 mM MgCl$_2$ was added to 1 μl of reservoir buffer (23% PEG MME 5000, 100 mM sodium citrate, 200 mM ammonium sulfate, 10 mM DTT, 10% glycerol, 5% Isopropanol, pH 5.6), and 0.4 μl 15% heptanetriol. The droplets were equilibrated with 0.5 ml of reservoir buffer.

X-ray Data Collection, Structure Determination, and Refinement:

Diffraction data were collected at the Brookhaven National Synchrotron Light Source, beamline X8C. Crystals were flash frozen in mother liquor at the beam line before data collection. All data were processed and reduced using DENZO and SCALEPACK (Otwinowski, Z. In *CCP4 Proceedings*. 56–62 (Daresbury Laboratory, Warrington, UK, 1993).

The coordinates of the MarR crystal without salicylate are shown in FIG. 8. Table 2 shows data collection, phasing, and refinement statistics for the MarR crystal.

TABLE 2

| Space group | C222 |
|---|---|
| Unit cell (Å) | a = 65.8, b = 137.7, c = 96.4 |
| Resolution | 50–2.7 |
| Rfree | 26.7% |
| Rcryst | 23.2% |
| Atoms/AU | |
| Protein | 2093 |
| Water | 14 |
| Average B (Å$^2$) | |
| main chain | 40.0 |
| side chain | 48.0 |
| Water | 32.6 |
| R.m.s. deviation | |
| Bonds (Å) | 0.009 |
| Angles (°) | 1.3 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference. The entire contents of Alekshun et al. "The Crystal Structure of MarR a Regulator of Multiple Antibiotic Resistance at 2.3 Å resolution," *Nature Structural Biology* 8(8) is hereby incorporated herein by reference.

---

The invention claimed is:

1. A co-crystallized regulator of multiple antibiotic resistance (MarR) and the inhibitor salicylate having unit cell dimensions of a=62.00 Å, b=62.00 Å and c=132.89 Å, wherein said co-crystallized MarR and salicylate are crystallized under appropriate conditions such that the three dimensional structure of MarR and salicylate can be determined, and wherein said three dimensional structure has/$4_1 22$ space group and a peptide sequence of MarR comprising SEQ ID NO: 2.

2. The crystallized MarR of claim 1, wherein said MarR is selected from the group consisting of MarR of *Escherichia coli* and MarR, of *Salmonella typhimurium*.

3. The co-crystallized MarR and salicylate of claim 1, wherein said three dimensional structure is determined to a maximum resolution of 2.3 Å or better.

4. The crystallized MarR of claim 1, wherein said MarR has a winged-helix structure.

5. A crystallized MarR defined by FIGS. 7-1 to 7-20, wherein the crystal comprises SEQ ID NO: 2 and the inhibitor salicylate.

6. A crystallized MarR defined by FIGS. 8-1 to 8-29, wherein the crystal comprises SEQ ID NO: 2.

7. A crystallized regulator of multiple antibiotic resistance (MarR) having unit cell dimensions of a=65.8 Å, b=137.7 Å and c=96.4 Å, wherein said crystallized MarR is crystallized under appropriate conditions such that the three dimensional structure or said MarR can be determined, and wherein said three dimensional structure has C222 space group and a peptide sequence of MarR comprising SEQ ID NO: 2.

8. The crystallized MarR of claim 7, wherein said MarR is selected from the group consisting of MarR of *Escherichia coli* and MarR of *Salmonella typhimurium*.

9. The crystallized MarR of claim 7, wherein said MarR has a winged-helix structure.

10. The crystallized MarR of claim 7, wherein said three dimensional structure is determined to a maximum resolution of 2.3 Å.

* * * * *